United States Patent
Anderson et al.

(10) Patent No.: US 11,220,537 B2
(45) Date of Patent: Jan. 11, 2022

(54) **ANTIBODIES AGAINST *CLOSTRIDIUM DIFFICILE* TOXINS AND METHODS OF USING THE SAME**

(71) Applicant: SANOFI PASTEUR BIOLOGICS, LLC, Cambridge, MA (US)

(72) Inventors: Stephen F. Anderson, Arlington, MA (US); Natalie Anosova, Lexington, MA (US); Nicola Beltraminelli, Lyons (FR); Pierre Garrone, Lyons (FR); Harold Kleanthous, Chelmsford, MA (US); Jianxin Zhang, Acton, MA (US); Majid Mehtali, Paris (FR)

(73) Assignee: SANOFI PASTEUR BIOLOGICS, LLC, Cambridge, MA (US)

( * ) Notice: Subject to any disclaimer, the term of this patent is extended or adjusted under 35 U.S.C. 154(b) by 0 days.

(21) Appl. No.: 16/204,624

(22) Filed: Nov. 29, 2018

(65) Prior Publication Data

US 2019/0153078 A1    May 23, 2019

Related U.S. Application Data

(63) Continuation of application No. 14/776,146, filed as application No. PCT/US2014/028637 on Mar. 14, 2014, now Pat. No. 10,160,797.

(60) Provisional application No. 61/794,071, filed on Mar. 15, 2013.

(51) Int. Cl.
*C07K 16/00* (2006.01)
*C07K 16/12* (2006.01)
*A61K 39/40* (2006.01)
*A61K 39/00* (2006.01)

(52) U.S. Cl.
CPC .......... *C07K 16/1282* (2013.01); *A61K 39/40* (2013.01); *A61K 2039/505* (2013.01); *A61K 2039/507* (2013.01); *C07K 2317/21* (2013.01); *C07K 2317/30* (2013.01); *C07K 2317/31* (2013.01); *C07K 2317/34* (2013.01); *C07K 2317/76* (2013.01); *C07K 2317/92* (2013.01)

(58) Field of Classification Search
CPC .................................................. C07K 16/1282
See application file for complete search history.

(56) References Cited

U.S. PATENT DOCUMENTS

| | | | |
|---|---|---|---|
| 6,596,541 | B2 | 7/2003 | Murphy et al. |
| 7,625,559 | B2 | 12/2009 | Ambrosino et al. |
| 8,236,311 | B2 | 8/2012 | Ambrosino et al. |
| 8,257,709 | B2 | 9/2012 | Ambrosino et al. |
| 2004/0137601 | A1 | 7/2004 | Von Eichel-Streiber et al. |
| 2009/0087478 | A1 | 4/2009 | Hansen et al. |
| 2010/0233181 | A1 | 9/2010 | Ambrosino et al. |
| 2012/0282274 | A1 | 11/2012 | Jin et al. |
| 2012/0288508 | A1 | 11/2012 | Ambrosino et al. |
| 2016/0039944 | A1 | 2/2016 | Shinkura |

FOREIGN PATENT DOCUMENTS

| | | |
|---|---|---|
| EP | 2184345 A1 | 5/2010 |
| WO | 2006/121422 A2 | 11/2006 |
| WO | 2011/130650 A2 | 10/2011 |
| WO | 2012/092469 A2 | 7/2012 |
| WO | 2012/143902 A1 | 10/2012 |
| WO | 2013/028810 A1 | 2/2013 |
| WO | 2014/060898 A2 | 4/2014 |

OTHER PUBLICATIONS

Paul (Fundamental Immunology, 3rd Edition, pp. 292-295) (Year: 1993).*
Bendig (Methods: A Companion Methods in Enzymology vol. 8, pp. 83-93) (Year: 1995).*
MacCallum et al (J. Mol. Biol. vol. 262, pp. 732-745) (Year: 1996).*
Casset et al (Biochemical and Biophysical Research Communications vol. 307, pp. 198-205) (Year: 2003).*
Wu et al (Journal of Molecular Biology vol. 294, pp. 151-162) (Year: 1999).*
Skolnick et al (Trends in Biotechnology vol. 18, pp. 34-39) (Year: 2000).*
Vajdos et al (Journal of Molecular Biology vol. 320, pp. 415-428) (Year: 2002).*
European Search Report dated Jul. 5, 2016 from European Patent Application No. 14762533.9, pp. 1-14.
Babcock et al., "Human Monoclonal Antibodies Directed against Toxins A and B Prevent Clostridium difficile-induced Mortality in Hamsters", Infection and Immunity, vol. 74, No. 11, Nov. 1, 2006, pp. 6339-6347.
Rothman et al., "Immunochemical and Structural Similarities in Toxin A and Toxin B of Clostridium Difficile Shown by Binding to Monoclonal Antibodies", Toxicon, vol. 26, No. 6, Jan. 1, 1988, pp. 583-597.
Demarest et al., "Neutralization of Clostridium difficile toxin A using antibody combinations", mAbs, vol. 2, No. 2, Mar. 2010, pp. 190-198.
Hussack et al., "Neutralization of Clostridium difficile toxin A with Single-domain Antibodies Targeting the Cell Receptor Binding Domain", Journal of Biological Chemistry, vol. 286, No. 11, Mar. 18, 2011, pp. 8961-8976.
Lowy et al., "Treatment with Monoclonal Antibodies against Clostridium difficile Toxins", The New England Journal of Medicine, vol. 362, No. 3, Jan. 21, 2010, pp. 197-205.
Marozsan et al., "Mechanistic Studies of Novel Monoclonal Antibodies against Clostridium difficile Toxins", Abstracts of the Interscience Conference on Antimicrobial Agents and Chemotherapy, vol. 50, 2010, Abstract, 1 Page.

(Continued)

*Primary Examiner* — Albert M Navarro
(74) *Attorney, Agent, or Firm* — MH2 Technology Law Group, LLP

(57) ABSTRACT

Monoclonal antibodies, or antigen-binding fragments thereof, that bind to *Clostridium difficile* (*C. difficile*) toxin A or toxin B and methods of using the same to detect or treat *C. difficile* infections and/or *C. difficile*-associated disease.

19 Claims, 12 Drawing Sheets

Specification includes a Sequence Listing.

(56) References Cited

OTHER PUBLICATIONS

Marozsan et al., "Humanized mAbs Against Clostridium difficile Toxins A and B Demonstrate Potent Neutralizing Activity In Vitro and Durable Protection from Lethal Disease In Vivo", Abstracts of the Interscience Conference on Antimicrobial Agents and Chemotherapy, vol. 51, 2011, Abstract, 2 Pages.
Marozsan et al., "Protection Against Clostridium difficile Infection With Broadly Neutralizing Antitoxin Monoclonal Antibodies", The Journal of Infectious Diseases, vol. 206, No. 5, Sep. 1, 2012, pp. 706-713.
Thomas Tiller, "Single B cell antibody technologies", New Biotechnology, vol. 28, No. 5, Sep. 2011, pp. 453-457.
Hussack et al., "Toxin-Specific Antibodies for the Treatment of Clostridium difficile: Current Status and Future Perspectives", Toxins, May 7, 2010, vol. 2, pp. 998-1018.
Vink et al., "A simple, robust and highly efficient transient expression system for producing antibodies", Methods, 2014, vol. 65, pp. 5-10.
Communication pursuant to Article 94(3) EPC dated Jun. 4, 2019 for European Patent Application No. 14 762 533.9, 7 pages.
Rupnik, Maja, "Heterogeneity of large clostridial toxins: importance of Clostridium difficile toxinotypes", FEMS Microbiology Reviews, vol. 32, No. 3, May 1, 2008, pp. 541-555.
Rupnik et al., "A novel toxinotyping scheme and correlation of toxinotypes with serogroups of Clostridium difficile isolates", Journal of Clinical Microbiology, vol. 36, No. 8, Aug. 1, 1998, pp. 2240-2247.

\* cited by examiner toxin A cytotox

FIG. 1A toxin B cytotox

FIG. 1B

Inhibition of Neutralization Activity of mAb A2 by
C. diff Toxin A CTD Fragments of Toxinotype
0, III, V, XII and XV

- A2
- A2 + TxA 0 CTD
- A2 + TxA III CTD
- A2 + TxA V CTD
- A2 + TxA XII CTD
- A2 + TxA XV CTD

FIG. 3

Toxin A CTD Inhibition of A2

- A2 + TXV CTD
- A2 + TXII CTD
- A2 + TV CTD
- A2 + TIII CTD
- A2 + T0 CTD
- A2

FIG. 4A

Toxin B CTD Inhibition of B6

- B6 + TXV CTD
- B6 + TXII CTD
- B6 + TVIII CTD
- B6 + TV CTD
- B6 + TIII CTD
- B6 + T0 CTD
- B6

FIG. 4B

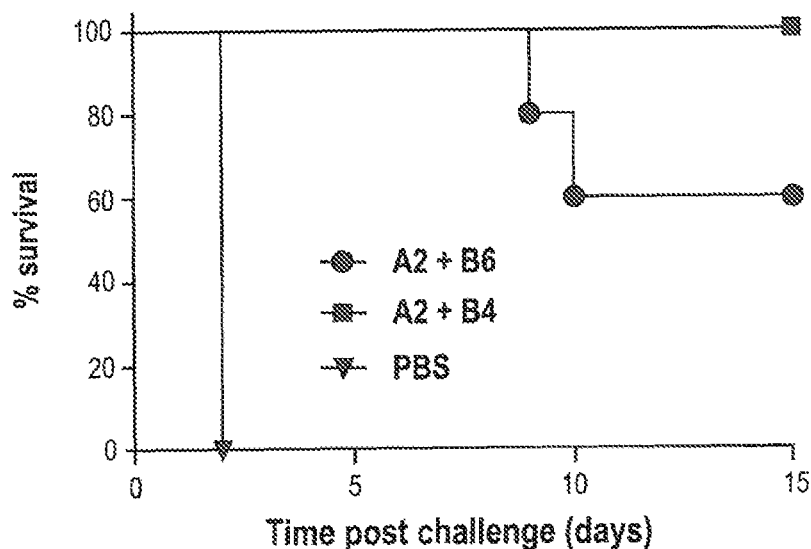
FIG. 5A
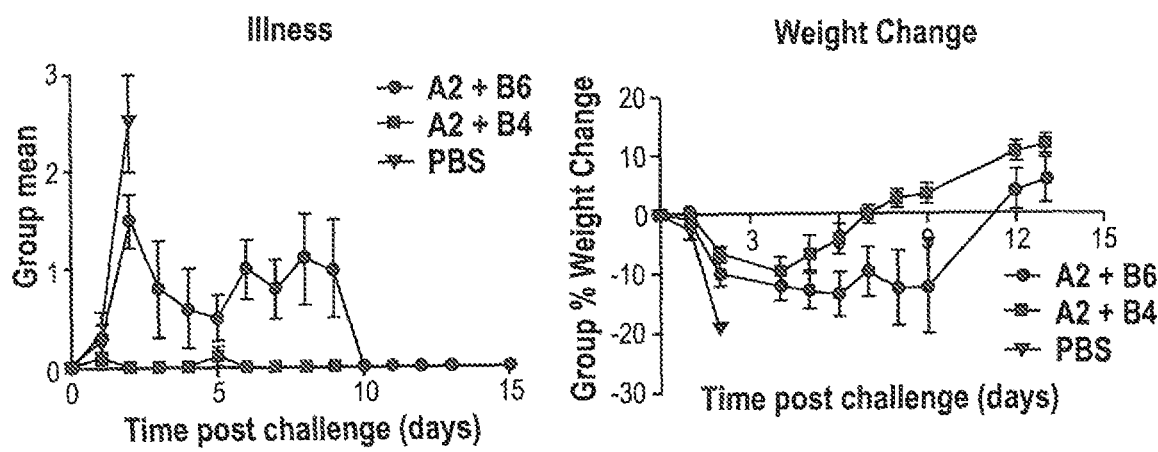
FIG. 5B
FIG. 5C

SEQUENCE LISTING

<160> NUMBER OF SEQ ID NOS: 340

<210> SEQ ID NO 1
<211> LENGTH: 1416
<212> TYPE: DNA
<213> ORGANISM: Homo sapiens

<400> SEQUENCE: 1

| | |
|---|---:|
| atgaaacatc tgtggttctt ccttctcctg gtggcagctc ccagatgggt cctgtcccag | 60 |
| gtgcagctgc aggagtcggg cccaggactg gtgaagcctt cggagaccct gtccctcacc | 120 |
| tgcactgtct ctggtggctc catcagtact tactactgga gctggatccg gcagtcccca | 180 |
| gggaagggac tggagtggat ggggtatatc tattatagtg ggagcaccaa ctacaacccc | 240 |
| tccctcgaga gtcgggtcac catagcagtg gacacgtcca agaatcagtt ctccctgcag | 300 |
| ttgacctctg tgactgctgc ggacacggcc gtgtattact gtgcgagagg agcggcggag | 360 |
| tggctacggt tcagggggtt ctttgactcc tggggccagg gaaccctggt caccgtctcc | 420 |
| tcagcctcca ccaagggccc atcggtcttc cccctggcac cctcctccaa gagcacctct | 480 |
| gggggcacag cggccctggg ctgcctggtc aaggactact ccccgaacc ggtgacggtg | 540 |
| tcgtggaact caggcgccct gaccagcggc gtgcacacct tcccggctgt cctacagtcc | 600 |
| tcaggactct actccctcag cagcgtggtg accgtgccct ccagcagctt gggcacccag | 660 |
| acctacatct gcaacgtgaa tcacaagccc agcaacacca aggtggacaa gaaagttgag | 720 |
| cccaaatctt gtgacaaaac tcacacatgc ccaccgtgcc cagcacctga actcctgggg | 780 |
| ggaccgtcag tcttcctctt ccccccaaaa cccaaggaca cctcatgat ctcccggacc | 840 |
| cctgaggtca catgcgtggt ggtggacgtg agccacgaag accctgaggt caagttcaac | 900 |
| tggtacgtgg acggcgtgga ggtgcataat gccaagacaa agccgcggga ggagcagtac | 960 |
| aacagcacgt accgggtggt cagcgtcctc accgtcctgc accaggactg gctgaatggc | 1020 |
| aaggagtaca agtgcaaggt ctccaacaaa gccctcccag cccccatcga gaaaaccatc | 1080 |
| tccaaagcca agggcagcc cgagaaccag gtgtaca ccctgccccc atcccgggat | 1140 |
| gagctgacca agaaccaggt cagcctgacc tgcctggtca aaggcttcta tcccagcgac | 1200 |
| atcgccgtgg agtgggagag caatgggcag ccggagaaca actacaagac cacgcctccc | 1260 |
| gtgctggact ccgacggctc cttcttcctc tacagcaagc tcaccgtgga caagagcagg | 1320 |
| tggcagcagg ggaacgtctt ctcatgctcc gtgatgcatg aggctctgca caaccactac | 1380 |
| acgcagaaga gcctctccct gtctccgggt aaatga | 1416 |

<210> SEQ ID NO 2
<211> LENGTH: 471
<212> TYPE: PRT
<213> ORGANISM: Homo sapiens

<400> SEQUENCE: 2

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

Ser Thr Tyr Tyr Trp Ser Trp Ile Arg Gln Ser Pro Gly Lys Gly Leu
    50                  55                  60

Glu Trp Met Gly Tyr Ile Tyr Tyr Ser Gly Ser Thr Asn Tyr Asn Pro

```
            65                  70                  75                  80
        Ser Leu Glu Ser Arg Val Thr Ile Ala Val Asp Thr Ser Lys Asn Gln
                        85                  90                  95

Phe Ser Leu Gln Leu Thr Ser Val Thr Ala Asp Thr Ala Val Tyr
                        100                 105                 110

Tyr Cys Ala Arg Gly Ala Ala Glu Trp Leu Arg Phe Arg Gly Phe Phe
                        115                 120                 125

Asp Ser Trp Gly Gln Gly Thr Leu Val Thr Val Ser Ser Ala Ser Thr
                    130                 135                 140

Lys Gly Pro Ser Val Phe Pro Leu Ala Pro Ser Ser Lys Ser Thr Ser
        145                 150                 155                 160

Gly Gly Thr Ala Ala Leu Gly Cys Leu Val Lys Asp Tyr Phe Pro Glu
                        165                 170                 175

Pro Val Thr Val Ser Trp Asn Ser Gly Ala Leu Thr Ser Gly Val His
                        180                 185                 190

Thr Phe Pro Ala Val Leu Gln Ser Ser Gly Leu Tyr Ser Leu Ser Ser
                    195                 200                 205

Val Val Thr Val Pro Ser Ser Ser Leu Gly Thr Gln Thr Tyr Ile Cys
                    210                 215                 220

Asn Val Asn His Lys Pro Ser Asn Thr Lys Val Asp Lys Lys Val Glu
        225                 230                 235                 240

Pro Lys Ser Cys Asp Lys Thr His Thr Cys Pro Pro Cys Pro Ala Pro
                        245                 250                 255

Glu Leu Leu Gly Gly Pro Ser Val Phe Leu Phe Pro Pro Lys Pro Lys
                        260                 265                 270

Asp Thr Leu Met Ile Ser Arg Thr Pro Glu Val Thr Cys Val Val Val
                    275                 280                 285

Asp Val Ser His Glu Asp Pro Glu Val Lys Phe Asn Trp Tyr Val Asp
                    290                 295                 300

Gly Val Glu Val His Asn Ala Lys Thr Lys Pro Arg Glu Glu Gln Tyr
        305                 310                 315                 320

Asn Ser Thr Tyr Arg Val Val Ser Val Leu Thr Val Leu His Gln Asp
                        325                 330                 335

Trp Leu Asn Gly Lys Glu Tyr Lys Cys Lys Val Ser Asn Lys Ala Leu
                        340                 345                 350

Pro Ala Pro Ile Glu Lys Thr Ile Ser Lys Ala Lys Gly Gln Pro Arg
                    355                 360                 365

Glu Pro Gln Val Tyr Thr Leu Pro Pro Ser Arg Asp Glu Leu Thr Lys
                    370                 375                 380

Asn Gln Val Ser Leu Thr Cys Leu Val Lys Gly Phe Tyr Pro Ser Asp
        385                 390                 395                 400

Ile Ala Val Glu Trp Glu Ser Asn Gly Gln Pro Glu Asn Asn Tyr Lys
                        405                 410                 415

Thr Thr Pro Pro Val Leu Asp Ser Asp Gly Ser Phe Phe Leu Tyr Ser
                        420                 425                 430

Lys Leu Thr Val Asp Lys Ser Arg Trp Gln Gln Gly Asn Val Phe Ser
                    435                 440                 445

Cys Ser Val Met His Glu Ala Leu His Asn His Tyr Thr Gln Lys Ser
                    450                 455                 460

Leu Ser Leu Ser Pro Gly Lys
        465                 470

<210> SEQ ID NO 3
```

```
<211> LENGTH: 705
<212> TYPE: DNA
<213> ORGANISM: Homo sapiens

<400> SEQUENCE: 3
atggaaaccc cagcgcagct tctcttcctc ctgctactct ggctcccaga gaccaccgga    60
gaaaatgtgt tgacgcagtc tccagggacc ctgtctttgt ctccagggga aagagccacc   120
ctctcctgca gggccagtca cagtgttacc aacaacttct tagcctggta ccagcaaaaa   180
cctggccagg ctcccaggct cctcatctat ggtgtgtcca gcagggccac tggcatccca   240
gacaggttca gtggcagtgg gtctgggaca gacttcactc tcaccatcag cagactggag   300
cctgaagatt ttgcagtgta ttactgtcag caatatggtg tctcagggac ttttggccag   360
gggaccaagc tggagatcaa acgaactgtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgccc tccaatcggg taactcccag   540
gagagtgtca cagagcagga cagcaaggac agcacctaca gcctcagcag caccctgacg   600
ctgagcaaag cagactacga gaaacacaaa gtctacgcct gcgaagtcac ccatcagggc   660
ctgagctcgc ccgtcacaaa gagcttcaac aggggagagt gttag                   705

<210> SEQ ID NO 4
<211> LENGTH: 234
<212> TYPE: PRT
<213> ORGANISM: Homo sapiens

<400> SEQUENCE: 4

Met Glu Thr Pro Ala Gln Leu Leu Phe Leu Leu Leu Trp Leu Pro
1               5                   10                  15

Glu Thr Thr Gly Glu Asn Val Leu Thr Gln Ser Pro Gly Thr Leu Ser
                20                  25                  30

Leu Ser Pro Gly Glu Arg Ala Thr Leu Ser Cys Arg Ala Ser His Ser
            35                  40                  45

Val Thr Asn Asn Phe Leu Ala Trp Tyr Gln Gln Lys Pro Gly Gln Ala
        50                  55                  60

Pro Arg Leu Leu Ile Tyr Gly Val Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
                100                 105                 110

Gly Val Ser Gly Thr Phe Gly Gln Gly Thr Lys Leu Glu Ile Lys Arg
            115                 120                 125

Thr Val Ala Ala Pro Ser Val Phe Ile Phe Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220
```

```
Val Thr Lys Ser Phe Asn Arg Gly Glu Cys
225                 230

<210> SEQ ID NO 5
<211> LENGTH: 25
<212> TYPE: PRT
<213> ORGANISM: Homo sapiens

<400> SEQUENCE: 5

Gln Val Gln Leu Gln Glu Ser Gly Pro Gly Leu Val Lys Pro Ser Glu
1               5                   10                  15

Thr Leu Ser Leu Thr Cys Thr Val Ser
            20                  25

<210> SEQ ID NO 6
<211> LENGTH: 10
<212> TYPE: PRT
<213> ORGANISM: Homo sapiens

<400> SEQUENCE: 6

Gly Gly Ser Ile Ser Thr Tyr Tyr Trp Ser
1               5                   10

<210> SEQ ID NO 7
<211> LENGTH: 14
<212> TYPE: PRT
<213> ORGANISM: Homo sapiens

<400> SEQUENCE: 7

Trp Ile Arg Gln Ser Pro Gly Lys Gly Leu Glu Trp Met Gly
1               5                   10

<210> SEQ ID NO 8
<211> LENGTH: 9
<212> TYPE: PRT
<213> ORGANISM: Homo sapiens

<400> SEQUENCE: 8

Tyr Ile Tyr Tyr Ser Gly Ser Thr Asn
1               5

<210> SEQ ID NO 9
<211> LENGTH: 39
<212> TYPE: PRT
<213> ORGANISM: Homo sapiens

<400> SEQUENCE: 9

Tyr Asn Pro Ser Leu Glu Ser Arg Val Thr Ile Ala Val Asp Thr Ser
1               5                   10                  15

Lys Asn Gln Phe Ser Leu Gln Leu Thr Ser Val Thr Ala Ala Asp Thr
            20                  25                  30

Ala Val Tyr Tyr Cys Ala Arg
            35

<210> SEQ ID NO 10
<211> LENGTH: 14
<212> TYPE: PRT
<213> ORGANISM: Homo sapiens

<400> SEQUENCE: 10

Gly Ala Ala Glu Trp Leu Arg Phe Arg Gly Phe Phe Asp Ser
1               5                   10
```

```
<210> SEQ ID NO 11
<211> LENGTH: 11
<212> TYPE: PRT
<213> ORGANISM: Homo sapiens

<400> SEQUENCE: 11

Trp Gly Gln Gly Thr Leu Val Thr Val Ser Ser
1               5                   10

<210> SEQ ID NO 12
<211> LENGTH: 23
<212> TYPE: PRT
<213> ORGANISM: Homo sapiens

<400> SEQUENCE: 12

Glu Asn Val Leu Thr Gln Ser Pro Gly Thr Leu Ser Leu Ser Pro Gly
1               5                   10                  15

Glu Arg Ala Thr Leu Ser Cys
            20

<210> SEQ ID NO 13
<211> LENGTH: 12
<212> TYPE: PRT
<213> ORGANISM: Homo sapiens

<400> SEQUENCE: 13

Arg Ala Ser His Ser Val Thr Asn Asn Phe Leu Ala
1               5                   10

<210> SEQ ID NO 14
<211> LENGTH: 15
<212> TYPE: PRT
<213> ORGANISM: Homo sapiens

<400> SEQUENCE: 14

Trp Tyr Gln Gln Lys Pro Gly Gln Ala Pro Arg Leu Leu Ile Tyr
1               5                   10                  15

<210> SEQ ID NO 15
<211> LENGTH: 7
<212> TYPE: PRT
<213> ORGANISM: Homo sapiens

<400> SEQUENCE: 15

Gly Val Ser Ser Arg Ala Thr
1               5

<210> SEQ ID NO 16
<211> LENGTH: 32
<212> TYPE: PRT
<213> ORGANISM: Homo sapiens

<400> SEQUENCE: 16

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 17
<211> LENGTH: 8
<212> TYPE: PRT
<213> ORGANISM: Homo sapiens

<400> SEQUENCE: 17
```

Gln Gln Tyr Gly Val Ser Gly Thr
1               5

<210> SEQ ID NO 18
<211> LENGTH: 10
<212> TYPE: PRT
<213> ORGANISM: Homo sapiens

<400> SEQUENCE: 18

Phe Gly Gln Gly Thr Lys Leu Glu Ile Lys
1               5                   10

<210> SEQ ID NO 19
<211> LENGTH: 1416
<212> TYPE: DNA
<213> ORGANISM: Homo sapiens

<400> SEQUENCE: 19

| | | | |
|---|---|---|---|
| atgaaacatc | tgtggttctt | ccttctcctg gtggcagccc ccagatgggt | cctgtcccag | 60 |
| gtgcacctgc | aggagtcggg | cccaggactg gtgaagcctt cggagaccct | gtccctcacc | 120 |
| tgcactgtct | ccggtgactc | catcagtact tactactgga gctggatccg | gcagccccca | 180 |
| gggaagggac | tggagtggat | tgggtatgtc tattacactg ggagcaccaa | ctacagccct | 240 |
| tccctcgagg | gtcgagtcac | cttatcagta gacacgtcca agaaccagtt | ctccctgaag | 300 |
| ttgaattctg | tgagtgctgc | ggacacggcc gtgtattact gtgcgagagg | cgcggcggag | 360 |
| tggctacgat | tcagggggtt | cttttgactac tggggccagg gaatcctggt | ctccgtctcc | 420 |
| tcagcctcca | ccaagggccc | atcggtcttc ccctggcac cctcctccaa | gagcacctct | 480 |
| gggggcacag | cggccctggg | ctgcctggtc aaggactact ccccgaacc | ggtgacggtg | 540 |
| tcgtggaact | caggcgccct | gaccagcggc gtgcacacct tcccggctgt | cctacagtcc | 600 |
| tcaggactct | actccctcag | cagcgtggtg accgtgccct ccagcagctt | gggcacccag | 660 |
| acctacatct | gcaacgtgaa | tcacaagccc agcaacacca aggtggacaa | gaaagttgag | 720 |
| cccaaatctt | gtgacaaaac | tcacacatgc ccaccgtgcc cagcacctga | actcctgggg | 780 |
| ggaccgtcag | tcttcctctt | ccccccaaaa cccaaggaca cctcatgat | ctcccggacc | 840 |
| cctgaggtca | catgcgtggt | ggtggacgtg agccacgaag accctgaggt | caagttcaac | 900 |
| tggtacgtgg | acggcgtgga | ggtgcataat gccaagacaa agccgcggga | ggagcagtac | 960 |
| aacagcacgt | accgggtggt | cagcgtcctc accgtcctgc accaggactg | gctgaatggc | 1020 |
| aaggagtaca | agtgcaaggt | ctccaacaaa gccctcccag cccccatcga | gaaaaccatc | 1080 |
| tccaaagcca | aagggcagcc | ccgagaacca caggtgtaca ccctgccccc | atcccgggat | 1140 |
| gagctgacca | agaaccaggt | cagcctgacc tgcctggtca aaggcttcta | tcccagcgac | 1200 |
| atcgccgtgg | agtgggagag | caatgggcag ccggagaaca actacaagac | cacgcctccc | 1260 |
| gtgctggact | ccgacggctc | cttcttcctc tacagcaagc tcaccgtgga | caagagcagg | 1320 |
| tggcagcagg | ggaacgtctt | ctcatgctcc gtgatgcatg aggctctgca | caaccactac | 1380 |
| acgcagaaga | gcctctccct | gtctccgggt aaatga | | 1416 |

<210> SEQ ID NO 20
<211> LENGTH: 471
<212> TYPE: PRT
<213> ORGANISM: Homo sapiens

<400> SEQUENCE: 20

```
Met Lys His Leu Trp Phe Phe Leu Leu Leu Val Ala Ala Pro Arg Trp
1               5                   10                  15

Val Leu Ser Gln Val His Leu Gln Glu Ser Gly Pro Gly Leu Val Lys
            20                  25                  30

Pro Ser Glu Thr Leu Ser Leu Thr Cys Thr Val Ser Gly Asp Ser Ile
        35                  40                  45

Ser Thr Tyr Tyr Trp Ser Trp Ile Arg Gln Pro Pro Gly Lys Gly Leu
    50                  55                  60

Glu Trp Ile Gly Tyr Val Tyr Tyr Thr Gly Thr Asn Tyr Ser Pro
65                  70                  75                  80

Ser Leu Glu Gly Arg Val Thr Leu Ser Val Asp Thr Ser Lys Asn Gln
                85                  90                  95

Phe Ser Leu Lys Leu Asn Ser Val Ser Ala Ala Asp Thr Ala Val Tyr
            100                 105                 110

Tyr Cys Ala Arg Gly Ala Ala Glu Trp Leu Arg Phe Arg Gly Phe Phe
            115                 120                 125

Asp Tyr Trp Gly Gln Gly Ile Leu Val Ser Val Ser Ser Ala Ser Thr
            130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
            165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
            195                 200                 205

Val Val Thr Val Pro Ser Ser Ser Leu Gly Thr Gln Thr Tyr Ile Cys
            210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val Asp
            290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Asp Glu Leu Thr Lys
            370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
```

```
                420             425             430
Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
        450                 455                 460

Leu Ser Leu Ser Pro Gly Lys
465                 470

<210> SEQ ID NO 21
<211> LENGTH: 705
<212> TYPE: DNA
<213> ORGANISM: Homo sapiens

<400> SEQUENCE: 21
atggaaaccc cagcgcagct tctcttcctc ctgctactct ggctcccaga taccaccgga      60
gaagttgtgt tgacgcagtc tccaggcacc ctgtctttgt ctccagggga aagagccacc     120
ctctcctgta gggccagtca gagtgttacc aacggcttct tagcctggta ccagcagaaa     180
cctggccagg ctcccagggt cctcatctat ggtgcgtcca gcagggccac tggcatccca     240
gacaggttca gtggcagtgg gtctgggaca gacttcactc tcaccatcag cagactggag     300
cctgaagatt ttgcaatgta ttactgtcag cagtatggtc tctcagggac ttttggccag     360
gggaccaagc tggagatcaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag caccctgacg     600
ctgagcaaag cagactacga gaaacacaaa gtctacgcct gcgaagtcac ccatcagggc     660
ctgagctcgc ccgtcacaaa gagcttcaac aggggagagt gttag                     705

<210> SEQ ID NO 22
<211> LENGTH: 234
<212> TYPE: PRT
<213> ORGANISM: Homo sapiens

<400> SEQUENCE: 22

Met Glu Thr Pro Ala Gln Leu Leu Phe Leu Leu Leu Trp Leu Pro
1               5                   10                  15

Asp Thr Thr Gly Glu Val Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Thr Asn Gly Phe Leu Ala Trp Tyr Gln Gln Lys Pro Gly Gln Ala
    50                  55                  60

Pro Arg Val Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Met Tyr Tyr Cys Gln Gln Tyr
            100                 105                 110

Gly Leu Ser Gly Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
```

```
145                 150                 155                 160
Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 23
<211> LENGTH: 25
<212> TYPE: PRT
<213> ORGANISM: Homo sapiens

<400> SEQUENCE: 23

Gln Val His Leu Gln Glu Ser Gly Pro Gly Leu Val Lys Pro Ser Glu
1               5                   10                  15

Thr Leu Ser Leu Thr Cys Thr Val Ser
            20                  25

<210> SEQ ID NO 24
<211> LENGTH: 10
<212> TYPE: PRT
<213> ORGANISM: Homo sapiens

<400> SEQUENCE: 24

Gly Asp Ser Ile Ser Thr Tyr Tyr Trp Ser
1               5                   10

<210> SEQ ID NO 25
<211> LENGTH: 14
<212> TYPE: PRT
<213> ORGANISM: Homo sapiens

<400> SEQUENCE: 25

Trp Ile Arg Gln Pro Pro Gly Lys Gly Leu Glu Trp Ile Gly
1               5                   10

<210> SEQ ID NO 26
<211> LENGTH: 9
<212> TYPE: PRT
<213> ORGANISM: Homo sapiens

<400> SEQUENCE: 26

Tyr Val Tyr Tyr Thr Gly Ser Thr Asn
1               5

<210> SEQ ID NO 27
<211> LENGTH: 39
<212> TYPE: PRT
<213> ORGANISM: Homo sapiens

<400> SEQUENCE: 27

Tyr Ser Pro Ser Leu Glu Gly Arg Val Thr Leu Ser Val Asp Thr Ser
1               5                   10                  15

Lys Asn Gln Phe Ser Leu Lys Leu Asn Ser Val Ser Ala Ala Asp Thr
            20                  25                  30

Ala Val Tyr Tyr Cys Ala Arg
```

<210> SEQ ID NO 28
<211> LENGTH: 14
<212> TYPE: PRT
<213> ORGANISM: Homo sapiens

<400> SEQUENCE: 28

Gly Ala Ala Glu Trp Leu Arg Phe Arg Gly Phe Phe Asp Tyr
1               5                   10

<210> SEQ ID NO 29
<211> LENGTH: 11
<212> TYPE: PRT
<213> ORGANISM: Homo sapiens

<400> SEQUENCE: 29

Trp Gly Gln Gly Ile Leu Val Ser Val Ser Ser
1               5                   10

<210> SEQ ID NO 30
<211> LENGTH: 23
<212> TYPE: PRT
<213> ORGANISM: Homo sapiens

<400> SEQUENCE: 30

Glu Val Val Leu Thr Gln Ser Pro Gly Thr Leu Ser Leu Ser Pro Gly
1               5                   10                  15

Glu Arg Ala Thr Leu Ser Cys
            20

<210> SEQ ID NO 31
<211> LENGTH: 12
<212> TYPE: PRT
<213> ORGANISM: Homo sapiens

<400> SEQUENCE: 31

Arg Ala Ser Gln Ser Val Thr Asn Gly Phe Leu Ala
1               5                   10

<210> SEQ ID NO 32
<211> LENGTH: 15
<212> TYPE: PRT
<213> ORGANISM: Homo sapiens

<400> SEQUENCE: 32

Trp Tyr Gln Gln Lys Pro Gly Gln Ala Pro Arg Val Leu Ile Tyr
1               5                   10                  15

<210> SEQ ID NO 33
<211> LENGTH: 7
<212> TYPE: PRT
<213> ORGANISM: Homo sapiens

<400> SEQUENCE: 33

Gly Ala Ser Ser Arg Ala Thr
1               5

<210> SEQ ID NO 34
<211> LENGTH: 32
<212> TYPE: PRT
<213> ORGANISM: Homo sapiens

<400> SEQUENCE: 34

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Met Tyr Tyr Cys
            20                  25                  30

<210> SEQ ID NO 35
<211> LENGTH: 8
<212> TYPE: PRT
<213> ORGANISM: Homo sapiens

<400> SEQUENCE: 35

Gln Gln Tyr Gly Leu Ser Gly Thr
1               5

<210> SEQ ID NO 36
<211> LENGTH: 10
<212> TYPE: PRT
<213> ORGANISM: Homo sapiens

<400> SEQUENCE: 36

Phe Gly Gln Gly Thr Lys Leu Glu Ile Lys
1               5                   10

<210> SEQ ID NO 37
<211> LENGTH: 1398
<212> TYPE: DNA
<213> ORGANISM: Homo sapiens

<400> SEQUENCE: 37

| | |
|---|---|
| atgcaactgc tggagtctgg gggaggcttg gtgaagcctg gggggtccct tagactctcc | 60 |
| tgtgcagcct ctggattcac tttcagtaac gcctggatga gttgggtccg ccagggtcca | 120 |
| gggaaggggc tggaatgggt tggccgtatt aaaagtaaaa ctgatggtgg acaacagac | 180 |
| tacgctgcac ccgtgaaagg cagattcagc atctcaagaa atgattcaaa taacacgctg | 240 |
| tttctgcaaa tgaacagcct gaaaaccgag gacacagccg tatattactg taccacaggt | 300 |
| cctcaaattg tagttgtagc aggtgctacc agtcgggacc agcctaacta ctactactac | 360 |
| ggtttggacg tctggggcct agggaccacg gtcaccgtct cgtcagcctc caccaagggc | 420 |
| ccatcggtct tccccctggc accctcctcc aagagcacct ctgggggcac agcggccctg | 480 |
| ggctgcctgg tcaaggacta cttccccgaa ccggtgacgg tgtcgtggaa ctcaggcgcc | 540 |
| ctgaccagcg gcgtgcacac cttcccggct gtcctacagt cctcaggact ctactccctc | 600 |
| agcagcgtgg tgaccgtgcc ctccagcagc ttgggcaccc agacctacat ctgcaacgtg | 660 |
| aatcacaagc ccagcaacac caaggtggac aagaaagttg agcccaaatc ttgtgacaaa | 720 |
| actcacacat gcccaccgtg cccagcacct gaactcctgg ggggaccgtc agtcttcctc | 780 |
| ttccccccaa aacccaagga caccctcatg atctcccgga cccctgaggt cacatgcgtg | 840 |
| gtggtggacg tgagccacga agaccctgag gtcaagttca actggtacgt ggacggcgtg | 900 |
| gaggtgcata atgccaagac aaagccgcgg gaggagcagt acaacagcac gtaccgggtg | 960 |
| gtcagcgtcc tcaccgtcct gcaccaggac tggctgaatg gcaaggagta caagtgcaag | 1020 |
| gtctccaaca aagccctccc agcccccatc gagaaaacca tctccaaagc caaagggcag | 1080 |
| ccccgagaac acaggtgta caccctgccc ccatcccggg atgagctgac caagaaccag | 1140 |
| gtcagcctga cctgcctggt caaaggcttc tatcccagcg acatcgccgt ggagtgggag | 1200 |
| agcaatgggc agccggagaa caactacaag accacgcctc ccgtgctgga ctccgacggc | 1260 |
| tccttcttcc tctacagcaa gctcaccgtg gacaagagca ggtggcagca ggggaacgtc | 1320 |

-continued

```
ttctcatgct ccgtgatgca tgaggctctg cacaaccact acacgcagaa gagcctctcc    1380
ctgtctccgg gtaaatga                                                  1398
```

<210> SEQ ID NO 38
<211> LENGTH: 465
<212> TYPE: PRT
<213> ORGANISM: Homo sapiens

<400> SEQUENCE: 38

| Met | Gln | Leu | Leu | Glu | Ser | Gly | Gly | Leu | Val | Lys | Pro | Gly | Gly | Ser |
|---|---|---|---|---|---|---|---|---|---|---|---|---|---|---|
| 1 | | | | 5 | | | | | 10 | | | | | 15 |

| Leu | Arg | Leu | Ser | Cys | Ala | Ala | Ser | Gly | Phe | Thr | Phe | Ser | Asn | Ala | Trp |
|---|---|---|---|---|---|---|---|---|---|---|---|---|---|---|---|
| | | | 20 | | | | | 25 | | | | | 30 | | |

| Met | Ser | Trp | Val | Arg | Gln | Gly | Pro | Gly | Lys | Gly | Leu | Glu | Trp | Val | Gly |
|---|---|---|---|---|---|---|---|---|---|---|---|---|---|---|---|
| | 35 | | | | | 40 | | | | | 45 | | | | |

| Arg | Ile | Lys | Ser | Lys | Thr | Asp | Gly | Gly | Thr | Thr | Asp | Tyr | Ala | Ala | Pro |
|---|---|---|---|---|---|---|---|---|---|---|---|---|---|---|---|
| 50 | | | | | 55 | | | | | 60 | | | | | |

| Val | Lys | Gly | Arg | Phe | Ser | Ile | Ser | Arg | Asn | Asp | Ser | Asn | Asn | Thr | Leu |
|---|---|---|---|---|---|---|---|---|---|---|---|---|---|---|---|
| 65 | | | | | 70 | | | | | 75 | | | | | 80 |

| Phe | Leu | Gln | Met | Asn | Ser | Leu | Lys | Thr | Glu | Asp | Thr | Ala | Val | Tyr | Tyr |
|---|---|---|---|---|---|---|---|---|---|---|---|---|---|---|---|
| | | | | 85 | | | | | 90 | | | | | 95 | |

| Cys | Thr | Thr | Gly | Pro | Gln | Ile | Val | Val | Ala | Gly | Ala | Thr | Ser | Arg |
|---|---|---|---|---|---|---|---|---|---|---|---|---|---|---|
| | | | 100 | | | | | 105 | | | | | 110 | |

| Asp | Gln | Pro | Asn | Tyr | Tyr | Tyr | Gly | Leu | Asp | Val | Trp | Gly | Leu | Gly |
|---|---|---|---|---|---|---|---|---|---|---|---|---|---|---|
| | | 115 | | | | | 120 | | | | | 125 | | |

| Thr | Thr | Val | Thr | Val | Ser | Ser | Ala | Ser | Thr | Lys | Gly | Pro | Ser | Val | Phe |
|---|---|---|---|---|---|---|---|---|---|---|---|---|---|---|---|
| | 130 | | | | | 135 | | | | | 140 | | | | |

| Pro | Leu | Ala | Pro | Ser | Ser | Lys | Ser | Thr | Ser | Gly | Gly | Thr | Ala | Ala | Leu |
|---|---|---|---|---|---|---|---|---|---|---|---|---|---|---|---|
| 145 | | | | | 150 | | | | | 155 | | | | | 160 |

| Gly | Cys | Leu | Val | Lys | Asp | Tyr | Phe | Pro | Glu | Pro | Val | Thr | Val | Ser | Trp |
|---|---|---|---|---|---|---|---|---|---|---|---|---|---|---|---|
| | | | | 165 | | | | | 170 | | | | | 175 | |

| Asn | Ser | Gly | Ala | Leu | Thr | Ser | Gly | Val | His | Thr | Phe | Pro | Ala | Val | Leu |
|---|---|---|---|---|---|---|---|---|---|---|---|---|---|---|---|
| | | | 180 | | | | | 185 | | | | | 190 | | |

| Gln | Ser | Ser | Gly | Leu | Tyr | Ser | Leu | Ser | Ser | Val | Val | Thr | Val | Pro | Ser |
|---|---|---|---|---|---|---|---|---|---|---|---|---|---|---|---|
| | | 195 | | | | | 200 | | | | | 205 | | | |

| Ser | Ser | Leu | Gly | Thr | Gln | Thr | Tyr | Ile | Cys | Asn | Val | Asn | His | Lys | Pro |
|---|---|---|---|---|---|---|---|---|---|---|---|---|---|---|---|
| 210 | | | | | 215 | | | | | 220 | | | | | |

| Ser | Asn | Thr | Lys | Val | Asp | Lys | Lys | Val | Glu | Pro | Lys | Ser | Cys | Asp | Lys |
|---|---|---|---|---|---|---|---|---|---|---|---|---|---|---|---|
| 225 | | | | | 230 | | | | | 235 | | | | | 240 |

| Thr | His | Thr | Cys | Pro | Pro | Cys | Pro | Ala | Pro | Glu | Leu | Leu | Gly | Gly | Pro |
|---|---|---|---|---|---|---|---|---|---|---|---|---|---|---|---|
| | | | | 245 | | | | | 250 | | | | | 255 | |

| Ser | Val | Phe | Leu | Phe | Pro | Pro | Lys | Pro | Lys | Asp | Thr | Leu | Met | Ile | Ser |
|---|---|---|---|---|---|---|---|---|---|---|---|---|---|---|---|
| | | | 260 | | | | | 265 | | | | | 270 | | |

| Arg | Thr | Pro | Glu | Val | Thr | Cys | Val | Val | Val | Asp | Val | Ser | His | Glu | Asp |
|---|---|---|---|---|---|---|---|---|---|---|---|---|---|---|---|
| | | 275 | | | | | 280 | | | | | 285 | | | |

| Pro | Glu | Val | Lys | Phe | Asn | Trp | Tyr | Val | Asp | Gly | Val | Glu | Val | His | Asn |
|---|---|---|---|---|---|---|---|---|---|---|---|---|---|---|---|
| | 290 | | | | | 295 | | | | | 300 | | | | |

| Ala | Lys | Thr | Lys | Pro | Arg | Glu | Glu | Gln | Tyr | Asn | Ser | Thr | Tyr | Arg | Val |
|---|---|---|---|---|---|---|---|---|---|---|---|---|---|---|---|
| 305 | | | | | 310 | | | | | 315 | | | | | 320 |

| Val | Ser | Val | Leu | Thr | Val | Leu | His | Gln | Asp | Trp | Leu | Asn | Gly | Lys | Glu |
|---|---|---|---|---|---|---|---|---|---|---|---|---|---|---|---|
| | | | | 325 | | | | | 330 | | | | | 335 | |

| Tyr | Lys | Cys | Lys | Val | Ser | Asn | Lys | Ala | Leu | Pro | Ala | Pro | Ile | Glu | Lys |
|---|---|---|---|---|---|---|---|---|---|---|---|---|---|---|---|
| | | | 340 | | | | | 345 | | | | | 350 | | |

```
Thr Ile Ser Lys Ala Lys Gly Gln Pro Arg Glu Pro Gln Val Tyr Thr
            355                 360                 365

Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
    435                 440                 445

Ala Leu His Asn His Tyr Thr Gln Lys Ser Leu Ser Leu Ser Pro Gly
    450                 455                 460

Lys
465

<210> SEQ ID NO 39
<211> LENGTH: 711
<212> TYPE: DNA
<213> ORGANISM: Homo sapiens

<400> SEQUENCE: 39
atggccagct tccctctcct cctcaccctc ctcactcact gtgcagggtc ctgggcccag      60
tctgtgctga ctcagccacc ctcagcgtct gggacccccg ggcagagggt caccatctct     120
tgttctggaa gcagctccaa catcggcatt aatactgtaa actggtacca gcagctccca     180
ggaacggccc ccaaactcct catatataag agtaatctgc gaccctcagg ggtccctgac     240
cgattctctg gctccaagtc tggcacctca gcctccctgg ccatcagtgg gctccggtct     300
gaggatgagg ctgattatta ctgtgcggca tgggatgaca gcctgactgg tctttatgtc     360
ttcggaactg ggaccaaggt caccgtccta ggtcagccca aggccaaccc cactgtcact     420
ctgttcccgc cctcctctga ggagctccaa gccaacaagg ccacactagt gtgtctgatc     480
agtgacttct acccgggagc tgtgacagtg gcttggaagg cagatggcag ccccgtcaag     540
gcgggagtgg agacgaccaa accctccaaa cagagcaaca acaagtacgc ggccagcagc     600
tacctgagcc tgacgcccga gcagtggaag tcccacagaa gctacagctg ccaggtcacg     660
catgaaggga gcaccgtgga agacagtgtg cccctacag aatgttcata g             711

<210> SEQ ID NO 40
<211> LENGTH: 236
<212> TYPE: PRT
<213> ORGANISM: Homo sapiens

<400> SEQUENCE: 40

Met Ala Ser Phe Pro Leu Leu Leu Thr Leu Leu Thr His Cys Ala Gly
1               5                   10                  15

Ser Trp Ala Gln Ser Val Leu Thr Gln Pro Pro Ser Ala Ser Gly Thr
            20                  25                  30

Pro Gly Gln Arg Val Thr Ile Ser Cys Ser Gly Ser Ser Ser Asn Ile
        35                  40                  45

Gly Ile Asn Thr Val Asn Trp Tyr Gln Gln Leu Pro Gly Thr Ala Pro
    50                  55                  60

Lys Leu Leu Ile Tyr Lys Ser Asn Leu Arg Pro Ser Gly Val Pro Asp
65                  70                  75                  80
```

Arg Phe Ser Gly Ser Lys Ser Gly Thr Ser Ala Ser Leu Ala Ile Ser
                85                  90                  95

Gly Leu Arg Ser Glu Asp Glu Ala Asp Tyr Tyr Cys Ala Ala Trp Asp
            100                 105                 110

Asp Ser Leu Thr Gly Leu Tyr Val Phe Gly Thr Gly Thr Lys Val Thr
        115                 120                 125

Val Leu Gly Gln Pro Lys Ala Asn Pro Thr Val Thr Leu Phe Pro Pro
    130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Gly
                165                 170                 175

Ser Pro Val Lys Ala Gly Val Glu Thr Thr Lys Pro Ser Lys Gln Ser
            180                 185                 190

Asn Asn Lys Tyr Ala Ala Ser Ser Tyr Leu Ser Leu Thr Pro Glu Gln
        195                 200                 205

Trp Lys Ser His Arg Ser Tyr Ser Cys Gln Val Thr His Glu Gly Ser
    210                 215                 220

Thr Val Glu Lys Thr Val Ala Pro Thr Glu Cys Ser
225                 230                 235

<210> SEQ ID NO 41
<211> LENGTH: 24
<212> TYPE: PRT
<213> ORGANISM: Homo sapiens

<400> SEQUENCE: 41

Met Gln Leu Leu Glu Ser Gly Gly Gly Leu Val Lys Pro Gly Gly Ser
1               5                   10                  15

Leu Arg Leu Ser Cys Ala Ala Ser
            20

<210> SEQ ID NO 42
<211> LENGTH: 10
<212> TYPE: PRT
<213> ORGANISM: Homo sapiens

<400> SEQUENCE: 42

Gly Phe Thr Phe Ser Asn Ala Trp Met Ser
1               5                   10

<210> SEQ ID NO 43
<211> LENGTH: 14
<212> TYPE: PRT
<213> ORGANISM: Homo sapiens

<400> SEQUENCE: 43

Trp Val Arg Gln Gly Pro Gly Lys Gly Leu Glu Trp Val Gly
1               5                   10

<210> SEQ ID NO 44
<211> LENGTH: 12
<212> TYPE: PRT
<213> ORGANISM: Homo sapiens

<400> SEQUENCE: 44

Arg Ile Lys Ser Lys Thr Asp Gly Gly Thr Thr Asp
1               5                   10

<210> SEQ ID NO 45

```
<211> LENGTH: 39
<212> TYPE: PRT
<213> ORGANISM: Homo sapiens

<400> SEQUENCE: 45

Tyr Ala Ala Pro Val Lys Gly Arg Phe Ser Ile Ser Arg Asn Asp Ser
1               5                   10                  15

Asn Asn Thr Leu Phe Leu Gln Met Asn Ser Leu Lys Thr Glu Asp Thr
            20                  25                  30

Ala Val Tyr Tyr Cys Thr Thr
        35

<210> SEQ ID NO 46
<211> LENGTH: 8
<212> TYPE: PRT
<213> ORGANISM: Homo sapiens

<400> SEQUENCE: 46

Gly Pro Gln Ile Val Val Val Ala
1               5

<210> SEQ ID NO 47
<211> LENGTH: 28
<212> TYPE: PRT
<213> ORGANISM: Homo sapiens

<400> SEQUENCE: 47

Gly Ala Thr Ser Arg Asp Gln Pro Asn Tyr Tyr Tyr Gly Leu Asp
1               5                   10                  15

Val Trp Gly Leu Gly Thr Thr Val Thr Val Ser Ser
            20                  25

<210> SEQ ID NO 48
<211> LENGTH: 22
<212> TYPE: PRT
<213> ORGANISM: Homo sapiens

<400> SEQUENCE: 48

Gln Ser Val Leu Thr Gln Pro Pro Ser Ala Ser Gly Thr Pro Gly Gln
1               5                   10                  15

Arg Val Thr Ile Ser Cys
            20

<210> SEQ ID NO 49
<211> LENGTH: 13
<212> TYPE: PRT
<213> ORGANISM: Homo sapiens

<400> SEQUENCE: 49

Ser Gly Ser Ser Ser Asn Ile Gly Ile Asn Thr Val Asn
1               5                   10

<210> SEQ ID NO 50
<211> LENGTH: 15
<212> TYPE: PRT
<213> ORGANISM: Homo sapiens

<400> SEQUENCE: 50

Trp Tyr Gln Gln Leu Pro Gly Thr Ala Pro Lys Leu Leu Ile Tyr
1               5                   10                  15

<210> SEQ ID NO 51
<211> LENGTH: 7
```

<212> TYPE: PRT
<213> ORGANISM: Homo sapiens

<400> SEQUENCE: 51

Lys Ser Asn Leu Arg Pro Ser
1               5

<210> SEQ ID NO 52
<211> LENGTH: 32
<212> TYPE: PRT
<213> ORGANISM: Homo sapiens

<400> SEQUENCE: 52

Gly Val Pro Asp Arg Phe Ser Gly Ser Lys Ser Gly Thr Ser Ala Ser
1               5                   10                  15

Leu Ala Ile Ser Gly Leu Arg Ser Glu Asp Glu Ala Asp Tyr Tyr Cys
            20                  25                  30

<210> SEQ ID NO 53
<211> LENGTH: 12
<212> TYPE: PRT
<213> ORGANISM: Homo sapiens

<400> SEQUENCE: 53

Ala Ala Trp Asp Asp Ser Leu Thr Gly Leu Tyr Val
1               5                   10

<210> SEQ ID NO 54
<211> LENGTH: 20
<212> TYPE: PRT
<213> ORGANISM: Homo sapiens

<400> SEQUENCE: 54

Phe Gly Thr Gly Thr Lys Val Thr Val Leu Gly Gln Pro Lys Ala Asn
1               5                   10                  15

Pro Thr Val Thr
            20

<210> SEQ ID NO 55
<211> LENGTH: 1431
<212> TYPE: DNA
<213> ORGANISM: Homo sapiens

<400> SEQUENCE: 55

```
atggagtttg ggctgagctg ggttttcctc gttgctcttt taagaggtgt ccagtgtcag      60
gtgcacctgg tggagtctgg gggaggcgtg gtccagcctg gaggtccct  gagactctcc     120
tgtgcaacct ttggactcaa cttcagtgac tatggttttc actgggtccg ccaggctcca     180
ggcaagggc  tggagtgggt ggcagttaca tcatatgatg aagcaacaa  atactacgca     240
gaattcgtga agggccgatt caccatctcc agagacaatt acaagaatac ggtgtatctg     300
caaatgaaca gcctgagact gaggacacg  gctgtgtatt actgtgcgag agatctcgcc     360
ccatacaatt tttggagtgg ttatgggaat aattggttcg acccctgggg ccagggaacc     420
ctggtcaccg tctcctcagc ctccaccaag ggcccatcgg tcttcccct  ggcaccctcc     480
tccaagagca cctctggggg cacagcggcc ctgggctgcc tggtcaagga ctacttcccc     540
gaaccggtga cggtgtcgtg gaactcaggc gccctgacca gcggcgtgca caccttcccg     600
gctgtcctac agtcctcagg actctactcc ctcagcagcg tggtgaccgt gccctccagc     660
agcttgggca cccagaccta catctgcaac gtgaatcaca agcccagcaa caccaaggtg     720
```

-continued

```
gacaagaaag ttgagcccaa atcttgtgac aaaactcaca catgcccacc gtgcccagca    780
cctgaactcc tggggggacc gtcagtcttc ctcttccccc caaaacccaa ggacaccctc    840
atgatctccc ggacccctga ggtcacatgc gtggtggtgg acgtgagcca cgaagaccct    900
gaggtcaagt tcaactggta cgtggacggc gtggaggtgc ataatgccaa gacaaagccg   960
cgggaggagc agtacaacag cacgtaccgg gtggtcagcg tcctcaccgt cctgcaccag   1020
gactggctga atggcaagga gtacaagtgc aaggtctcca acaaagccct cccagccccc   1080
atcgagaaaa ccatctccaa agccaaaggg cagccccgag aaccacaggt gtacaccctg   1140
cccccatccc gggatgagct gaccaagaac caggtcagcc tgacctgcct ggtcaaaggc   1200
ttctatccca gcgacatcgc cgtggagtgg gagagcaatg ggcagccgga gaacaactac   1260
aagaccacgc ctcccgtgct ggactccgac ggctccttct tcctctacag caagctcacc   1320
gtggacaaga gcaggtggca gcaggggaac gtcttctcat gctccgtgat gcatgaggct   1380
ctgcacaacc actacacgca gaagagcctc tccctgtctc cgggtaaatg a           1431
```

<210> SEQ ID NO 56
<211> LENGTH: 476
<212> TYPE: PRT
<213> ORGANISM: Homo sapiens

<400> SEQUENCE: 56

```
Met Glu Phe Gly Leu Ser Trp Val Phe Leu Val Ala Leu Leu Arg Gly
1               5                   10                  15

Val Gln Cys Gln Val His Leu Val Glu Ser Gly Gly Gly Val Val Gln
                20                  25                  30

Pro Gly Arg Ser Leu Arg Leu Ser Cys Ala Thr Phe Gly Leu Asn Phe
        35                  40                  45

Ser Asp Tyr Gly Phe His Trp Val Arg Gln Ala Pro Gly Lys Gly Leu
    50                  55                  60

Glu Trp Val Ala Val Thr Ser Tyr Asp Gly Ser Asn Lys Tyr Tyr Ala
65                  70                  75                  80

Glu Phe Val Lys Gly Arg Phe Thr Ile Ser Arg Asp Asn Tyr Lys Asn
                85                  90                  95

Thr Val Tyr Leu Gln Met Asn Ser Leu Arg Leu Glu Asp Thr Ala Val
            100                 105                 110

Tyr Tyr Cys Ala Arg Asp Leu Ala Pro Tyr Asn Phe Trp Ser Gly Tyr
        115                 120                 125

Gly Asn Asn Trp Phe Asp Pro Trp Gly Gln Gly Thr Leu Val Thr Val
    130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Leu Gly Thr
    210                 215                 220

Gln Thr Tyr Ile Cys Asn Val Asn His Lys Pro Ser Asn Thr Lys Val
225                 230                 235                 240

Asp Lys Lys Val Glu Pro Lys Ser Cys Asp Lys Thr His Thr Cys Pro
                245                 250                 255
```

Pro Cys Pro Ala Pro Glu Leu Leu Gly Gly Pro Ser Val Phe Leu Phe
                260                 265                 270

Pro Pro Lys Pro Lys Asp Thr Leu Met Ile Ser Arg Thr Pro Glu Val
            275                 280                 285

Thr Cys Val Val Val Asp Val Ser His Glu Asp Pro Glu Val Lys Phe
        290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
        450                 455                 460

Tyr Thr Gln Lys Ser Leu Ser Leu Ser Pro Gly Lys
465                 470                 475

<210> SEQ ID NO 57
<211> LENGTH: 711
<212> TYPE: DNA
<213> ORGANISM: Homo sapiens

<400> SEQUENCE: 57
atggaaaccc cagcgcagct tctcttcctc ctgctactct ggctcccaga taccaccgga      60
gaaattgtgt tgacgcagtc tccaggcacc ctgtctttgt ctccagggga aagagccacc     120
ctctcctgca gggccagtca gagtgttact ggcacctcct agcctggtt ccagcagaaa      180 cctggccagg ctcccggct cctcatctat ggtgcatcca gcagggccac tggcatccca     240
gacaggttca gtggcagtgg gtctgggaca gacttcactc tcaccatcag cagactggag     300
cctgaagatt ttgcagtgta ttactgtcag cagtatggta gctcacctag actcactttc     360
ggcggaggga ccaaggtgga gatcaaacga actgtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata acgccctcca atcgggtaac     540
tcccaggaga gtgtcacaga gcaggacagc aaggacagca cctacagcct cagcagcacc     600
ctgacgctga gcaaagcaga ctacgagaaa cacaaagtct acgcctgcga agtcaccccat     660 cagggcctga gctcgcccgt cacaaagagc ttcaacaggg gagagtgtta g              711

<210> SEQ ID NO 58
<211> LENGTH: 236
<212> TYPE: PRT

<213> ORGANISM: Homo sapiens

<400> SEQUENCE: 58

Met Glu Thr Pro Ala Gln Leu Leu Phe Leu Leu Leu Trp Leu Pro
1               5                   10                  15
Asp Thr Thr Gly Glu Ile Val Leu Thr Gln Ser Pro Gly Thr Leu Ser
            20                  25                  30
Leu Ser Pro Gly Glu Arg Ala Thr Leu Ser Cys Arg Ala Ser Gln Ser
        35                  40                  45
Val Thr Gly Thr Ser Leu Ala Trp Phe Gln Gln Lys Pro Gly Gln Ala
    50                  55                  60
Pro Arg Leu Leu Ile Tyr Gly Ala Ser Ser Arg Ala Thr Gly Ile Pro
65                  70                  75                  80
Asp Arg Phe Ser Gly Ser Gly Ser Gly Thr Asp Phe Thr Leu Thr Ile
                85                  90                  95
Ser Arg Leu Glu Pro Glu Asp Phe Ala Val Tyr Tyr Cys Gln Gln Tyr
            100                 105                 110
Gly Ser Ser Pro Arg Leu Thr Phe Gly Gly Gly Thr Lys Val Glu Ile
        115                 120                 125
Lys Arg Thr Val Ala Ala Pro Ser Val Phe Ile Phe Pro Pro Ser Asp
130                 135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
                165                 170                 175
Gln Ser Gly Asn Ser Gln Glu Ser Val Thr Glu Gln Asp Ser Lys Asp
            180                 185                 190
Ser Thr Tyr Ser Leu Ser Ser Thr Leu Thr Leu Ser Lys Ala Asp Tyr
        195                 200                 205
Glu Lys His Lys Val Tyr Ala Cys Glu Val Thr His Gln Gly Leu Ser
    210                 215                 220
Ser Pro Val Thr Lys Ser Phe Asn Arg Gly Glu Cys
225                 230                 235

<210> SEQ ID NO 59
<211> LENGTH: 25
<212> TYPE: PRT
<213> ORGANISM: Homo sapiens

<400> SEQUENCE: 59

Gln Val His Leu Val Glu Ser Gly Gly Gly Val Val Gln Pro Gly Arg
1               5                   10                  15
Ser Leu Arg Leu Ser Cys Ala Thr Phe
            20                  25

<210> SEQ ID NO 60
<211> LENGTH: 10
<212> TYPE: PRT
<213> ORGANISM: Homo sapiens

<400> SEQUENCE: 60

Gly Leu Asn Phe Ser Asp Tyr Gly Phe His
1               5                   10

<210> SEQ ID NO 61
<211> LENGTH: 14
<212> TYPE: PRT
<213> ORGANISM: Homo sapiens

```
<400> SEQUENCE: 61

Trp Val Arg Gln Ala Pro Gly Lys Gly Leu Glu Trp Val Ala
1               5                   10

<210> SEQ ID NO 62
<211> LENGTH: 9
<212> TYPE: PRT
<213> ORGANISM: Homo sapiens

<400> SEQUENCE: 62

Val Thr Ser Tyr Asp Gly Ser Asn Lys
1               5

<210> SEQ ID NO 63
<211> LENGTH: 40
<212> TYPE: PRT
<213> ORGANISM: Homo sapiens

<400> SEQUENCE: 63

Tyr Tyr Ala Glu Phe Val Lys Gly Arg Phe Thr Ile Ser Arg Asp Asn
1               5                   10                  15

Tyr Lys Asn Thr Val Tyr Leu Gln Met Asn Ser Leu Arg Leu Glu Asp
            20                  25                  30

Thr Ala Val Tyr Tyr Cys Ala Arg
        35                  40

<210> SEQ ID NO 64
<211> LENGTH: 18
<212> TYPE: PRT
<213> ORGANISM: Homo sapiens

<400> SEQUENCE: 64

Asp Leu Ala Pro Tyr Asn Phe Trp Ser Gly Tyr Gly Asn Asn Trp Phe
1               5                   10                  15

Asp Pro

<210> SEQ ID NO 65
<211> LENGTH: 11
<212> TYPE: PRT
<213> ORGANISM: Homo sapiens

<400> SEQUENCE: 65

Trp Gly Gln Gly Thr Leu Val Thr Val Ser Ser
1               5                   10

<210> SEQ ID NO 66
<211> LENGTH: 23
<212> TYPE: PRT
<213> ORGANISM: Homo sapiens

<400> SEQUENCE: 66

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 67
<211> LENGTH: 12
<212> TYPE: PRT
<213> ORGANISM: Homo sapiens

<400> SEQUENCE: 67
```

Arg Ala Ser Gln Ser Val Thr Gly Thr Ser Leu Ala
1               5                   10

<210> SEQ ID NO 68
<211> LENGTH: 15
<212> TYPE: PRT
<213> ORGANISM: Homo sapiens

<400> SEQUENCE: 68

Trp Phe Gln Gln Lys Pro Gly Gln Ala Pro Arg Leu Leu Ile Tyr
1               5                   10                  15

<210> SEQ ID NO 69
<211> LENGTH: 7
<212> TYPE: PRT
<213> ORGANISM: Homo sapiens

<400> SEQUENCE: 69

Gly Ala Ser Ser Arg Ala Thr
1               5

<210> SEQ ID NO 70
<211> LENGTH: 32
<212> TYPE: PRT
<213> ORGANISM: Homo sapiens

<400> SEQUENCE: 70

Gly Ile Pro Asp Arg Phe Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 71
<211> LENGTH: 10
<212> TYPE: PRT
<213> ORGANISM: Homo sapiens

<400> SEQUENCE: 71

Gln Gln Tyr Gly Ser Ser Pro Arg Leu Thr
1               5                   10

<210> SEQ ID NO 72
<211> LENGTH: 10
<212> TYPE: PRT
<213> ORGANISM: Homo sapiens

<400> SEQUENCE: 72

Phe Gly Gly Gly Thr Lys Val Glu Ile Lys
1               5                   10

<210> SEQ ID NO 73
<211> LENGTH: 1431
<212> TYPE: DNA
<213> ORGANISM: Homo sapiens

<400> SEQUENCE: 73
atggagtttg ggctgagctg ggttttcctc gttgctcttt taagaggtgt ccagtgtcag      60
gtgcacctgg tggagtctgg gggaggcgtg gtccagcctg ggaggtccct gagactctcc     120
tgtgcaacct ttggactcaa cttcagtgac tatggttttc actgggtccg ccaggctcca     180 ggcaagggc tggagtgggt ggcagttaca tcatatgatg aagcaacaa atactacgca      240 gaattcgtga agggccgatt caccatctcc agagacaatt acaagaatac ggtgtatctg     300

```
caaatgaaca gcctgagact tgaggacacg gctgtgtatt actgtgcgag agatctcgcc    360
ccatacaatt tttggagtgg ttatgggaat aattggttcg accccctggg ccagggaacc    420
ctggtcaccg tctcctcagc ctccaccaag ggcccatcgg tcttccccct ggcaccctcc    480
tccaagagca cctctggggg cacagcggcc ctgggctgcc tggtcaagga ctacttcccc    540
gaaccggtga cggtgtcgtg gaactcaggc gccctgacca gcggcgtgca caccttcccg    600
gctgtcctac agtcctcagg actctactcc ctcagcagcg tggtgaccgt gccctccagc    660
agcttgggca cccagaccta catctgcaac gtgaatcaca agcccagcaa caccaaggtg    720
gacaagaaag ttgagcccaa atcttgtgac aaaactcaca catgcccacc gtgcccagca    780
cctgaactcc tggggggacc gtcagtcttc ctcttccccc caaaacccaa ggacaccctc    840
atgatctccc ggacccctga ggtcacatgc gtggtggtgg acgtgagcca cgaagaccct    900
gaggtcaagt tcaactggta cgtggacggc gtggaggtgc ataatgccaa gacaaagccg    960
cgggaggagc agtacaacag cacgtaccgg gtggtcagcg tcctcaccgt cctgcaccag   1020
gactggctga atggcaagga gtacaagtgc aaggtctcca acaaagccct cccagccccc   1080
atcgagaaaa ccatctccaa agccaaaggg cagccccgag aaccacaggt gtacaccctg   1140
cccccatccc gggatgagct gaccaagaac caggtcagcc tgacctgcct ggtcaaaggc   1200
ttctatccca gcgacatcgc cgtggagtgg gagagcaatg ggcagccgga gaacaactac   1260
aagaccacgc ctcccgtgct ggactccgac ggctccttct tcctctacag caagctcacc   1320
gtggacaaga gcaggtggca gcaggggaac gtcttctcat gctccgtgat gcatgaggct   1380
ctgcacaacc actacacgca gaagagcctc tccctgtctc cgggtaaatg a            1431
```

<210> SEQ ID NO 74
<211> LENGTH: 476
<212> TYPE: PRT
<213> ORGANISM: Homo sapiens

<400> SEQUENCE: 74

```
Met Glu Phe Gly Leu Ser Trp Val Phe Leu Val Ala Leu Leu Arg Gly
1               5                   10                  15

Val Gln Cys Gln Val His Leu Val Glu Ser Gly Gly Gly Val Val Gln
            20                  25                  30

Pro Gly Arg Ser Leu Arg Leu Ser Cys Ala Thr Phe Gly Leu Asn Phe
        35                  40                  45

Ser Asp Tyr Gly Phe His Trp Val Arg Gln Ala Pro Gly Lys Gly Leu
    50                  55                  60

Glu Trp Val Ala Val Thr Ser Tyr Asp Gly Ser Asn Lys Tyr Tyr Ala
65                  70                  75                  80

Glu Phe Val Lys Gly Arg Phe Thr Ile Ser Arg Asp Asn Tyr Lys Asn
                85                  90                  95

Thr Val Tyr Leu Gln Met Asn Ser Leu Arg Leu Glu Asp Thr Ala Val
            100                 105                 110

Tyr Tyr Cys Ala Arg Asp Leu Ala Pro Tyr Asn Phe Trp Ser Gly Tyr
        115                 120                 125

Gly Asn Asn Trp Phe Asp Pro Trp Gly Gln Gly Thr Leu Val Thr Val
    130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175
```

-continued

```
Asp Tyr Phe Pro Glu Pro Val Thr Val Ser Trp Asn Ser Gly Ala Leu
                180                 185                 190
Thr Ser Gly Val His Thr Phe Pro Ala Val Leu Gln Ser Ser Gly Leu
            195                 200                 205
Tyr Ser Leu Ser Ser Val Val Thr Val Pro Ser Ser Leu Gly Thr
    210                 215                 220
Gln Thr Tyr Ile Cys Asn Val Asn His Lys Pro Ser Asn Thr Lys Val
225                 230                 235                 240
Asp Lys Lys Val Glu Pro Lys Ser Cys Asp Lys Thr His Thr Cys Pro
                245                 250                 255
Pro Cys Pro Ala Pro Glu Leu Leu Gly Gly Pro Ser Val Phe Leu Phe
            260                 265                 270
Pro Pro Lys Pro Lys Asp Thr Leu Met Ile Ser Arg Thr Pro Glu Val
        275                 280                 285
Thr Cys Val Val Val Asp Val Ser His Glu Asp Pro Glu Val Lys Phe
    290                 295                 300
Asn Trp Tyr Val Asp Gly Val Glu Val His Asn Ala Lys Thr Lys Pro
305                 310                 315                 320
Arg Glu Glu Gln Tyr Asn Ser Thr Tyr Arg Val Val Ser Val Leu Thr
                325                 330                 335
Val Leu His Gln Asp Trp Leu Asn Gly Lys Glu Tyr Lys Cys Lys Val
            340                 345                 350
Ser Asn Lys Ala Leu Pro Ala Pro Ile Glu Lys Thr Ile Ser Lys Ala
        355                 360                 365
Lys Gly Gln Pro Arg Glu Pro Gln Val Tyr Thr Leu Pro Pro Ser Arg
    370                 375                 380
Asp Glu Leu Thr Lys Asn Gln Val Ser Leu Thr Cys Leu Val Lys Gly
385                 390                 395                 400
Phe Tyr Pro Ser Asp Ile Ala Val Glu Trp Glu Ser Asn Gly Gln Pro
                405                 410                 415
Glu Asn Asn Tyr Lys Thr Thr Pro Pro Val Leu Asp Ser Asp Gly Ser
            420                 425                 430
Phe Phe Leu Tyr Ser Lys Leu Thr Val Asp Lys Ser Arg Trp Gln Gln
        435                 440                 445
Gly Asn Val Phe Ser Cys Ser Val Met His Glu Ala Leu His Asn His
    450                 455                 460
Tyr Thr Gln Lys Ser Leu Ser Leu Ser Pro Gly Lys
465                 470                 475
```

<210> SEQ ID NO 75
<211> LENGTH: 705
<212> TYPE: DNA
<213> ORGANISM: Homo sapiens

<400> SEQUENCE: 75

```
atggaagccc agcgcagct tctcttcctc ctgctactct ggctcccaga taccactgga      60
gaaatagtga tgacgcagtc tccagccacc ctgtctgtct ctccaggaga aagagccacc    120
ctctcctgca gggccagtca gagtattagc agcaacttag cctggtacca gcagaaacct    180
ggccaggctc ccagactcct catctatgat gcatccacca gggccactgg tatcccagcc    240
aggttcagtg gcagtgggtc tgggacagag ttcactctca ccatcagcag cctgcagtct    300
gaagattttg cagtttatta ctgtcagcaa tacaatgact ggcttgtgac gttcggccaa    360
gggaccaaag tggaaatcaa acgaactgtg gctgcaccat ctgtcttcat cttcccgcca    420
```

```
tctgatgagc agttgaaatc tggaactgcc tctgttgtgt gcctgctgaa taacttctat    480
cccagagagg ccaaagtaca gtggaaggtg ataacgccc tccaatcggg taactcccag     540
gagagtgtca cagagcagga cagcaaggac agcacctaca gcctcagcag cacctgacg     600 ctgagcaaag cagactacga gaaacacaaa gtctacgcct gcgaagtcac ccatcagggc    660
ctgagctcgc ccgtcacaaa gagcttcaac aggggagagt gttag                   705
```

<210> SEQ ID NO 76
<211> LENGTH: 234
<212> TYPE: PRT
<213> ORGANISM: Homo sapiens

<400> SEQUENCE: 76

```
Met Glu Ala Pro Ala Gln Leu Leu Phe Leu Leu Leu Leu Trp Leu Pro
1               5                   10                  15

Asp Thr Thr Gly Glu Ile Val Met Thr Gln Ser Pro Ala Thr Leu Ser
                20                  25                  30

Val Ser Pro Gly Glu Arg Ala Thr Leu Ser Cys Arg Ala Ser Gln Ser
            35                  40                  45

Ile Ser Ser Asn Leu Ala Trp Tyr Gln Gln Lys Pro Gly Gln Ala Pro
        50                  55                  60

Arg Leu Leu Ile Tyr Asp Ala Ser Thr Arg Ala Thr Gly Ile Pro Ala
65                  70                  75                  80

Arg Phe Ser Gly Ser Gly Ser Gly Thr Glu Phe Thr Leu Thr Ile Ser
                85                  90                  95

Ser Leu Gln Ser Glu Asp Phe Ala Val Tyr Tyr Cys Gln Gln Tyr Asn
            100                 105                 110

Asp Trp Leu Val Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 77
<211> LENGTH: 25
<212> TYPE: PRT
<213> ORGANISM: Homo sapiens

<400> SEQUENCE: 77

```
Gln Val His Leu Val Glu Ser Gly Gly Gly Val Val Gln Pro Gly Arg
1               5                   10                  15

Ser Leu Arg Leu Ser Cys Ala Thr Phe
            20                  25
```

```
<210> SEQ ID NO 78
<211> LENGTH: 10
<212> TYPE: PRT
<213> ORGANISM: Homo sapiens

<400> SEQUENCE: 78

Gly Leu Asn Phe Ser Asp Tyr Gly Phe His
1               5                   10

<210> SEQ ID NO 79
<211> LENGTH: 14
<212> TYPE: PRT
<213> ORGANISM: Homo sapiens

<400> SEQUENCE: 79

Trp Val Arg Gln Ala Pro Gly Lys Gly Leu Glu Trp Val Ala
1               5                   10

<210> SEQ ID NO 80
<211> LENGTH: 9
<212> TYPE: PRT
<213> ORGANISM: Homo sapiens

<400> SEQUENCE: 80

Val Thr Ser Tyr Asp Gly Ser Asn Lys
1               5

<210> SEQ ID NO 81
<211> LENGTH: 40
<212> TYPE: PRT
<213> ORGANISM: Homo sapiens

<400> SEQUENCE: 81

Tyr Tyr Ala Glu Phe Val Lys Gly Arg Phe Thr Ile Ser Arg Asp Asn
1               5                   10                  15

Tyr Lys Asn Thr Val Tyr Leu Gln Met Asn Ser Leu Arg Leu Glu Asp
            20                  25                  30

Thr Ala Val Tyr Tyr Cys Ala Arg
        35                  40

<210> SEQ ID NO 82
<211> LENGTH: 18
<212> TYPE: PRT
<213> ORGANISM: Homo sapiens

<400> SEQUENCE: 82

Asp Leu Ala Pro Tyr Asn Phe Trp Ser Gly Tyr Gly Asn Asn Trp Phe
1               5                   10                  15

Asp Pro

<210> SEQ ID NO 83
<211> LENGTH: 11
<212> TYPE: PRT
<213> ORGANISM: Homo sapiens

<400> SEQUENCE: 83

Trp Gly Gln Gly Thr Leu Val Thr Val Ser Ser
1               5                   10

<210> SEQ ID NO 84
<211> LENGTH: 23
<212> TYPE: PRT
<213> ORGANISM: Homo sapiens
```

<400> SEQUENCE: 84

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 85
<211> LENGTH: 11
<212> TYPE: PRT
<213> ORGANISM: Homo sapiens

<400> SEQUENCE: 85

Arg Ala Ser Gln Ser Ile Ser Ser Asn Leu Ala
1               5                   10

<210> SEQ ID NO 86
<211> LENGTH: 15
<212> TYPE: PRT
<213> ORGANISM: Homo sapiens

<400> SEQUENCE: 86

Trp Tyr Gln Gln Lys Pro Gly Gln Ala Pro Arg Leu Leu Ile Tyr
1               5                   10                  15

<210> SEQ ID NO 87
<211> LENGTH: 7
<212> TYPE: PRT
<213> ORGANISM: Homo sapiens

<400> SEQUENCE: 87

Asp Ala Ser Thr Arg Ala Thr
1               5

<210> SEQ ID NO 88
<211> LENGTH: 32
<212> TYPE: PRT
<213> ORGANISM: Homo sapiens

<400> SEQUENCE: 88

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 89
<211> LENGTH: 9
<212> TYPE: PRT
<213> ORGANISM: Homo sapiens

<400> SEQUENCE: 89

Gln Gln Tyr Asn Asp Trp Leu Val Thr
1               5

<210> SEQ ID NO 90
<211> LENGTH: 10
<212> TYPE: PRT
<213> ORGANISM: Homo sapiens

<400> SEQUENCE: 90

Phe Gly Gln Gly Thr Lys Val Glu Ile Lys
1               5                   10

<210> SEQ ID NO 91

<211> LENGTH: 1413
<212> TYPE: DNA
<213> ORGANISM: Homo sapiens

<400> SEQUENCE: 91

```
atgaaacacc tgtggttctt cgtcctcctg gtggcagctc ccagatgggt cctgtcccag    60
gtgcaactac tgcagggggg cgcaggactg ttgaagcctt cggagaccct gtccctcacg   120
tgcgctgtct atggtgggtc ctttagtgaa cactattgga gttggatccg ccagccccca   180
gggaagggc tggagtggat tgggaaatc aattatggtg gaaacaccaa ctacaacccg    240
tccctcgaga gtcgaatctc catctcagtg gacacatcaa agaaccaggt cttcctgaga   300
gtgagatttg tgacagctgc ggacacggct gtgtattttt gttcgggagg ccggcgagca   360
gcagtacatg gccggacttt tgctatctgg ggccaaggga caatggtcac cgtctcttca   420
gcctccacca agggcccatc ggtcttcccc ctggcaccct cctccaagag cacctctggg   480
ggcacagcgg ccctgggctg cctggtcaag gactacttcc ccgaaccggt gacggtgtcg   540
tggaactcag gcgccctgac cagcggcgtg cacaccttcc cggctgtcct acagtcctca   600
ggactctact ccctcagcag cgtggtgacc gtgccctcca gcagcttggg cacccagacc   660
tacatctgca acgtgaatca caagcccagc aacaccaagg tggacaagaa agttgagccc   720
aaatcttgtg acaaaactca cacatgccca ccgtgcccag cacctgaact cctggggggga   780
ccgtcagtct tcctcttccc cccaaaaccc aaggacaccc tcatgatctc ccggacccct   840
gaggtcacat gcgtggtggt ggacgtgagc cacgaagacc ctgaggtcaa gttcaactgg   900
tacgtggacg gcgtggaggt gcataatgcc aagacaaagc cgcgggagga gcagtacaac   960
agcacgtacc gggtggtcag cgtcctcacc gtcctgcacc aggactggct gaatggcaag  1020
gagtacaagt gcaaggtctc caacaaagcc ctcccagccc ccatcgagaa aaccatctcc  1080
aaagccaaag gcagccccg agaaccacag gtgtacaccc tgcccccatc ccgggatgag  1140
ctgaccaaga accaggtcag cctgacctgc ctggtcaaag gcttctatcc cagcgacatc  1200
gccgtggagt gggagagcaa tgggcagccg gagaacaact acaagaccac gcctcccgtg  1260
ctggactccg acggctcctt cttcctctac agcaagctca ccgtggacaa gagcaggtgg  1320
cagcagggga acgtcttctc atgctccgtg atgcatgagg ctctgcacaa ccactacacg  1380
cagaagagcc tctccctgtc tccgggtaaa tga                              1413
```

<210> SEQ ID NO 92
<211> LENGTH: 470
<212> TYPE: PRT
<213> ORGANISM: Homo sapiens

<400> SEQUENCE: 92

```
Met Lys His Leu Trp Phe Phe Val Leu Leu Val Ala Ala Pro Arg Trp
 1               5                  10                  15

Val Leu Ser Gln Val Gln Leu Leu Gln Gly Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Glu His Tyr Trp Ser Trp Ile Arg Gln Pro Pro Gly Lys Gly Leu
    50                  55                  60

Glu Trp Ile Gly Glu Ile Asn Tyr Gly Gly Asn Thr Asn Tyr Asn Pro
65                  70                  75                  80

Ser Leu Glu Ser Arg Ile Ser Ile Ser Val Asp Thr Ser Lys Asn Gln
                85                  90                  95
```

```
Val Phe Leu Arg Val Arg Phe Val Thr Ala Ala Asp Thr Ala Val Tyr
            100                 105                 110

Phe Cys Ser Gly Gly Arg Arg Ala Val His Gly Arg Thr Phe Ala
            115                 120                 125

Ile Trp Gly Gln Gly Thr Met Val Thr Val Ser Ser Ala Ser Thr Lys
            130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                    165                 170                 175

Val Thr Val Ser Trp Asn Ser Gly Ala Leu Thr Ser Gly Val His Thr
                    180                 185                 190

Phe Pro Ala Val Leu Gln Ser Ser Gly Leu Tyr Ser Leu Ser Ser Val
                    195                 200                 205

Val Thr Val Pro Ser Ser Ser Leu Gly Thr Gln Thr Tyr Ile Cys Asn
            210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                    245                 250                 255

Leu Leu Gly Gly Pro Ser Val Phe Leu Phe Pro Pro Lys Pro Lys Asp
                    260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
            290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                    325                 330                 335

Leu Asn Gly Lys Glu Tyr Lys Cys Lys Val Ser Asn Lys Ala Leu Pro
                    340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
            370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                    405                 410                 415

Thr Pro Pro Val Leu Asp Ser Asp Gly Ser Phe Phe Leu Tyr Ser Lys
                    420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
            450                 455                 460

Ser Leu Ser Pro Gly Lys
465                 470

<210> SEQ ID NO 93
<211> LENGTH: 720
<212> TYPE: DNA
<213> ORGANISM: Homo sapiens
```

-continued

```
<400> SEQUENCE: 93
atgaggctcc ctgctcagct cctggggctg ctaatgctct gggtctccgg gtccagtggg      60
gatattgtga tgacgcagtc tccactctcc ctgcccgtca cccctggaga gccggcctcc     120
atctcctgca ggtctagtca gagcctgctt catactaatg aaacaactta tttggtatgg     180
tatctgcaga agccagggca ggctccacat ctcctgatct atctgggatc taatcgggcc     240
tccggggtcc ctggcaggtt cagtggcagt ggatcaggca cagattttac actgaaaatc     300
agcagagtgg aggtcgagga tgttggggtt tattactgca tgcaatctct acaaactcct     360 cccactttg gccaggggac caagctggag atcaaacgaa ctgtggctgc accatctgtc      420
ttcatcttcc cgccatctga tgagcagttg aaatctggaa ctgcctctgt tgtgtgcctg     480
ctgaataact tctatcccag agaggccaaa gtacagtgga aggtggataa cgccctccaa     540
tcgggtaact cccaggagag tgtcacagag caggacagca aggacagcac ctacagcctc     600
agcagcaccc tgacgctgag caaagcagac tacgagaaac acaaagtcta cgcctgcgaa     660
gtcacccatc agggcctgag ctcgcccgtc acaaagagct tcaacagggg agagtgttag     720

<210> SEQ ID NO 94
<211> LENGTH: 239
<212> TYPE: PRT
<213> ORGANISM: Homo sapiens

<400> SEQUENCE: 94

Met Arg Leu Pro Ala Gln Leu Gly Leu Leu Met Leu Trp Val Ser
1               5                   10                  15

Gly Ser Ser Gly Asp Ile Val Met Thr Gln Ser Pro Leu Ser Leu Pro
                20                  25                  30

Val Thr Pro Gly Glu Pro Ala Ser Ile Ser Cys Arg Ser Ser Gln Ser
            35                  40                  45

Leu Leu His Thr Asn Gly Asn Asn Tyr Leu Val Trp Tyr Leu Gln Lys
        50                  55                  60

Pro Gly Gln Ala Pro His Leu Leu Ile Tyr Leu Gly Ser Asn Arg Ala
65                  70                  75                  80

Ser Gly Val Pro Gly Arg Phe Ser Gly Ser Gly Ser Gly Thr Asp Phe
                85                  90                  95

Thr Leu Lys Ile Ser Arg Val Glu Val Glu Asp Val Gly Val Tyr Tyr
            100                 105                 110

Cys Met Gln Ser Leu Gln Thr Pro Thr Phe Gly Gln Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 95
<211> LENGTH: 25
<212> TYPE: PRT
<213> ORGANISM: Homo sapiens

<400> SEQUENCE: 95

Gln Val Gln Leu Leu Gln Gly Gly Ala Gly Leu Leu Lys Pro Ser Glu
1               5                   10                  15

Thr Leu Ser Leu Thr Cys Ala Val Tyr
            20                  25

<210> SEQ ID NO 96
<211> LENGTH: 10
<212> TYPE: PRT
<213> ORGANISM: Homo sapiens

<400> SEQUENCE: 96

Gly Gly Ser Phe Ser Glu His Tyr Trp Ser
1               5                   10

<210> SEQ ID NO 97
<211> LENGTH: 14
<212> TYPE: PRT
<213> ORGANISM: Homo sapiens

<400> SEQUENCE: 97

Trp Ile Arg Gln Pro Pro Gly Lys Gly Leu Glu Trp Ile Gly
1               5                   10

<210> SEQ ID NO 98
<211> LENGTH: 9
<212> TYPE: PRT
<213> ORGANISM: Homo sapiens

<400> SEQUENCE: 98

Glu Ile Asn Tyr Gly Gly Asn Thr Asn
1               5

<210> SEQ ID NO 99
<211> LENGTH: 39
<212> TYPE: PRT
<213> ORGANISM: Homo sapiens

<400> SEQUENCE: 99

Tyr Asn Pro Ser Leu Glu Ser Arg Ile Ser Ile Ser Val Asp Thr Ser
1               5                   10                  15

Lys Asn Gln Val Phe Leu Arg Val Arg Phe Val Thr Ala Ala Asp Thr
            20                  25                  30

Ala Val Tyr Phe Cys Ser Gly
        35

<210> SEQ ID NO 100
<211> LENGTH: 13
<212> TYPE: PRT
<213> ORGANISM: Homo sapiens

<400> SEQUENCE: 100

Gly Arg Arg Ala Ala Val His Gly Arg Thr Phe Ala Ile
1               5                   10

<210> SEQ ID NO 101
<211> LENGTH: 11
<212> TYPE: PRT

```
<213> ORGANISM: Homo sapiens

<400> SEQUENCE: 101

Trp Gly Gln Gly Thr Met Val Thr Val Ser Ser
1               5                   10

<210> SEQ ID NO 102
<211> LENGTH: 23
<212> TYPE: PRT
<213> ORGANISM: Homo sapiens

<400> SEQUENCE: 102

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 103
<211> LENGTH: 16
<212> TYPE: PRT
<213> ORGANISM: Homo sapiens

<400> SEQUENCE: 103

Arg Ser Ser Gln Ser Leu Leu His Thr Asn Gly Asn Asn Tyr Leu Val
1               5                   10                  15

<210> SEQ ID NO 104
<211> LENGTH: 15
<212> TYPE: PRT
<213> ORGANISM: Homo sapiens

<400> SEQUENCE: 104

Trp Tyr Leu Gln Lys Pro Gly Gln Ala Pro His Leu Leu Ile Tyr
1               5                   10                  15

<210> SEQ ID NO 105
<211> LENGTH: 7
<212> TYPE: PRT
<213> ORGANISM: Homo sapiens

<400> SEQUENCE: 105

Leu Gly Ser Asn Arg Ala Ser
1               5

<210> SEQ ID NO 106
<211> LENGTH: 32
<212> TYPE: PRT
<213> ORGANISM: Homo sapiens

<400> SEQUENCE: 106

Gly Val Pro Gly Arg Phe Ser Gly Ser Gly Ser Gly Thr Asp Phe Thr
1               5                   10                  15

Leu Lys Ile Ser Arg Val Glu Val Glu Asp Val Gly Val Tyr Tyr Cys
            20                  25                  30

<210> SEQ ID NO 107
<211> LENGTH: 9
<212> TYPE: PRT
<213> ORGANISM: Homo sapiens

<400> SEQUENCE: 107

Met Gln Ser Leu Gln Thr Pro Pro Thr
1               5
```

<210> SEQ ID NO 108
<211> LENGTH: 10
<212> TYPE: PRT
<213> ORGANISM: Homo sapiens

<400> SEQUENCE: 108

Phe Gly Gln Gly Thr Lys Leu Glu Ile Lys
1               5                   10

<210> SEQ ID NO 109
<211> LENGTH: 1395
<212> TYPE: DNA
<213> ORGANISM: Homo sapiens

<400> SEQUENCE: 109

| | | | | | |
|---|---|---|---|---|---|
| atggagtttg | gcctgagctg | ggttttcctt | gttgccattt | taaaaggtgt | ccagtgtgag | 60 |
| gtgcagctgg | tggagtccgg | gggaggctta | gttcagcctg | gggggtccct | gagactctcc | 120 |
| tgtgcagcct | ctggattcac | tttcagaagt | tactggatgc | actgggtccg | ccaagttcca | 180 |
| gggaaggggc | tggtgtgggt | gtcatgtatt | aataaagaag | ggagtagcac | aacctacgcg | 240 |
| gactccgtga | agggccgatt | caccatctcc | agagacaacg | ccaagaacac | gctgtatttg | 300 |
| gaaatgaaca | gtctgagagc | cgacgacacg | gctgtgtatt | attgtctaag | gggatacgat | 360 |
| gttgactact | ggggccaggg | aacgctggtc | accgtctcct | cagcctccac | caagggccca | 420 |
| tcggtcttcc | ccctggcacc | ctcctccaag | agcacctctg | ggggcacagc | ggccctgggc | 480 |
| tgcctggtca | aggactactt | ccccgaaccg | gtgacggtgt | cgtggaactc | aggcgccctg | 540 |
| accagcggcg | tgcacacctt | cccggctgtc | ctacagtcct | caggactcta | ctccctcagc | 600 |
| agcgtggtga | ccgtgccctc | cagcagcttg | ggcacccaga | cctacatctg | caacgtgaat | 660 |
| cacaagccca | gcaacaccaa | ggtggacaag | aaagttgagc | ccaaatcttg | tgacaaaact | 720 |
| cacacatgcc | caccgtgccc | agcacctgaa | ctcctggggg | gaccgtcagt | cttcctcttc | 780 |
| cccccaaaac | ccaaggacac | cctcatgatc | tcccggaccc | ctgaggtcac | atgcgtggtg | 840 |
| gtggacgtga | gccacgaaga | ccctgaggtc | aagttcaact | ggtacgtgga | cggcgtggag | 900 |
| gtgcataatg | ccaagacaaa | gccgcgggag | gagcagtaca | acagcacgta | ccgggtggtc | 960 |
| agcgtcctca | ccgtcctgca | ccaggactgg | ctgaatggca | aggagtacaa | gtgcaaggtc | 1020 |
| tccaacaaag | ccctcccagc | ccccatcgag | aaaaccatct | ccaaagccaa | agggcagccc | 1080 |
| cgagaaccac | aggtgtacac | cctgcccca | tcccgggatg | agctgaccaa | gaaccaggtc | 1140 |
| agcctgacct | gcctggtcaa | aggcttctat | cccagcgaca | tcgccgtgga | gtgggagagc | 1200 |
| aatgggcagc | cggagaacaa | ctacaagacc | acgcctcccg | tgctggactc | cgacggctcc | 1260 |
| ttcttcctct | acagcaagct | caccgtggac | aagagcaggt | ggcagcaggg | gaacgtcttc | 1320 |
| tcatgctccg | tgatgcatga | ggctctgcac | aaccactaca | cgcagaagag | cctctccctg | 1380 |
| tctccgggta | aatga | | | | | 1395 |

<210> SEQ ID NO 110
<211> LENGTH: 464
<212> TYPE: PRT
<213> ORGANISM: Homo sapiens

<400> SEQUENCE: 110

Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Gly Leu Val Gln

```
            20                  25                  30
Pro Gly Gly Ser Leu Arg Leu Ser Cys Ala Ala Ser Gly Phe Thr Phe
            35                  40                  45
Arg Ser Tyr Trp Met His Trp Val Arg Gln Val Pro Gly Lys Gly Leu
50                  55                  60
Val Trp Val Ser Cys Ile Asn Lys Glu Gly Ser Ser Thr Thr Tyr Ala
65                  70                  75                  80
Asp Ser Val Lys Gly Arg Phe Thr Ile Ser Arg Asp Asn Ala Lys Asn
                85                  90                  95
Thr Leu Tyr Leu Glu Met Asn Ser Leu Arg Ala Asp Thr Ala Val
            100                 105                 110
Tyr Tyr Cys Leu Arg Gly Tyr Asp Val Asp Tyr Trp Gly Gln Gly Thr
            115                 120                 125
Leu Val Thr Val Ser Ser Ala Ser Thr Lys Gly Pro Ser Val Phe Pro
            130                 135                 140
Leu Ala Pro Ser Ser Lys Ser Thr Ser Gly Gly Thr Ala Ala Leu Gly
145                 150                 155                 160
Cys Leu Val Lys Asp Tyr Phe Pro Glu Pro Val Thr Val Ser Trp Asn
                165                 170                 175
Ser Gly Ala Leu Thr Ser Gly Val His Thr Phe Pro Ala Val Leu Gln
            180                 185                 190
Ser Ser Gly Leu Tyr Ser Leu Ser Ser Val Val Thr Val Pro Ser Ser
            195                 200                 205
Ser Leu Gly Thr Gln Thr Tyr Ile Cys Asn Val Asn His Lys Pro Ser
            210                 215                 220
Asn Thr Lys Val Asp Lys Lys Val Glu Pro Lys Ser Cys Asp Lys Thr
225                 230                 235                 240
His Thr Cys Pro Pro Cys Pro Ala Pro Glu Leu Leu Gly Gly Pro Ser
                245                 250                 255
Val Phe Leu Phe Pro Pro Lys Pro Lys Asp Thr Leu Met Ile Ser Arg
            260                 265                 270
Thr Pro Glu Val Thr Cys Val Val Val Asp Val Ser His Glu Asp Pro
            275                 280                 285
Glu Val Lys Phe Asn Trp Tyr Val Asp Gly Val Glu Val His Asn Ala
            290                 295                 300
Lys Thr Lys Pro Arg Glu Glu Gln Tyr Asn Ser Thr Tyr Arg Val Val
305                 310                 315                 320
Ser Val Leu Thr Val Leu His Gln Asp Trp Leu Asn Gly Lys Glu Tyr
                325                 330                 335
Lys Cys Lys Val Ser Asn Lys Ala Leu Pro Ala Pro Ile Glu Lys Thr
            340                 345                 350
Ile Ser Lys Ala Lys Gly Gln Pro Arg Glu Pro Gln Val Tyr Thr Leu
            355                 360                 365
Pro Pro Ser Arg Asp Glu Leu Thr Lys Asn Gln Val Ser Leu Thr Cys
            370                 375                 380
Leu Val Lys Gly Phe Tyr Pro Ser Asp Ile Ala Val Glu Trp Glu Ser
385                 390                 395                 400
Asn Gly Gln Pro Glu Asn Asn Tyr Lys Thr Thr Pro Pro Val Leu Asp
                405                 410                 415
Ser Asp Gly Ser Phe Phe Leu Tyr Ser Lys Leu Thr Val Asp Lys Ser
            420                 425                 430
Arg Trp Gln Gln Gly Asn Val Phe Ser Cys Ser Val Met His Glu Ala
            435                 440                 445
```

Leu His Asn His Tyr Thr Gln Lys Ser Leu Ser Leu Ser Pro Gly Lys
            450                 455                 460

<210> SEQ ID NO 111
<211> LENGTH: 723
<212> TYPE: DNA
<213> ORGANISM: Homo sapiens

<400> SEQUENCE: 111
atggcctgga ctcctctcct cctcctgttc ctctctcact gcacaggttc cctctcgcag     60
gctgtgctga ctcagccgtc ctccctctct gcatctcccg gagcatcagt cagtctcacc    120
tgcaccttgc gcagtggcat caatgttggt acctacagga tatactggta tcagcagaag    180
ccagggagtc ctcccegtta tctcctgagg tacaaatcag gcttagataa acaccagggc    240
tctggagtcc ccagccgctt ctctggatcc aaagatgatt cggccaatgc agggattta    300 ttcatttctg gctccagtc tgaggatgag gctgattatt actgtttgat ttggcacagc    360
agcgctgtgg tattcggcgg agggaccaag ctgaccgtcc taggtcagcc caaggctgcc    420
ccctcggtca ctctgttccc gccctcctct gaggagcttc aagccaacaa ggccacacta    480
gtgtgtctga tcagtgactt ctacccggga gctgtgacag tggcttggaa ggcagatggc    540
agccccgtca aggcgggagt ggagacgacc aaaccctcca acagagcaa caacaagtac    600 gcggccagca gctacctgag cctgacgccc agcagtgga agtcccacag aagctacagc    660
tgccaggtca cgcatgaagg gagcaccgtg gagaagacag tggcccctac agaatgttca    720
tag                                                                  723

<210> SEQ ID NO 112
<211> LENGTH: 240
<212> TYPE: PRT
<213> ORGANISM: Homo sapiens

<400> SEQUENCE: 112

Met Ala Trp Thr Pro Leu Leu Leu Phe Leu Ser His Cys Thr Gly
1               5                  10                  15

Ser Leu Ser Gln Ala Val Leu Thr Gln Pro Ser Ser Leu Ser Ala Ser
            20                  25                  30

Pro Gly Ala Ser Val Ser Leu Thr Cys Thr Leu Arg Ser Gly Ile Asn
        35                  40                  45

Val Gly Thr Tyr Arg Ile Tyr Trp Tyr Gln Gln Lys Pro Gly Ser Pro
    50                  55                  60

Pro Arg Tyr Leu Leu Arg Tyr Lys Ser Gly Leu Asp Lys His Gln Gly
65                  70                  75                  80

Ser Gly Val Pro Ser Arg Phe Ser Gly Ser Lys Asp Asp Ser Ala Asn
                85                  90                  95

Ala Gly Ile Leu Phe Ile Ser Gly Leu Gln Ser Glu Asp Glu Ala Asp
            100                 105                 110

Tyr Tyr Cys Leu Ile Trp His Ser Ser Ala Val Val Phe Gly Gly Gly
        115                 120                 125

Thr Lys Leu Thr Val Leu Gly Gln Pro Lys Ala Ala Pro Ser Val Thr
    130                 135                 140

Leu Phe Pro Pro Ser Ser Glu Glu Leu Gln Ala Asn Lys Ala Thr Leu
145                 150                 155                 160

Val Cys Leu Ile Ser Asp Phe Tyr Pro Gly Ala Val Thr Val Ala Trp
                165                 170                 175

-continued

```
Lys Ala Asp Gly Ser Pro Val Lys Ala Gly Val Glu Thr Thr Lys Pro
            180                 185                 190

Ser Lys Gln Ser Asn Asn Lys Tyr Ala Ala Ser Ser Tyr Leu Ser Leu
        195                 200                 205

Thr Pro Glu Gln Trp Lys Ser His Arg Ser Tyr Ser Cys Gln Val Thr
    210                 215                 220

His Glu Gly Ser Thr Val Glu Lys Thr Val Ala Pro Thr Glu Cys Ser
225                 230                 235                 240

<210> SEQ ID NO 113
<211> LENGTH: 25
<212> TYPE: PRT
<213> ORGANISM: Homo sapiens

<400> SEQUENCE: 113

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 114
<211> LENGTH: 10
<212> TYPE: PRT
<213> ORGANISM: Homo sapiens

<400> SEQUENCE: 114

Gly Phe Thr Phe Arg Ser Tyr Trp Met His
1               5                   10

<210> SEQ ID NO 115
<211> LENGTH: 14
<212> TYPE: PRT
<213> ORGANISM: Homo sapiens

<400> SEQUENCE: 115

Trp Val Arg Gln Val Pro Gly Lys Gly Leu Val Trp Val Ser
1               5                   10

<210> SEQ ID NO 116
<211> LENGTH: 10
<212> TYPE: PRT
<213> ORGANISM: Homo sapiens

<400> SEQUENCE: 116

Cys Ile Asn Lys Glu Gly Ser Ser Thr Thr
1               5                   10

<210> SEQ ID NO 117
<211> LENGTH: 39
<212> TYPE: PRT
<213> ORGANISM: Homo sapiens

<400> SEQUENCE: 117

Tyr Ala Asp Ser Val Lys Gly Arg Phe Thr Ile Ser Arg Asp Asn Ala
1               5                   10                  15

Lys Asn Thr Leu Tyr Leu Glu Met Asn Ser Leu Arg Ala Asp Asp Thr
            20                  25                  30

Ala Val Tyr Tyr Cys Leu Arg
            35

<210> SEQ ID NO 118
<211> LENGTH: 8
```

```
<212> TYPE: PRT
<213> ORGANISM: Homo sapiens

<400> SEQUENCE: 118

Gly Tyr Asp Val Asp Tyr Trp Gly
1               5

<210> SEQ ID NO 119
<211> LENGTH: 9
<212> TYPE: PRT
<213> ORGANISM: Homo sapiens

<400> SEQUENCE: 119

Gln Gly Thr Leu Val Thr Val Ser Ser
1               5

<210> SEQ ID NO 120
<211> LENGTH: 25
<212> TYPE: PRT
<213> ORGANISM: Homo sapiens

<400> SEQUENCE: 120

Gln Ala Val Leu Thr Gln Pro Ser Ser Leu Ser Ala Ser Pro Gly Ala
1               5                   10                  15

Ser Val Ser Leu Thr Cys Thr Leu Arg
            20                  25

<210> SEQ ID NO 121
<211> LENGTH: 11
<212> TYPE: PRT
<213> ORGANISM: Homo sapiens

<400> SEQUENCE: 121

Ser Gly Ile Asn Val Gly Thr Tyr Arg Ile Tyr
1               5                   10

<210> SEQ ID NO 122
<211> LENGTH: 14
<212> TYPE: PRT
<213> ORGANISM: Homo sapiens

<400> SEQUENCE: 122

Trp Tyr Gln Gln Lys Pro Gly Ser Pro Pro Arg Tyr Leu Leu
1               5                   10

<210> SEQ ID NO 123
<211> LENGTH: 9
<212> TYPE: PRT
<213> ORGANISM: Homo sapiens

<400> SEQUENCE: 123

Arg Tyr Lys Ser Gly Leu Asp Lys His
1               5

<210> SEQ ID NO 124
<211> LENGTH: 39
<212> TYPE: PRT
<213> ORGANISM: Homo sapiens

<400> SEQUENCE: 124

Gln Gly Ser Gly Val Pro Ser Arg Phe Ser Gly Ser Lys Asp Asp Ser
1               5                   10                  15

Ala Asn Ala Gly Ile Leu Phe Ile Ser Gly Leu Gln Ser Glu Asp Glu
            20                  25                  30
```

Ala Asp Tyr Tyr Cys Leu Ile
         35

<210> SEQ ID NO 125
<211> LENGTH: 8
<212> TYPE: PRT
<213> ORGANISM: Homo sapiens

<400> SEQUENCE: 125

Trp His Ser Ser Ala Val Val Phe
1               5

<210> SEQ ID NO 126
<211> LENGTH: 19
<212> TYPE: PRT
<213> ORGANISM: Homo sapiens

<400> SEQUENCE: 126

Gly Gly Gly Thr Lys Leu Thr Val Leu Gly Gln Pro Lys Ala Ala Pro
1               5                   10                  15

Ser Val Thr

<210> SEQ ID NO 127
<211> LENGTH: 1413
<212> TYPE: DNA
<213> ORGANISM: Homo sapiens

<400> SEQUENCE: 127

| | | | | | |
|---|---|---|---|---|---|
| atggagttgg | ggctgtgctg | ggttttcctt | gttgctattt | tagaaggtgt | ccagtgtgag | 60 |
| gtgcagctgg | tggagtctgg | gggaggcttg | gtacagccgg | gggggtccct | gagactctcc | 120 |
| tgtgcagcct | ctggattcac | cttcactacc | tctaccatga | actgggtccg | ccaggctcca | 180 |
| gggaaggggc | tggagtgggt | ttcatacatt | actaggacca | gcactgtcat | atactatgca | 240 |
| gactctgtga | agggccgatt | caccatctcc | agagacaatg | ccaagaactc | actgtatctg | 300 |
| caaatgagca | gcctgagagc | cgaggacacg | gctgtgtatt | attgtgcgag | aggggtgagg | 360 |
| gacattggcg | gaaacggttt | tgactactgg | ggccagggaa | ccctggtcac | cgtctcctca | 420 |
| gcctccacca | agggcccatc | ggtcttcccc | ctggcaccct | cctccaagag | cacctctggg | 480 |
| ggcacagcgg | ccctgggctg | cctggtcaag | gactacttcc | ccgaaccggt | gacggtgtcg | 540 |
| tggaactcag | gcgccctgac | cagcggcgtg | cacaccttcc | cggctgtcct | acagtcctca | 600 |
| ggactctact | ccctcagcag | cgtggtgacc | gtgccctcca | gcagcttggg | cacccagacc | 660 |
| tacatctgca | acgtgaatca | caagcccagc | aacaccaagg | tggacaagaa | agttgagccc | 720 |
| aaatcttgtg | acaaaactca | cacatgccca | ccgtgcccag | cacctgaact | cctgggggga | 780 |
| ccgtcagtct | tcctcttccc | cccaaaaccc | aaggacaccc | tcatgatctc | ccggacccct | 840 |
| gaggtcacat | gcgtggtggt | ggacgtgagc | cacgaagacc | ctgaggtcaa | gttcaactgg | 900 |
| tacgtggacg | gcgtggaggt | gcataatgcc | aagacaaagc | cgcgggagga | gcagtacaac | 960 |
| agcacgtacc | gggtggtcag | cgtcctcacc | gtcctgcacc | aggactggct | gaatggcaag | 1020 |
| gagtacaagt | gcaaggtctc | caacaaagcc | ctcccagccc | ccatcgagaa | aaccatctcc | 1080 |
| aaagccaaag | ggcagccccg | agaaccacag | gtgtacaccc | tgcccccatc | ccgggatgag | 1140 |
| ctgaccaaga | accaggtcag | cctgacctgc | ctggtcaaag | gcttctatcc | cagcgacatc | 1200 |
| gccgtggagt | gggagagcaa | tgggcagccg | gagaacaact | acaagaccac | gcctcccgtg | 1260 |
| ctggactccg | acggctcctt | cttcctctac | agcaagctca | ccgtggacaa | gagcaggtgg | 1320 | cagcagggga acgtcttctc atgctccgtg atgcatgagg ctctgcacaa ccactacacg    1380 cagaagagcc tctccctgtc tccgggtaaa tga                                 1413

<210> SEQ ID NO 128
<211> LENGTH: 470
<212> TYPE: PRT
<213> ORGANISM: Homo sapiens

<400> SEQUENCE: 128

Met Glu Leu Gly Leu Cys Trp Val Phe Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Thr Thr Ser Thr Met Asn Trp Val Arg Gln Ala Pro Gly Lys Gly Leu
    50                  55                  60

Glu Trp Val Ser Tyr Ile Thr Arg Thr Ser Thr Val Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Ser Ser Leu Arg Ala Glu Asp Thr Ala Val
            100                 105                 110

Tyr Tyr Cys Ala Arg Gly Val Arg Asp Ile Gly Gly Asn Gly Phe Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
    450                 455                 460

Ser Leu Ser Pro Gly Lys
465             470

<210> SEQ ID NO 129
<211> LENGTH: 711
<212> TYPE: DNA
<213> ORGANISM: Homo sapiens

<400> SEQUENCE: 129
atggaaaccc cagcgcagct tctcttcctc ctgctactct ggctcccaga taccaccgga      60
gaaattgtgt tgacgcagtc tccaggcacc ctctctttgt ctccagggga agagccacc     120 ctctcctgca gggccagtca gagtgtaacc agcagttact tagcctggta ccagcagaaa     180
actggccagg ctcccaggct cctcatctac ggcgcatcca gcagggccac tggcatccca     240
gacaggttca gtggcagtgg gtctgggaca gacttcactc tcaccatcgc cagactggag     300
cctgaagatt ttgcggtgta ttactgtcag cagtatggta gctcgcctcc gtacactttt     360
ggccagggga ccaagctgga gatcaaacga actgtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata acgccctcca atcgggtaac     540
tcccaggaga gtgtcacaga gcaggacagc aaggacagca cctacagcct cagcagcacc     600
ctgacgctga gcaaagcaga ctacgagaaa cacaaagtct acgcctgcga agtcacccat     660
cagggcctga gctcgcccgt cacaaagagc ttcaacaggg gagagtgtta g             711

<210> SEQ ID NO 130
<211> LENGTH: 236
<212> TYPE: PRT
<213> ORGANISM: Homo sapiens

<400> SEQUENCE: 130

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Ala Ser Gln Ser
            35                  40                  45

Val Thr Ser Ser Tyr Leu Ala Trp Tyr Gln Gln Lys Thr Gly Gln Ala
    50                  55                  60

Pro Arg Leu Leu Ile Tyr Gly Ala Ser Ser Arg Ala Thr Gly Ile Pro
65                  70                  75                  80

```
Asp Arg Phe Ser Gly Ser Gly Ser Gly Thr Asp Phe Thr Leu Thr Ile
            85                  90                  95

Ala Arg Leu Glu Pro Glu Asp Phe Ala Val Tyr Tyr Cys Gln Gln Tyr
            100                 105                 110

Gly Ser Ser Pro Pro Tyr Thr Phe Gly Gln Gly Thr Lys Leu Glu Ile
            115                 120                 125

Lys Arg Thr Val Ala Ala Pro Ser Val Phe Ile Phe Pro Pro Ser Asp
            130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
            165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
            210                 215                 220

Ser Pro Val Thr Lys Ser Phe Asn Arg Gly Glu Cys
225                 230                 235

<210> SEQ ID NO 131
<211> LENGTH: 25
<212> TYPE: PRT
<213> ORGANISM: Homo sapiens

<400> SEQUENCE: 131

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 132
<211> LENGTH: 10
<212> TYPE: PRT
<213> ORGANISM: Homo sapiens

<400> SEQUENCE: 132

Gly Phe Thr Phe Thr Thr Ser Thr Met Asn
1               5                   10

<210> SEQ ID NO 133
<211> LENGTH: 14
<212> TYPE: PRT
<213> ORGANISM: Homo sapiens

<400> SEQUENCE: 133

Trp Val Arg Gln Ala Pro Gly Lys Gly Leu Glu Trp Val Ser
1               5                   10

<210> SEQ ID NO 134
<211> LENGTH: 9
<212> TYPE: PRT
<213> ORGANISM: Homo sapiens

<400> SEQUENCE: 134

Tyr Ile Thr Arg Thr Ser Thr Val Ile
1               5

<210> SEQ ID NO 135
```

```
<211> LENGTH: 40
<212> TYPE: PRT
<213> ORGANISM: Homo sapiens

<400> SEQUENCE: 135

Tyr Tyr Ala Asp Ser Val Lys Gly Arg Phe Thr Ile Ser Arg Asp Asn
1               5                   10                  15

Ala Lys Asn Ser Leu Tyr Leu Gln Met Ser Ser Leu Arg Ala Glu Asp
            20                  25                  30

Thr Ala Val Tyr Tyr Cys Ala Arg
        35                  40

<210> SEQ ID NO 136
<211> LENGTH: 12
<212> TYPE: PRT
<213> ORGANISM: Homo sapiens

<400> SEQUENCE: 136

Gly Val Arg Asp Ile Gly Gly Asn Gly Phe Asp Tyr
1               5                   10

<210> SEQ ID NO 137
<211> LENGTH: 11
<212> TYPE: PRT
<213> ORGANISM: Homo sapiens

<400> SEQUENCE: 137

Trp Gly Gln Gly Thr Leu Val Thr Val Ser Ser
1               5                   10

<210> SEQ ID NO 138
<211> LENGTH: 23
<212> TYPE: PRT
<213> ORGANISM: Homo sapiens

<400> SEQUENCE: 138

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 139
<211> LENGTH: 11
<212> TYPE: PRT
<213> ORGANISM: Homo sapiens

<400> SEQUENCE: 139

Arg Ala Ser Gln Ser Ile Ser Ser Asn Leu Ala
1               5                   10

<210> SEQ ID NO 140
<211> LENGTH: 15
<212> TYPE: PRT
<213> ORGANISM: Homo sapiens

<400> SEQUENCE: 140

Trp Tyr Gln Gln Lys Pro Gly Gln Ala Pro Arg Leu Leu Ile Tyr
1               5                   10                  15

<210> SEQ ID NO 141
<211> LENGTH: 7
<212> TYPE: PRT
<213> ORGANISM: Homo sapiens
```

<400> SEQUENCE: 141

Asp Ala Ser Thr Arg Ala Thr
1               5

<210> SEQ ID NO 142
<211> LENGTH: 32
<212> TYPE: PRT
<213> ORGANISM: Homo sapiens

<400> SEQUENCE: 142

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 143
<211> LENGTH: 9
<212> TYPE: PRT
<213> ORGANISM: Homo sapiens

<400> SEQUENCE: 143

Gln Gln Tyr Asn Asp Trp Leu Val Thr
1               5

<210> SEQ ID NO 144
<211> LENGTH: 10
<212> TYPE: PRT
<213> ORGANISM: Homo sapiens

<400> SEQUENCE: 144

Phe Gly Gln Gly Thr Lys Val Glu Ile Lys
1               5                   10

<210> SEQ ID NO 145
<211> LENGTH: 1407
<212> TYPE: DNA
<213> ORGANISM: Homo sapiens

<400> SEQUENCE: 145

```
atggaactgg ggctccgctg ggttttcctt gttgctattt tagaaggtgt ccagtgtgag     60
gtgcagctgg tggagtctgg gggaggcctg gtcaagcctg gggggtccct gagagtctcc    120
tgtgcagcct ctggattcac cttcagtagc tatagcatga actggatccg ccaggctcca    180
gggaaggggc tggagtgggt ctcatccatt agtagtaata gtagttacat atactacgca    240
gactcagtta agggccgatt caccatctcc agagacaacg ccaagaactc actgtatctg    300
caaatgaaca gcctgagagc cgaggacacg gctgtttatt actgtgcgag agatcgggac    360
tacagtaact accttaccgc gtggggccag ggaaccctgg tcaccgtctc ctcagcctcc    420
accaagggcc catcggtctt ccccctggca ccctcctcca agagcacctc tgggggcaca    480
gcggccctgg gctgcctggt caaggactac ttccccgaac cggtgacggt gtcgtggaac    540
tcaggcgccc tgaccagcgg cgtgcacacc ttcccggctg tcctacagtc ctcaggactc    600
tactccctca gcagcgtggt gaccgtgccc tccagcagct tgggcaccca gacctacatc    660
tgcaacgtga atcacaagcc cagcaacacc aaggtggaca agaaagttga gcccaaatct    720
tgtgacaaaa ctcacacatg cccaccgtgc ccagcacctg aactcctggg gggaccgtca    780
gtcttcctct tccccccaaa acccaaggac accctcatga tctcccggac ccctgaggtc    840
acatgcgtgg tggtggacgt gagccacgaa gaccctgagg tcaagttcaa ctggtacgtg    900
```

```
gacggcgtgg aggtgcataa tgccaagaca aagccgcggg aggagcagta caacagcacg    960
taccgggtgg tcagcgtcct caccgtcctg caccaggact ggctgaatgg caaggagtac   1020
aagtgcaagg tctccaacaa agccctccca gccccatcg agaaaaccat ctccaaagcc   1080
aaagggcagc cccgagaacc acaggtgtac accctgcccc catcccggga tgagctgacc   1140
aagaaccagg tcagcctgac ctgcctggtc aaaggcttct atcccagcga catcgccgtg   1200
gagtgggaga gcaatgggca gccggagaac aactacaaga ccacgcctcc cgtgctggac   1260
tccgacggct ccttcttcct ctacagcaag ctcaccgtgg acaagagcag gtggcagcag   1320
gggaacgtct tctcatgctc cgtgatgcat gaggctctgc acaaccacta cacgcagaag   1380
agcctctccc tgtctccggg taaatga                                       1407

<210> SEQ ID NO 146
<211> LENGTH: 468
<212> TYPE: PRT
<213> ORGANISM: Homo sapiens

<400> SEQUENCE: 146
```

Met Glu Leu Gly Leu Arg Trp Val Phe Leu Val Ala Ile Leu Glu Gly
1               5                   10                  15

Val Gln Cys Glu Val Gln Leu Val Glu Ser Gly Gly Gly Leu Val Lys
            20                  25                  30

Pro Gly Gly Ser Leu Arg Val Ser Cys Ala Ala Ser Gly Phe Thr Phe
        35                  40                  45

Ser Ser Tyr Ser Met Asn Trp Ile Arg Gln Ala Pro Gly Lys Gly Leu
    50                  55                  60

Glu Trp Val Ser Ser Ile Ser Ser Asn Ser Ser Tyr Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Asp Arg Asp Tyr Ser Asn Tyr Leu Thr Ala Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
        290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
450                 455                 460

Ser Pro Gly Lys
465

<210> SEQ ID NO 147
<211> LENGTH: 711
<212> TYPE: DNA
<213> ORGANISM: Homo sapiens

<400> SEQUENCE: 147
atggcctggt ctcctctcct cctcactctc ctcgctcact gcacagggtc ctgggcccag      60
tctgtgctga cgcagccgcc ctcagtgtct ggggccccag gcagagggt caccatctcc      120 tgcactggga gcagctccaa catcggggca ggttatgatg tacactggta ccgccaactt      180
ccaggaacag ccccaaaact cctcatctat ggtaagaaca atcggcctc agggtccct      240 aaccgattct ctggctccaa gtctggcacc tcagcctccc tggccatcac tggcctccag      300
gctgaggatg aggctgatta ttactgtcag tcctatgaca gcagcctgag tggttcggta      360
ttcggcggag ggaccaagct gaccgtccta ggtcagccca aggctgcccc ctcggtcact      420
ctgttcccgc cctcctctga ggagcttcaa gccaacaagg ccacactagt gtgtctgatc      480
agtgacttct acccgggagc tgtgacagtg gcttggaagg cagatggcag ccccgtcaag      540
gcgggagtgg agacgaccaa acctccaaa cagagcaaca acaagtacgc ggccagcagc      600
tacctgagcc tgacgcccga gcagtggaag tcccacagaa gctacagctg ccaggtcacg      660
catgaaggga gcaccgtgga agacagtg gcccctacag aatgttcata g              711

<210> SEQ ID NO 148
<211> LENGTH: 236
<212> TYPE: PRT
<213> ORGANISM: Homo sapiens

<400> SEQUENCE: 148

Met Ala Trp Ser Pro Leu Leu Leu Thr Leu Leu Ala His Cys Thr Gly
1               5                   10                  15

```
Ser Trp Ala Gln Ser Val Leu Thr Gln Pro Pro Ser Val Ser Gly Ala
         20                  25                  30

Pro Gly Gln Arg Val Thr Ile Ser Cys Thr Gly Ser Ser Ser Asn Ile
             35                  40                  45

Gly Ala Gly Tyr Asp Val His Trp Tyr Arg Gln Leu Pro Gly Thr Ala
 50                  55                  60

Pro Lys Leu Leu Ile Tyr Gly Lys Asn Asn Arg Pro Ser Gly Val Pro
 65                  70                  75                  80

Asn Arg Phe Ser Gly Ser Lys Ser Gly Thr Ser Ala Ser Leu Ala Ile
             85                  90                  95

Thr Gly Leu Gln Ala Glu Asp Glu Ala Asp Tyr Tyr Cys Gln Ser Tyr
            100                 105                 110

Asp Ser Ser Leu Ser Gly Ser Val Phe Gly Gly Gly Thr Lys Leu Thr
            115                 120                 125

Val Leu Gly Gln Pro Lys Ala Ala Pro Ser Val Thr Leu Phe Pro Pro
130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Gly
                165                 170                 175

Ser Pro Val Lys Ala Gly Val Glu Thr Thr Lys Pro Ser Lys Gln Ser
            180                 185                 190

Asn Asn Lys Tyr Ala Ala Ser Ser Tyr Leu Ser Leu Thr Pro Glu Gln
            195                 200                 205

Trp Lys Ser His Arg Ser Tyr Ser Cys Gln Val Thr His Glu Gly Ser
    210                 215                 220

Thr Val Glu Lys Thr Val Ala Pro Thr Glu Cys Ser
225                 230                 235

<210> SEQ ID NO 149
<211> LENGTH: 25
<212> TYPE: PRT
<213> ORGANISM: Homo sapiens

<400> SEQUENCE: 149

Glu Val Gln Leu Val Glu Ser Gly Gly Gly Leu Val Lys Pro Gly Gly
1               5                   10                  15

Ser Leu Arg Val Ser Cys Ala Ala Ser
            20                  25

<210> SEQ ID NO 150
<211> LENGTH: 10
<212> TYPE: PRT
<213> ORGANISM: Homo sapiens

<400> SEQUENCE: 150

Gly Phe Thr Phe Ser Ser Tyr Ser Met Asn
1               5                   10

<210> SEQ ID NO 151
<211> LENGTH: 14
<212> TYPE: PRT
<213> ORGANISM: Homo sapiens

<400> SEQUENCE: 151

Trp Ile Arg Gln Ala Pro Gly Lys Gly Leu Glu Trp Val Ser
1               5                   10
```

<210> SEQ ID NO 152
<211> LENGTH: 9
<212> TYPE: PRT
<213> ORGANISM: Homo sapiens

<400> SEQUENCE: 152

Ser Ile Ser Ser Asn Ser Ser Tyr Ile
1               5

<210> SEQ ID NO 153
<211> LENGTH: 40
<212> TYPE: PRT
<213> ORGANISM: Homo sapiens

<400> SEQUENCE: 153

Tyr Tyr Ala Asp Ser Val Lys Gly Arg Phe Thr Ile Ser Arg Asp Asn
1               5                   10                  15

Ala Lys Asn Ser Leu Tyr Leu Gln Met Asn Ser Leu Arg Ala Glu Asp
            20                  25                  30

Thr Ala Val Tyr Tyr Cys Ala Arg
        35                  40

<210> SEQ ID NO 154
<211> LENGTH: 10
<212> TYPE: PRT
<213> ORGANISM: Homo sapiens

<400> SEQUENCE: 154

Asp Arg Asp Tyr Ser Asn Tyr Leu Thr Ala
1               5                   10

<210> SEQ ID NO 155
<211> LENGTH: 11
<212> TYPE: PRT
<213> ORGANISM: Homo sapiens

<400> SEQUENCE: 155

Trp Gly Gln Gly Thr Leu Val Thr Val Ser Ser
1               5                   10

<210> SEQ ID NO 156
<211> LENGTH: 22
<212> TYPE: PRT
<213> ORGANISM: Homo sapiens

<400> SEQUENCE: 156

Gln Ser Val Leu Thr Gln Pro Pro Ser Val Ser Gly Ala Pro Gly Gln
1               5                   10                  15

Arg Val Thr Ile Ser Cys
            20

<210> SEQ ID NO 157
<211> LENGTH: 14
<212> TYPE: PRT
<213> ORGANISM: Homo sapiens

<400> SEQUENCE: 157

Thr Gly Ser Ser Ser Asn Ile Gly Ala Gly Tyr Asp Val His
1               5                   10

<210> SEQ ID NO 158
<211> LENGTH: 15
<212> TYPE: PRT

-continued

<213> ORGANISM: Homo sapiens

<400> SEQUENCE: 158

Trp Tyr Arg Gln Leu Pro Gly Thr Ala Pro Lys Leu Leu Ile Tyr
1               5                   10                  15

<210> SEQ ID NO 159
<211> LENGTH: 7
<212> TYPE: PRT
<213> ORGANISM: Homo sapiens

<400> SEQUENCE: 159

Gly Lys Asn Asn Arg Pro Ser
1               5

<210> SEQ ID NO 160
<211> LENGTH: 32
<212> TYPE: PRT
<213> ORGANISM: Homo sapiens

<400> SEQUENCE: 160

Gly Val Pro Asn Arg Phe Ser Gly Ser Lys Ser Gly Thr Ser Ala Ser
1               5                   10                  15

Leu Ala Ile Thr Gly Leu Gln Ala Glu Asp Glu Ala Asp Tyr Tyr Cys
            20                  25                  30

<210> SEQ ID NO 161
<211> LENGTH: 11
<212> TYPE: PRT
<213> ORGANISM: Homo sapiens

<400> SEQUENCE: 161

Gln Ser Tyr Asp Ser Ser Leu Ser Gly Ser Val
1               5                   10

<210> SEQ ID NO 162
<211> LENGTH: 20
<212> TYPE: PRT
<213> ORGANISM: Homo sapiens

<400> SEQUENCE: 162

Phe Gly Gly Gly Thr Lys Leu Thr Val Leu Gly Gln Pro Lys Ala Ala
1               5                   10                  15

Pro Ser Val Thr
            20

<210> SEQ ID NO 163
<211> LENGTH: 1395
<212> TYPE: DNA
<213> ORGANISM: Homo sapiens

<400> SEQUENCE: 163
atggagtttg ggctgagctg ggttttcctt gttgccattt taaaaggtgt ccagtgtgag      60
gtgcagctgg tggagtccgg gggaggctta gttcagcctg gggggtccct gagactctcc    120
tgttcagcct ctggattcac tttcagaagt tactggatgc actgggtccg ccaagttcca    180
gggaaggggc tggtatgggt ctcatgtatt aataaagaag gagtagcac aacctacgcg     240 gactccgtga agggccgatt caccatctcc agagacaacg ccaagaacac gctgtatttg    300
caaatgaaca gtctgagagc cgacgacacg gctgtgtatt actgtctaag gggatacgat    360
gttgactact ggggccaggg aaccctggtc accgtctcct cagcctccac caagggccca    420

```
tcggtcttcc ccctggcacc ctcctccaag agcacctctg ggggcacagc ggccctgggc    480
tgcctggtca aggactactt ccccgaaccg gtgacggtgt cgtggaactc aggcgccctg    540
accagcggcg tgcacacctt cccggctgtc ctacagtcct caggactcta ctccctcagc    600
agcgtggtga ccgtgccctc cagcagcttg ggcacccaga cctacatctg caacgtgaat    660
cacaagccca gcaacaccaa ggtggacaag aaagttgagc ccaaatcttg tgacaaaact    720
cacacatgcc caccgtgccc agcacctgaa ctcctggggg gaccgtcagt cttcctcttc    780
cccccaaaac ccaaggacac cctcatgatc tcccggaccc ctgaggtcac atgcgtggtg    840
gtggacgtga gccacgaaga ccctgaggtc aagttcaact ggtacgtgga cggcgtggag    900
gtgcataatg ccaagacaaa gccgcgggag gagcagtaca acagcacgta ccgggtggtc    960
agcgtcctca ccgtcctgca ccaggactgg ctgaatggca aggagtacaa gtgcaaggtc   1020
tccaacaaag ccctcccagc ccccatcgag aaaaccatct ccaaagccaa agggcagccc   1080
cgagaaccac aggtgtacac cctgccccca tcccgggatg agctgaccaa gaaccaggtc   1140
agcctgacct gcctggtcaa aggcttctat cccagcgaca tcgccgtgga gtgggagagc   1200
aatgggcagc cggagaacaa ctacaagacc acgcctcccg tgctggactc cgacggctcc   1260
ttcttcctct acagcaagct caccgtggac aagagcaggt ggcagcaggg gaacgtcttc   1320
tcatgctccg tgatgcatga ggctctgcac aaccactaca cgcagaagag cctctccctg   1380
tctccgggta aatga                                                    1395
```

<210> SEQ ID NO 164
<211> LENGTH: 464
<212> TYPE: PRT
<213> ORGANISM: Homo sapiens

<400> SEQUENCE: 164

```
Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Gly Leu Val Gln
                20                  25                  30

Pro Gly Gly Ser Leu Arg Leu Ser Cys Ser Ala Ser Gly Phe Thr Phe
            35                  40                  45

Arg Ser Tyr Trp Met His Trp Val Arg Gln Val Pro Gly Lys Gly Leu
        50                  55                  60

Val Trp Val Ser Cys Ile Asn Lys Glu Gly Ser Ser Thr Thr Tyr Ala
65                  70                  75                  80

Asp Ser Val Lys Gly Arg Phe Thr Ile Ser Arg Asp Asn Ala Lys Asn
                85                  90                  95

Thr Leu Tyr Leu Gln Met Asn Ser Leu Arg Ala Asp Asp Thr Ala Val
            100                 105                 110

Tyr Tyr Cys Leu Arg Gly Tyr Asp Val Asp Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
```

```
        195                 200                 205
Ser Leu Gly Thr Gln Thr Tyr Ile Cys Asn Val Asn His Lys Pro Ser
    210                 215                 220

Asn Thr Lys Val Asp Lys Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Asp Glu Leu Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

<210> SEQ ID NO 165
<211> LENGTH: 723
<212> TYPE: DNA
<213> ORGANISM: Homo sapiens

<400> SEQUENCE: 165
atggcctgga ctcctctcct cctcctgttc ctctctcact gcacaggttc cctctcgcag    60
gctgtgctga ctcagccgtc ctccctctct gcatctcccg gagcatcagt cagtctcacc   120
tgcaccttgc gcagtggcgt caatgttggt tcctacagga tatactggta tcagcagaag   180
ccagggagtc ctccccggta tctcctgagg tacaaatcag cttagataa acaccagggc   240 tctggagtcc ccagccgctt ctctggatcc aaagatgatt cggccaatgc agggatttta   300
ttcatttctg ggctccagtc tgagaatgat gctgattatt actgtttgat ttggcacaac   360
agcgctgtgg tattcggcgg agggaccaag ctgaccgtcc taggtcagcc caaggctgcc   420
ccctcggtca ctctgttccc gccctcctct gaggagcttc aagccaacaa ggccacactg   480
gtgtgtctga tcagtgactt ctaccccgga gctgtgacag tggcttggaa ggcagatggc   540
agccccgtca aggcgggagt ggagacgacc aaaccctcca aacagagcaa caacaagtac   600
gcggccagca gctacctgag cctgacgccc gagcagtgga agtcccacag aagctacagc   660
```

```
tgccaggtca cgcatgaagg gagcaccgtg gagaagacag tggcccctac agaatgttca    720
tag                                                                  723
```

<210> SEQ ID NO 166
<211> LENGTH: 240
<212> TYPE: PRT
<213> ORGANISM: Homo sapiens

<400> SEQUENCE: 166

```
Met Ala Trp Thr Pro Leu Leu Leu Phe Leu Ser His Cys Thr Gly
1               5                   10                  15

Ser Leu Ser Gln Ala Val Leu Thr Gln Pro Ser Ser Leu Ser Ala Ser
                20                  25                  30

Pro Gly Ala Ser Val Ser Leu Thr Cys Thr Leu Arg Ser Gly Val Asn
            35                  40                  45

Val Gly Ser Tyr Arg Ile Tyr Trp Tyr Gln Gln Lys Pro Gly Ser Pro
    50                  55                  60

Pro Arg Tyr Leu Leu Arg Tyr Lys Ser Gly Leu Asp Lys His Gln Gly
65                  70                  75                  80

Ser Gly Val Pro Ser Arg Phe Ser Gly Ser Lys Asp Asp Ser Ala Asn
                85                  90                  95

Ala Gly Ile Leu Phe Ile Ser Gly Leu Gln Ser Glu Asn Asp Ala Asp
            100                 105                 110

Tyr Tyr Cys Leu Ile Trp His Asn Ser Ala Val Val Phe Gly Gly Gly
        115                 120                 125

Thr Lys Leu Thr Val Leu Gly Gln Pro Lys Ala Ala Pro Ser Val Thr
130                 135                 140

Leu Phe Pro Pro Ser Ser Glu Glu Leu Gln Ala Asn Lys Ala Thr Leu
145                 150                 155                 160

Val Cys Leu Ile Ser Asp Phe Tyr Pro Gly Ala Val Thr Val Ala Trp
                165                 170                 175

Lys Ala Asp Gly Ser Pro Val Lys Ala Gly Val Glu Thr Thr Lys Pro
            180                 185                 190

Ser Lys Gln Ser Asn Asn Lys Tyr Ala Ala Ser Ser Tyr Leu Ser Leu
        195                 200                 205

Thr Pro Glu Gln Trp Lys Ser His Arg Ser Tyr Ser Cys Gln Val Thr
    210                 215                 220

His Glu Gly Ser Thr Val Glu Lys Thr Val Ala Pro Thr Glu Cys Ser
225                 230                 235                 240
```

<210> SEQ ID NO 167
<211> LENGTH: 25
<212> TYPE: PRT
<213> ORGANISM: Homo sapiens

<400> SEQUENCE: 167

```
Glu Val Gln Leu Val Glu Ser Gly Gly Gly Leu Val Gln Pro Gly Gly
1               5                   10                  15

Ser Leu Arg Leu Ser Cys Ser Ala Ser
            20                  25
```

<210> SEQ ID NO 168
<211> LENGTH: 10
<212> TYPE: PRT
<213> ORGANISM: Homo sapiens

<400> SEQUENCE: 168

Gly Phe Thr Phe Arg Ser Tyr Trp Met His
1               5                   10

<210> SEQ ID NO 169
<211> LENGTH: 14
<212> TYPE: PRT
<213> ORGANISM: Homo sapiens

<400> SEQUENCE: 169

Trp Val Arg Gln Val Pro Gly Lys Gly Leu Val Trp Val Ser
1               5                   10

<210> SEQ ID NO 170
<211> LENGTH: 10
<212> TYPE: PRT
<213> ORGANISM: Homo sapiens

<400> SEQUENCE: 170

Cys Ile Asn Lys Glu Gly Ser Ser Thr Thr
1               5                   10

<210> SEQ ID NO 171
<211> LENGTH: 39
<212> TYPE: PRT
<213> ORGANISM: Homo sapiens

<400> SEQUENCE: 171

Tyr Ala Asp Ser Val Lys Gly Arg Phe Thr Ile Ser Arg Asp Asn Ala
1               5                   10                  15

Lys Asn Thr Leu Tyr Leu Gln Met Asn Ser Leu Arg Ala Asp Asp Thr
            20                  25                  30

Ala Val Tyr Tyr Cys Leu Arg
        35

<210> SEQ ID NO 172
<211> LENGTH: 8
<212> TYPE: PRT
<213> ORGANISM: Homo sapiens

<400> SEQUENCE: 172

Gly Tyr Asp Val Asp Tyr Trp Gly
1               5

<210> SEQ ID NO 173
<211> LENGTH: 9
<212> TYPE: PRT
<213> ORGANISM: Homo sapiens

<400> SEQUENCE: 173

Gln Gly Thr Leu Val Thr Val Ser Ser
1               5

<210> SEQ ID NO 174
<211> LENGTH: 25
<212> TYPE: PRT
<213> ORGANISM: Homo sapiens

<400> SEQUENCE: 174

Gln Ala Val Leu Thr Gln Pro Ser Ser Leu Ser Ala Ser Pro Gly Ala
1               5                   10                  15

Ser Val Ser Leu Thr Cys Thr Leu Arg
            20                  25

<210> SEQ ID NO 175
<211> LENGTH: 11
<212> TYPE: PRT
<213> ORGANISM: Homo sapiens

<400> SEQUENCE: 175

Ser Gly Val Asn Val Gly Ser Tyr Arg Ile Tyr
1               5                   10

<210> SEQ ID NO 176
<211> LENGTH: 14
<212> TYPE: PRT
<213> ORGANISM: Homo sapiens

<400> SEQUENCE: 176

Trp Tyr Gln Gln Lys Pro Gly Ser Pro Pro Arg Tyr Leu Leu
1               5                   10

<210> SEQ ID NO 177
<211> LENGTH: 9
<212> TYPE: PRT
<213> ORGANISM: Homo sapiens

<400> SEQUENCE: 177

Arg Tyr Lys Ser Gly Leu Asp Lys His
1               5

<210> SEQ ID NO 178
<211> LENGTH: 39
<212> TYPE: PRT
<213> ORGANISM: Homo sapiens

<400> SEQUENCE: 178

Gln Gly Ser Gly Val Pro Ser Arg Phe Ser Gly Ser Lys Asp Asp Ser
1               5                   10                  15

Ala Asn Ala Gly Ile Leu Phe Ile Ser Gly Leu Gln Ser Glu Asn Asp
            20                  25                  30

Ala Asp Tyr Tyr Cys Leu Ile
        35

<210> SEQ ID NO 179
<211> LENGTH: 8
<212> TYPE: PRT
<213> ORGANISM: Homo sapiens

<400> SEQUENCE: 179

Trp His Asn Ser Ala Val Val Phe
1               5

<210> SEQ ID NO 180
<211> LENGTH: 19
<212> TYPE: PRT
<213> ORGANISM: Homo sapiens

<400> SEQUENCE: 180

Gly Gly Gly Thr Lys Leu Thr Val Leu Gly Gln Pro Lys Ala Ala Pro
1               5                   10                  15

Ser Val Thr

<210> SEQ ID NO 181
<211> LENGTH: 1416
<212> TYPE: DNA
<213> ORGANISM: Homo sapiens

<400> SEQUENCE: 181

```
atgaaacacc tgtggttctt cctcctcctg gtggcagctc ccagatgggt cctgtctcag    60
gtgcatctgc aggagtcggg cccaggactg gtgaagcctt cggggaccct gtccctcacc   120
tgcgctgtct ctggtggctc catcagttac actaactggt ggagttgggt ccgcctgccc   180
ccagggaagg gctggagtg gatagggga atctatcata gtaggagcac caactacaac    240
ccgtccctca gagtcgagt caccatgtca atagacaagt ccaagaatct gttctccctg   300
aagctgaact ctgtgaccgc cgcggacacg gccatctatt actgtgctaa gccgcttac    360
acaagggatg aatacagcc ttttgacaac tggggccagg gaaccctggt caccgtctcc   420
tcagcctcca ccaagggccc atcggtcttc ccctggcac cctcctccaa gagcacctct   480
ggggggcacag cggccctggg ctgcctggtc aaggactact ccccgaacc ggtgacggtg   540
tcgtggaact caggcgccct gaccagcggc gtgcacacct tcccggctgt cctacagtcc   600
tcaggactct actccctcag cagcgtggtg accgtgccct ccagcagctt gggcacccag   660
acctacatct gcaacgtgaa tcacaagccc agcaacacca aggtggacaa gaaagttgag   720
cccaaatctt gtgacaaaac tcacacatgc ccaccgtgcc cagcacctga actcctgggg   780
ggaccgtcag tcttcctctt ccccccaaaa cccaaggaca cctcatgat ctcccggacc   840
cctgaggtca catgcgtggt ggtggacgtg agccacgaag accctgaggt caagttcaac   900
tggtacgtgg acggcgtgga ggtgcataat gccaagacaa agccgcggga ggagcagtac   960
aacagcacgt accgggtggt cagcgtcctc accgtcctgc accaggactg gctgaatggc  1020
aaggagtaca agtgcaaggt ctccaacaaa gccctcccag cccccatcga gaaaaccatc  1080
tccaaagcca aagggcagcc ccgagaacca caggtgtaca ccctgccccc atcccgggat  1140
gagctgacca agaaccaggt cagcctgacc tgcctggtca aaggcttcta tcccagcgac  1200
atcgccgtgg agtgggagag caatgggcag ccggagaaca actacaagac cacgcctccc  1260
gtgctggact ccgacggctc cttcttcctc tacagcaagc tcaccgtgga caagagcagg  1320
tggcagcagg ggaacgtctt ctcatgctcc gtgatgcatg aggctctgca caaccactac  1380
acgcagaaga gcctctccct gtctccgggt aaatga                            1416
```

<210> SEQ ID NO 182
<211> LENGTH: 471
<212> TYPE: PRT
<213> ORGANISM: Homo sapiens

<400> SEQUENCE: 182

```
Met Lys His Leu Trp Phe Phe Leu Leu Val Ala Ala Pro Arg Trp
1               5                   10                  15

Val Leu Ser Gln Val His Leu Gln Glu Ser Gly Pro Gly Leu Val Lys
                20                  25                  30

Pro Ser Gly Thr Leu Ser Leu Thr Cys Ala Val Ser Gly Gly Ser Ile
            35                  40                  45

Ser Tyr Thr Asn Trp Trp Ser Trp Val Arg Leu Pro Pro Gly Lys Gly
        50                  55                  60

Leu Glu Trp Ile Gly Glu Ile Tyr His Ser Arg Ser Thr Asn Tyr Asn
65                  70                  75                  80

Pro Ser Leu Lys Ser Arg Val Thr Met Ser Ile Asp Lys Ser Lys Asn
                85                  90                  95

Leu Phe Ser Leu Lys Leu Asn Ser Val Thr Ala Ala Asp Thr Ala Ile
            100                 105                 110
```

```
Tyr Tyr Cys Ala Lys Ala Ala Tyr Thr Arg Asp Gly Ile Gln Pro Phe
            115                 120                 125

Asp Asn Trp Gly Gln Gly Thr Leu Val Thr Val Ser Ser Ala Ser Thr
        130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 183
<211> LENGTH: 723
<212> TYPE: DNA
<213> ORGANISM: Homo sapiens

<400> SEQUENCE: 183
atggtgttgc agacccaggt cttcatttct ctgttgctct ggatctctgg tgcctacggg    60
```

```
gacatcgtga tgacccagtc tccagactcc ctggctgtgt ctctgggcga gagggccacc    120
atcaactgca agtccagcca gagtgtttta aagagctcca acaataagaa ctacttagct    180
tggtaccagc agaaaccagg acagcctcct aagctgctca ttttctgggc atcgacccgg    240
gaatccgggg tccctgaccg attcagtggc agcgggtctg ggacagattt cactctcacc    300
atcagcagcc tgcaggctga agatgtggca gtttattact gtcagcaata ttctagtgct    360
cctcgaactt tcggcggagg gaccaacgta gaaatcagac gaactgtggc tgcaccatct    420
gtcttcatct tcccgccatc tgatgagcag ttgaaatctg gaactgcctc tgttgtgtgc    480
ctgctgaata acttctatcc cagagaggcc aaagtacagt ggaaggtgga taacgccctc    540
caatcgggta actcccagga gagtgtcaca gagcaggaca gcaaggacag cacctacagc    600
ctcagcagca ccctgacgct gagcaaagca gactacgaga aacacaaagt ctacgcctgc    660
gaagtcaccc atcagggcct gagctcgccc gtcacaaaga gcttcaacag gggagagtgt    720
tag                                                                  723
```

<210> SEQ ID NO 184
<211> LENGTH: 240
<212> TYPE: PRT
<213> ORGANISM: Homo sapiens

<400> SEQUENCE: 184

```
Met Val Leu Gln Thr Gln Val Phe Ile Ser Leu Leu Leu Trp Ile Ser
 1               5                  10                  15

Gly Ala Tyr Gly Asp Ile Val Met Thr Gln Ser Pro Asp Ser Leu Ala
                20                  25                  30

Val Ser Leu Gly Glu Arg Ala Thr Ile Asn Cys Lys Ser Ser Gln Ser
            35                  40                  45

Val Leu Lys Ser Ser Asn Asn Lys Asn Tyr Leu Ala Trp Tyr Gln Gln
        50                  55                  60

Lys Pro Gly Gln Pro Pro Lys Leu Leu Ile Phe Trp Ala Ser Thr Arg
 65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
               100                 105                 110

Tyr Cys Gln Gln Tyr Ser Ser Ala Pro Arg Thr Phe Gly Gly Gly Thr
           115                 120                 125

Asn Val Glu Ile Arg Arg Thr Val Ala Ala Pro Ser Val Phe Ile Phe
       130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
               165                 170                 175

Asp Asn Ala Leu Gln Ser Gly Asn Ser Gln Glu Ser Val Thr Glu Gln
           180                 185                 190

Asp Ser Lys Asp Ser Thr Tyr Ser Leu Ser Ser Thr Leu Thr Leu Ser
       195                 200                 205

Lys Ala Asp Tyr Glu Lys His Lys Val Tyr Ala Cys Glu Val Thr His
   210                 215                 220

Gln Gly Leu Ser Ser Pro Val Thr Lys Ser Phe Asn Arg Gly Glu Cys
225                 230                 235                 240
```

```
<210> SEQ ID NO 185
<211> LENGTH: 25
<212> TYPE: PRT
<213> ORGANISM: Homo sapiens

<400> SEQUENCE: 185

Gln Val His Leu Gln Glu Ser Gly Pro Gly Leu Val Lys Pro Ser Gly
1               5                   10                  15

Thr Leu Ser Leu Thr Cys Ala Val Ser
            20                  25

<210> SEQ ID NO 186
<211> LENGTH: 11
<212> TYPE: PRT
<213> ORGANISM: Homo sapiens

<400> SEQUENCE: 186

Gly Gly Ser Ile Ser Tyr Thr Asn Trp Trp Ser
1               5                   10

<210> SEQ ID NO 187
<211> LENGTH: 14
<212> TYPE: PRT
<213> ORGANISM: Homo sapiens

<400> SEQUENCE: 187

Trp Val Arg Leu Pro Pro Gly Lys Gly Leu Glu Trp Ile Gly
1               5                   10

<210> SEQ ID NO 188
<211> LENGTH: 9
<212> TYPE: PRT
<213> ORGANISM: Homo sapiens

<400> SEQUENCE: 188

Glu Ile Tyr His Ser Arg Ser Thr Asn
1               5

<210> SEQ ID NO 189
<211> LENGTH: 39
<212> TYPE: PRT
<213> ORGANISM: Homo sapiens

<400> SEQUENCE: 189

Tyr Asn Pro Ser Leu Lys Ser Arg Val Thr Met Ser Ile Asp Lys Ser
1               5                   10                  15

Lys Asn Leu Phe Ser Leu Lys Leu Asn Ser Val Thr Ala Ala Asp Thr
            20                  25                  30

Ala Ile Tyr Tyr Cys Ala Lys
        35

<210> SEQ ID NO 190
<211> LENGTH: 13
<212> TYPE: PRT
<213> ORGANISM: Homo sapiens

<400> SEQUENCE: 190

Ala Ala Tyr Thr Arg Asp Gly Ile Gln Pro Phe Asp Asn
1               5                   10

<210> SEQ ID NO 191
<211> LENGTH: 11
<212> TYPE: PRT
<213> ORGANISM: Homo sapiens
```

```
<400> SEQUENCE: 191

Trp Gly Gln Gly Thr Leu Val Thr Val Ser Ser
1               5                  10

<210> SEQ ID NO 192
<211> LENGTH: 23
<212> TYPE: PRT
<213> ORGANISM: Homo sapiens

<400> SEQUENCE: 192

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 193
<211> LENGTH: 17
<212> TYPE: PRT
<213> ORGANISM: Homo sapiens

<400> SEQUENCE: 193

Lys Ser Ser Gln Ser Val Leu Lys Ser Ser Asn Asn Lys Asn Tyr Leu
1               5                   10                  15

Ala

<210> SEQ ID NO 194
<211> LENGTH: 15
<212> TYPE: PRT
<213> ORGANISM: Homo sapiens

<400> SEQUENCE: 194

Trp Tyr Gln Gln Lys Pro Gly Gln Pro Pro Lys Leu Leu Ile Phe
1               5                   10                  15

<210> SEQ ID NO 195
<211> LENGTH: 7
<212> TYPE: PRT
<213> ORGANISM: Homo sapiens

<400> SEQUENCE: 195

Trp Ala Ser Thr Arg Glu Ser
1               5

<210> SEQ ID NO 196
<211> LENGTH: 32
<212> TYPE: PRT
<213> ORGANISM: Homo sapiens

<400> SEQUENCE: 196

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 197
<211> LENGTH: 9
<212> TYPE: PRT
<213> ORGANISM: Homo sapiens

<400> SEQUENCE: 197

Gln Gln Tyr Ser Ser Ala Pro Arg Thr
1               5
```

<210> SEQ ID NO 198
<211> LENGTH: 10
<212> TYPE: PRT
<213> ORGANISM: Homo sapiens

<400> SEQUENCE: 198

Phe Gly Gly Gly Thr Asn Val Glu Ile Arg
1               5                   10

<210> SEQ ID NO 199
<211> LENGTH: 24
<212> TYPE: PRT
<213> ORGANISM: Clostridium difficile

<400> SEQUENCE: 199

Ser Gly Ser Gly His Leu Gly Phe Lys Ile Ile Asp Asn Lys Thr Tyr
1               5                   10                  15

Tyr Tyr Asp Glu Asp Ser Lys Leu
            20

<210> SEQ ID NO 200
<211> LENGTH: 24
<212> TYPE: PRT
<213> ORGANISM: Clostridium difficile

<400> SEQUENCE: 200

Ser Gly Ser Gly Val Thr Gly Trp Gln Thr Ile Asn Gly Lys Lys Tyr
1               5                   10                  15

Tyr Phe Asp Ile Asn Thr Gly Ala
            20

<210> SEQ ID NO 201
<211> LENGTH: 24
<212> TYPE: PRT
<213> ORGANISM: Clostridium difficile

<400> SEQUENCE: 201

Ser Gly Ser Gly Leu Thr Ser Tyr Lys Ile Ile Asn Gly Lys His Phe
1               5                   10                  15

Tyr Phe Asn Asn Asp Gly Val Met
            20

<210> SEQ ID NO 202
<211> LENGTH: 24
<212> TYPE: PRT
<213> ORGANISM: Clostridium difficile

<400> SEQUENCE: 202

Ser Gly Ser Gly Gln Ser Lys Phe Leu Thr Leu Asn Gly Lys Lys Tyr
1               5                   10                  15

Tyr Phe Asp Asn Asn Ser Lys Ala
            20

<210> SEQ ID NO 203
<211> LENGTH: 24
<212> TYPE: PRT
<213> ORGANISM: Clostridium difficile

<400> SEQUENCE: 203

Ser Gly Ser Gly Val Thr Gly Trp Arg Ile Ile Asn Asn Glu Lys Tyr
1               5                   10                  15

```
Tyr Phe Asn Pro Asn Asn Ala Ile
            20
```

<210> SEQ ID NO 204
<211> LENGTH: 24
<212> TYPE: PRT
<213> ORGANISM: Clostridium difficile

<400> SEQUENCE: 204

```
Ser Gly Ser Gly Ala Val Gly Leu Gln Val Ile Asp Asn Asn Lys Tyr
1               5                   10                  15

Tyr Phe Asn Pro Asp Thr Ala Ile
            20
```

<210> SEQ ID NO 205
<211> LENGTH: 24
<212> TYPE: PRT
<213> ORGANISM: Clostridium difficile

<400> SEQUENCE: 205

```
Ser Gly Ser Gly Ser Lys Gly Trp Gln Thr Val Asn Gly Ser Arg Tyr
1               5                   10                  15

Tyr Phe Asp Thr Asp Thr Ala Ile
            20
```

<210> SEQ ID NO 206
<211> LENGTH: 24
<212> TYPE: PRT
<213> ORGANISM: Clostridium difficile

<400> SEQUENCE: 206

```
Ser Gly Ser Gly Phe Asn Gly Tyr Lys Thr Ile Asp Gly Lys His Phe
1               5                   10                  15

Tyr Phe Asp Ser Asp Cys Val Val
            20
```

<210> SEQ ID NO 207
<211> LENGTH: 24
<212> TYPE: PRT
<213> ORGANISM: Clostridium difficile

<400> SEQUENCE: 207

```
Ser Gly Ser Gly Val Thr Gly Leu Gln Thr Ile Asp Ser Lys Lys Tyr
1               5                   10                  15

Tyr Phe Asn Thr Asn Thr Ala Glu
            20
```

<210> SEQ ID NO 208
<211> LENGTH: 24
<212> TYPE: PRT
<213> ORGANISM: Clostridium difficile

<400> SEQUENCE: 208

```
Ser Gly Ser Gly Ala Thr Gly Trp Gln Thr Ile Asp Gly Lys Lys Tyr
1               5                   10                  15

Tyr Phe Asn Thr Asn Thr Ala Glu
            20
```

<210> SEQ ID NO 209
<211> LENGTH: 24
<212> TYPE: PRT
<213> ORGANISM: Clostridium difficile -continued

```
<400> SEQUENCE: 209

Ser Gly Ser Gly Ala Thr Gly Trp Gln Thr Ile Asp Gly Lys Lys Tyr
1               5                   10                  15

Tyr Phe Asn Thr Asn Thr Ala Ile
            20

<210> SEQ ID NO 210
<211> LENGTH: 24
<212> TYPE: PRT
<213> ORGANISM: Clostridium difficile

<400> SEQUENCE: 210

Ser Gly Ser Gly Ser Thr Gly Tyr Thr Ile Ile Asn Gly Lys His Phe
1               5                   10                  15

Tyr Phe Asn Thr Asp Gly Ile Met
            20

<210> SEQ ID NO 211
<211> LENGTH: 24
<212> TYPE: PRT
<213> ORGANISM: Clostridium difficile

<400> SEQUENCE: 211

Ser Gly Ser Gly Gln Asn Glu Phe Leu Thr Leu Asn Gly Lys Lys Tyr
1               5                   10                  15

Tyr Phe Gly Ser Asp Ser Lys Ala
            20

<210> SEQ ID NO 212
<211> LENGTH: 24
<212> TYPE: PRT
<213> ORGANISM: Clostridium difficile

<400> SEQUENCE: 212

Ser Gly Ser Gly Val Thr Gly Trp Arg Ile Ile Asn Asn Lys Lys Tyr
1               5                   10                  15

Tyr Phe Asn Pro Asn Asn Ala Ile
            20

<210> SEQ ID NO 213
<211> LENGTH: 24
<212> TYPE: PRT
<213> ORGANISM: Clostridium difficile

<400> SEQUENCE: 213

Ser Gly Ser Gly Ala Ile His Leu Cys Thr Ile Asn Asn Asp Lys Tyr
1               5                   10                  15

Tyr Phe Ser Tyr Asp Gly Ile Leu
            20

<210> SEQ ID NO 214
<211> LENGTH: 24
<212> TYPE: PRT
<213> ORGANISM: Clostridium difficile

<400> SEQUENCE: 214

Ser Gly Ser Gly Gln Asn Gly Tyr Ile Thr Ile Glu Arg Asn Asn Phe
1               5                   10                  15

Tyr Phe Asp Ala Asn Asn Glu Ser
            20
```

```
<210> SEQ ID NO 215
<211> LENGTH: 24
<212> TYPE: PRT
<213> ORGANISM: Clostridium difficile

<400> SEQUENCE: 215

Ser Gly Ser Gly Gln Asn Lys Phe Leu Thr Leu Asn Gly Lys Lys Tyr
1               5                   10                  15

Tyr Phe Asp Asn Asp Ser Lys Ala
            20

<210> SEQ ID NO 216
<211> LENGTH: 24
<212> TYPE: PRT
<213> ORGANISM: Clostridium difficile

<400> SEQUENCE: 216

Ser Gly Ser Gly Val Thr Gly Trp Gln Thr Ile Asp Gly Lys Lys Tyr
1               5                   10                  15

Tyr Phe Asn Leu Asn Thr Ala Glu
            20

<210> SEQ ID NO 217
<211> LENGTH: 24
<212> TYPE: PRT
<213> ORGANISM: Clostridium difficile

<400> SEQUENCE: 217

Ser Gly Ser Gly Ala Thr Gly Trp Gln Thr Ile Asp Gly Lys Lys Tyr
1               5                   10                  15

Tyr Phe Asn Leu Asn Thr Ala Glu
            20

<210> SEQ ID NO 218
<211> LENGTH: 24
<212> TYPE: PRT
<213> ORGANISM: Clostridium difficile

<400> SEQUENCE: 218

Ser Gly Ser Gly Ala Thr Gly Trp Gln Thr Ile Asp Gly Lys Lys Tyr
1               5                   10                  15

Tyr Phe Asn Thr Asn Thr Phe Ile
            20

<210> SEQ ID NO 219
<211> LENGTH: 24
<212> TYPE: PRT
<213> ORGANISM: Clostridium difficile

<400> SEQUENCE: 219

Ser Gly Ser Gly Ser Thr Gly Tyr Thr Ser Ile Asn Gly Lys His Phe
1               5                   10                  15

Tyr Phe Asn Thr Asp Gly Ile Met
            20

<210> SEQ ID NO 220
<211> LENGTH: 24
<212> TYPE: PRT
<213> ORGANISM: Clostridium difficile

<400> SEQUENCE: 220

Ser Gly Ser Gly Gln Asn Lys Phe Leu Thr Leu Asn Gly Lys Lys Tyr
1               5                   10                  15
```

Tyr Phe Gly Ser Asp Ser Lys Ala
            20

<210> SEQ ID NO 221
<211> LENGTH: 24
<212> TYPE: PRT
<213> ORGANISM: Clostridium difficile

<400> SEQUENCE: 221

Ser Gly Ser Gly Val Thr Gly Leu Arg Thr Ile Asp Gly Lys Lys Tyr
1               5                   10                  15

Tyr Phe Asn Thr Asn Thr Ala Val
            20

<210> SEQ ID NO 222
<211> LENGTH: 24
<212> TYPE: PRT
<213> ORGANISM: Clostridium difficile

<400> SEQUENCE: 222

Ser Gly Ser Gly Val Thr Gly Trp Gln Thr Ile Asn Gly Lys Lys Tyr
1               5                   10                  15

Tyr Phe Asn Thr Asn Thr Ser Ile
            20

<210> SEQ ID NO 223
<211> LENGTH: 24
<212> TYPE: PRT
<213> ORGANISM: Clostridium difficile

<400> SEQUENCE: 223

Ser Gly Ser Gly Ser Thr Gly Tyr Thr Ile Ile Ser Gly Lys His Phe
1               5                   10                  15

Tyr Phe Asn Thr Asp Gly Ile Met
            20

<210> SEQ ID NO 224
<211> LENGTH: 24
<212> TYPE: PRT
<213> ORGANISM: Clostridium difficile

<400> SEQUENCE: 224

Ser Gly Ser Gly Gln Asn Arg Phe Leu Tyr Leu His Asp Asn Ile Tyr
1               5                   10                  15

Tyr Phe Gly Asn Asn Ser Lys Ala
            20

<210> SEQ ID NO 225
<211> LENGTH: 24
<212> TYPE: PRT
<213> ORGANISM: Clostridium difficile

<400> SEQUENCE: 225

Ser Gly Ser Gly Ala Thr Gly Trp Val Thr Ile Asp Gly Asn Arg Tyr
1               5                   10                  15

Tyr Phe Glu Pro Asn Thr Ala Met
            20

<210> SEQ ID NO 226
<211> LENGTH: 24
<212> TYPE: PRT
<213> ORGANISM: Clostridium difficile

<400> SEQUENCE: 226

Ser Gly Ser Gly Ala Asn Gly Tyr Lys Thr Ile Asp Asn Lys Asn Phe
1               5                   10                  15

Tyr Phe Arg Asn Gly Leu Pro Gln
            20

<210> SEQ ID NO 227
<211> LENGTH: 24
<212> TYPE: PRT
<213> ORGANISM: Clostridium difficile

<400> SEQUENCE: 227

Ser Gly Ser Gly Gln Asn Arg Phe Leu His Leu Leu Gly Lys Ile Tyr
1               5                   10                  15

Tyr Phe Gly Asn Asn Ser Lys Ala
            20

<210> SEQ ID NO 228
<211> LENGTH: 24
<212> TYPE: PRT
<213> ORGANISM: Clostridium difficile

<400> SEQUENCE: 228

Ser Gly Ser Gly Val Thr Gly Trp Gln Thr Ile Asn Gly Lys Val Tyr
1               5                   10                  15

Tyr Phe Met Pro Asp Thr Ala Met
            20

<210> SEQ ID NO 229
<211> LENGTH: 24
<212> TYPE: PRT
<213> ORGANISM: Clostridium difficile

<400> SEQUENCE: 229

Ser Gly Ser Gly Ala Gly Gly Leu Phe Glu Ile Asp Gly Val Ile Tyr
1               5                   10                  15

Phe Phe Gly Val Asp Gly Val Lys
            20

<210> SEQ ID NO 230
<211> LENGTH: 2710
<212> TYPE: PRT
<213> ORGANISM: Clostridium difficile

<400> SEQUENCE: 230

Met Ser Leu Ile Ser Lys Glu Glu Leu Ile Lys Leu Ala Tyr Ser Ile
1               5                   10                  15

Arg Pro Arg Glu Asn Glu Tyr Lys Thr Ile Leu Thr Asn Leu Asp Glu
            20                  25                  30

Tyr Asn Lys Leu Thr Thr Asn Asn Asn Glu Asn Lys Tyr Leu Gln Leu
        35                  40                  45

Lys Lys Leu Asn Glu Ser Ile Asp Val Phe Met Asn Lys Tyr Lys Thr
    50                  55                  60

Ser Ser Arg Asn Arg Ala Leu Ser Asn Leu Lys Lys Asp Ile Leu Lys
65                  70                  75                  80

Glu Val Ile Leu Ile Lys Asn Ser Asn Thr Ser Pro Val Glu Lys Asn
                85                  90                  95

Leu His Phe Val Trp Ile Gly Gly Glu Val Ser Asp Ile Ala Leu Glu
            100                 105                 110

```
Tyr Ile Lys Gln Trp Ala Asp Ile Asn Ala Glu Tyr Asn Ile Lys Leu
        115                 120                 125

Trp Tyr Asp Ser Glu Ala Phe Leu Val Asn Thr Leu Lys Lys Ala Ile
        130                 135                 140

Val Glu Ser Ser Thr Thr Glu Ala Leu Gln Leu Leu Glu Glu Glu Ile
145                 150                 155                 160

Gln Asn Pro Gln Phe Asp Asn Met Lys Phe Tyr Lys Lys Arg Met Glu
        165                 170                 175

Phe Ile Tyr Asp Arg Gln Lys Arg Phe Ile Asn Tyr Tyr Lys Ser Gln
        180                 185                 190

Ile Asn Lys Pro Thr Val Pro Thr Ile Asp Asp Ile Ile Lys Ser His
        195                 200                 205

Leu Val Ser Glu Tyr Asn Arg Asp Glu Thr Val Leu Glu Ser Tyr Arg
        210                 215                 220

Thr Asn Ser Leu Arg Lys Ile Asn Ser Asn His Gly Ile Asp Ile Arg
225                 230                 235                 240

Ala Asn Ser Leu Phe Thr Glu Gln Glu Leu Leu Asn Ile Tyr Ser Gln
        245                 250                 255

Glu Leu Leu Asn Arg Gly Asn Leu Ala Ala Ser Asp Ile Val Arg
        260                 265                 270

Leu Leu Ala Leu Lys Asn Phe Gly Gly Val Tyr Leu Asp Val Asp Met
        275                 280                 285

Leu Pro Gly Ile His Ser Asp Leu Phe Lys Thr Ile Ser Arg Pro Ser
        290                 295                 300

Ser Ile Gly Leu Asp Arg Trp Glu Met Ile Lys Leu Glu Ala Ile Met
305                 310                 315                 320

Lys Tyr Lys Lys Tyr Ile Asn Asn Tyr Thr Ser Glu Asn Phe Asp Lys
        325                 330                 335

Leu Asp Gln Gln Leu Lys Asp Asn Phe Lys Leu Ile Ile Glu Ser Lys
        340                 345                 350

Ser Glu Lys Ser Glu Ile Phe Ser Lys Leu Glu Asn Leu Asn Val Ser
        355                 360                 365

Asp Leu Glu Ile Lys Ile Ala Phe Ala Leu Gly Ser Val Ile Asn Gln
        370                 375                 380

Ala Leu Ile Ser Lys Gln Gly Ser Tyr Leu Thr Asn Leu Val Ile Glu
385                 390                 395                 400

Gln Val Lys Asn Arg Tyr Gln Phe Leu Asn Gln His Leu Asn Pro Ala
        405                 410                 415

Ile Glu Ser Asp Asn Asn Phe Thr Asp Thr Thr Lys Ile Phe His Asp
        420                 425                 430

Ser Leu Phe Asn Ser Ala Thr Ala Glu Asn Ser Met Phe Leu Thr Lys
        435                 440                 445

Ile Ala Pro Tyr Leu Gln Val Gly Phe Met Pro Glu Ala Arg Ser Thr
        450                 455                 460

Ile Ser Leu Ser Gly Pro Gly Ala Tyr Ala Ser Ala Tyr Tyr Asp Phe
465                 470                 475                 480

Ile Asn Leu Gln Glu Asn Thr Ile Glu Lys Thr Leu Lys Ala Ser Asp
        485                 490                 495

Leu Ile Glu Phe Lys Phe Pro Glu Asn Asn Leu Ser Gln Leu Thr Glu
        500                 505                 510

Gln Glu Ile Asn Ser Leu Trp Ser Phe Asp Gln Ala Ser Ala Lys Tyr
        515                 520                 525
```

```
Gln Phe Glu Lys Tyr Val Arg Asp Tyr Thr Gly Gly Ser Leu Ser Glu
    530                 535                 540

Asp Asn Gly Val Asp Phe Asn Lys Asn Thr Ala Leu Asp Lys Asn Tyr
545                 550                 555                 560

Leu Leu Asn Asn Lys Ile Pro Ser Asn Val Glu Glu Ala Gly Ser
                565                 570                 575

Lys Asn Tyr Val His Tyr Ile Ile Gln Leu Gln Gly Asp Asp Ile Ser
            580                 585                 590

Tyr Glu Ala Thr Cys Asn Leu Phe Ser Lys Asn Pro Lys Asn Ser Ile
        595                 600                 605

Ile Ile Gln Arg Asn Met Asn Glu Ser Ala Lys Ser Tyr Phe Leu Ser
    610                 615                 620

Asp Asp Gly Glu Ser Ile Leu Glu Leu Asn Lys Tyr Arg Ile Pro Glu
625                 630                 635                 640

Arg Leu Lys Asn Lys Glu Lys Val Lys Val Thr Phe Ile Gly His Gly
                645                 650                 655

Lys Asp Glu Phe Asn Thr Ser Glu Phe Ala Arg Leu Ser Val Asp Ser
            660                 665                 670

Leu Ser Asn Glu Ile Ser Ser Phe Leu Asp Thr Ile Lys Leu Asp Ile
        675                 680                 685

Ser Pro Lys Asn Val Glu Val Asn Leu Leu Gly Cys Asn Met Phe Ser
    690                 695                 700

Tyr Asp Phe Asn Val Glu Glu Thr Tyr Pro Gly Lys Leu Leu Leu Ser
705                 710                 715                 720

Ile Met Asp Lys Ile Thr Ser Thr Leu Pro Asp Val Asn Lys Asn Ser
                725                 730                 735

Ile Thr Ile Gly Ala Asn Gln Tyr Glu Val Arg Ile Asn Ser Glu Gly
            740                 745                 750

Arg Lys Glu Leu Leu Ala His Ser Gly Lys Trp Ile Asn Lys Glu Glu
        755                 760                 765

Ala Ile Met Ser Asp Leu Ser Ser Lys Glu Tyr Ile Phe Phe Asp Ser
    770                 775                 780

Ile Asp Asn Lys Leu Lys Ala Lys Ser Lys Asn Ile Pro Gly Leu Ala
785                 790                 795                 800

Ser Ile Ser Glu Asp Ile Lys Thr Leu Leu Leu Asp Ala Ser Val Ser
                805                 810                 815

Pro Asp Thr Lys Phe Ile Leu Asn Asn Leu Lys Leu Asn Ile Glu Ser
            820                 825                 830

Ser Ile Gly Asp Tyr Ile Tyr Tyr Glu Lys Leu Glu Pro Val Lys Asn
        835                 840                 845

Ile Ile His Asn Ser Ile Asp Asp Leu Ile Asp Glu Phe Asn Leu Leu
    850                 855                 860

Glu Asn Val Ser Asp Glu Leu Tyr Glu Leu Lys Lys Leu Asn Asn Leu
865                 870                 875                 880

Asp Glu Lys Tyr Leu Ile Ser Phe Glu Asp Ile Ser Lys Asn Asn Ser
                885                 890                 895

Thr Tyr Ser Val Arg Phe Ile Asn Lys Ser Asn Gly Glu Ser Val Tyr
            900                 905                 910

Val Glu Thr Glu Lys Glu Ile Phe Ser Lys Tyr Ser Glu His Ile Thr
        915                 920                 925

Lys Glu Ile Ser Thr Ile Lys Asn Ser Ile Ile Thr Asp Val Asn Gly
    930                 935                 940

Asn Leu Leu Asp Asn Ile Gln Leu Asp His Thr Ser Gln Val Asn Thr
```

```
                945                 950                 955                 960
Leu Asn Ala Ala Phe Phe Ile Gln Ser Leu Ile Asp Tyr Ser Ser Asn
                965                 970                 975
Lys Asp Val Leu Asn Asp Leu Ser Thr Ser Val Lys Val Gln Leu Tyr
                980                 985                 990
Ala Gln Leu Phe Ser Thr Gly Leu Asn Thr Ile Tyr Asp Ser Ile Gln
                995                1000                1005
Leu Val Asn Leu Ile Ser Asn Ala Val Asn Asp Thr Ile Asn Val Leu
               1010                1015                1020
Pro Thr Ile Thr Glu Gly Ile Pro Ile Val Ser Thr Ile Leu Asp Gly
1025                1030                1035                1040
Ile Asn Leu Gly Ala Ala Ile Lys Glu Leu Leu Asp Glu His Asp Pro
               1045                1050                1055
Leu Leu Lys Lys Glu Leu Glu Ala Lys Val Gly Val Leu Ala Ile Asn
               1060                1065                1070
Met Ser Leu Ser Ile Ala Ala Thr Val Ala Ser Ile Val Gly Ile Gly
               1075                1080                1085
Ala Glu Val Thr Ile Phe Leu Leu Pro Ile Ala Gly Ile Ser Ala Gly
               1090                1095                1100
Ile Pro Ser Leu Val Asn Asn Glu Leu Ile Leu His Asp Lys Ala Thr
1105                1110                1115                1120
Ser Val Val Asn Tyr Phe Asn His Leu Ser Glu Ser Lys Lys Tyr Gly
               1125                1130                1135
Pro Leu Lys Thr Glu Asp Asp Lys Ile Leu Val Pro Ile Asp Asp Leu
               1140                1145                1150
Val Ile Ser Glu Ile Asp Phe Asn Asn Asn Ser Ile Lys Leu Gly Thr
               1155                1160                1165
Cys Asn Ile Leu Ala Met Glu Gly Gly Ser Gly His Thr Val Thr Gly
               1170                1175                1180
Asn Ile Asp His Phe Phe Ser Ser Pro Ser Ile Ser Ser His Ile Pro
1185                1190                1195                1200
Ser Leu Ser Ile Tyr Ser Ala Ile Gly Ile Glu Thr Glu Asn Leu Asp
               1205                1210                1215
Phe Ser Lys Lys Ile Met Met Leu Pro Asn Ala Pro Ser Arg Val Phe
               1220                1225                1230
Trp Trp Glu Thr Gly Ala Val Pro Gly Leu Arg Ser Leu Glu Asn Asp
               1235                1240                1245
Gly Thr Arg Leu Leu Asp Ser Ile Arg Asp Leu Tyr Pro Gly Lys Phe
               1250                1255                1260
Tyr Trp Arg Phe Tyr Ala Phe Phe Asp Tyr Ala Ile Thr Thr Leu Lys
1265                1270                1275                1280
Pro Val Tyr Glu Asp Thr Asn Ile Lys Ile Lys Leu Asp Lys Asp Thr
               1285                1290                1295
Arg Asn Phe Ile Met Pro Thr Ile Thr Thr Asn Glu Ile Arg Asn Lys
               1300                1305                1310
Leu Ser Tyr Ser Phe Asp Gly Ala Gly Gly Thr Tyr Ser Leu Leu Leu
               1315                1320                1325
Ser Ser Tyr Pro Ile Ser Thr Asn Ile Asn Leu Ser Lys Asp Asp Leu
               1330                1335                1340
Trp Ile Phe Asn Ile Asp Asn Glu Val Arg Glu Ile Ser Ile Glu Asn
1345                1350                1355                1360
Gly Thr Ile Lys Lys Gly Lys Leu Ile Lys Asp Val Leu Ser Lys Ile
               1365                1370                1375
```

```
Asp Ile Asn Lys Asn Lys Leu Ile Ile Gly Asn Gln Thr Ile Asp Phe
            1380                1385                1390

Ser Gly Asp Ile Asp Asn Lys Asp Arg Tyr Ile Phe Leu Thr Cys Glu
            1395                1400                1405

Leu Asp Asp Lys Ile Ser Leu Ile Ile Glu Ile Asn Leu Val Ala Lys
    1410                1415                1420

Ser Tyr Ser Leu Leu Leu Ser Gly Asp Lys Asn Tyr Leu Ile Ser Asn
1425                1430                1435                1440

Leu Ser Asn Thr Ile Glu Lys Ile Asn Thr Leu Gly Leu Asp Ser Lys
            1445                1450                1455

Asn Ile Ala Tyr Asn Tyr Thr Asp Glu Ser Asn Lys Tyr Phe Gly
            1460                1465                1470

Ala Ile Ser Lys Thr Ser Gln Lys Ser Ile Ile His Tyr Lys Lys Asp
            1475                1480                1485

Ser Lys Asn Ile Leu Glu Phe Tyr Asn Asp Ser Thr Leu Glu Phe Asn
    1490                1495                1500

Ser Lys Asp Phe Ile Ala Glu Asp Ile Asn Val Phe Met Lys Asp Asp
1505                1510                1515                1520

Ile Asn Thr Ile Thr Gly Lys Tyr Tyr Val Asp Asn Asn Thr Asp Lys
            1525                1530                1535

Ser Ile Asp Phe Ser Ile Ser Leu Val Ser Lys Asn Gln Val Lys Val
            1540                1545                1550

Asn Gly Leu Tyr Leu Asn Glu Ser Val Tyr Ser Ser Tyr Leu Asp Phe
            1555                1560                1565

Val Lys Asn Ser Asp Gly His His Asn Thr Ser Asn Phe Met Asn Leu
            1570                1575                1580

Phe Leu Asp Asn Ile Ser Phe Trp Lys Leu Phe Gly Phe Glu Asn Ile
1585                1590                1595                1600

Asn Phe Val Ile Asp Lys Tyr Phe Thr Leu Val Gly Lys Thr Asn Leu
            1605                1610                1615

Gly Tyr Val Glu Phe Ile Cys Asp Asn Asn Lys Asn Ile Asp Ile Tyr
            1620                1625                1630

Phe Gly Glu Trp Lys Thr Ser Ser Ser Lys Ser Thr Ile Phe Ser Gly
            1635                1640                1645

Asn Gly Arg Asn Val Val Val Glu Pro Ile Tyr Asn Pro Asp Thr Gly
            1650                1655                1660

Glu Asp Ile Ser Thr Ser Leu Asp Phe Ser Tyr Glu Pro Leu Tyr Gly
1665                1670                1675                1680

Ile Asp Arg Tyr Ile Asn Lys Val Leu Ile Ala Pro Asp Leu Tyr Thr
            1685                1690                1695

Ser Leu Ile Asn Ile Asn Thr Asn Tyr Tyr Ser Asn Glu Tyr Tyr Pro
            1700                1705                1710

Glu Ile Ile Val Leu Asn Pro Asn Thr Phe His Lys Lys Val Asn Ile
            1715                1720                1725

Asn Leu Asp Ser Ser Ser Phe Glu Tyr Lys Trp Ser Thr Glu Gly Ser
            1730                1735                1740

Asp Phe Ile Leu Val Arg Tyr Leu Glu Glu Ser Asn Lys Lys Ile Leu
1745                1750                1755                1760

Gln Lys Ile Arg Ile Lys Gly Ile Leu Ser Asn Thr Gln Ser Phe Asn
            1765                1770                1775

Lys Met Ser Ile Asp Phe Lys Asp Ile Lys Lys Leu Ser Leu Gly Tyr
            1780                1785                1790
```

-continued

Ile Met Ser Asn Phe Lys Ser Phe Asn Ser Glu Asn Glu Leu Asp Arg
        1795                1800                1805

Asp His Leu Gly Phe Lys Ile Ile Asp Asn Lys Thr Tyr Tyr Tyr Asp
        1810                1815                1820

Glu Asp Ser Lys Leu Val Lys Gly Leu Ile Asn Ile Asn Asn Ser Leu
1825                1830                1835                1840

Phe Tyr Phe Asp Pro Ile Glu Phe Asn Leu Val Thr Gly Trp Gln Thr
            1845                1850                1855

Ile Asn Gly Lys Lys Tyr Tyr Phe Asp Ile Asn Thr Gly Ala Ala Leu
        1860                1865                1870

Thr Ser Tyr Lys Ile Ile Asn Gly Lys His Phe Tyr Phe Asn Asn Asp
        1875                1880                1885

Gly Val Met Gln Leu Gly Val Phe Lys Gly Pro Asp Gly Phe Glu Tyr
        1890                1895                1900

Phe Ala Pro Ala Asn Thr Gln Asn Asn Asn Ile Glu Gly Gln Ala Ile
1905                1910                1915                1920

Val Tyr Gln Ser Lys Phe Leu Thr Leu Asn Gly Lys Lys Tyr Tyr Phe
                1925                1930                1935

Asp Asn Asn Ser Lys Ala Val Thr Gly Trp Arg Ile Ile Asn Asn Glu
            1940                1945                1950

Lys Tyr Tyr Phe Asn Pro Asn Asn Ala Ile Ala Ala Val Gly Leu Gln
        1955                1960                1965

Val Ile Asp Asn Asn Lys Tyr Tyr Phe Asn Pro Asp Thr Ala Ile Ile
        1970                1975                1980

Ser Lys Gly Trp Gln Thr Val Asn Gly Ser Arg Tyr Tyr Phe Asp Thr
1985                1990                1995                2000

Asp Thr Ala Ile Ala Phe Asn Gly Tyr Lys Thr Ile Asp Gly Lys His
            2005                2010                2015

Phe Tyr Phe Asp Ser Asp Cys Val Val Lys Ile Gly Val Phe Ser Thr
            2020                2025                2030

Ser Asn Gly Phe Glu Tyr Phe Ala Pro Ala Asn Thr Tyr Asn Asn Asn
        2035                2040                2045

Ile Glu Gly Gln Ala Ile Val Tyr Gln Ser Lys Phe Leu Thr Leu Asn
2050                2055                2060

Gly Lys Lys Tyr Tyr Phe Asp Asn Asn Ser Lys Ala Val Thr Gly Leu
2065                2070                2075                2080

Gln Thr Ile Asp Ser Lys Lys Tyr Tyr Phe Asn Thr Asn Thr Ala Glu
            2085                2090                2095

Ala Ala Thr Gly Trp Gln Thr Ile Asp Gly Lys Lys Tyr Tyr Phe Asn
        2100                2105                2110

Thr Asn Thr Ala Glu Ala Ala Thr Gly Trp Gln Thr Ile Asp Gly Lys
        2115                2120                2125

Lys Tyr Tyr Phe Asn Thr Asn Thr Ala Ile Ala Ser Thr Gly Tyr Thr
        2130                2135                2140

Ile Ile Asn Gly Lys His Phe Tyr Phe Asn Thr Asp Gly Ile Met Gln
2145                2150                2155                2160

Ile Gly Val Phe Lys Gly Pro Asn Gly Phe Glu Tyr Phe Ala Pro Ala
            2165                2170                2175

Asn Thr Asp Ala Asn Asn Ile Glu Gly Gln Ala Ile Leu Tyr Gln Asn
            2180                2185                2190

Glu Phe Leu Thr Leu Asn Gly Lys Lys Tyr Tyr Phe Gly Ser Asp Ser
        2195                2200                2205

Lys Ala Val Thr Gly Trp Arg Ile Ile Asn Asn Lys Lys Tyr Tyr Phe

```
               2210                2215                2220
Asn Pro Asn Asn Ala Ile Ala Ala Ile His Leu Cys Thr Ile Asn Asn
2225                2230                2235                2240
Asp Lys Tyr Tyr Phe Ser Tyr Asp Gly Ile Leu Gln Asn Gly Tyr Ile
                2245                2250                2255
Thr Ile Glu Arg Asn Asn Phe Tyr Phe Asp Ala Asn Asn Glu Ser Lys
                2260                2265                2270
Met Val Thr Gly Val Phe Lys Gly Pro Asn Gly Phe Glu Tyr Phe Ala
                2275                2280                2285
Pro Ala Asn Thr His Asn Asn Ile Glu Gly Gln Ala Ile Val Tyr
                2290                2295                2300
Gln Asn Lys Phe Leu Thr Leu Asn Gly Lys Lys Tyr Tyr Phe Asp Asn
2305                2310                2315                2320
Asp Ser Lys Ala Val Thr Gly Trp Gln Thr Ile Asp Gly Lys Lys Tyr
                2325                2330                2335
Tyr Phe Asn Leu Asn Thr Ala Glu Ala Ala Thr Gly Trp Gln Thr Ile
                2340                2345                2350
Asp Gly Lys Lys Tyr Tyr Phe Asn Leu Asn Thr Ala Glu Ala Ala Thr
                2355                2360                2365
Gly Trp Gln Thr Ile Asp Gly Lys Lys Tyr Tyr Phe Asn Thr Asn Thr
                2370                2375                2380
Phe Ile Ala Ser Thr Gly Tyr Thr Ser Ile Asn Gly Lys His Phe Tyr
2385                2390                2395                2400
Phe Asn Thr Asp Gly Ile Met Gln Ile Gly Val Phe Lys Gly Pro Asn
                2405                2410                2415
Gly Phe Glu Tyr Phe Ala Pro Ala Asn Thr Asp Ala Asn Asn Ile Glu
                2420                2425                2430
Gly Gln Ala Ile Leu Tyr Gln Asn Lys Phe Leu Thr Leu Asn Gly Lys
                2435                2440                2445
Lys Tyr Tyr Phe Gly Ser Asp Ser Lys Ala Val Thr Gly Leu Arg Thr
                2450                2455                2460
Ile Asp Gly Lys Lys Tyr Tyr Phe Asn Thr Asn Thr Ala Val Ala Val
2465                2470                2475                2480
Thr Gly Trp Gln Thr Ile Asn Gly Lys Lys Tyr Tyr Phe Asn Thr Asn
                2485                2490                2495
Thr Ser Ile Ala Ser Thr Gly Tyr Thr Ile Ile Ser Gly Lys His Phe
                2500                2505                2510
Tyr Phe Asn Thr Asp Gly Ile Met Gln Ile Gly Val Phe Lys Gly Pro
                2515                2520                2525
Asp Gly Phe Glu Tyr Phe Ala Pro Ala Asn Thr Asp Ala Asn Asn Ile
                2530                2535                2540
Glu Gly Gln Ala Ile Arg Tyr Gln Asn Arg Phe Leu Tyr Leu His Asp
2545                2550                2555                2560
Asn Ile Tyr Tyr Phe Gly Asn Asn Ser Lys Ala Ala Thr Gly Trp Val
                2565                2570                2575
Thr Ile Asp Gly Asn Arg Tyr Tyr Phe Glu Pro Asn Thr Ala Met Gly
                2580                2585                2590
Ala Asn Gly Tyr Lys Thr Ile Asp Asn Lys Asn Phe Tyr Phe Arg Asn
                2595                2600                2605
Gly Leu Pro Gln Ile Gly Val Phe Lys Gly Ser Asn Gly Phe Glu Tyr
                2610                2615                2620
Phe Ala Pro Ala Asn Thr Asp Ala Asn Asn Ile Glu Gly Gln Ala Ile
2625                2630                2635                2640
```

<210> SEQ ID NO 231
<211> LENGTH: 2366
<212> TYPE: PRT
<213> ORGANISM: Clostridium difficile

<400> SEQUENCE: 231

Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
            20                  25                  30

Glu Tyr His Asn Met Ser Glu Asn Thr Val Val Glu Lys Tyr Leu Lys
        35                  40                  45

Leu Lys Asp Ile Asn Ser Leu Thr Asp Ile Tyr Ile Asp Thr Tyr Lys
    50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
            180                 185                 190

Gln Arg Glu Glu Asn Pro Glu Leu Ile Ile Asp Asp Ile Val Lys Thr
        195                 200                 205

Tyr Leu Ser Asn Glu Tyr Ser Lys Glu Ile Asp Glu Leu Asn Thr Tyr
    210                 215                 220

Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
                245                 250                 255

Gln Glu Leu Val Glu Arg Trp Asn Leu Ala Ala Ala Ser Asp Ile Leu
            260                 265                 270

Arg Ile Ser Ala Leu Lys Glu Ile Gly Gly Met Tyr Leu Asp Val Asp
        275                 280                 285

Met Leu Pro Gly Ile Gln Pro Asp Leu Phe Glu Ser Ile Glu Lys Pro

```
              290                 295                 300
Ser Ser Val Thr Val Asp Phe Trp Glu Met Thr Lys Leu Glu Ala Ile
305                 310                 315                 320

Met Lys Tyr Lys Glu Tyr Ile Pro Glu Tyr Thr Ser Glu His Phe Asp
                325                 330                 335

Met Leu Asp Glu Val Gln Ser Ser Phe Glu Ser Val Leu Ala Ser
                340                 345                 350

Lys Ser Asp Lys Ser Glu Ile Phe Ser Ser Leu Gly Asp Met Glu Ala
                355                 360                 365

Ser Pro Leu Glu Val Lys Ile Ala Phe Asn Ser Lys Gly Ile Ile Asn
        370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Thr Phe Ile
                420                 425                 430

Asp Ser Ile Met Ala Glu Ala Asn Ala Asp Asn Gly Arg Phe Met Met
        435                 440                 445

Glu Leu Gly Lys Tyr Leu Arg Val Gly Phe Phe Pro Asp Val Lys Thr
450                 455                 460

Thr Ile Asn Leu Ser Gly Pro Glu Ala Tyr Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
                500                 505                 510

Glu Gln Glu Met Ala Ser Leu Trp Ser Phe Asp Asp Ala Arg Ala Lys
                515                 520                 525

Ala Gln Phe Glu Glu Tyr Lys Arg Asn Tyr Phe Glu Gly Ser Leu Gly
                530                 535                 540

Glu Asp Asp Asn Leu Asp Phe Ser Gln Asn Ile Val Val Asp Lys Glu
545                 550                 555                 560

Tyr Leu Leu Glu Lys Ile Ser Ser Leu Ala Arg Ser Ser Glu Arg Gly
                565                 570                 575

Tyr Ile His Tyr Ile Val Gln Leu Gln Gly Asp Lys Ile Ser Tyr Glu
                580                 585                 590

Ala Ala Cys Asn Leu Phe Ala Lys Thr Pro Tyr Asp Ser Val Leu Phe
        595                 600                 605

Gln Lys Asn Ile Glu Asp Ser Glu Ile Ala Tyr Tyr Tyr Asn Pro Gly
        610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
                645                 650                 655

Glu Phe Asn Thr Asp Ile Phe Ala Gly Phe Asp Val Asp Ser Leu Ser
                660                 665                 670

Thr Glu Ile Glu Ala Ala Ile Asp Leu Ala Lys Glu Asp Ile Ser Pro
                675                 680                 685

Lys Ser Ile Glu Ile Asn Leu Leu Gly Cys Asn Met Phe Ser Tyr Ser
        690                 695                 700

Ile Asn Val Glu Glu Thr Tyr Pro Gly Lys Leu Leu Leu Lys Val Lys
705                 710                 715                 720
```

```
Asp Lys Ile Ser Glu Leu Met Pro Ser Ile Ser Gln Asp Ser Ile Ile
            725                 730                 735

Val Ser Ala Asn Gln Tyr Glu Val Arg Ile Asn Ser Glu Gly Arg Arg
            740                 745                 750

Glu Leu Leu Asp His Ser Gly Glu Trp Ile Asn Lys Glu Ser Ile
            755                 760                 765

Ile Lys Asp Ile Ser Ser Lys Glu Tyr Ile Ser Phe Asn Pro Lys Glu
            770                 775                 780

Asn Lys Ile Thr Val Lys Ser Lys Asn Leu Pro Glu Leu Ser Thr Leu
785                 790                 795                 800

Leu Gln Glu Ile Arg Asn Asn Ser Asn Ser Asp Ile Glu Leu Glu
                    805                 810                 815

Glu Lys Val Met Leu Thr Glu Cys Glu Ile Asn Val Ile Ser Asn Ile
            820                 825                 830

Asp Thr Gln Ile Val Glu Glu Arg Ile Glu Glu Ala Lys Asn Leu Thr
            835                 840                 845

Ser Asp Ser Ile Asn Tyr Ile Lys Asp Glu Phe Lys Leu Ile Glu Ser
850                 855                 860

Ile Ser Asp Ala Leu Cys Asp Leu Lys Gln Gln Asn Glu Leu Glu Asp
865                 870                 875                 880

Ser His Phe Ile Ser Phe Glu Asp Ile Ser Glu Thr Asp Glu Gly Phe
                    885                 890                 895

Ser Ile Arg Phe Ile Asn Lys Glu Thr Gly Glu Ser Ile Phe Val Glu
                    900                 905                 910

Thr Glu Lys Thr Ile Phe Ser Glu Tyr Ala Asn His Ile Thr Glu Glu
            915                 920                 925

Ile Ser Lys Ile Lys Gly Thr Ile Phe Asp Thr Val Asn Gly Lys Leu
            930                 935                 940

Val Lys Lys Val Asn Leu Asp Thr Thr His Glu Val Asn Thr Leu Asn
945                 950                 955                 960

Ala Ala Phe Phe Ile Gln Ser Leu Ile Glu Tyr Asn Ser Ser Lys Glu
                    965                 970                 975

Ser Leu Ser Asn Leu Ser Val Ala Met Lys Val Gln Val Tyr Ala Gln
            980                 985                 990

Leu Phe Ser Thr Gly Leu Asn Thr Ile Thr Asp Ala Ala Lys Val Val
            995                 1000                1005

Glu Leu Val Ser Thr Ala Leu Asp Glu Thr Ile Asp Leu Leu Pro Thr
    1010                1015                1020

Leu Ser Glu Gly Leu Pro Ile Ile Ala Thr Ile Ile Asp Gly Val Ser
1025                1030                1035                1040

Leu Gly Ala Ala Ile Lys Glu Leu Ser Glu Thr Ser Asp Pro Leu Leu
                    1045                1050                1055

Arg Gln Glu Ile Glu Ala Lys Ile Gly Ile Met Ala Val Asn Leu Thr
                    1060                1065                1070

Thr Ala Thr Thr Ala Ile Ile Thr Ser Ser Leu Gly Ile Ala Ser Gly
            1075                1080                1085

Phe Ser Ile Leu Leu Val Pro Leu Ala Gly Ile Ser Ala Gly Ile Pro
            1090                1095                1100

Ser Leu Val Asn Asn Glu Leu Val Leu Arg Asp Lys Ala Thr Lys Val
1105                1110                1115                1120

Val Asp Tyr Phe Lys His Val Ser Leu Val Glu Thr Glu Gly Val Phe
            1125                1130                1135
```

-continued

```
Thr Leu Leu Asp Asp Lys Ile Met Met Pro Gln Asp Leu Val Ile
        1140                1145                1150

Ser Glu Ile Asp Phe Asn Asn Asn Ser Ile Val Leu Gly Lys Cys Glu
    1155                1160                1165

Ile Trp Arg Met Glu Gly Gly Ser Gly His Thr Val Thr Asp Asp Ile
    1170                1175                1180

Asp His Phe Phe Ser Ala Pro Ser Ile Thr Tyr Arg Glu Pro His Leu
1185                1190                1195                1200

Ser Ile Tyr Asp Val Leu Glu Val Gln Lys Glu Leu Asp Leu Ser
        1205                1210                1215

Lys Asp Leu Met Val Leu Pro Asn Ala Pro Asn Arg Val Phe Ala Trp
        1220                1225                1230

Glu Thr Gly Trp Thr Pro Gly Leu Arg Ser Leu Glu Asn Asp Gly Thr
        1235                1240                1245

Lys Leu Leu Asp Arg Ile Arg Asp Asn Tyr Glu Gly Glu Phe Tyr Trp
        1250                1255                1260

Arg Tyr Phe Ala Phe Ile Ala Asp Ala Leu Ile Thr Thr Leu Lys Pro
1265                1270                1275                1280

Arg Tyr Glu Asp Thr Asn Ile Arg Ile Asn Leu Asp Ser Asn Thr Arg
        1285                1290                1295

Ser Phe Ile Val Pro Ile Ile Thr Thr Glu Tyr Ile Arg Glu Lys Leu
        1300                1305                1310

Ser Tyr Ser Phe Tyr Gly Ser Gly Gly Thr Tyr Ala Leu Ser Leu Ser
        1315                1320                1325

Gln Tyr Asn Met Gly Ile Asn Ile Glu Leu Ser Glu Ser Asp Val Trp
        1330                1335                1340

Ile Ile Asp Val Asp Asn Val Val Arg Asp Val Thr Ile Glu Ser Asp
1345                1350                1355                1360

Lys Ile Lys Lys Gly Asp Leu Ile Glu Gly Ile Leu Ser Thr Leu Ser
        1365                1370                1375

Ile Glu Glu Asn Lys Ile Ile Leu Asn Ser His Glu Ile Asn Phe Ser
        1380                1385                1390

Gly Glu Val Asn Gly Ser Asn Gly Phe Val Ser Leu Thr Phe Ser Ile
        1395                1400                1405

Leu Glu Gly Ile Asn Ala Ile Ile Glu Val Asp Leu Leu Ser Lys Ser
        1410                1415                1420

Tyr Lys Leu Leu Ile Ser Gly Glu Leu Lys Ile Leu Met Leu Asn Ser
1425                1430                1435                1440

Asn His Ile Gln Gln Lys Ile Asp Tyr Ile Gly Phe Asn Ser Glu Leu
        1445                1450                1455

Gln Lys Asn Ile Pro Tyr Ser Phe Val Asp Ser Glu Gly Lys Glu Asn
        1460                1465                1470

Gly Phe Ile Asn Gly Ser Thr Lys Glu Gly Leu Phe Val Ser Glu Leu
        1475                1480                1485

Pro Asp Val Val Leu Ile Ser Lys Val Tyr Met Asp Asp Ser Lys Pro
        1490                1495                1500

Ser Phe Gly Tyr Tyr Ser Asn Asn Leu Lys Asp Val Lys Val Ile Thr
1505                1510                1515                1520

Lys Asp Asn Val Asn Ile Leu Thr Gly Tyr Tyr Leu Lys Asp Asp Ile
        1525                1530                1535

Lys Ile Ser Leu Ser Leu Thr Leu Gln Asp Glu Lys Thr Ile Lys Leu
        1540                1545                1550

Asn Ser Val His Leu Asp Glu Ser Gly Val Ala Glu Ile Leu Lys Phe
```

-continued

```
            1555                1560                1565

Met Asn Arg Lys Gly Asn Thr Asn Thr Ser Asp Ser Leu Met Ser Phe
        1570                1575                1580

Leu Glu Ser Met Asn Ile Lys Ser Ile Phe Val Asn Phe Leu Gln Ser
1585                1590                1595                1600

Asn Ile Lys Phe Ile Leu Asp Ala Asn Phe Ile Ile Ser Gly Thr Thr
            1605                1610                1615

Ser Ile Gly Gln Phe Glu Phe Ile Cys Asp Glu Asn Asp Asn Ile Gln
            1620                1625                1630

Pro Tyr Phe Ile Lys Phe Asn Thr Leu Glu Thr Asn Tyr Thr Leu Tyr
            1635                1640                1645

Val Gly Asn Arg Gln Asn Met Ile Val Glu Pro Asn Tyr Asp Leu Asp
            1650                1655                1660

Asp Ser Gly Asp Ile Ser Ser Thr Val Ile Asn Phe Ser Gln Lys Tyr
1665                1670                1675                1680

Leu Tyr Gly Ile Asp Ser Cys Val Asn Lys Val Val Ile Ser Pro Asn
            1685                1690                1695

Ile Tyr Thr Asp Glu Ile Asn Ile Thr Pro Val Tyr Glu Thr Asn Asn
            1700                1705                1710

Thr Tyr Pro Glu Val Ile Val Leu Asp Ala Asn Tyr Ile Asn Glu Lys
            1715                1720                1725

Ile Asn Val Asn Ile Asn Asp Leu Ser Ile Arg Tyr Val Trp Ser Asn
            1730                1735                1740

Asp Gly Asn Asp Phe Ile Leu Met Ser Thr Ser Glu Glu Asn Lys Val
1745                1750                1755                1760

Ser Gln Val Lys Ile Arg Phe Val Asn Val Phe Lys Asp Lys Thr Leu
            1765                1770                1775

Ala Asn Lys Leu Ser Phe Asn Phe Ser Asp Lys Gln Asp Val Pro Val
            1780                1785                1790

Ser Glu Ile Ile Leu Ser Phe Thr Pro Ser Tyr Tyr Glu Asp Gly Leu
            1795                1800                1805

Ile Gly Tyr Asp Leu Gly Leu Val Ser Leu Tyr Asn Glu Lys Phe Tyr
            1810                1815                1820

Ile Asn Asn Phe Gly Met Met Val Ser Gly Leu Ile Tyr Ile Asn Asp
1825                1830                1835                1840

Ser Leu Tyr Tyr Phe Lys Pro Pro Val Asn Asn Leu Ile Thr Gly Phe
            1845                1850                1855

Val Thr Val Gly Asp Asp Lys Tyr Tyr Phe Asn Pro Ile Asn Gly Gly
            1860                1865                1870

Ala Ala Ser Ile Gly Glu Thr Ile Ile Asp Asp Lys Asn Tyr Tyr Phe
            1875                1880                1885

Asn Gln Ser Gly Val Leu Gln Thr Gly Val Phe Ser Thr Glu Asp Gly
            1890                1895                1900

Phe Lys Tyr Phe Ala Pro Ala Asn Thr Leu Asp Glu Asn Leu Glu Gly
1905                1910                1915                1920

Glu Ala Ile Asp Phe Thr Gly Lys Leu Ile Ile Asp Glu Asn Ile Tyr
            1925                1930                1935

Tyr Phe Asp Asp Asn Tyr Arg Gly Ala Val Glu Trp Lys Glu Leu Asp
            1940                1945                1950

Gly Glu Met His Tyr Phe Ser Pro Glu Thr Gly Lys Ala Phe Lys Gly
            1955                1960                1965

Leu Asn Gln Ile Gly Asp Tyr Lys Tyr Tyr Phe Asn Ser Asp Gly Val
            1970                1975                1980
```

Met Gln Lys Gly Phe Val Ser Ile Asn Asp Asn Lys His Tyr Phe Asp
1985                1990                1995                2000

Asp Ser Gly Val Met Lys Val Gly Tyr Thr Glu Ile Asp Gly Lys His
            2005                2010                2015

Phe Tyr Phe Ala Glu Asn Gly Glu Met Gln Ile Gly Val Phe Asn Thr
        2020                2025                2030

Glu Asp Gly Phe Lys Tyr Phe Ala His His Asn Glu Asp Leu Gly Asn
            2035                2040                2045

Glu Glu Gly Glu Glu Ile Ser Tyr Ser Gly Ile Leu Asn Phe Asn Asn
        2050                2055                2060

Lys Ile Tyr Tyr Phe Asp Asp Ser Phe Thr Ala Val Val Gly Trp Lys
2065                2070                2075                2080

Asp Leu Glu Asp Gly Ser Lys Tyr Tyr Phe Asp Glu Asp Thr Ala Glu
            2085                2090                2095

Ala Tyr Ile Gly Leu Ser Leu Ile Asn Asp Gly Gln Tyr Tyr Phe Asn
        2100                2105                2110

Asp Asp Gly Ile Met Gln Val Gly Phe Val Thr Ile Asn Asp Lys Val
            2115                2120                2125

Phe Tyr Phe Ser Asp Ser Gly Ile Ile Glu Ser Gly Val Gln Asn Ile
        2130                2135                2140

Asp Asp Asn Tyr Phe Tyr Ile Asp Asp Asn Gly Ile Val Gln Ile Gly
2145                2150                2155                2160

Val Phe Asp Thr Ser Asp Gly Tyr Lys Tyr Phe Ala Pro Ala Asn Thr
            2165                2170                2175

Val Asn Asp Asn Ile Tyr Gly Gln Ala Val Glu Tyr Ser Gly Leu Val
        2180                2185                2190

Arg Val Gly Glu Asp Val Tyr Tyr Phe Gly Glu Thr Tyr Thr Ile Glu
            2195                2200                2205

Thr Gly Trp Ile Tyr Asp Met Glu Asn Glu Ser Asp Lys Tyr Tyr Phe
        2210                2215                2220

Asn Pro Glu Thr Lys Lys Ala Cys Lys Gly Ile Asn Leu Ile Asp Asp
2225                2230                2235                2240

Ile Lys Tyr Tyr Phe Asp Glu Lys Gly Ile Met Arg Thr Gly Leu Ile
            2245                2250                2255

Ser Phe Glu Asn Asn Asn Tyr Tyr Phe Asn Glu Asn Gly Glu Met Gln
        2260                2265                2270

Phe Gly Tyr Ile Asn Ile Glu Asp Lys Met Phe Tyr Phe Gly Glu Asp
            2275                2280                2285

Gly Val Met Gln Ile Gly Val Phe Asn Thr Pro Asp Gly Phe Lys Tyr
        2290                2295                2300

Phe Ala His Gln Asn Thr Leu Asp Glu Asn Phe Glu Gly Glu Ser Ile
2305                2310                2315                2320

Asn Tyr Thr Gly Trp Leu Asp Leu Asp Glu Lys Arg Tyr Tyr Phe Thr
            2325                2330                2335

Asp Glu Tyr Ile Ala Ala Thr Gly Ser Val Ile Ile Asp Gly Glu Glu
            2340                2345                2350

Tyr Tyr Phe Asp Pro Asp Thr Ala Gln Leu Val Ile Ser Glu
            2355                2360                2365

<210> SEQ ID NO 232
<211> LENGTH: 7
<212> TYPE: PRT
<213> ORGANISM: Clostridium difficile
<220> FEATURE:

<220> FEATURE:
<221> NAME/KEY: MOD_RES
<222> LOCATION: 1..1
<223> OTHER INFORMATION: Ala or Val

<400> SEQUENCE: 232

Xaa Thr Gly Trp Gln Thr Ile
1               5

<210> SEQ ID NO 233
<211> LENGTH: 14
<212> TYPE: PRT
<213> ORGANISM: Clostridium difficile
<220> FEATURE:
<221> NAME/KEY: MOD_RES
<222> LOCATION: 1..1
<223> OTHER INFORMATION: Ala or Val
<220> FEATURE:
<221> NAME/KEY: MOD_RES
<222> LOCATION: 8..8
<223> OTHER INFORMATION: Asn or Asp
<220> FEATURE:
<221> NAME/KEY: MOD_RES
<222> LOCATION: 11..11
<223> OTHER INFORMATION: Lys or Val

<400> SEQUENCE: 233

Xaa Thr Gly Trp Gln Thr Ile Xaa Gly Lys Xaa Tyr Tyr Phe
1               5                   10

<210> SEQ ID NO 234
<211> LENGTH: 5
<212> TYPE: PRT
<213> ORGANISM: Clostridium difficile

<400> SEQUENCE: 234

Ser Gly Arg Asn Lys
1               5

<210> SEQ ID NO 235
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
caccatggga tttaaaataa tagataataa aacttattac                          40

<210> SEQ ID NO 236
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
gccatatatc ccaggggc                                                  18

<210> SEQ ID NO 237
<211> LENGTH: 932
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

```
Met Gly Phe Lys Ile Ile Asp Asn Lys Thr Tyr Tyr Asp Glu Asp
1               5                   10                  15

Ser Lys Leu Val Lys Gly Leu Ile Asn Ile Asn Ser Leu Phe Tyr
                20                  25                  30

Phe Asp Pro Ile Glu Phe Asn Leu Val Thr Gly Trp Gln Thr Ile Asn
            35                  40                  45

Gly Lys Lys Tyr Tyr Phe Asp Ile Asn Thr Gly Ala Ala Leu Thr Ser
        50                  55                  60

Tyr Lys Ile Ile Asn Gly Lys His Phe Tyr Phe Asn Asn Asp Gly Val
65                      70                  75                  80

Met Gln Leu Gly Val Phe Lys Gly Pro Asp Gly Phe Glu Tyr Phe Ala
                85                  90                  95

Pro Ala Asn Thr Gln Asn Asn Asn Ile Glu Gly Gln Ala Ile Val Tyr
                100                 105                 110

Gln Ser Lys Phe Leu Thr Leu Asn Gly Lys Lys Tyr Tyr Phe Asp Asn
            115                 120                 125

Asn Ser Lys Ala Val Thr Gly Trp Arg Ile Ile Asn Asn Glu Lys Tyr
        130                 135                 140

Tyr Phe Asn Pro Asn Asn Ala Ile Ala Ala Val Gly Leu Gln Val Ile
145                 150                 155                 160

Asp Asn Asn Lys Tyr Tyr Phe Asn Pro Asp Thr Ala Ile Ile Ser Lys
                165                 170                 175

Gly Trp Gln Thr Val Asn Gly Ser Arg Tyr Tyr Phe Asp Thr Asp Thr
            180                 185                 190

Ala Ile Ala Phe Asn Gly Tyr Lys Thr Ile Asp Gly Lys His Phe Tyr
        195                 200                 205

Phe Asp Ser Asp Cys Val Val Lys Ile Gly Val Phe Ser Thr Ser Asn
210                 215                 220

Gly Phe Glu Tyr Phe Ala Pro Ala Asn Thr Tyr Asn Asn Asn Ile Glu
225                 230                 235                 240

Gly Gln Ala Ile Val Tyr Gln Ser Lys Phe Leu Thr Leu Asn Gly Lys
                245                 250                 255

Lys Tyr Tyr Phe Asp Asn Asn Ser Lys Ala Val Thr Gly Leu Gln Thr
            260                 265                 270

Ile Asp Ser Lys Lys Tyr Tyr Phe Asn Thr Asn Thr Ala Glu Ala Ala
            275                 280                 285

Thr Gly Trp Gln Thr Ile Asp Gly Lys Lys Tyr Tyr Phe Asn Thr Asn
        290                 295                 300

Thr Ala Glu Ala Ala Thr Gly Trp Gln Thr Ile Asp Gly Lys Lys Tyr
305                 310                 315                 320

Tyr Phe Asn Thr Asn Thr Ala Ile Ala Ser Thr Gly Tyr Thr Ile Ile
            325                 330                 335

Asn Gly Lys His Phe Tyr Phe Asn Thr Asp Gly Ile Met Gln Ile Gly
            340                 345                 350

Val Phe Lys Gly Pro Asn Gly Phe Glu Tyr Phe Ala Pro Ala Asn Thr
            355                 360                 365

Asp Ala Asn Asn Ile Glu Gly Gln Ala Ile Leu Tyr Gln Asn Glu Phe
            370                 375                 380

Leu Thr Leu Asn Gly Lys Lys Tyr Tyr Phe Gly Ser Asp Ser Lys Ala
385                 390                 395                 400

Val Thr Gly Trp Arg Ile Ile Asn Asn Lys Lys Tyr Tyr Phe Asn Pro
            405                 410                 415
```

```
Asn Asn Ala Ile Ala Ala Ile His Leu Cys Thr Ile Asn Asn Asp Lys
                420                 425                 430

Tyr Tyr Phe Ser Tyr Asp Gly Ile Leu Gln Asn Gly Tyr Ile Thr Ile
            435                 440                 445

Glu Arg Asn Asn Phe Tyr Phe Asp Ala Asn Asn Glu Ser Lys Met Val
        450                 455                 460

Thr Gly Val Phe Lys Gly Pro Asn Gly Phe Glu Tyr Phe Ala Pro Ala
465                 470                 475                 480

Asn Thr His Asn Asn Asn Ile Glu Gly Gln Ala Ile Val Tyr Gln Asn
                485                 490                 495

Lys Phe Leu Thr Leu Asn Gly Lys Lys Tyr Tyr Phe Asp Asn Asp Ser
            500                 505                 510

Lys Ala Val Thr Gly Trp Gln Thr Ile Asp Gly Lys Lys Tyr Tyr Phe
        515                 520                 525

Asn Leu Asn Thr Ala Glu Ala Ala Thr Gly Trp Gln Thr Ile Asp Gly
            530                 535                 540

Lys Lys Tyr Tyr Phe Asn Leu Asn Thr Ala Glu Ala Ala Thr Gly Trp
545                 550                 555                 560

Gln Thr Ile Asp Gly Lys Lys Tyr Tyr Phe Asn Thr Asn Thr Phe Ile
            565                 570                 575

Ala Ser Thr Gly Tyr Thr Ser Ile Asn Gly Lys His Phe Tyr Phe Asn
            580                 585                 590

Thr Asp Gly Ile Met Gln Ile Gly Val Phe Lys Gly Pro Asn Gly Phe
            595                 600                 605

Glu Tyr Phe Ala Pro Ala Asn Thr Asp Ala Asn Asn Ile Glu Gly Gln
        610                 615                 620

Ala Ile Leu Tyr Gln Asn Lys Phe Leu Thr Leu Asn Gly Lys Lys Tyr
625                 630                 635                 640

Tyr Phe Gly Ser Asp Ser Lys Ala Val Thr Gly Leu Arg Thr Ile Asp
            645                 650                 655

Gly Lys Lys Tyr Tyr Phe Asn Thr Asn Thr Ala Val Ala Val Thr Gly
            660                 665                 670

Trp Gln Thr Ile Asn Gly Lys Lys Tyr Tyr Phe Asn Thr Asn Thr Ser
        675                 680                 685

Ile Ala Ser Thr Gly Tyr Thr Ile Ile Ser Gly Lys His Phe Tyr Phe
        690                 695                 700

Asn Thr Asp Gly Ile Met Gln Ile Gly Val Phe Lys Gly Pro Asp Gly
705                 710                 715                 720

Phe Glu Tyr Phe Ala Pro Ala Asn Thr Asp Ala Asn Asn Ile Glu Gly
                725                 730                 735

Gln Ala Ile Arg Tyr Gln Asn Arg Phe Leu Tyr Leu His Asp Asn Ile
            740                 745                 750

Tyr Tyr Phe Gly Asn Asn Ser Lys Ala Ala Thr Gly Trp Val Thr Ile
            755                 760                 765

Asp Gly Asn Arg Tyr Tyr Phe Glu Pro Asn Thr Ala Met Gly Ala Asn
            770                 775                 780

Gly Tyr Lys Thr Ile Asp Asn Lys Asn Phe Tyr Phe Arg Asn Gly Leu
785                 790                 795                 800

Pro Gln Ile Gly Val Phe Lys Gly Ser Asn Gly Phe Glu Tyr Phe Ala
                805                 810                 815

Pro Ala Asn Thr Asp Ala Asn Asn Ile Glu Gly Gln Ala Ile Arg Tyr
            820                 825                 830

Gln Asn Arg Phe Leu His Leu Leu Gly Lys Ile Tyr Tyr Phe Gly Asn
```

```
                  835                 840                 845
Asn Ser Lys Ala Val Thr Gly Trp Gln Thr Ile Asn Gly Lys Val Tyr
    850                 855                 860

Tyr Phe Met Pro Asp Thr Ala Met Ala Ala Gly Gly Leu Phe Glu
865             870                 875                 880

Ile Asp Gly Val Ile Tyr Phe Phe Gly Val Asp Gly Val Lys Ala Pro
                    885                 890                 895

Gly Ile Tyr Gly Lys Gly Glu Leu Asn Ser Lys Leu Glu Gly Lys Pro
                900                 905                 910

Ile Pro Asn Pro Leu Leu Gly Leu Asp Ser Thr Arg Thr Gly His His
                915                 920                 925

His His His His
        930
```

<210> SEQ ID NO 238
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 238
cggatccgaa ttcattctta tgtcaactag tgaagaaaat aagg    44

<210> SEQ ID NO 239
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 239
gtggtggtgc tcgagagctg tatcaggatc aaaataatac    40

<210> SEQ ID NO 240
<211> LENGTH: 617
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 240

```
Met Ser Thr Ser Glu Glu Asn Lys Val Ser Gln Val Lys Ile Arg Phe
1               5                   10                  15

Val Asn Val Phe Lys Asp Lys Thr Leu Ala Asn Lys Leu Ser Phe Asn
                20                  25                  30

Phe Ser Asp Lys Gln Asp Val Pro Val Ser Glu Ile Ile Leu Ser Phe
            35                  40                  45

Thr Pro Ser Tyr Tyr Glu Asp Gly Leu Ile Gly Tyr Asp Leu Gly Leu
        50                  55                  60

Val Ser Leu Tyr Asn Glu Lys Phe Tyr Ile Asn Asn Phe Gly Met Met
65                  70                  75                  80

Val Ser Gly Leu Ile Tyr Ile Asn Asp Ser Leu Tyr Tyr Phe Lys Pro
                85                  90                  95

Pro Val Asn Asn Leu Ile Thr Gly Phe Val Thr Val Gly Asp Asp Lys
                100                 105                 110

Tyr Tyr Phe Asn Pro Ile Asn Gly Gly Ala Ala Ser Ile Gly Glu Thr
```

```
                115                 120                 125
Ile Ile Asp Asp Lys Asn Tyr Tyr Phe Asn Gln Ser Gly Val Leu Gln
                130                 135                 140
Thr Gly Val Phe Ser Thr Glu Asp Gly Phe Lys Tyr Phe Ala Pro Ala
145                 150                 155                 160
Asn Thr Leu Asp Glu Asn Leu Glu Gly Glu Ala Ile Asp Phe Thr Gly
                165                 170                 175
Lys Leu Ile Ile Asp Glu Asn Ile Tyr Tyr Phe Asp Asp Asn Tyr Arg
                180                 185                 190
Gly Ala Val Glu Trp Lys Glu Leu Asp Gly Glu Met His Tyr Phe Ser
                195                 200                 205
Pro Glu Thr Gly Lys Ala Phe Lys Gly Leu Asn Gln Ile Gly Asp Tyr
                210                 215                 220
Lys Tyr Tyr Phe Asn Ser Asp Gly Val Met Gln Lys Gly Phe Val Ser
225                 230                 235                 240
Ile Asn Asp Asn Lys His Tyr Phe Asp Asp Ser Gly Val Met Lys Val
                245                 250                 255
Gly Tyr Thr Glu Ile Asp Gly Lys His Phe Tyr Phe Ala Glu Asn Gly
                260                 265                 270
Glu Met Gln Ile Gly Val Phe Asn Thr Glu Asp Gly Phe Lys Tyr Phe
                275                 280                 285
Ala His His Asn Glu Asp Leu Gly Asn Glu Glu Gly Glu Glu Ile Ser
                290                 295                 300
Tyr Ser Gly Ile Leu Asn Phe Asn Asn Lys Ile Tyr Tyr Phe Asp Asp
305                 310                 315                 320
Ser Phe Thr Ala Val Val Gly Trp Lys Asp Leu Glu Asp Gly Ser Lys
                325                 330                 335
Tyr Tyr Phe Asp Glu Asp Thr Ala Glu Ala Tyr Ile Gly Leu Ser Leu
                340                 345                 350
Ile Asn Asp Gly Gln Tyr Tyr Phe Asn Asp Asp Gly Ile Met Gln Val
                355                 360                 365
Gly Phe Val Thr Ile Asn Asp Lys Val Phe Tyr Phe Ser Asp Ser Gly
                370                 375                 380
Ile Ile Glu Ser Gly Val Gln Asn Ile Asp Asp Asn Tyr Phe Tyr Ile
385                 390                 395                 400
Asp Asp Asn Gly Ile Val Gln Ile Gly Val Phe Asp Thr Ser Asp Gly
                405                 410                 415
Tyr Lys Tyr Phe Ala Pro Ala Asn Thr Val Asn Asp Asn Ile Tyr Gly
                420                 425                 430
Gln Ala Val Glu Tyr Ser Gly Leu Val Arg Val Gly Glu Asp Val Tyr
                435                 440                 445
Tyr Phe Gly Glu Thr Tyr Thr Ile Glu Thr Gly Trp Ile Tyr Asp Met
                450                 455                 460
Glu Asn Glu Ser Asp Lys Tyr Tyr Phe Asn Pro Glu Thr Lys Lys Ala
465                 470                 475                 480
Cys Lys Gly Ile Asn Leu Ile Asp Asp Ile Lys Tyr Tyr Phe Asp Glu
                485                 490                 495
Lys Gly Ile Met Arg Thr Gly Leu Ile Ser Phe Glu Asn Asn Asn Tyr
                500                 505                 510
Tyr Phe Asn Glu Asn Gly Glu Met Gln Phe Gly Tyr Ile Asn Ile Glu
                515                 520                 525
Asp Lys Met Phe Tyr Phe Gly Glu Asp Gly Val Met Gln Ile Gly Val
                530                 535                 540
```

```
Phe Asn Thr Pro Asp Gly Phe Lys Tyr Phe Ala His Gln Asn Thr Leu
545                 550                 555                 560

Asp Glu Asn Phe Glu Gly Glu Ser Ile Asn Tyr Thr Gly Trp Leu Asp
                565                 570                 575

Leu Asp Glu Lys Arg Tyr Tyr Phe Thr Asp Glu Tyr Ile Ala Ala Thr
            580                 585                 590

Gly Ser Val Ile Ile Asp Gly Glu Tyr Tyr Phe Asp Pro Asp Thr
        595                 600                 605

Ala Leu Glu His His His His His His
    610                 615

<210> SEQ ID NO 241
<211> LENGTH: 20
<212> TYPE: PRT
<213> ORGANISM: Clostridium difficile

<400> SEQUENCE: 241

Val Thr Gly Trp Gln Thr Ile Asn Gly Lys Lys Tyr Tyr Phe Asp Ile
1               5                   10                  15

Asn Thr Gly Ala
            20

<210> SEQ ID NO 242
<211> LENGTH: 20
<212> TYPE: PRT
<213> ORGANISM: Clostridium difficile

<400> SEQUENCE: 242

Val Thr Gly Trp Gln Thr Ile Asp Gly Lys Lys Tyr Tyr Phe Asn Leu
1               5                   10                  15

Asn Thr Ala Glu
            20

<210> SEQ ID NO 243
<211> LENGTH: 20
<212> TYPE: PRT
<213> ORGANISM: Clostridium difficile

<400> SEQUENCE: 243

Val Thr Gly Trp Gln Thr Ile Asn Gly Lys Val Tyr Tyr Phe Met Pro
1               5                   10                  15

Asp Thr Ala Met
            20

<210> SEQ ID NO 244
<211> LENGTH: 15
<212> TYPE: PRT
<213> ORGANISM: Clostridium difficile

<400> SEQUENCE: 244

Thr Asp Ile Cys Ile Asp Thr Tyr Lys Lys Ser Gly Arg Asn Lys
1               5                   10                  15

<210> SEQ ID NO 245
<211> LENGTH: 15
<212> TYPE: PRT
<213> ORGANISM: Clostridium difficile

<400> SEQUENCE: 245

Asp Thr Tyr Lys Lys Ser Gly Arg Asn Lys Ala Leu Lys Lys Phe
1               5                   10                  15
```

```
<210> SEQ ID NO 246
<211> LENGTH: 15
<212> TYPE: PRT
<213> ORGANISM: Clostridium difficile

<400> SEQUENCE: 246

Ser Gly Arg Asn Lys Ala Leu Lys Lys Phe Lys Glu Tyr Leu Val
1               5                   10                  15

<210> SEQ ID NO 247
<211> LENGTH: 19
<212> TYPE: PRT
<213> ORGANISM: Clostridium difficile

<400> SEQUENCE: 247

Ser Gly Ser Gly Met Ser Leu Val Asn Arg Lys Gln Leu Glu Lys Met
1               5                   10                  15

Ala Asn Val

<210> SEQ ID NO 248
<211> LENGTH: 19
<212> TYPE: PRT
<213> ORGANISM: Clostridium difficile

<400> SEQUENCE: 248

Ser Gly Ser Gly Arg Lys Gln Leu Glu Lys Met Ala Asn Val Arg Phe
1               5                   10                  15

Arg Thr Gln

<210> SEQ ID NO 249
<211> LENGTH: 19
<212> TYPE: PRT
<213> ORGANISM: Clostridium difficile

<400> SEQUENCE: 249

Ser Gly Ser Gly Lys Met Ala Asn Val Arg Phe Arg Thr Gln Glu Asp
1               5                   10                  15

Glu Tyr Val

<210> SEQ ID NO 250
<211> LENGTH: 19
<212> TYPE: PRT
<213> ORGANISM: Clostridium difficile

<400> SEQUENCE: 250

Ser Gly Ser Gly Arg Phe Arg Thr Gln Glu Asp Glu Tyr Val Ala Ile
1               5                   10                  15

Leu Asp Ala

<210> SEQ ID NO 251
<211> LENGTH: 19
<212> TYPE: PRT
<213> ORGANISM: Clostridium difficile

<400> SEQUENCE: 251

Ser Gly Ser Gly Glu Asp Glu Tyr Val Ala Ile Leu Asp Ala Leu Glu
1               5                   10                  15

Glu Tyr His

<210> SEQ ID NO 252
```

<211> LENGTH: 19
<212> TYPE: PRT
<213> ORGANISM: Clostridium difficile

<400> SEQUENCE: 252

Ser Gly Ser Gly Ala Ile Leu Asp Ala Leu Glu Glu Tyr His Asn Met
1               5                   10                  15
Ser Glu Asn

<210> SEQ ID NO 253
<211> LENGTH: 19
<212> TYPE: PRT
<213> ORGANISM: Clostridium difficile

<400> SEQUENCE: 253

Ser Gly Ser Gly Leu Glu Glu Tyr His Asn Met Ser Glu Asn Thr Val
1               5                   10                  15
Val Glu Lys

<210> SEQ ID NO 254
<211> LENGTH: 19
<212> TYPE: PRT
<213> ORGANISM: Clostridium difficile

<400> SEQUENCE: 254

Ser Gly Ser Gly Asn Met Ser Glu Asn Thr Val Val Glu Lys Tyr Leu
1               5                   10                  15
Lys Leu Lys

<210> SEQ ID NO 255
<211> LENGTH: 19
<212> TYPE: PRT
<213> ORGANISM: Clostridium difficile

<400> SEQUENCE: 255

Ser Gly Ser Gly Thr Val Val Glu Lys Tyr Leu Lys Leu Lys Asp Ile
1               5                   10                  15
Asn Ser Leu

<210> SEQ ID NO 256
<211> LENGTH: 19
<212> TYPE: PRT
<213> ORGANISM: Clostridium difficile

<400> SEQUENCE: 256

Ser Gly Ser Gly Tyr Leu Lys Leu Lys Asp Ile Asn Ser Leu Thr Asp
1               5                   10                  15
Ile Cys Ile

<210> SEQ ID NO 257
<211> LENGTH: 19
<212> TYPE: PRT
<213> ORGANISM: Clostridium difficile

<400> SEQUENCE: 257

Ser Gly Ser Gly Asp Ile Asn Ser Leu Thr Asp Ile Cys Ile Asp Thr
1               5                   10                  15
Tyr Lys Lys

<210> SEQ ID NO 258
<211> LENGTH: 19

```
<212> TYPE: PRT
<213> ORGANISM: Clostridium difficile

<400> SEQUENCE: 258

Ser Gly Ser Gly Thr Asp Ile Cys Ile Asp Thr Tyr Lys Lys Ser Gly
1               5                   10                  15

Arg Asn Lys

<210> SEQ ID NO 259
<211> LENGTH: 19
<212> TYPE: PRT
<213> ORGANISM: Clostridium difficile

<400> SEQUENCE: 259

Ser Gly Ser Gly Asp Thr Tyr Lys Lys Ser Gly Arg Asn Lys Ala Leu
1               5                   10                  15

Lys Lys Phe

<210> SEQ ID NO 260
<211> LENGTH: 19
<212> TYPE: PRT
<213> ORGANISM: Clostridium difficile

<400> SEQUENCE: 260

Ser Gly Ser Gly Ser Gly Arg Asn Lys Ala Leu Lys Lys Phe Lys Glu
1               5                   10                  15

Tyr Leu Val

<210> SEQ ID NO 261
<211> LENGTH: 19
<212> TYPE: PRT
<213> ORGANISM: Clostridium difficile

<400> SEQUENCE: 261

Ser Gly Ser Gly Ala Leu Lys Lys Phe Lys Glu Tyr Leu Val Thr Glu
1               5                   10                  15

Val Leu Glu

<210> SEQ ID NO 262
<211> LENGTH: 19
<212> TYPE: PRT
<213> ORGANISM: Clostridium difficile

<400> SEQUENCE: 262

Ser Gly Ser Gly Lys Glu Tyr Leu Val Thr Glu Val Leu Glu Leu Lys
1               5                   10                  15

Asn Asn Asn

<210> SEQ ID NO 263
<211> LENGTH: 19
<212> TYPE: PRT
<213> ORGANISM: Clostridium difficile

<400> SEQUENCE: 263

Ser Gly Ser Gly Thr Glu Val Leu Glu Leu Lys Asn Asn Asn Leu Thr
1               5                   10                  15

Pro Val Glu

<210> SEQ ID NO 264
<211> LENGTH: 19
<212> TYPE: PRT
```

<213> ORGANISM: Clostridium difficile

<400> SEQUENCE: 264

Ser Gly Ser Gly Leu Lys Asn Asn Asn Leu Thr Pro Val Glu Lys Asn
1               5                   10                  15

Leu His Phe

<210> SEQ ID NO 265
<211> LENGTH: 19
<212> TYPE: PRT
<213> ORGANISM: Clostridium difficile

<400> SEQUENCE: 265

Ser Gly Ser Gly Lys Asn Leu His Phe Val Trp Ile Gly Gly Gln Ile
1               5                   10                  15

Asn Asp Thr

<210> SEQ ID NO 266
<211> LENGTH: 19
<212> TYPE: PRT
<213> ORGANISM: Clostridium difficile

<400> SEQUENCE: 266

Ser Gly Ser Gly Val Trp Ile Gly Gly Gln Ile Asn Asp Thr Ala Ile
1               5                   10                  15

Asn Tyr Ile

<210> SEQ ID NO 267
<211> LENGTH: 19
<212> TYPE: PRT
<213> ORGANISM: Clostridium difficile

<400> SEQUENCE: 267

Ser Gly Ser Gly Gln Ile Asn Asp Thr Ala Ile Asn Tyr Ile Asn Gln
1               5                   10                  15

Trp Lys Asp

<210> SEQ ID NO 268
<211> LENGTH: 19
<212> TYPE: PRT
<213> ORGANISM: Clostridium difficile

<400> SEQUENCE: 268

Ser Gly Ser Gly Ala Ile Asn Tyr Ile Asn Gln Trp Lys Asp Val Asn
1 5 10 15

Ser Asp Tyr

<210> SEQ ID NO 269
<211> LENGTH: 19
<212> TYPE: PRT
<213> ORGANISM: Clostridium difficile

<400> SEQUENCE: 269

Ser Gly Ser Gly Asn Gln Trp Lys Asp Val Asn Ser Asp Tyr Asn Val
1 5 10 15

Asn Val Phe

<210> SEQ ID NO 270
<211> LENGTH: 19
<212> TYPE: PRT
<213> ORGANISM: Clostridium difficile

<400> SEQUENCE: 270

Ser Gly Ser Gly Val Asn Ser Asp Tyr Asn Val Asn Val Phe Tyr Asp
1               5                   10                  15

Ser Asn Ala

<210> SEQ ID NO 271
<211> LENGTH: 19
<212> TYPE: PRT
<213> ORGANISM: Clostridium difficile

<400> SEQUENCE: 271

Ser Gly Ser Gly Leu Lys Lys Thr Val Val Glu Ser Ala Ile Asn Asp
1               5                   10                  15

Thr Leu Glu

<210> SEQ ID NO 272
<211> LENGTH: 19
<212> TYPE: PRT
<213> ORGANISM: Clostridium difficile

<400> SEQUENCE: 272

Ser Gly Ser Gly Val Glu Ser Ala Ile Asn Asp Thr Leu Glu Ser Phe
1               5                   10                  15

Arg Glu Asn

<210> SEQ ID NO 273
<211> LENGTH: 19
<212> TYPE: PRT
<213> ORGANISM: Clostridium difficile

<400> SEQUENCE: 273

Ser Gly Ser Gly Asn Asp Thr Leu Glu Ser Phe Arg Glu Asn Leu Asn
1               5                   10                  15

Asp Pro Arg

<210> SEQ ID NO 274
<211> LENGTH: 19
<212> TYPE: PRT
<213> ORGANISM: Clostridium difficile

<400> SEQUENCE: 274

Ser Gly Ser Gly Ser Phe Arg Glu Asn Leu Asn Asp Pro Arg Phe Asp
1               5                   10                  15

Tyr Asn Lys

<210> SEQ ID NO 275
<211> LENGTH: 19
<212> TYPE: PRT
<213> ORGANISM: Clostridium difficile

<400> SEQUENCE: 275

Ser Gly Ser Gly Leu Asn Asp Pro Arg Phe Asp Tyr Asn Lys Phe Phe
1               5                   10                  15

Arg Lys Arg

<210> SEQ ID NO 276
<211> LENGTH: 19
<212> TYPE: PRT
<213> ORGANISM: Clostridium difficile -continued

```
<400> SEQUENCE: 276

Ser Gly Ser Gly Phe Asp Tyr Asn Lys Phe Arg Lys Arg Met Glu
1               5                   10                  15

Ile Ile Tyr

<210> SEQ ID NO 277
<211> LENGTH: 19
<212> TYPE: PRT
<213> ORGANISM: Clostridium difficile

<400> SEQUENCE: 277

Ser Gly Ser Gly Phe Phe Arg Lys Arg Met Glu Ile Ile Tyr Asp Lys
1               5                   10                  15

Gln Lys Asn

<210> SEQ ID NO 278
<211> LENGTH: 19
<212> TYPE: PRT
<213> ORGANISM: Clostridium difficile

<400> SEQUENCE: 278

Ser Gly Ser Gly Met Glu Ile Ile Tyr Asp Lys Gln Lys Asn Phe Ile
1               5                   10                  15

Asn Tyr Tyr

<210> SEQ ID NO 279
<211> LENGTH: 19
<212> TYPE: PRT
<213> ORGANISM: Clostridium difficile

<400> SEQUENCE: 279

Ser Gly Ser Gly Asp Lys Gln Lys Asn Phe Ile Asn Tyr Tyr Lys Ala
1               5                   10                  15

Gln Arg Glu

<210> SEQ ID NO 280
<211> LENGTH: 19
<212> TYPE: PRT
<213> ORGANISM: Clostridium difficile

<400> SEQUENCE: 280

Ser Gly Ser Gly Phe Ile Asn Tyr Tyr Lys Ala Gln Arg Glu Glu Asn
1               5                   10                  15

Pro Glu Leu

<210> SEQ ID NO 281
<211> LENGTH: 19
<212> TYPE: PRT
<213> ORGANISM: Clostridium difficile

<400> SEQUENCE: 281

Ser Gly Ser Gly Lys Ala Gln Arg Glu Glu Asn Pro Glu Leu Ile Ile
1               5                   10                  15

Asp Asp Ile

<210> SEQ ID NO 282
<211> LENGTH: 19
<212> TYPE: PRT
<213> ORGANISM: Clostridium difficile

<400> SEQUENCE: 282
```

Ser Gly Ser Gly Glu Asn Pro Glu Leu Ile Ile Asp Asp Ile Val Lys
1               5                   10                  15

Thr Tyr Leu

<210> SEQ ID NO 283
<211> LENGTH: 19
<212> TYPE: PRT
<213> ORGANISM: Clostridium difficile

<400> SEQUENCE: 283

Ser Gly Ser Gly Ile Ile Asp Asp Ile Val Lys Thr Tyr Leu Ser Asn
1               5                   10                  15

Glu Tyr Ser

<210> SEQ ID NO 284
<211> LENGTH: 19
<212> TYPE: PRT
<213> ORGANISM: Clostridium difficile

<400> SEQUENCE: 284

Ser Gly Ser Gly Val Lys Thr Tyr Leu Ser Asn Glu Tyr Ser Lys Glu
1               5                   10                  15

Ile Asp Glu

<210> SEQ ID NO 285
<211> LENGTH: 19
<212> TYPE: PRT
<213> ORGANISM: Clostridium difficile

<400> SEQUENCE: 285

Ser Gly Ser Gly Ser Asn Glu Tyr Ser Lys Glu Ile Asp Glu Leu Asn
1               5                   10                  15

Thr Tyr Ile

<210> SEQ ID NO 286
<211> LENGTH: 19
<212> TYPE: PRT
<213> ORGANISM: Clostridium difficile

<400> SEQUENCE: 286

Ser Gly Ser Gly Lys Glu Ile Asp Glu Leu Asn Thr Tyr Ile Glu Glu
1               5                   10                  15

Ser Leu Asn

<210> SEQ ID NO 287
<211> LENGTH: 19
<212> TYPE: PRT
<213> ORGANISM: Clostridium difficile

<400> SEQUENCE: 287

Ser Gly Ser Gly Leu Asn Thr Tyr Ile Glu Glu Ser Leu Asn Lys Ile
1               5                   10                  15

Thr Gln Asn

<210> SEQ ID NO 288
<211> LENGTH: 19
<212> TYPE: PRT
<213> ORGANISM: Clostridium difficile

<400> SEQUENCE: 288

```
Ser Gly Ser Gly Glu Glu Ser Leu Asn Lys Ile Thr Gln Asn Ser Gly
1               5                   10                  15

Asn Asp Val
```

<210> SEQ ID NO 289
<211> LENGTH: 19
<212> TYPE: PRT
<213> ORGANISM: Clostridium difficile

<400> SEQUENCE: 289

```
Ser Gly Ser Gly Lys Ile Thr Gln Asn Ser Gly Asn Asp Val Arg Asn
1               5                   10                  15

Phe Gly Glu
```

<210> SEQ ID NO 290
<211> LENGTH: 19
<212> TYPE: PRT
<213> ORGANISM: Clostridium difficile

<400> SEQUENCE: 290

```
Ser Gly Ser Gly Ser Gly Asn Asp Val Arg Asn Phe Gly Glu Phe Lys
1               5                   10                  15

Asn Gly Glu
```

<210> SEQ ID NO 291
<211> LENGTH: 19
<212> TYPE: PRT
<213> ORGANISM: Clostridium difficile

<400> SEQUENCE: 291

```
Ser Gly Ser Gly Arg Asn Phe Gly Glu Phe Lys Asn Gly Glu Ser Phe
1               5                   10                  15

Asn Leu Tyr
```

<210> SEQ ID NO 292
<211> LENGTH: 19
<212> TYPE: PRT
<213> ORGANISM: Clostridium difficile

<400> SEQUENCE: 292

```
Ser Gly Ser Gly Phe Lys Asn Gly Glu Ser Phe Asn Leu Tyr Glu Gln
1               5                   10                  15

Glu Leu Val
```

<210> SEQ ID NO 293
<211> LENGTH: 19
<212> TYPE: PRT
<213> ORGANISM: Clostridium difficile

<400> SEQUENCE: 293

```
Ser Gly Ser Gly Asp Val Asp Met Leu Pro Gly Ile Gln Pro Asp Leu
1               5                   10                  15

Phe Glu Ser
```

<210> SEQ ID NO 294
<211> LENGTH: 19
<212> TYPE: PRT
<213> ORGANISM: Clostridium difficile

<400> SEQUENCE: 294

```
Ser Gly Ser Gly Pro Gly Ile Gln Pro Asp Leu Phe Glu Ser Ile Glu
```

```
                1               5                  10                 15

Lys Pro Ser

<210> SEQ ID NO 295
<211> LENGTH: 19
<212> TYPE: PRT
<213> ORGANISM: Clostridium difficile

<400> SEQUENCE: 295

Ser Gly Ser Gly Asp Leu Phe Glu Ser Ile Glu Lys Pro Ser Ser Val
1               5                  10                 15

Thr Val Asp

<210> SEQ ID NO 296
<211> LENGTH: 19
<212> TYPE: PRT
<213> ORGANISM: Clostridium difficile

<400> SEQUENCE: 296

Ser Gly Ser Gly Ile Glu Lys Pro Ser Ser Val Thr Val Asp Phe Trp
1               5                  10                 15

Glu Met Thr

<210> SEQ ID NO 297
<211> LENGTH: 19
<212> TYPE: PRT
<213> ORGANISM: Clostridium difficile

<400> SEQUENCE: 297

Ser Gly Ser Gly Ser Val Thr Val Asp Phe Trp Glu Met Thr Lys Leu
1               5                  10                 15

Glu Ala Ile

<210> SEQ ID NO 298
<211> LENGTH: 19
<212> TYPE: PRT
<213> ORGANISM: Clostridium difficile

<400> SEQUENCE: 298

Ser Gly Ser Gly Lys Leu Glu Ala Ile Met Lys Tyr Lys Glu Tyr Ile
1               5                  10                 15

Pro Glu Tyr

<210> SEQ ID NO 299
<211> LENGTH: 19
<212> TYPE: PRT
<213> ORGANISM: Clostridium difficile

<400> SEQUENCE: 299

Ser Gly Ser Gly Met Lys Tyr Lys Glu Tyr Ile Pro Glu Tyr Thr Ser
1               5                  10                 15

Glu His Phe

<210> SEQ ID NO 300
<211> LENGTH: 19
<212> TYPE: PRT
<213> ORGANISM: Clostridium difficile

<400> SEQUENCE: 300

Ser Gly Ser Gly Tyr Ile Pro Glu Tyr Thr Ser Glu His Phe Asp Met
1               5                  10                 15
```

Leu Asp Glu

<210> SEQ ID NO 301
<211> LENGTH: 19
<212> TYPE: PRT
<213> ORGANISM: Clostridium difficile

<400> SEQUENCE: 301

Ser Gly Ser Gly Thr Ser Glu His Phe Asp Met Leu Asp Glu Val
1               5                   10                  15

Gln Ser Ser

<210> SEQ ID NO 302
<211> LENGTH: 19
<212> TYPE: PRT
<213> ORGANISM: Clostridium difficile

<400> SEQUENCE: 302

Ser Gly Ser Gly Asp Met Leu Asp Glu Glu Val Gln Ser Ser Phe Glu
1               5                   10                  15

Ser Val Leu

<210> SEQ ID NO 303
<211> LENGTH: 19
<212> TYPE: PRT
<213> ORGANISM: Clostridium difficile

<400> SEQUENCE: 303

Ser Gly Ser Gly Glu Val Gln Ser Ser Phe Glu Ser Val Leu Ala Ser
1               5                   10                  15

Lys Ser Asp

<210> SEQ ID NO 304
<211> LENGTH: 19
<212> TYPE: PRT
<213> ORGANISM: Clostridium difficile

<400> SEQUENCE: 304

Ser Gly Ser Gly Phe Glu Ser Val Leu Ala Ser Lys Ser Asp Lys Ser
1               5                   10                  15

Glu Ile Phe

<210> SEQ ID NO 305
<211> LENGTH: 19
<212> TYPE: PRT
<213> ORGANISM: Clostridium difficile

<400> SEQUENCE: 305

Ser Gly Ser Gly Ala Ser Lys Ser Asp Lys Ser Glu Ile Phe Ser Ser
1               5                   10                  15

Leu Gly Asp

<210> SEQ ID NO 306
<211> LENGTH: 19
<212> TYPE: PRT
<213> ORGANISM: Clostridium difficile

<400> SEQUENCE: 306

Ser Gly Ser Gly Lys Ser Glu Ile Phe Ser Ser Leu Gly Asp Met Glu
1               5                   10                  15

Ala Ser Pro

<210> SEQ ID NO 307
<211> LENGTH: 19
<212> TYPE: PRT
<213> ORGANISM: Clostridium difficile

<400> SEQUENCE: 307

Ser Gly Ser Gly Ser Ser Leu Gly Asp Met Glu Ala Ser Pro Leu Glu
1               5                   10                  15

Val Lys Ile

<210> SEQ ID NO 308
<211> LENGTH: 19
<212> TYPE: PRT
<213> ORGANISM: Clostridium difficile

<400> SEQUENCE: 308

Ser Gly Ser Gly Met Glu Ala Ser Pro Leu Glu Val Lys Ile Ala Phe
1               5                   10                  15

Asn Ser Lys

<210> SEQ ID NO 309
<211> LENGTH: 19
<212> TYPE: PRT
<213> ORGANISM: Clostridium difficile

<400> SEQUENCE: 309

Ser Gly Ser Gly Leu Glu Val Lys Ile Ala Phe Asn Ser Lys Gly Ile
1               5                   10                  15

Ile Asn Gln

<210> SEQ ID NO 310
<211> LENGTH: 19
<212> TYPE: PRT
<213> ORGANISM: Clostridium difficile

<400> SEQUENCE: 310

Ser Gly Ser Gly Ala Phe Asn Ser Lys Gly Ile Ile Asn Gln Gly Leu
1               5                   10                  15

Ile Ser Val

<210> SEQ ID NO 311
<211> LENGTH: 19
<212> TYPE: PRT
<213> ORGANISM: Clostridium difficile

<400> SEQUENCE: 311

Ser Gly Ser Gly Lys Asp Ser Tyr Cys Ser Asn Leu Ile Val Lys Gln
1               5                   10                  15

Ile Glu Asn

<210> SEQ ID NO 312
<211> LENGTH: 19
<212> TYPE: PRT
<213> ORGANISM: Clostridium difficile

<400> SEQUENCE: 312

Ser Gly Ser Gly Lys Gln Ile Glu Asn Arg Tyr Lys Ile Leu Asn Asn
1               5                   10                  15

Ser Leu Asn

-continued

<210> SEQ ID NO 313
<211> LENGTH: 19
<212> TYPE: PRT
<213> ORGANISM: Clostridium difficile

<400> SEQUENCE: 313

Ser Gly Ser Gly Arg Tyr Lys Ile Leu Asn Asn Ser Leu Asn Pro Ala
1               5                   10                  15

Ile Ser Glu

<210> SEQ ID NO 314
<211> LENGTH: 19
<212> TYPE: PRT
<213> ORGANISM: Clostridium difficile

<400> SEQUENCE: 314

Ser Gly Ser Gly Asn Asn Ser Leu Asn Pro Ala Ile Ser Glu Asp Asn
1               5                   10                  15

Asp Phe Asn

<210> SEQ ID NO 315
<211> LENGTH: 19
<212> TYPE: PRT
<213> ORGANISM: Clostridium difficile

<400> SEQUENCE: 315

Ser Gly Ser Gly Pro Ala Ile Ser Glu Asp Asn Asp Phe Asn Thr Thr
1               5                   10                  15

Thr Asn Thr

<210> SEQ ID NO 316
<211> LENGTH: 19
<212> TYPE: PRT
<213> ORGANISM: Clostridium difficile

<400> SEQUENCE: 316

Ser Gly Ser Gly Asp Asn Asp Phe Asn Thr Thr Thr Asn Thr Phe Ile
1               5                   10                  15

Asp Ser Ile

<210> SEQ ID NO 317
<211> LENGTH: 19
<212> TYPE: PRT
<213> ORGANISM: Clostridium difficile

<400> SEQUENCE: 317

Ser Gly Ser Gly Thr Thr Thr Asn Thr Phe Ile Asp Ser Ile Met Ala
1               5                   10                  15

Glu Ala Asn

<210> SEQ ID NO 318
<211> LENGTH: 19
<212> TYPE: PRT
<213> ORGANISM: Clostridium difficile

<400> SEQUENCE: 318

Ser Gly Ser Gly Phe Ile Asp Ser Ile Met Ala Glu Ala Asn Ala Asp
1               5                   10                  15

Asn Gly Arg

<210> SEQ ID NO 319
<211> LENGTH: 19
<212> TYPE: PRT
<213> ORGANISM: Clostridium difficile

<400> SEQUENCE: 319

Ser Gly Ser Gly Met Ala Glu Ala Asn Ala Asp Asn Gly Arg Phe Met
1               5                   10                  15

Met Glu Leu

<210> SEQ ID NO 320
<211> LENGTH: 19
<212> TYPE: PRT
<213> ORGANISM: Clostridium difficile

<400> SEQUENCE: 320

Ser Gly Ser Gly Ala Asp Asn Gly Arg Phe Met Met Glu Leu Gly Lys
1               5                   10                  15

Tyr Leu Arg

<210> SEQ ID NO 321
<211> LENGTH: 19
<212> TYPE: PRT
<213> ORGANISM: Clostridium difficile

<400> SEQUENCE: 321

Ser Gly Ser Gly Leu Leu Met Phe Lys Glu Gly Ser Met Asn Ile His
1               5                   10                  15

Leu Ile Glu

<210> SEQ ID NO 322
<211> LENGTH: 19
<212> TYPE: PRT
<213> ORGANISM: Clostridium difficile

<400> SEQUENCE: 322

Ser Gly Ser Gly Glu Gly Ser Met Asn Ile His Leu Ile Glu Ala Asp
1               5                   10                  15

Leu Arg Asn

<210> SEQ ID NO 323
<211> LENGTH: 19
<212> TYPE: PRT
<213> ORGANISM: Clostridium difficile

<400> SEQUENCE: 323

Ser Gly Ser Gly Ile His Leu Ile Glu Ala Asp Leu Arg Asn Phe Glu
1               5                   10                  15

Ile Ser Lys

<210> SEQ ID NO 324
<211> LENGTH: 19
<212> TYPE: PRT
<213> ORGANISM: Clostridium difficile

<400> SEQUENCE: 324

Ser Gly Ser Gly Ala Asp Leu Arg Asn Phe Glu Ile Ser Lys Thr Asn
1               5                   10                  15

Ile Ser Gln

```
<210> SEQ ID NO 325
<211> LENGTH: 19
<212> TYPE: PRT
<213> ORGANISM: Clostridium difficile

<400> SEQUENCE: 325

Ser Gly Ser Gly Phe Glu Ile Ser Lys Thr Asn Ile Ser Gln Ser Thr
1               5                   10                  15

Glu Gln Glu

<210> SEQ ID NO 326
<211> LENGTH: 19
<212> TYPE: PRT
<213> ORGANISM: Clostridium difficile

<400> SEQUENCE: 326

Ser Gly Ser Gly Thr Asn Ile Ser Gln Ser Thr Glu Gln Glu Met Ala
1               5                   10                  15

Ser Leu Trp

<210> SEQ ID NO 327
<211> LENGTH: 19
<212> TYPE: PRT
<213> ORGANISM: Clostridium difficile

<400> SEQUENCE: 327

Ser Gly Ser Gly Ser Thr Glu Gln Glu Met Ala Ser Leu Trp Ser Phe
1               5                   10                  15

Asp Asp Ala

<210> SEQ ID NO 328
<211> LENGTH: 19
<212> TYPE: PRT
<213> ORGANISM: Clostridium difficile

<400> SEQUENCE: 328

Ser Gly Ser Gly Met Ala Ser Leu Trp Ser Phe Asp Asp Ala Arg Ala
1               5                   10                  15

Lys Ala Gln

<210> SEQ ID NO 329
<211> LENGTH: 19
<212> TYPE: PRT
<213> ORGANISM: Clostridium difficile

<400> SEQUENCE: 329

Ser Gly Ser Gly Ser Phe Asp Asp Ala Arg Ala Lys Ala Gln Phe Glu
1               5                   10                  15

Glu Tyr Lys

<210> SEQ ID NO 330
<211> LENGTH: 19
<212> TYPE: PRT
<213> ORGANISM: Clostridium difficile

<400> SEQUENCE: 330

Ser Gly Ser Gly Arg Ala Lys Ala Gln Phe Glu Glu Tyr Lys Arg Asn
1               5                   10                  15

Tyr Phe Glu

<210> SEQ ID NO 331
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Gly Gly Gly Gly Ser Gly Gly Gly Ser Gly Gly Gly Gly Ser
1               5                   10                  15

<210> SEQ ID NO 332
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 332

His His His His His His
1               5

<210> SEQ ID NO 333
<211> LENGTH: 20
<212> TYPE: PRT
<213> ORGANISM: Clostridium difficile

<400> SEQUENCE: 333

Ala Thr Gly Trp Gln Thr Ile Asp Gly Lys Lys Tyr Tyr Phe Asn Leu
1               5                   10                  15

Asn Thr Ala Glu
            20

<210> SEQ ID NO 334
<211> LENGTH: 20
<212> TYPE: PRT
<213> ORGANISM: Clostridium difficile

<400> SEQUENCE: 334

Ala Thr Gly Trp Gln Thr Ile Asp Gly Lys Lys Tyr Tyr Phe Asn Thr
1               5                   10                  15

Asn Thr Phe Ile
            20

<210> SEQ ID NO 335
<211> LENGTH: 20
<212> TYPE: PRT
<213> ORGANISM: Clostridium difficile

<400> SEQUENCE: 335

Val Thr Gly Trp Gln Thr Ile Asn Gly Lys Lys Tyr Tyr Phe Asn Thr
1               5                   10                  15

Asn Thr Ser Ile
            20

<210> SEQ ID NO 336
<211> LENGTH: 5
<212> TYPE: PRT
<213> ORGANISM: Artificial Sequence
<220> FEATURE:
<223> OTHER INFORMATION: Description of Artificial Sequence: Synthetic
      motif which allows for sortase-catalyzed conjugation of labels,
      such as biotin

<400> SEQUENCE: 336
```

Leu Pro Glu Thr Gly
1               5

<210> SEQ ID NO 337
<211> LENGTH: 5
<212> TYPE: PRT
<213> ORGANISM: Artificial Sequence
<220> FEATURE:
<223> OTHER INFORMATION: Description of Artificial Sequence: Synthetic
      mutated peptide

<400> SEQUENCE: 337

Ala Gly Ala Asn Lys
1               5

<210> SEQ ID NO 338
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 338

Met Ser Gly Leu Val Pro Arg Gly Ser His Met Ser Leu Val Asn Arg
1               5                   10                  15

Lys Gln Leu Glu Lys Met Ala Asn Val Arg Phe Arg Thr Gln Glu Asp
            20                  25                  30

Glu Tyr Val Ala Ile Leu Asp Ala Leu Glu Glu Tyr His Asn Met Ser
        35                  40                  45

Glu Asn Thr Val Val Glu Lys Tyr Leu Lys Leu Lys Asp Ile Asn Ser
    50                  55                  60

Leu Thr Asp Ile Tyr Ile Asp Thr Tyr Lys Lys Ser Gly Arg Asn Lys
65                  70                  75                  80

Ala Leu Lys Lys Phe Lys Glu Tyr Leu Val Thr Glu Val Leu Glu Leu
                85                  90                  95

Lys Asn Asn Asn Leu Leu Pro Glu Thr Gly Gly His His His His
            100                 105                 110

His

<210> SEQ ID NO 339
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 339

Met Ser Gly Leu Val Pro Arg Gly Ser His Met Ser Leu Val Asn Arg
1               5                   10                  15

Lys Gln Leu Glu Lys Met Ala Asn Val Arg Phe Arg Thr Gln Glu Asp
            20                  25                  30

Glu Tyr Val Ala Ile Leu Asp Ala Leu Glu Glu Tyr His Asn Met Ser
        35                  40                  45

Glu Asn Thr Val Val Glu Lys Tyr Leu Lys Leu Lys Asp Ile Asn Ser
    50                  55                  60

Leu Thr Asp Ile Tyr Ile Asp Thr Tyr Lys Lys Ala Gly Ala Asn Lys
65                  70                  75                  80

Ala Leu Lys Lys Phe Lys Glu Tyr Leu Val Thr Glu Val Leu Glu Leu

```
                85                  90                  95
Lys Asn Asn Leu Leu Pro Glu Thr Gly His His His His
            100                 105                 110
His
```

<210> SEQ ID NO 340
<211> LENGTH: 464
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 340

```
Met Glu Lys Asn Leu His Phe Val Trp Ile Gly Gly Gln Ile Asn Asp
1               5                   10                  15

Thr Ala Ile Asn Tyr Ile Asn Gln Trp Lys Asp Val Asn Ser Asp Tyr
            20                  25                  30

Asn Val Asn Val Phe Tyr Asp Ser Asn Ala Phe Leu Ile Asn Thr Leu
        35                  40                  45

Lys Lys Thr Val Val Glu Ser Ala Ile Asn Asp Thr Leu Glu Ser Phe
50                  55                  60

Arg Glu Asn Leu Asn Asp Pro Arg Phe Asp Tyr Asn Lys Phe Phe Arg
65                  70                  75                  80

Lys Arg Met Glu Ile Ile Tyr Asp Lys Gln Lys Asn Phe Ile Asn Tyr
                85                  90                  95

Tyr Lys Ala Gln Arg Glu Glu Asn Pro Glu Leu Ile Ile Asp Asp Ile
            100                 105                 110

Val Lys Thr Tyr Leu Ser Asn Glu Tyr Ser Lys Glu Ile Asp Glu Leu
        115                 120                 125

Asn Thr Tyr Ile Glu Glu Ser Leu Asn Lys Ile Thr Gln Asn Ser Gly
130                 135                 140

Asn Asp Val Arg Asn Phe Glu Glu Phe Lys Asn Gly Glu Ser Phe Asn
145                 150                 155                 160

Leu Tyr Glu Gln Glu Leu Val Glu Arg Trp Asn Leu Ala Ala Ala Ser
                165                 170                 175

Asp Ile Leu Arg Ile Ser Ala Leu Lys Glu Ile Gly Gly Met Tyr Leu
            180                 185                 190

Asp Val Asp Met Leu Pro Gly Ile Gln Pro Asp Leu Phe Glu Ser Ile
        195                 200                 205

Glu Lys Pro Ser Ser Val Thr Val Asp Phe Trp Glu Met Thr Lys Leu
210                 215                 220

Glu Ala Ile Met Lys Tyr Lys Glu Tyr Ile Pro Glu Tyr Thr Ser Glu
225                 230                 235                 240

His Phe Asp Met Leu Asp Glu Val Gln Ser Ser Phe Glu Ser Val
                245                 250                 255

Leu Ala Ser Lys Ser Asp Lys Ser Glu Ile Phe Ser Ser Leu Gly Asp
            260                 265                 270

Met Glu Ala Ser Pro Leu Glu Val Lys Ile Ala Phe Asn Ser Lys Gly
        275                 280                 285

Ile Ile Asn Gln Gly Leu Ile Ser Val Lys Asp Ser Tyr Cys Ser Asn
290                 295                 300

Leu Ile Val Lys Gln Ile Glu Asn Arg Tyr Lys Ile Leu Asn Asn Ser
305                 310                 315                 320

Leu Asn Pro Ala Ile Ser Glu Asp Asn Asp Phe Asn Thr Thr Thr Asn
```

-continued

```
                325                 330                 335
Thr Phe Ile Asp Ser Ile Met Ala Glu Ala Asn Ala Asp Asn Gly Arg
            340                 345                 350

Phe Met Met Glu Leu Gly Lys Tyr Leu Arg Val Gly Phe Phe Pro Asp
        355                 360                 365

Val Lys Thr Thr Ile Asn Leu Ser Gly Pro Glu Ala Tyr Ala Ala Ala
    370                 375                 380

Tyr Gln Asp Leu Leu Met Phe Lys Glu Gly Ser Met Asn Ile His Leu
385                 390                 395                 400

Ile Glu Ala Asp Leu Arg Asn Phe Glu Ile Ser Lys Thr Asn Ile Ser
            405                 410                 415

Gln Ser Thr Glu Gln Glu Met Ala Ser Leu Trp Ser Phe Asp Asp Ala
            420                 425                 430

Arg Ala Lys Ala Gln Phe Glu Glu Tyr Lys Arg Asn Tyr Phe Glu Gly
        435                 440                 445

Ser Leu Gly Glu Leu Pro Glu Thr Gly Gly His His His His His His
    450                 455                 460
```

ANTIBODIES AGAINST *CLOSTRIDIUM DIFFICILE* TOXINS AND METHODS OF USING THE SAME

CROSS-REFERENCE TO RELATED APPLICATIONS

This application is a continuation of U.S. application Ser. No. 14/776,146, now U.S. Pat. No. 10,160,797, filed 14 Sep. 2015, which is a U.S. National Stage application of PCT/US2014/028637 filed 14 Mar. 2014, which claims the benefit of, and relies on the filing date of, U.S. provisional patent application No. 61/794,071, filed 15 Mar. 2013, the entire disclosure of which is incorporated herein by reference.

SEQUENCE LISTING

The instant application contains a Sequence Listing which has been submitted electronically in ASCII format and is hereby incorporated by reference in its entirety. Said ASCII copy, created on 17 Sep. 2018, is named 0171-0002-US-Substitute-SL and is 219 kilobytes in size.

FIELD

This application relates generally to antibodies against *Clostridium difficile* (*C. difficile*) toxins and methods of using the same to detect or treat *C. difficile* infections and/or *C. difficile*-associated disease.

BACKGROUND

*C. difficile* is a gram positive, anaerobic bacterium that causes gastrointestinal disease in humans. The bacteria are transmitted through feces and spread to food and other surfaces when people who are infected do not thoroughly wash their hands. *C. difficile* form spores that can persist outside of a human body for weeks or even months. Symptoms of *C. difficile* infection can range from diarrhea to life-threatening inflammation of the colon. *C. difficile* infections are the most common cause of infectious diarrhea in the healthcare setting (Cohen S H et al., Infect Control Hosp Epidemiol 2010; 31:431-55).

*C. difficile* infections are more frequent in older adults in a hospital or long-term care facility and commonly occur during or following antibiotic treatment, which disrupts the normal flora of the gut and permits the opportunistic *C. difficile* to colonize the gut. In more severe infections, the colon can become inflamed (colitis) or form patches of raw tissue that can bleed or produce pus (pseudomembranous colitis). Symptoms of severe *C. difficile* infection include watery diarrhea, abdominal cramping and pain, nausea, fever, dehydration, and weight loss.

*C. difficile* produces two cytotoxic enterotoxins, toxin A and toxin B, that have been identified as targets for therapeutic intervention. Toxins A and B are released by the bacteria into the gut and believed to be involved in causing *C. difficile*-associated disease (CDAD) or the symptoms associated with CDAD. Symptoms of CDAD can be reproduced in animal models by transfer of the toxins. Toxins A and B have glucosyl transferase activity, which is capable of transferring glucose residues from UDP-glucose to Rho-GTPases, thereby inactivating the GTPase proteins found inside the target host cell. Inhibition of the Rho-GTPases results in depolymerization of actin filaments within the host cell, leading to dysregulation of actin cytoskeleton and tight junction integrity, which in turn produces increased cell permeability and loss of barrier function, diarrhea, inflammation, and an influx of molecules associated with the innate immune response. Toxins A and B are found in fecal samples and can be used to diagnose *C. difficile* infection.

Once a *C. difficile* infection has been identified, it is best, if possible, to stop taking the antibiotic that caused the infection. The typical treatment for *C. difficile* is another antibiotic, usually metronidazole or fidaxomicin, for mild to moderate illness, or vancomycin for more severe symptoms. If effective, these antibiotics prevent *C. difficile* from growing and allow the normal flora to return and colonize the gut. However, in recent years, strains resistant to these antibiotics have been identified, as well as higher recurrence or reinfection rates. Another approach is taking probiotics. Probiotics are non-pathogenic microorganisms, such as bacteria or yeast that compete with *C. difficile* and help restore balance to the intestinal tract. For patients with severe pain or inflammation, another option is surgery to remove the diseased portion of the colon.

Therapeutic antibodies have been a rapidly emerging field in recent years and provide another possible strategy for treating *C. difficile* infections. Patients infected with *C. difficile* experience a wide range of symptoms, the reasons for which are not fully understood. However, antibodies may play a role, as patients who experience milder symptoms tend to possess high titers of anti-toxin A antibody serum titers, while patients susceptible to recurring infections have demonstrated low titers of circulating anti-toxin A antibodies (Hussack and Tanha, Toxins, 2010, (2): 998-1018). US2012/0269841 describes murine antibodies that bind mutant *C. difficile* toxin-A or anti-toxin B. WO2011/130650 describes murine anti toxin-A and anti-toxin B antibodies that were optionally humanized to reduce their immunogenicity, including the lead anti-toxin A antibody, PA-50, and the lead anti-toxin B antibody, PA-41. U.S. Pat. No. 8,257,709 describes anti toxin-A and anti-toxin B antibodies that were generated in transgenic mice, including the lead anti-toxin A antibody, 3D8, and the lead anti-toxin B antibody, 124-152. The transgenic mice contain human immunoglobulin genes encoding certain unrearranged human heavy chain and kappa light chain sequences and, thus, are less immunogenic than murine antibodies.

There remains an unmet need for effective treatment of *C. difficile* infection, particularly non-invasive treatments that are effective against antibiotic-resistant strains of *C. difficile* and/or against high-toxin producing strains, including therapeutic antibodies that present reduced immunogenicity while providing high binding affinity for *C. difficile* toxin A or toxin B and/or potent neutralization activity.

SUMMARY

The present disclosure provides antibodies that bind to *C. difficile* toxin A or *C. difficile* toxin B and can be used, for example, in methods of detecting or treating *C. difficile* infection.

One embodiment is directed to monoclonal antibodies that bind to *C. difficile* toxin A. The anti-toxin A antibodies are preferably human antibodies. In one embodiment, the anti-toxin A antibodies are recombinant antibodies.

One embodiment is directed to an isolated monoclonal antibody that binds to an epitope in the C-terminal receptor domain (CTD) of *C. difficile* toxin A, wherein the epitope comprises the amino acid sequence $X_1$TGWQTI (SEQ ID NO:232), where $X_1$ is A or V or the amino acid sequence of $X_2$TGWQTIX$_3$GKX$_4$YYF (SEQ ID NO:233), where $X_2$ is A or V, $X_3$ is N or D and $X_4$ is K or V.

Another embodiment is directed to an isolated monoclonal antibody that binds to *C. difficile* toxin A, wherein said antibody comprises a heavy chain variable domain and a light chain variable domain, and (a) wherein the heavy chain variable domain comprises a complementarity determining region 1 (CDR1) comprising the amino acid sequence of SEQ ID NO:6; a CDR2 comprising the amino acid sequence of SEQ ID NO:8; and a CDR3 comprising the amino acid sequence of SEQ ID NO:10; and wherein the light chain variable domain comprises: a CDR1 comprising the amino acid sequence of SEQ ID NO:13; a CDR2 comprising the amino acid sequence of SEQ ID NO:15; and a CDR3 comprising the amino acid sequence of SEQ ID NO:17;

(b) wherein the heavy chain variable domain comprises a CDR1 comprising the amino acid sequence of SEQ ID NO:24; a CDR2 comprising the amino acid sequence of SEQ ID NO:26; and a CDR3 comprising the amino acid sequence of SEQ ID NO:28; and wherein the light chain variable domain comprises: a CDR1 comprising the amino acid sequence of SEQ ID NO:31; a CDR2 comprising the amino acid sequence of SEQ ID NO:33; and a CDR3 comprising the amino acid sequence of SEQ ID NO:35;

(c) wherein the heavy chain variable domain comprises a CDR1 comprising the amino acid sequence of SEQ ID NO:42; a CDR2 comprising the amino acid sequence of SEQ ID NO:44; and a CDR3 comprising the amino acid sequence of SEQ ID NO:46; and wherein the light chain variable domain comprises: a CDR1 comprising the amino acid sequence of SEQ ID NO:49; a CDR2 comprising the amino acid sequence of SEQ ID NO:51; and a CDR3 comprising the amino acid sequence of SEQ ID NO:53;

(d) wherein the heavy chain variable domain comprises a CDR1 comprising the amino acid sequence of SEQ ID NO:60; a CDR2 comprising the amino acid sequence of SEQ ID NO:62; and a CDR3 comprising the amino acid sequence of SEQ ID NO:64; and wherein the light chain variable domain comprises: a CDR1 comprising the amino acid sequence of SEQ ID NO:67; a CDR2 comprising the amino acid sequence of SEQ ID NO:69; and a CDR3 comprising the amino acid sequence of SEQ ID NO:71; or (e) wherein the heavy chain variable domain comprises a CDR1 comprising the amino acid sequence of SEQ ID NO:78; a CDR2 comprising the amino acid sequence of SEQ ID NO:80; and a CDR3 comprising the amino acid sequence of SEQ ID NO:82; and wherein the light chain variable domain comprises: a CDR1 comprising the amino acid sequence of SEQ ID NO:85; a CDR2 comprising the amino acid sequence of SEQ ID NO:87; and a CDR3 comprising the amino acid sequence of SEQ ID NO:89.

Another embodiment is directed to an isolated monoclonal antibody that binds to *Clostridium difficile* toxin A, wherein said antibody comprises a heavy chain variable domain comprising the amino acid sequence of SEQ ID NO:2, SEQ ID NO:20, SEQ ID NO:38, SEQ ID NO:56, or SEQ ID NO:74 or a light chain variable domain comprising the amino acid sequence of SEQ ID NO:4, SEQ ID NO:22, SEQ ID NO:40, SEQ ID NO:58, or SEQ ID NO:76.

Another embodiment is directed to an isolated monoclonal antibody that binds to *C. difficile* toxin A, wherein said antibody comprises a heavy chain variable domain and a light chain variable domain, and (a) wherein the heavy chain variable domain comprises the amino acid sequence of SEQ ID NO:2 and the light chain variable domain comprises the amino acid sequence of SEQ ID NO:4;

(b) wherein the heavy chain variable domain comprises the amino acid sequence of SEQ ID NO:20 and the light chain variable domain comprises the amino acid sequence of SEQ ID NO:22;

(c) wherein the heavy chain variable domain comprises the amino acid sequence of SEQ ID NO:38 and the light chain variable domain comprises the amino acid sequence of SEQ ID NO:40;

(d) wherein the heavy chain variable domain comprises the amino acid sequence of SEQ ID NO:56 and the light chain variable domain comprises the amino acid sequence of SEQ ID NO:58; or (e) wherein the heavy chain variable domain comprises the amino acid sequence of SEQ ID NO:74 and the light chain variable domain comprises the amino acid sequence of SEQ ID NO:76.

Yet another embodiment is directed to an isolated, human monoclonal antibody that binds to the same epitope of *C. difficile* toxin A recognized by:

(a) an antibody having a heavy chain variable domain comprising the amino acid sequence of SEQ ID NO:2 and a light chain variable domain comprising the amino acid sequence of SEQ ID NO:4;

(b) an antibody having a heavy chain variable domain comprising the amino acid sequence of SEQ ID NO:20 and a light chain variable domain comprising the amino acid sequence of SEQ ID NO:22;

(c) an antibody having a heavy chain variable domain comprising the amino acid sequence of SEQ ID NO:38 and a light chain variable domain comprising the amino acid sequence of SEQ ID NO:40;

(d) an antibody having a heavy chain variable domain comprising the amino acid sequence of SEQ ID NO:56 and a light chain variable domain comprising the amino acid sequence of SEQ ID NO:58; or (e) an antibody having a heavy chain variable domain comprising the amino acid sequence of SEQ ID NO:74 and a light chain variable domain comprising the amino acid sequence of SEQ ID NO:76.

In another embodiment, the antibody is an isolated, human monoclonal antibody comprising at least one of the following characteristics:

(a) the antibody binds to *C. difficile* toxin A with a dissociation constant ($K_D$) equal to or less than 10 pM ($10^{-11}$M);

(b) the antibody neutralizes the in vitro cytotoxicity of *C. difficile* toxin A in the Vero monkey kidney cell line with an NT50 equal to or less than 3000 pM;

(c) the antibody neutralizes the *C. difficile* toxin A induced loss of transepithelial electrical resistance (TEER) in the T-84 cell line with an NT50 equal to or less than 6 nM; and/or (d) the antibody binds to toxin A produced by the strains of toxinotypes 0, III, V, XII, and XV.

The antibody may have at least two, at least three, or all four of the above-identified characteristics.

Another aspect is drawn to monoclonal antibodies that bind to *C. difficile* toxin B. The anti-toxin B antibodies are preferably human antibodies. In one embodiment, the anti-toxin B antibodies are recombinant antibodies.

One embodiment is directed to an isolated monoclonal antibody that binds to an epitope in the glucosyl transferase domain of *C. difficile* toxin B, wherein the epitope comprises the amino acid sequence SGRNK (SEQ ID NO:234), amino acids 56-80 of SEQ ID NO:231, or amino acids 10-520 of SEQ ID NO:231.

Another embodiment is directed to an isolated monoclonal antibody that binds to an epitope in the N-terminal translocation domain of *C. difficile* toxin B, wherein the epitope comprises amino acids 1110-1530 of SEQ ID NO:231.

Another embodiment is directed to an isolated monoclonal antibody that binds to an epitope in the receptor binding domain of *C. difficile* toxin B, wherein the epitope comprises amino acids 1750-2360 of SEQ ID NO:231.

Yet another embodiment is directed to an isolated monoclonal antibody that binds to *C. difficile* toxin B, wherein said antibody comprises a heavy chain variable domain and a light chain variable domain, and (a) wherein the heavy chain variable domain comprises a complementarity determining region 1 (CDR1) comprising the amino acid sequence of SEQ ID NO:96; a CDR2 comprising the amino acid sequence of SEQ ID NO:98; and a CDR3 comprising the amino acid sequence of SEQ ID NO:100; and wherein the light chain variable domain comprises: a CDR1 comprising the amino acid sequence of SEQ ID NO:103; a CDR2 comprising the amino acid sequence of SEQ ID NO:105; and a CDR3 comprising the amino acid sequence of SEQ ID NO:107;

(b) wherein the heavy chain variable domain comprises a CDR1 comprising the amino acid sequence of SEQ ID NO:114; a CDR2 comprising the amino acid sequence of SEQ ID NO:116; and a CDR3 comprising the amino acid sequence of SEQ ID NO:118; and wherein the light chain variable domain comprises: a CDR1 comprising the amino acid sequence of SEQ ID NO:121; a CDR2 comprising the amino acid sequence of SEQ ID NO:123; and a CDR3 comprising the amino acid sequence of SEQ ID NO:125;

(c) wherein the heavy chain variable domain comprises a CDR1 comprising the amino acid sequence of SEQ ID NO:132; a CDR2 comprising the amino acid sequence of SEQ ID NO:134; and a CDR3 comprising the amino acid sequence of SEQ ID NO:136; and wherein the light chain variable domain comprises: a CDR1 comprising the amino acid sequence of SEQ ID NO:139; a CDR2 comprising the amino acid sequence of SEQ ID NO:141; and a CDR3 comprising the amino acid sequence of SEQ ID NO:143;

(d) wherein the heavy chain variable domain comprises a CDR1 comprising the amino acid sequence of SEQ ID NO:150; a CDR2 comprising the amino acid sequence of SEQ ID NO:152; and a CDR3 comprising the amino acid sequence of SEQ ID NO:154; and wherein the light chain variable domain comprises: a CDR1 comprising the amino acid sequence of SEQ ID NO:157; a CDR2 comprising the amino acid sequence of SEQ ID NO:159; and a CDR3 comprising the amino acid sequence of SEQ ID NO:161;

(e) wherein the heavy chain variable domain comprises a CDR1 comprising the amino acid sequence of SEQ ID NO:168; a CDR2 comprising the amino acid sequence of SEQ ID NO:170; and a CDR3 comprising the amino acid sequence of SEQ ID NO:172; and wherein the light chain variable domain comprises: a CDR1 comprising the amino acid sequence of SEQ ID NO:175; a CDR2 comprising the amino acid sequence of SEQ ID NO:177; and a CDR3 comprising the amino acid sequence of SEQ ID NO:179; or (f) wherein the heavy chain variable domain comprises a CDR1 comprising the amino acid sequence of SEQ ID NO:186; a CDR2 comprising the amino acid sequence of SEQ ID NO:188; and a CDR3 comprising the amino acid sequence of SEQ ID NO:190; and wherein the light chain variable domain comprises: a CDR1 comprising the amino acid sequence of SEQ ID NO:193; a CDR2 comprising the amino acid sequence of SEQ ID NO:195; and a CDR3 comprising the amino acid sequence of SEQ ID NO:197.

One embodiment is directed to an isolated, monoclonal antibody that binds to *Clostridium difficile* toxin B, wherein said antibody comprises a heavy chain variable domain comprising the amino acid sequence of SEQ ID NO:92, SEQ ID NO:110, SEQ ID NO:128, SEQ ID NO:146, SEQ ID NO:164, or SEQ ID NO:182 or a light chain variable domain comprising the amino acid sequence of SEQ ID NO:94, SEQ ID NO:112, SEQ ID NO:130, SEQ ID NO:148, SEQ ID NO:166, or SEQ ID NO:184.

Another embodiment is directed to an isolated, monoclonal antibody that binds to *C. difficile* toxin B, wherein said antibody comprises a heavy chain variable domain and a light chain variable domain, and (a) wherein the heavy chain variable domain comprises the amino acid sequence of SEQ ID NO:92 and the light chain variable domain comprises the amino acid sequence of SEQ ID NO:94;

(b) wherein the heavy chain variable domain comprises the amino acid sequence of SEQ ID NO:110 and the light chain variable domain comprises the amino acid sequence of SEQ ID NO:112;

(c) wherein the heavy chain variable domain comprises the amino acid sequence of SEQ ID NO:128 and the light chain variable domain comprises the amino acid sequence of SEQ ID NO:130;

(d) wherein the heavy chain variable domain comprises the amino acid sequence of SEQ ID NO:146 and the light chain variable domain comprises the amino acid sequence of SEQ ID NO:148;

(e) wherein the heavy chain variable domain comprises the amino acid sequence of SEQ ID NO:164 and the light chain variable domain comprises the amino acid sequence of SEQ ID NO:166; or (f) wherein the heavy chain variable domain comprises the amino acid sequence of SEQ ID NO:182 and the light chain variable domain comprises the amino acid sequence of SEQ ID NO:184.

Yet another embodiment is directed to an isolated monoclonal antibody that binds to the same epitope of *C. difficile* toxin B recognized by:

(a) an antibody having a heavy chain variable domain comprising the amino acid sequence of SEQ ID NO:92 and a light chain variable domain comprising the amino acid sequence of SEQ ID NO:94;

(b) an antibody having a heavy chain variable domain comprising the amino acid sequence of SEQ ID NO:110 and a light chain variable domain comprising the amino acid sequence of SEQ ID NO:112;

(c) an antibody having a heavy chain variable domain comprising the amino acid sequence of SEQ ID NO:128 and a light chain variable domain comprising the amino acid sequence of SEQ ID NO:130;

(d) an antibody having a heavy chain variable domain comprising the amino acid sequence of SEQ ID NO:146 and a light chain variable domain comprising the amino acid sequence of SEQ ID NO:148;

(e) an antibody having a heavy chain variable domain comprising the amino acid sequence of SEQ ID NO:164 and a light chain variable domain comprising the amino acid sequence of SEQ ID NO:166; or (f) an antibody having a heavy chain variable domain comprising the amino acid sequence of SEQ ID NO:182 and a light chain variable domain comprising the amino acid sequence of SEQ ID NO:184.

In another embodiment, the antibody is an isolated, human monoclonal antibody comprising at least one of the following characteristics:
- (a) the antibody binds to *C. difficile* toxin B with a dissociation constant ($K_D$) equal to or less than 100 pM;
- (b) the antibody neutralizes the in vitro cytotoxicity of *C. difficile* toxin B in the Vero monkey kidney cell line with an NT50 equal to or less than 1000 pM;
- (c) the antibody neutralizes the *C. difficile* toxin B induced loss of transepithelial resistance electrical (TEER) in the T-84 cell line with an NT50 equal to or less than 200 pM; and/or
- (d) the antibody binds to toxin B produced by at least the strains of toxinotypes 0, III, and V.

The antibody may have at least two, at least three, or all four of the above-identified characteristics.

In another embodiment, the antibody binds to toxin B produced by at least the strains of toxinotypes 0, III, V, and VIII. In another embodiment, the antibody binds to toxin B produced by at least the strains of toxinotypes 0, III, V, VIII, and XII. In another embodiment, the antibody binds to toxin B produced by at least the strains of toxinotypes 0, III, V, VIII, XII, and XV.

In one embodiment, the antibody is a bispecific antibody, where the bispecific antibody comprises 1) a first antigen binding site comprising the heavy chain variable domain and light chain variable domain of an antibody that binds to *C. difficile* toxin A, as described herein, and 2) a second antigen binding site comprising the heavy chain variable domain and light chain variable domain of an antibody that binds to *C. difficile* toxin B, as described herein. In an alternative embodiment, the antibody is a bispecific antibody, where the bispecific antibody comprises two antigen binding sites, each antigen binding site comprising the heavy chain variable domain from an antibody that binds to *C. difficile* toxin A, as described herein, and the light chain variable domain from an antibody that binds to *C. difficile* B, as described herein. In a further alternative embodiment, the antibody is a bispecific antibody, where the bispecific antibody comprises two antigen binding sites, each antigen binding site comprising the heavy chain variable domain from an antibody that binds to *C. difficile* toxin B, as described herein, and the light chain variable domain from an antibody that binds to *C. difficile* toxin A, as described herein. In a further alternative embodiment, the antibody is a bispecific antibody, where the bispecific antibody comprises two antigen binding sites, each antigen binding site comprising the heavy chain variable domain from an antibody that binds to *C. difficile* toxin B, such as B1, and as further described herein, and the light chain variable domain from an antibody that binds to a different part of *C. difficile* toxin B, such as B2, and as further described herein.

In one embodiment of the bispecific antibody, the first antigen binding site comprises the heavy chain variable domain and light chain variable domain of the A1, A2, A3, A4, or A5 antibody. In another embodiment of the bispecific antibody, the second antigen binding site comprises the heavy chain variable domain and light chain variable domain of the B1, B2, B3, B4, B5, or B6 antibody. In yet another embodiment of the bispecific antibody, the first antigen binding site comprises the heavy chain variable domain and light chain variable domain of the A1, A2, A3, A4, or A5 antibody and the second antigen binding site comprises the heavy chain variable domain and light chain variable domain of the B1, B2, B3, B4, B5, or B6 antibody.

In another embodiment, the antibody is a bispecific antibody, where the bispecific antibody comprises 1) a first antigen binding site, wherein the first antigen binding site comprises the heavy chain variable domain and light chain variable domain of an antibody that binds to *C. difficile* toxin B, as described herein and 2) a second antigen binding site, wherein the second antigen binding site comprises the heavy chain variable domain and light chain variable domain of an antibody that binds to *C. difficile* toxin B, as described herein, wherein the first and second antigen binding sites are different. Preferably, the first and second antigen binding sites comprise the heavy chain variable domain and light chain variable domain of the B1, B2, B3, B4, B5, or B6 antibody, wherein the first and second antigen binding sites are different. In yet another embodiment of the bispecific antibody, the first antigen binding site comprises the heavy chain variable domain and light chain variable domain of the B1 antibody and the second antigen binding site comprises the heavy chain variable domain and light chain variable domain of the B2 antibody.

In a further embodiment, the antibody is a bispecific antibody, where the bispecific antibody comprises 1) a first antigen binding site, wherein the first antigen binding site comprises the heavy chain variable domain and light chain variable domain of an antibody that binds to *C. difficile* toxin A, as described herein and 2) a second antigen binding site, wherein the second antigen binding site comprises the heavy chain variable domain and light chain variable domain of an antibody that binds to *C. difficile* toxin A, as described herein, wherein the first and second antigen binding sites are different. Preferably, the first and second antigen binding sites comprise the heavy chain variable domain and light chain variable domain of the A1, A2, A3, A4, or A5 antibody, wherein the first and second antigen binding sites are different.

Another aspect is related to compositions comprising one or more of the A1, A2, A3, A4, A5, B1, B2, B3, B4, B5, or B6 antibodies, which compositions can be used, by way of example, for treating a *C. difficile* infection. In certain embodiments, the composition comprises one antibody that binds to *C. difficile* toxin A and one antibody that binds to *C. difficile* toxin B, as described herein. In one embodiment, the composition comprises at least one antibody that binds to *C. difficile* toxin A and at least one antibody that binds to *C. difficile* toxin B, wherein the at least one antibody that binds to *C. difficile* toxin A is preferably one or more of the A1, A2, A3, A4, and A5 antibodies. In another embodiment, the composition comprises at least one antibody that binds to *C. difficile* toxin A and at least one antibody that binds to *C. difficile* toxin B, wherein the at least one antibody that binds to *C. difficile* toxin B is preferably one or more of the B1, B2, B3, B4, B5, or B6 antibodies. In yet another embodiment, the at least one antibody that binds to *C. difficile* toxin A is preferably one or more of the A1, A2, A3, A4, and A5 antibodies and the at least one antibody that binds to *C. difficile* toxin B is preferably one or more of the B1, B2, B3, B4, B5, or B6 antibodies. These compositions can be used, by way of example, for treating a *C. difficile* infection. In one embodiment, the at least one antibody that binds to *C. difficile* toxin A is the A2 antibody and the at least one antibody that binds to *C. difficile* toxin B is one or more of the B1, B2, B3, B4, B5, or B6 antibodies, preferably one or more of B1, B2, B4 or B6. Thus, in certain embodiments, the composition comprises the A2 and B1 antibodies, the A2 and B2 antibodies, the A2 and B4 antibodies, or the A2 and B6 antibodies. In another embodiment, the at least one antibody that binds to *C. difficile* toxin A is the A1 antibody and the at least one antibody that binds to *C. difficile* toxin B is one or more of the B1, B2, B3, B4, B5, or B6 antibodies, preferably one or more of B1, B2, B4 or B6. Thus, in certain other embodiments, the composition comprises the A1 and B1 antibodies, the A1 and B2 antibodies, the A1 and B4 antibodies, or the A1 and B6 antibodies. In other embodiments, the composition further comprises a pharmaceutically acceptable excipient.

In other embodiments, the composition comprises a combination of at least three antibodies. In one embodiment, the composition comprises two antibodies that bind to *C. difficile* toxin A, as described herein, and one antibody that binds to *C. difficile* toxin B, as described herein. Alternatively, the composition comprises one antibody that binds to *C. difficile* toxin A, as described herein, and two antibodies that bind to *C. difficile* toxin B, as described herein.

In a further embodiment the composition comprises a three antibody combination comprising one antibody that binds to *C. difficile* toxin A, as described herein, and preferably selected from the A1, A2, A3, A4, and A5 antibodies, and two antibodies that bind to *C. difficile* toxin B, as described herein, which are preferably selected from the B1, B2, B3, B4, B5, or B6 antibodies. In one embodiment, the composition comprises the A2, B1 and B2 antibodies. In another embodiment, the composition comprises the A2, B2, and B4 antibodies. In another embodiment, the composition comprises the A2, B2, and B6 antibodies.

In another embodiment, the composition comprises a first antibody that binds to *C. difficile* toxin A, as described herein, which is preferably selected from the A1, A2, A3, A4, and A5 antibodies, more preferably the A2 antibody, and a second antibody, wherein the second antibody is a bispecific antibody that binds to *C. difficile* toxin B and wherein the bispecific antibody comprises 1) a first antigen binding site, wherein the first antigen binding site comprises the heavy chain variable domain and light chain variable domain of the B1, B2, B3, B4, B5, or B6 antibody and 2) a second antigen binding site, wherein the second antigen binding site comprises the heavy chain variable domain and light chain variable domain of the B1, B2, B3, B4, B5, or B6 antibody, wherein the first and second antigen binding sites are different. In one embodiment, the composition comprises the A2 antibody and a bispecific B1+B2 antibody, a bispecific B2+B4 antibody, or a bispecific B2+B6 antibody. In another embodiment, the composition comprises the A1 antibody and a bispecific B1+B2 antibody, a bispecific B2+B4 antibody, or a bispecific B2+B6 antibody.

Another aspect is directed to methods of using antibodies that bind to *C. difficile* toxin A and/or *C. difficile* toxin B to treat *C. difficile* infection. In one embodiment, the method of treating a *C. difficile* infection comprises administering to a subject one or more of the A1, A2, A3, A4, A5, B1, B2, B3, B4, B5, or B6 antibodies or a bispecific antibody derived therefrom, including, for example, a bispecific B1+B2 antibody, a bispecific B2+B4 antibody, or a bispecific B2+B6 antibody in an amount effective to treat the *C. difficile* infection. In another embodiment, the method of treating a *C. difficile* infection comprises administering a composition to the subject in an amount effective to treat the *C. difficile* infection, wherein the composition comprises at least one antibody that binds to *C. difficile* toxin A selected from the A1, A2, A3, A4, and A5 antibodies and at least one antibody that binds to *C. difficile* toxin B selected from the B1, B2, B3, B4, B5, or B6 antibodies or a bispecific antibody derived therefrom, including, for example, a bispecific B1+B2 antibody, a bispecific B2+B4 antibody, or a bispecific B2+B6 antibody. In one embodiment, the at least one antibody that binds to *C. difficile* toxin A is the A2 antibody and the at least one antibody that binds to *C. difficile* toxin B is one or more of the B1, B2, B3, B4, B5, or B6 antibodies or a bispecific antibody derived therefrom, preferably one or more of B1, B2, or B4, or a bispecific antibody selected from B1+B2 or B2+B4.

Another aspect is directed to nucleic acids that encode an antibody of interest, or portion(s) thereof. One embodiment is directed to an isolated nucleic acid that encodes the amino acid sequence of one or more of the CDRs of the light and/or heavy chain variable regions of an A2, A2, A3, A4, A5, B1, B2, B3, B4, B5, or B6 antibody, or a bispecific antibody derived therefrom, including, for example, a bispecific B1+B2 antibody, a bispecific B2+B4 antibody, or a bispecific B2+B6 antibody. Another embodiment is directed to an isolated nucleic acid that encodes an amino acid sequence of the light and/or heavy chain variable regions of the A1, A2, A3, A4, A5, B1, B2, B3, B4, B5, or B6 monoclonal antibody or a bispecific antibody derived therefrom, including, for example, a bispecific B1+B2 antibody, a bispecific B2+B4 antibody, or a bispecific B2+B6 antibody. Other embodiments are directed to a recombinant expression vector comprising the nucleic acid or an isolated host cell comprising the recombinant expression vector.

BRIEF DESCRIPTION OF THE DRAWINGS

The accompanying drawings, which are incorporated in and constitute a part of this specification, illustrate certain embodiments, and together with the written description, serve to explain certain principles of the antibodies and methods disclosed herein.

FIGS. 1A-B show the results of the Vero cell cytotoxicity assay for various antibodies with potency (NT50) represented on the x-axis and percent completion represented on the y-axis. FIG. 1A shows the results for the anti-toxin A antibodies A1, A2, A3, A4, and A5 and FIG. 1B shows the results for the anti-toxin B antibodies B1, B2, B3, B5, and B4+B6 (tested as combination).

FIG. 2A shows the results for the anti-toxin A antibodies A1, A2, A3, A4, and A5 while FIG. 2B shows the results for the anti-toxin B antibodies B1, B2, B3, B4, B5, and B6. The asterisks ("*") in FIG. 2A indicates that the plateau for these antibodies was never reached and, thus, these values (for % completion) represent minimum values.

FIG. 3 shows that *C. difficile* toxin A CTD fragments from strains of toxinotypes 0, III, V, XII, and XV inhibit the potent neutralization activity of the A2 antibody against toxin A of toxinotype 0 in Vero cells, demonstrating that the A2 antibody recognizes toxin A produced by the strains of toxinotypes 0, III, V, XII, and XV by this highly sensitive in vitro functional assay.

FIGS. 4A-B show the results of the T-84 cell TEER assay. FIG. 4A shows the results for the A2 antibody and *C. difficile* toxin A CTD fragments from strains of toxinotypes 0, III, V, XII, and XV, while FIG. 4B shows the results of the B6 antibody and *C. difficile* toxin B CTD fragments from strains of toxinotypes 0, III, V, VIII, XII, and XV, with the CTD fragments inhibiting the potent neutralization activity of the A2 antibody against toxin A of toxinotype 0 and the potent neutralization activity of the B6 antibody against toxin B of toxinotype 0 in T-84 cells.

FIGS. 5A-C show the therapeutic effects of antibody combinations A2+B6 or A2+B4 at a dosage of 50 mg/kg in a hamster model of CDAD. FIG. 5A shows the effects of the antibody combinations on survival, while FIG. 5B shows the effects on disease symptoms, where 0=no illness, 1=loose feces, 2=wet tail and perianal region, and 3=wet tail and lower abdomen. FIG. 5C shows weight change post-challenge with *C. difficile* spores (toxinotype 0 strain 630).

FIG. 10A shows the effects of the A2+B2 antibody combination on survival against infection with the toxinotype 0 strain VPI10463. FIG. 10B shows the effects of the A2+B2 antibody combination on survival against infection with the toxinotype III (ribotype 027) strain 13695 #7.

FIG. 11A shows the effects of antibody combinations at low dosage (6 mg/kg) on survival while FIG. 11B shows the effects of antibody combinations at high dosage (50 mg/kg) on survival.

FIG. 12A shows the effects of antibody combinations at low dosage (6 mg/kg) on illness while FIG. 12B shows the effects of antibody combinations at high dosage (50 mg/kg) on illness, where 0=no illness, 1=loose feces, 2=wet tail and perianal region, and 3=wet tail and lower abdomen.

DETAILED DESCRIPTION

Figure 2A:
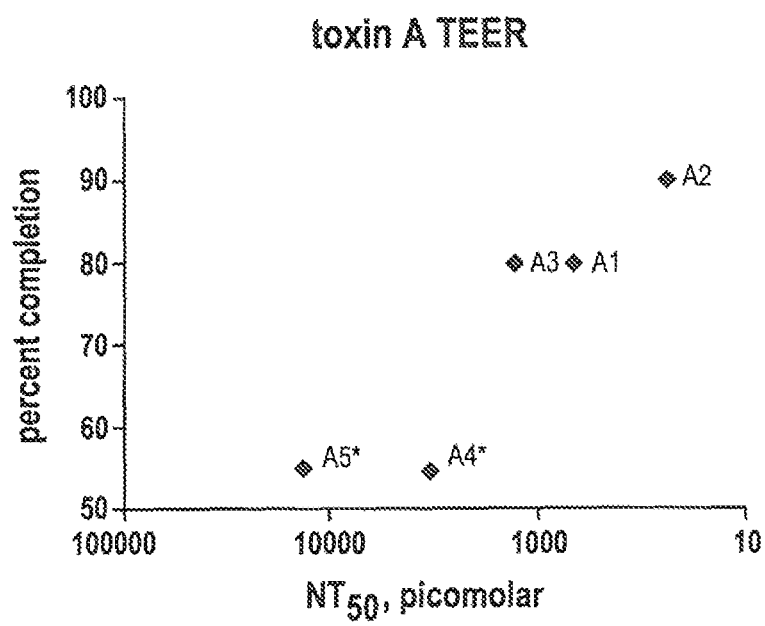
FIGS. 2A-B show the results of the T-84 cell TEER assay for various antibodies with potency (NT50) represented on the x-axis and percent completion represented on the y-axis.

Reference will now be made in detail to various exemplary embodiments, examples of which are illustrated in the accompanying drawings. It is to be understood that the following detailed description is provided to give the reader a fuller understanding of certain embodiments, features, and details of aspects of the invention, and should not be interpreted as a limitation of the scope of the invention.

1. Definitions

In order that the present invention may be more readily understood, certain terms are first defined. Additional definitions are set forth throughout the detailed description.

The term "antibody" as used in this disclosure refers to an immunoglobulin or an antigen-binding fragment thereof. Unless otherwise specified, the term includes, but is not limited to, polyclonal, monoclonal, monospecific, polyspecific, humanized, human, single-chain, chimeric, synthetic, recombinant, hybrid, mutated, grafted, and in vitro generated antibodies. The antibody can include a constant region, or a portion thereof, such as the kappa, lambda, alpha, gamma, delta, epsilon and mu constant region genes. For example, heavy chain constant regions of the various isotypes can be used, including: $IgG_1$, $IgG_2$, $IgG_3$, $IgG_4$, IgM, $IgA_1$, $IgA_2$, IgD, and IgE. By way of example, the light chain constant region can be kappa or lambda.

The terms "antigen-binding domain" and "antigen-binding fragment" refer to a part of an antibody molecule that comprises amino acids responsible for the specific binding between antibody and antigen. For certain antigens, the antigen-binding domain or antigen-binding fragment may only bind to a part of the antigen. The part of the antigen that is specifically recognized and bound by the antibody is referred to as the "epitope" or "antigenic determinant." Antigen-binding domains and antigen-binding fragments include Fab (Fragment antigen-binding); a F(ab')$_2$ fragment, a bivalent fragment having two Fab fragments linked by a disulfide bridge at the hinge region; Fv fragment; a single chain Fv fragment (scFv) see e.g., Bird et al. (1988) *Science* 242:423-426; and Huston et al. (1988) *Proc. Natl. Acad. Sci. USA* 85:5879-5883); a Fd fragment having the two $V_H$ and $C_H1$ domains; dAb (Ward et al., (1989) *Nature* 341:544-546), and other antibody fragments that retain antigen-binding function. The Fab fragment has $V_H$-$C_H1$ and $V_L$-$C_L$ domains covalently linked by a disulfide bond between the constant regions. The $F_v$ fragment is smaller and has $V_H$ and $V_L$ domains non-covalently linked. To overcome the tendency of non-covalently linked domains to dissociate, a $scF_v$ can be constructed. The $scF_v$ contains a flexible polypeptide that links (1) the C-terminus of $V_H$ to the N-terminus of $V_L$, or (2) the C-terminus of $V_L$ to the N-terminus of $V_H$. A 15-mer (Gly$_4$Ser)$_3$ (SEQ ID NO:331) peptide may be used as a linker, but other linkers are known in the art. These antibody fragments are obtained using conventional techniques known to those with skill in the art, and the fragments are evaluated for function in the same manner as are intact antibodies.

The terms "(cross)-block," "(cross)-blocked," "(cross)-blocking," "competitive binding," "(cross)-compete," "(cross)-competing," and "(cross)-competition" are used interchangeably herein to mean the ability of an antibody to interfere with the binding of other antibodies to a given target. The extent to which one antibody is able to interfere with the binding of another antibody to the target, and therefore whether it can be said to cross-block, as used herein, can be determined using competition binding assays. One particularly suitable quantitative cross-blocking assay uses a Biacore instrument which can measure the extent of interactions using surface plasmon resonance technology.

The following generally describes a suitable Biacore assay for determining whether an antibody cross-blocks or is capable of cross-blocking. It will be appreciated that the assay can be used with any of antibodies described herein. The Biacore instrument (for example the Biacore 3000) is operated in line with the manufacturer's recommendations. Thus in one cross-blocking assay, the target protein (e.g.

toxin A or toxin B) is coupled to a CMS Biacore chip using standard amine coupling chemistry to generate a surface that is coated with the target. Typically 200-800 resonance units of the target would be coupled to the chip (an amount that gives easily measurable levels of binding but that is readily saturable by the concentrations of test reagent being used), Two test binding agents {termed A* and B*} to be assessed for their ability to cross-block each other are mixed at a one to one molar ratio of binding sites in a suitable buffer to create the test mixture. When calculating the concentrations on a binding site basis the molecular weight of a binding agent is assumed to be the total molecular weight of the binding agent divided by the number of target binding sites on that binding agent. The concentration of each binding agent in the test mix should be high enough to readily saturate the binding sites for that binding agent on the target molecules captured on the Biacore chip. The binding agents in the mixture are at the same molar concentration (on a binding basis) and that concentration would typically be between 1.00 and 1.5 micromolar (on a binding site basis). Separate solutions containing A* alone and B* alone are also prepared. A* and B* in these solutions should be in the same buffer and at the same concentration as in the test mix. The test mixture is passed over the target-coated Biacore chip and the total amount of binding recorded. The chip is then treated in such a way as to remove the bound binding agents without damaging the chip-bound target. Typically this is done by treating the chip with 30 mM HCl for 60 seconds. The solution of A* alone is then passed over the target-coated surface and the amount of binding recorded. The chip is again treated to remove all of the bound binding agents without damaging the chip-bound target. The solution of B* alone is then passed over the target-coated surface and the amount of binding recorded. The maximum theoretical binding of the mixture of A* and B* is next calculated, and is the sum of the binding of each binding agent when passed over the target surface a lone. If the actual recorded binding of the mixture is less than this theoretical maximum then the two binding agents are said to cross-block each other. Thus, in general, a cross-blocking antibody is one which will bind to the target in the above Biacore cross-blocking assay such that during the assay and in the presence of a second antibody the recorded binding is between 80% and 0.1% of maximum theoretical binding {as defined above) of the two antibodies in combination. Other affinity assays may also be used, including the Octet assay, as described in the examples that follow.

As used herein, a "therapeutically effective amount" of an antibody refers to an amount of an antibody that is effective, upon single or multiple dose administration to a subject (such as a human patient) at treating *C. difficile* infection.

The terms "treatment of *C. difficile* infection" or "treating *C. difficile* infection" and the like refer to any treatment of any disease (e.g., CDAD) or condition in a subject caused by *C. difficile* infection and includes inhibiting a disease, condition, or symptom of a *C. difficile* infection, e.g., arresting its development and/or delaying or preventing its onset or manifestation in the subject; relieving a disease, condition, or symptom of a *C. difficile* infection, e.g., causing regression of the condition or disease and/or one or more of its symptoms (e.g., diarrhea, colitis, and/or abdominal pain); or preventing or reducing the recurrence or relapse of a disease, condition, or symptom of a *C. difficile* infection.

The terms "subject," "host," "patient," and "individual" are used interchangeably herein to refer to any mammalian subject for whom diagnosis or therapy is desired, particularly humans.

The term "pharmaceutically acceptable excipient" means solvents, diluents, dispersion media, coatings, antibacterial agents and antifungal agents, isotonic agents, solid and liquid fillers, and absorption delaying agents, and the like, that are suitable for administration into a human. The use of such media and agents for pharmaceutically active substances is well known in the art.

The term "human antibody" refers to an antibody having variable and constant regions corresponding substantially to human germline immunoglobulin sequences. A human antibody may also include amino acid residues not encoded by human germline immunoglobulin sequences (e.g., mutations introduced by random or site-specific mutagenesis in vitro or by somatic mutation in vivo), for example in the CDRs, and in particular, CDR3.

The term "recombinant antibody" refers to an antibody produced or expressed using a recombinant expression vector, where the expression vector comprises a nucleic acid encoding the recombinant antibody, such that introduction of the expression vector into an appropriate host cell results in the production or expression of the recombinant antibody.

The term "bispecific" or "bifunctional antibody" refers to an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992). For example, the bispecific antibody can comprises a first antigen binding site, such as a Fab' fragment, that binds to *C. difficile* toxin A and a second antigen binding site, such as a Fab' fragment, that binds to *C. difficile* toxin B. The first and second antigen binding site may be linked using any available technique, including, for example, an immunoglobulin constant region.

The term "neutralizing antibody" refers to an antibody whose binding an antigen results in inhibition of the biological activity of that antigen, respectively. For example, "toxin A neutralizing antibody" or "toxin B neutralizing antibody" (or an "antibody that neutralizes toxin A or toxin B activity") refers to an antibody whose binding to toxin A or toxin B results in the inhibition of the biological activity of toxin A or toxin B. This inhibition of the biological activity of toxin A or toxin B can be assessed by measuring one or more indicators of toxin A or toxin B biological activity, such as toxin A- or toxin B-induced cytotoxicity or loss of transepithelial electrical resistance (TEER), as demonstrated in the examples.

The term "isolated antibody," refers to an antibody that is substantially free of its natural environment, including other antibodies having different antigenic specificities (e.g., an isolated antibody that specifically binds *C. difficile* toxin A is substantially free of antibodies that specifically bind antigens other than *C. difficile* toxin A, unless the isolated antibody is combined with one or more isolated antibodies of interest, such as an antibody that specifically binds *C. difficile* toxin B).

The term "isolated nucleic acid," as used in the context of a nucleic acid encoding an antibody, or antigen-binding fragment thereof, refers to a nucleic acid molecule in which the nucleotide sequences encoding the antibody or antibody, or antigen-binding fragment thereof, are free of other nucleotide sequences encoding antibodies or portions thereof that bind antigens other than *C. difficile* toxin A or toxin B, which other sequences may naturally flank the nucleic acid in human genomic DNA. Thus, for example, an isolated nucleic acid encoding a VH region of an anti-toxin A antibody contains no other sequences encoding other VH regions that bind antigens other than *C. difficile* toxin A.

The term "identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. "Identity" and "similarity" can be readily calculated by known methods, including, but not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., Siam J. Applied Math., 48:1073 (1988). In addition, values for percentage identity can be obtained from amino acid and nucleotide sequence alignments generated using the default settings for the AlignX component of Vector NTI Suite 8.0 (Informax, Frederick, Md.).

Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12(1): 387 (1984)), BLASTP, BLASTN, and FASTA (Atschul, S. F. et al., J. Molec. Biol. 215:403-410 (1990). The BLAST X program is publicly available from NCBI and other sources (BLAST Manual, Altschul, S., et al., NCBINLM NIH Bethesda, Md. 20894: Altschul, S., et al., J. Mol. Biol. 215:403-410 (1990). The well-known Smith Waterman algorithm may also be used to determine identity.

2. Overview

The present application provides monoclonal antibodies that bind to either *C. difficile* toxin A or *C. difficile* toxin B with high affinity and exhibit potent neutralizing activity in both in vitro assays (Vero cell-based toxin neutralization assay and T-84 cell-based TEER assay) and in an art-recognized, in vivo animal model for *C. difficile* infection. Using a unique antibody discovery strategy, tens of millions of antibody producing B lymphocytes from selected human subjects were screened for binding to and/or neutralizing activity against *C. difficile* toxin A or B, selected for cloning and recombinant expression, and further characterization to identify specific human antibodies with high binding affinity for and strong neutralizing activity against either *C. difficile* toxin A or *C. difficile* toxin B, preferably with a broad spectrum of binding to various *C. difficile* toxinotypes, such as 0, III, V, VIII, XII, and XV. The human A1, A2, A3, A4, and A5 antibodies bind and neutralize *C. difficile* toxin A of toxinotype 0 and also recognize toxin A from toxinotypes III, V, XII, and XV. The human B1, B2, B3, B4, B5, and B6 antibodies bind and neutralize *C. difficile* toxin B from toxinotype 0 and also recognize toxin B from at least toxinotype III, and, in some instances, toxin B from at least toxinotypes, III, V, and VIII. These antibodies have therapeutic activity against active disease caused by or associated with *C. difficile* and can be used either singularly, or in combination, to treat *C. difficile* infections and/or to protect against the illness.

3. Antibodies

Antibodies, also known as immunoglobulins, are typically tetrameric glycosylated proteins composed of two light (L) chains of approximately 25 kDa each and two heavy (H) chains of approximately 50 kDa each. Two types of light chain, termed lambda and kappa, may be found in antibodies. Depending on the amino acid sequence of the constant domain of heavy chains, immunoglobulins can be assigned to five major classes: A, D, E, G, and M, and several of these may be further divided into subclasses (isotypes), e.g., $IgG_1$, $IgG_2$, $IgG_3$, $IgG_4$, $IgA_1$, and $IgA_2$. Each light chain includes an N-terminal variable (V) domain (VL) and a constant (C) domain (CL). Each heavy chain includes an N-terminal V domain (VH), three or four C domains (CHs), and a hinge region. The CH domain most proximal to VH is designated as CH1. The VH and VL domains consist of four regions of relatively conserved sequences called framework regions (FR1, FR2, FR3, and FR4), which form a scaffold for three regions of hypervariable sequences (complementarity determining regions, CDRs). The CDRs contain most of the residues responsible for specific interactions of the antibody with the antigen. CDRs are referred to as CDR1, CDR2, and CDR3. Accordingly, CDR constituents on the heavy chain are referred to as H1, H2, and H3, while CDR constituents on the light chain are referred to as L1, L2, and L3. Identification and numbering of framework and CDR residues is as described by Chothia et al., Structural determinants in the sequences of immunoglobulin variable domain, J Mol Biol 1998, 278:457-79, which is hereby incorporated by reference in its entirety.

CDR3 is typically the greatest source of molecular diversity within the antibody-binding site. H3, for example, can be as short as two amino acid residues or greater than 26 amino acids. The subunit structures and three-dimensional configurations of different classes of immunoglobulins are well known in the art. For a review of the antibody structure, see *Antibodies: A Laboratory Manual, Cold Spring Harbor Laboratory*, eds. Harlow et al., 1988. One of skill in the art will recognize that each subunit structure, e.g., a CH, VH, CL, VL, CDR, FR structure, comprises active fragments, e.g., the portion of the VH, VL, or CDR subunit the binds to the antigen, i.e., the antigen-binding fragment, or, e.g., the portion of the CH subunit that binds to and/or activates, e.g., an Fc receptor and/or complement. The CDRs typically refer to the Kabat CDRs, as described in *Sequences of Proteins of Immunological Interest, US Department of Health and Human Services* (1991), eds. Kabat et al. Another standard for characterizing the antigen binding site is to refer to the hypervariable loops as described by Chothia. See, e.g., Chothia, D. et al. (1992) *J. Mol. Biol.* 227:799-817; and Tomlinson et al. (1995) *EMBO J.* 14:4628-4638. Still another standard is the AbM definition used by Oxford Molecular's AbM antibody modeling software. See, generally, e.g., *Protein Sequence and Structure Analysis of Antibody Variable Domains*. In: *Antibody Engineering Lab Manual* (Ed. Duebel, S. and Kontermann, R., Springer-Verlag, Heidelberg). Embodiments described with respect to Kabat CDRs can alternatively be implemented using similar described relationships with respect to Chothia hypervariable loops or to the AbM-defined loops. Another standard for residue numbering that can be used is IMGT (Lefranc et al., Dev & Comp Immunol, 27(1):55-77 (2003).

The Fab fragment (Fragment antigen-binding) consists of $V_H$-$C_H1$ and $V_L$-$C_L$ domains covalently linked by a disulfide bond between the constant regions. The $F_v$ fragment is smaller and consists of $V_H$ and $V_L$ domains non-covalently linked. To overcome the tendency of non-covalently linked domains to dissociate, a single chain $F_v$ fragment (sc$F_v$) can be constructed. The sc$F_v$ contains a flexible connector, usually a polypeptide, that links (1) the C-terminus of $V_H$ to the N-terminus of $V_L$, or (2) the C-terminus of $V_L$ to the N-terminus of $V_H$. A 15-mer (Gly$_4$Ser)$_3$ (SEQ ID NO:331) peptide may be used as a linker, but other linkers are known in the art.

It is possible to modify an antibody to increase productivity and/or when relevant, to decrease possible immunogenicity. In addition, monoclonal antibodies may be modified at either the DNA sequence level to improve expression by removing hairpins or other secondary structure, by optimizing codon utilization, or at the amino acid level to improve expression or stability. For example, it is possible to remove residues such as unpaired cysteines to reduce aggregation, to alter glycosylation sites, or to substitute residues prone to deamidation or oxidization.

It may also be desirable to modify an antibody to improve effector function, e.g., so as to enhance antigen-dependent cell-mediated cytotoxicity (ADCC) and/or complement dependent cytotoxicity (CDC) of the antagonist. One or more amino acid substitutions or the introduction of cysteine in the Fc region may be made, thereby improving internalization capability and/or increased complement-mediated cell killing and ADCC. See Caron et al., J. Ex. Med. 176:1191-1195 (1991) and Shopes, B. J. Immunol. 148: 2918-2022 (1992), incorporated herein by reference in their entirety. An antibody fusion protein may be prepared that has dual Fc regions with both enhanced complement lysis and ADCC capabilities. Typical Fc receptors that bind to an Fc region of an antibody (e.g., an IgG antibody) include, but are not limited to, receptors of the FcγRI, FcγRII, and FcγRIII and FcRn subclasses, including allelic variants and alternatively spliced forms of these receptors. Fc receptors are reviewed in Ravetch and Kinet, *Annu. Rev. Immunol* 9:457-92, 1991; Capel et al., *Immunomethods* 4:25-34,1994; and de Haas et al., *J. Lab. Clin. Med.* 126:330-41, 1995). It is also possible to couple or join an antibody to another agent, such as a cytotoxic agent, drug, or therapeutic.

Anti-toxin A or anti-toxin B antibodies described in this application may optionally comprise antibody constant regions or parts thereof. For example, a $V_L$ domain may be attached at its C-terminal end to a light chain constant domain like Cκ or Cλ. Similarly, a $V_H$ domain or portion thereof may be attached to all or part of a heavy chain like IgA, IgD, IgE, IgG, and IgM, and any isotype subclass. Constant regions are known in the art (see, for example, Kabat et al., Sequences of Proteins of Immunological Interest, No. 91-3242, National Institutes of Health Publications, Bethesda, Md. (1991)).

VHH molecules (or nanobodies), as known to the skilled artisan, are heavy chain variable domains derived from immunoglobulins naturally devoid of light chains, such as those derived from Camelidae as described in WO 9404678, incorporated herein by reference. Such a VHH molecule can be derived from antibodies raised in Camelidae species, for example in camel, llama, dromedary, alpaca and guanaco and is sometimes called a camelid or camelized variable domain. See e.g., Muyldermans., *J. Biotechnology* (2001) 74(4):277-302, incorporated herein by reference. Other species besides Camelidae may produce heavy chain antibodies naturally devoid of light chain. VHH molecules are about 10 times smaller than IgG molecules. They are single polypeptides and very stable, resisting extreme pH and temperature conditions. Moreover, they are resistant to the action of proteases which is not the case for conventional antibodies. Furthermore, in vitro expression of VHHs produces high yield, properly folded functional VHHs. In addition, antibodies generated in Camelids will recognize epitopes other than those recognized by antibodies generated in vitro through the use of antibody libraries or via immunization of mammals other than Camelids (see WO 9749805, which is incorporated herein by reference).

The disclosed antibodies can be modified to alter their glycosylation; that is, at least one carbohydrate moiety can be deleted or added to the antibody. Deletion or addition of glycosylation sites can be accomplished by changing amino acid sequence to delete or create glycosylation consensus sites, which are well known in the art. Another means of adding carbohydrate moieties is the chemical or enzymatic coupling of glycosides to amino acid residues of the antibody (see WO 87/05330 and Aplin et al. (1981) *CRC Crit. Rev. Biochem.*, 22: 259-306). Removal of carbohydrate moieties can also be accomplished chemically or enzymatically (see Hakimuddin et al. (1987) *Arch. Biochem. Biophys.*, 259: 52; Edge et al. (1981) *Anal. Biochem.*, 118: 131; Thotakura et al. (1987) *Meth. Enzymol.*, 138: 350).

The antibodies of this invention may be tagged with a detectable or functional label. These labels include radiolabels (e.g., $^{131}$I or $^{99}$Tc), enzymatic labels (e.g., horseradish peroxidase or alkaline phosphatase), fluorescent labels, chemiluminescent labels, bioluminescent labels, and other chemical moieties (e.g., streptavidin/biotin, avidin/biotin).

4. *C. difficile* Toxin A and Toxin B

*C. difficile* produces two cytotoxic enterotoxins, toxins A and toxin B that are released by the bacteria into the gut and believed to be involved in causing the symptoms associated with *C. difficile* infection. The genes encoding toxins A and B, tcdA and tcdB, respectively, are located in the 19.6 kb *C. difficile* pathogenicity locus (PaLoc). Toxins A and B are high molecular weight proteins (about 308 and 270 kDa, respectively) consisting of four major structural domains, the N-terminal glucosyl transferase domain, a protease domain, a central, hydrophobic translocation domain, and a C-terminal receptor binding domain. The C terminus is responsible for toxin binding to the surface of epithelial cells and contains repeating oligopeptides that mediate binding to sugar moieties on the surface of target cells. After binding the cell surface receptor, the toxins enter the target cell via receptor-mediate endocytosis. The amino terminal domain contains the glucosyl transferase active site that modifies and inactivates the Rho/Ras superfamily of GTPase proteins found inside the target host cell. Inhibition of the Rho-GTPases results in depolymerization of actin filaments within the host cell, leading to dysregulation of actin cytoskeleton and tight junction integrity, which in turn produces increased cell permeability and loss of barrier function, resulting in diarrhea, inflammation, and an influx of innate immune response molecules.

The amino acid sequences of *C. difficile* toxin A are known. For example, the amino acid sequence of toxin A from Strain VPI10463 is set forth below.

(SEQ ID NO: 230)

```
   1 msliskeeli klaysirpre neyktiltnl deynklttnn nenkylqlkk lnesidvfmn
  61 kyktssrnra lsnlkkdilk eviliknsnt spveknlhfv wiggevsdia leyikqwadi
 121 naeyniklwy dseaflvntl kkaivesstt ealqlleeei qnpqfdnmkf ykkrmefiyd
 181 rqkrfinyyk sqinkptvpt iddiikshlv seynrdetvl esyrtnslrk insnhgidir
 241 anslfteqel lniysqelln rgnlaaasdi vrllalknfg gvyldvdmlp gihsdlfkti
 301 srpssigldr wemikleaim kykkyinnyt senfdkldqq lkdnfkliie sksekseifs
 361 klenlnvsdl eikiafalgs vinqaliskq gsyltnlvie qvknryqfln qhlnpaiesd
 421 nnftdttkif hdslfnsata ensmfltkia pylqvgfmpe arstislsgp gayasayydf
 481 inlqentiek tlkasdlief kfpennlsql teqeinslws fdqasakyqf ekyvrdytgg
 541 slsedngvdf nkntaldkny llnnkipsnn veeagsknyv hyiiqlqgdd isyeatcnlf
 601 sknpknsiii qrnmnesaks yflsddgesi lelnkyripe rlknkekvkv tfighgkdef
 661 ntsefarlsv dslsneissf ldtikldisp knvevnllgc nmfsydfnve etypgkllls
 721 imdkitstlp dvnknsitig anqyevrins egrkellahs gkwinkeeai msdlsskeyi
 781 ffdsidnklk aksknipgla sisediktll ldasvspdtk filnnlklni essigdyiyy
 841 eklepvknii hnsiddlide fnllenvsde lyelkklnnl dekylisfed isknnstysv
 901 rfinksnges vyvetekeif skysehitke istiknsiit dvngnlldni qldhtsqvnt
 961 lnaaffiqsl idyssnkdvl ndlstsvkvq lyaqlfstgl ntiydsiqlv nlisnavndt
1021 invlptiteg ipivstildg inlgaaikel ldehdpllkk eleakvgvla inmslsiaat
1081 vasivgigae vtifllpiag isagipslvn nelilhdkat svvnyfnhls eskkygplkt
1141 eddkilvpid dlviseidfn nnsiklgtcn ilameggsgh tvtgnidhff sspsisship
1201 slsiysaigi etenldfskk immlpnapsr vfwwetgavp glrslendgt rlldsirdly
1261 pgkfywrfya ffdyaittlk pvyedtniki kldkdtrnfi mptittneir nklsysfdga
1321 ggtyslllss ypistninls kddlwifnid nevreisien gtikkgklik dvlskidink
1381 nkliignqti dfsgdidnkd ryifltceld dkisliiein lvaksyslll sgdknylisn
1441 lsntiekint lgldskniay nytdesnnky fgaisktsqk siihykkdsk nilefyndst
1501 lefnskdfia edinvfmkdd intitgkyyv dnntdksidf sislvsknqv kvnglylnes
1561 vyssyldfvk nsdghhntsn fmnlfldnis fwklfgfeni nfvidkyftl vgktnlgyve
1621 ficdnnknid iyfgewktss skstifsgng rnvvvepiyn pdtgedists ldfsyeplyg
1681 idryinkvli apdlytslin intnyysney ypeiivlnpn tfhkkvninl dsssfeykws
1741 tegsdfilvr yleesnkkil qkirikgils ntqsfnkmsi dfkdikklsl gyimsnfksf
1801 nseneldrdh lgfkiidnkt yyydedsklv kglininnsl fyfdpiefnl vtgwqtingk
1861 kyyfdintga altsykiing khfyfnndgv mqlgvfkgpd gfeyfapant qnnniegqai
1921 vyqskfltln gkkyyfdnns kavtgwriin nekyyfnpnn aiaavglqvi dnnkyyfnpd
1981 taiiskgwqt vngsryyfdt dtaiafngyk tidgkhfyfd sdcvvkigvf stsngfeyfa
2041 pantynnnie gqaivyqskf ltlngkkyyf dnnskavtgl qtidskkyyf ntntaeaatg
2101 wqtidgkkyy fntntaeaat gwqtidgkky yfntntaias tgytiingkh fyfntdgimq
2161 igvfkgpngf eyfapantda nniegqaily qnefltlngk kyyfgsdska vtgwriinnk
2221 kyyfnpnnai aaihlctinn dkyyfsydgi lqngyitier nnfyfdanne skmvtgvfkg
2281 pngfeyfapa nthnnniegq aivyqnkflt lngkkyyfdn dskavtgwqt idgkkyyfnl
2341 ntaeaatgwq tidgkkyyfn lntaeaatgw qtidgkkyyf ntntfiastg ytsingkhfy
```

```
2401 fntdgimqig vfkgpngfey fapantdann iegqailyqn kfltlngkky yfgsdskavt 2461 glrtidgkky yfntntavav tgwqtingkk yyfntntsia stgytiisgk hfyfntdgim 2521 qigvfkgpdg feyfapantd anniegqair yqnrflylhd niyyfgnnsk aatgwvtidg 2581 nryyfepnta mgangyktid nknfyfrngl pqigvfkgsn gfeyfapant danniegqai 2641 ryqnrflhll gkiyyfgnns kavtgwqtin gkvyyfmpdt amaaagglfe idgviyffgv 2701 dgvkapgiyg
```

Similarly, the amino acid sequences of *C. difficile* toxin B are known. For example, the amino acid sequence of toxin B from Strain VPI10463 is set forth below.

```
                                                              (SEQ ID NO: 231)
   1 mslvnrkqle kmanvrfrtq edeyvailda leeyhnmsen tvvekylklk dinsltdiyi 61 dtykksgrnk alkkfkeylv tevlelknnn ltpveknlhf vwiggqindt ainyinqwkd 121 vnsdynvnvf ydsnaflint lkktvvesai ndtlesfren lndprfdynk ffrkrmeiiy 181 dkqknfinyy kaqreenpel iiddivktyl sneyskeide lntyieesln kitqnsgndv 241 rnfeefknge sfnlyeqelv erwnlaaasd ilrisalkei ggmyldvdml pgiqpdlfes 301 iekpssvtvd fwemtkleai mkykeyipey tsehfdmlde evqssfesvl asksdkseif 361 sslgdmeasp levkiafnsk giinqglisv kdsycsnliv kqienrykil nnslnpaise 421 dndfntttnt fidsimaean adngrfmmel gkylrvgffp dvkttinlsg peayaaayqd 481 llmfkegsmn ihlieadlrn feisktnisq steqemaslw sfddarakaq feeykrnyfe 541 gslgeddnld fsqnivvdke yllekissla rssergyihy ivqlqgdkis yeaacnlfak 601 tpydsvlfqk niedseiayy ynpgdgeiqe idkykipsii sdrpkikltf ighgkdefnt 661 difagfdvds lsteieaaid lakedispks ieinllgcnm fsysinveet ypgklllkvk 721 dkiselmpsi sqdsiivsan qyevrinseg rrelldhsge winkeesiik disskeyisf 781 npkenkitvk sknlpelstl lqeirnnsns sdieleekvm lteceinvis nidtqiveer 841 ieeaknltsd sinyikdefk liesisdalc dlkqqneled shfisfedis etdegfsirf 901 inketgesif vetektifse yanhiteeis kikgtifdtv ngklvkkvnl dtthevntln 961 aaffiqslie ynsskeslsn lsvamkvqvy aqlfstglnt itdaakvvel vstaldetid 1021 llptlseglp iiatiidgvs lgaaikelse tsdpllrqei eakigimavn lttattaiit 1081 sslgiasgfs illvplagis agipslvnne lvlrdkatkv vdyfkhvslv etegvftlld 1141 dkimmpqddl viseidfnnn sivlgkceiw rmeggsghtv tddidhffsa psityrephl 1201 siydvlevqk eeldlskdlm vlpnapnrvf awetgwtpgl rslendgtkl ldrirdnyeg 1261 efywryfafi adalittlkp ryedtnirin ldsntrsfiv piitteyire klsysfygsg 1321 gtyalslsqy nmginielse sdvwiidvdn vvrdvtiesd kikkgdlieg ilstlsieen 1381 kiilnshein fsgevngsng fvsltfsile ginaiievdl lsksykllis gelkilmlns 1441 nhiqqkidyi gfnselqkni pysfvdsegk engfingstk eglfvselpd vvliskvymd 1501 dskpsfgyys nnlkdvkvit kdnvniltgy ylkddikisl sltlqdekti klnsvhldes 1561 gvaeilkfmn rkgntntsds lmsflesmni ksifvnflqs nikfildanf iisgttsigq 1621 feficdendn iqpyfikfnt letnytlyvg nrqnmivepn ydlddsgdis stvinfsqky 1681 lygidscvnk vvispniytd einitpvyet nntypevivl danyinekin vnindlsiry 1741 vwsndgndfi lmstseenkv sqvkirfvnv fkdktlankl sfnfsdkqdv pvseiilsft 1801 psyyedglig ydlglvslyn ekfyinnfgm mvsgliyind slyyfkppvn nlitgfvtvg
```

```
1861 ddkyyfnpin ggaasigeti iddknyyfnq sgvlqtgvfs tedgfkyfap antldenleg 1921 eaidftgkli ideniyyfdd nyrgavewke ldgemhyfsp etgkafkgln qigdykyyfn 1981 sdgvmqkgfv sindnkhyfd dsgvmkvgyt eidgkhfyfa engemqigvf ntedgfkyfa 2041 hhnedlgnee geeisysgil nfnnkiyyfd dsftavvgwk dledgskyyf dedtaeayig 2101 lslindgqyy fnddgimqvg fvtindkvfy fsdsgiiesg vqniddnyfy iddngivqig 2161 vfdtsdgyky fapantvndn iygqaveysg lvrvgedvyy fgetytietg wiydmenesd 2221 kyyfnpetkk ackginlidd ikyyfdekgi mrtglisfen nnyyfnenge mqfgyinied 2281 kmfyfgedgv mqigvfntpd gfkyfahqnt ldenfegesi nytgwldlde kryyftdeyi 2341 aatgsviidg eeyyfdpdta qlvise
```

C. difficile strains are classified into variant toxinotypes according to variations in restriction sites within the DNA sequence of the PaLoc encoding toxins A and B. Currently 27 such variant toxinotypes are recognized (I to XXVII). Toxinotype 0 includes strains with restriction patterns identical to the reference laboratory strain VPI 10463 (ATCC43255) and is the most prevalent toxinotype. In a survey of strains in various culture collections worldwide, the toxinotypes 0, III, V, and VIII (toxin B only) are the most common. (Rupnik, FEMS Microbiol Rev 32 (2008) 541-555.)

5. Anti-Toxin A Antibodies

This disclosure provides antibodies that bind to C. difficile toxin A, including human, monoclonal antibodies having 1) high binding affinity, 2) potent in vitro neutralization activity, and 3) optionally with a broad spectrum of binding to various toxinotypes. Thus, in one embodiment, the antibody has at least one of the following characteristics:

(a) the antibody binds to C. difficile toxin A with a dissociation constant ($K_D$) equal to or less than 10 pM ($10^{-11}$M);

(b) the antibody neutralizes the in vitro cytotoxicity of C. difficile toxin A in the Vero monkey kidney cell line with an NT50 equal to or less than 3000 pM;

(c) the antibody neutralizes the C. difficile toxin A induced loss of transepithelial electrical resistance (TEER) in the T-84 cell line with an NT50 equal to or less than 6 nM; and/or (d) the antibody binds to toxin A produced by strains of toxinotypes 0, III, V, XII, and XV.

The antibody may have at least two, at least three, or all 4 of the above-identified characteristics.

In one embodiment, the human, monoclonal antibody binds to C. difficile toxin A with a dissociation constant ($K_D$) equal to or less than 500 pM, 250 pM, 200 pM, 150 pM, 100 pM ($10^{-10}$M) 10 pM ($10^{-11}$M), 1 pM ($10^{-12}$M, 0.1 pM ($10^{-13}$M), 0.01 pM ($10^{-14}$M), or 0.001 pM ($10^{-15}$M). The dissociation constant may be measured using techniques known in the art. In one embodiment, the dissociation constant is measured using biolayer interferometry, as described in the examples of this application.

In another embodiment, the human, monoclonal antibody neutralizes the in vitro cytotoxicity of C. difficile toxin A at 2.4 ng/mL in the Vero monkey kidney cell line with an NT50 equal to or less than 3000 pM, 2000 pM, 1000 pM, 100 pM, 60 pM, or 50 pM. For the sake of consistency, when measuring the neutralizing activity in the Vero monkey kidney cell line, Vero cells ($2.5 \times 10^4$ cells/well with 5% heat-inactivated FBS) are seeded in a 96-well tissue culture microtiter plates and incubated 37° C. overnight. An equal volume (80 µl) of 4.8 ng/mL (8×MC50) C. difficile toxin A solution and individual dilutions of the antibody solutions (80 µl) in Vero cell medium are combined in a new 96-well plate, and incubated at 37° C., 5% $CO_2$ for 1 hour before 100 µl of the toxin/antibody solutions are added to the Vero cells, and incubated at 37° C. for 72 hours. After incubating for 72 hours, the cells are washed twice with 120 µl/each of MEM medium that does not contain phenol, L-glutamine and FBS before adding 100 µl MEM medium that does not contain phenol, L-glutamine and FBS and 10 µl of Alamar Blue® (Life Technologies) to each well. The plates are lightly mixed and incubated at 37° C. for 4 hours before reading fluorescence at 560-590 nm with a cut off at 590 nm.

In yet another embodiment, the human, monoclonal antibody neutralizes the C. difficile toxin A (at 200 ng/mL applied apically) induced loss of transepithelial electrical resistance (TEER) in the T-84 cell line with an NT50 equal to or less than 6 nM, 5 nM, 2 nM, or 1.5 nM. For the sake of consistency, when measuring TEER, T-84 cells are seeded into 0.4 micron polyester transwell plates at a seeding density of $3.6 \times 10^5$ cells/$cm^2$ and maintained at 37° C., 5% $CO_2$ in 10% heat-inactivated FBS in DMEM/F12 culture media for 10-12 days until stable TEER achieved and media is replaced in both apical and basolateral compartments of the transwells daily from day 6 and on the day of assay. The C. difficile toxin A (final concentration of 200 ng/mL) is combined 1:1 with an antibody and incubated at 37° C. with gentle rocking for 30 minutes before replacing the media in the apical compartment with the toxin/antibody samples. Transepithelial electrical resistance of the T-84 cells is measured at $T_0$ immediately before sample addition and after 2.5 hours ($T_{150}$) incubation at 37° C. 5% $CO_2$.

In another embodiment, the human, monoclonal antibody binds to toxin A produced by the strains of toxinotypes 0, III, V, XII, and XV. Toxinotype binding may be measured using techniques known in the art, including the techniques described in the examples of this application, such as Western analysis. In another embodiment, for antibodies that bind to an epitope in the C-terminal domain (CTD) of toxin A or toxin B, the toxinotype can be measured using a CTD competition assay, as described in the examples of this application.

In another embodiment, the human, monoclonal anti-toxin A antibody has an on rate constant ($K_{on}$) to toxin A of at least $10^5 M^{-1} s^{-1}$. In another embodiment, the human, monoclonal anti-toxin A antibody has an off rate constant ($K_{off}$) to toxin A of $10^{-4} s^{-1}$, $10^{-5} s^{-1}$, $10^{-6} s^{-1}$, $10^{-7} s^{-1}$, or $10^{-8} s^{-1}$, or less. The $K_{on}$ and $K_{off}$ may be measured using techniques known in the art. In one embodiment, the dissociation constant is measured using biolayer interferometry, as described in the examples of this application.

In one embodiment, the antibody is an isolated A1 antibody. As used herein, the term "A1" refers to a monoclonal antibody, or antigen-binding fragment thereof, that binds to *C. difficile* toxin A, wherein the antibody comprises 1) a heavy chain variable domain comprising the amino acid sequence of SEQ ID NO:20 and a light chain variable domain comprising the amino acid sequence of SEQ ID NO:22; or 2) a heavy chain variable domain comprising a CDR1 comprising the amino acid sequence of SEQ ID NO:24, a CDR2 comprising the amino acid sequence of SEQ ID NO:26, and a CDR3 comprising the amino acid sequence of SEQ ID NO:28 and a light chain variable domain comprising a CDR1 comprising the amino acid sequence of SEQ ID NO:31, a CDR2 comprising the amino acid sequence of SEQ ID NO:33, and a CDR3 comprising the amino acid sequence of SEQ ID NO:35. In one embodiment, the monoclonal antibody comprises a heavy chain variable domain comprising a FR1 comprising the amino acid sequence SEQ ID NO:23, a CDR1 comprising the amino acid sequence of SEQ ID NO:24, a FR2 comprising the amino acid sequence SEQ ID NO:25, a CDR2 comprising the amino acid sequence of SEQ ID NO:26, a FR3 comprising the amino acid sequence SEQ ID NO:27, a CDR3 comprising the amino acid sequence of SEQ ID NO:28, and a FR4 comprising the amino acid sequence SEQ ID NO:29 and a light chain variable domain comprising a FR1 comprising the amino acid sequence SEQ ID NO:30, a CDR1 comprising the amino acid sequence of SEQ ID NO:31, a FR2 comprising the amino acid sequence SEQ ID NO:32, a CDR2 comprising the amino acid sequence of SEQ ID NO:33, a FR3 comprising the amino acid sequence SEQ ID NO:34, a CDR3 comprising the amino acid sequence of SEQ ID NO:35, and a FR4 comprising the amino acid sequence SEQ ID NO:36. In yet another embodiment, the antibody is a monoclonal antibody that binds to a *C. difficile* toxin A epitope that is recognized by the A1 antibody, such that the monoclonal antibody competitively inhibits, or cross-blocks, the binding of the A1 antibody to *C. difficile* toxin A.

In another embodiment, the antibody is an isolated A2 antibody. As used herein, the term "A2" refers to a monoclonal antibody, or antigen-binding fragment thereof, that binds to *C. difficile* toxin A, wherein the antibody comprises 1) a heavy chain variable domain comprising the amino acid sequence of SEQ ID NO:2 and a light chain variable domain comprising the amino acid sequence of SEQ ID NO:4; or 2) a heavy chain variable domain comprising a CDR1 comprising the amino acid sequence of SEQ ID NO:6, a CDR2 comprising the amino acid sequence of SEQ ID NO:8, and a CDR3 comprising the amino acid sequence of SEQ ID NO:10 and a light chain variable domain comprising a CDR1 comprising the amino acid sequence of SEQ ID NO:13, a CDR2 comprising the amino acid sequence of SEQ ID NO:15, and a CDR3 comprising the amino acid sequence of SEQ ID NO:17. In one embodiment, the monoclonal antibody comprises a heavy chain variable domain comprising a FR1 comprising the amino acid sequence SEQ ID NO:5, a CDR1 comprising the amino acid sequence of SEQ ID NO:6, a FR2 comprising the amino acid sequence SEQ ID NO:7, a CDR2 comprising the amino acid sequence of SEQ ID NO:8, a FR3 comprising the amino acid sequence SEQ ID NO:9, a CDR3 comprising the amino acid sequence of SEQ ID NO:10, and a FR4 comprising the amino acid sequence SEQ ID NO:11 and a light chain variable domain comprising a FR1 comprising the amino acid sequence SEQ ID NO:12, a CDR1 comprising the amino acid sequence of SEQ ID NO:13, a FR2 comprising the amino acid sequence SEQ ID NO:14, a CDR2 comprising the amino acid sequence of SEQ ID NO:15, a FR3 comprising the amino acid sequence of SEQ ID NO:16, a CDR3 comprising the amino acid sequence of SEQ ID NO:17, and a FR4 comprising the amino acid sequence SEQ ID NO:18. In yet another embodiment, the antibody is a monoclonal antibody that binds to a *C. difficile* toxin A epitope that is recognized by the A2 antibody, such that the monoclonal antibody competitively inhibits, or cross-blocks, the binding of the A2 antibody to *C. difficile* toxin A.

The A2 antibody binds to an epitope in the C-terminal receptor domain of *C. difficile* toxin A that comprises the amino acid sequence of $X_1$TGWQTI (SEQ ID NO:232), where $X_1$ is A or V or the amino acid sequence of $X_2$TGWQTI$X_3$GK$X_4$YYF (SEQ ID NO:233), where $X_2$ is A or V, $X_3$ is N or D and $X_4$ is K or V. Thus, another embodiment is directed to an isolated monoclonal antibody that binds to an epitope in the C-terminal receptor domain of *C. difficile* toxin A that comprises the amino acid sequence of $X_1$TGWQTI (SEQ ID NO:232), where $X_1$ is A or V or the amino acid sequence of $X_2$TGWQTI$X_3$GK$X_4$YYF (SEQ ID NO:233), where $X_2$ is A or V, $X_3$ is N or D and $X_4$ is K or V.

In another embodiment, the antibody is an isolated A3 antibody. As used herein, the term "A3" refers to a monoclonal antibody, or antigen-binding fragment thereof, that binds to *C. difficile* toxin A, wherein the antibody comprises 1) a heavy chain variable domain comprising the amino acid sequence of SEQ ID NO:38 and a light chain variable domain comprising the amino acid sequence of SEQ ID NO:40; or 2) a heavy chain variable domain comprising a CDR1 comprising the amino acid sequence of SEQ ID NO:42, a CDR2 comprising the amino acid sequence of SEQ ID NO:44, and a CDR3 comprising the amino acid sequence of SEQ ID NO:46 and a light chain variable domain comprising a CDR1 comprising the amino acid sequence of SEQ ID NO:49, a CDR2 comprising the amino acid sequence of SEQ ID NO:51, and a CDR3 comprising the amino acid sequence of SEQ ID NO:53. In one embodiment, the monoclonal antibody comprises a heavy chain variable domain comprising a FR1 comprising the amino acid sequence SEQ ID NO:41, a CDR1 comprising the amino acid sequence of SEQ ID NO:42, a FR2 comprising the amino acid sequence SEQ ID NO:43, a CDR2 comprising the amino acid sequence of SEQ ID NO:44, a FR3 comprising the amino acid sequence SEQ ID NO:45, a CDR3 comprising the amino acid sequence of SEQ ID NO:46, and a FR4 comprising the amino acid sequence SEQ ID NO:47 and a light chain variable domain comprising a FR1 comprising the amino acid sequence SEQ ID NO:48, a CDR1 comprising the amino acid sequence of SEQ ID NO:49, a FR2 comprising the amino acid sequence SEQ ID NO:50, a CDR2 comprising the amino acid sequence of SEQ ID NO:51, a FR3 comprising the amino acid sequence SEQ ID NO:52, a CDR3 comprising the amino acid sequence of SEQ ID NO:53, and a FR4 comprising the amino acid sequence SEQ ID NO:54. In yet another embodiment, the antibody is a monoclonal antibody that binds to a *C. difficile* toxin A epitope that is recognized by the A3 antibody, such that the monoclonal antibody competitively inhibits, or cross-blocks, the binding of the A3 antibody to *C. difficile* toxin A.

In another embodiment, the antibody is an isolated A4 antibody. As used herein, the term "A4" refers to a monoclonal antibody, or antigen-binding fragment thereof, that binds to *C. difficile* toxin A, wherein the antibody comprises 1) a heavy chain variable domain comprising the amino acid sequence of SEQ ID NO:56 and a light chain variable domain comprising the amino acid sequence of SEQ ID NO:58; or 2) a heavy chain variable domain comprising a CDR1 comprising the amino acid sequence of SEQ ID NO:60, a CDR2 comprising the amino acid sequence of SEQ ID NO:62, and a CDR3 comprising the amino acid sequence of SEQ ID NO:64 and a light chain variable domain comprising a CDR1 comprising the amino acid sequence of SEQ ID NO:67, a CDR2 comprising the amino acid sequence of SEQ ID NO:69, and a CDR3 comprising the amino acid sequence of SEQ ID NO:71. In one embodiment, the monoclonal antibody comprises a heavy chain variable domain comprising a FR1 comprising the amino acid sequence SEQ ID NO:59, a CDR1 comprising the amino acid sequence of SEQ ID NO:60, a FR2 comprising the amino acid sequence SEQ ID NO:61, a CDR2 comprising the amino acid sequence of SEQ ID NO:62, a FR3 comprising the amino acid sequence SEQ ID NO:63, a CDR3 comprising the amino acid sequence of SEQ ID NO:64, and a FR4 comprising the amino acid sequence SEQ ID NO:65 and a light chain variable domain comprising a FR1 comprising the amino acid sequence SEQ ID NO:66, a CDR1 comprising the amino acid sequence of SEQ ID NO:67, a FR2 comprising the amino acid sequence SEQ ID NO:68, a CDR2 comprising the amino acid sequence of SEQ ID NO:69, a FR3 comprising the amino acid sequence SEQ ID NO:70, a CDR3 comprising the amino acid sequence of SEQ ID NO:71, and a FR4 comprising the amino acid sequence SEQ ID NO:72. In yet another embodiment, the antibody is a monoclonal antibody that binds to a *C. difficile* toxin A epitope that is recognized by the A4 antibody, such that the monoclonal antibody competitively inhibits, or cross-blocks, the binding of the A4 antibody to *C. difficile* toxin A.

In another embodiment, the antibody is an isolated A5 antibody. As used herein, the term "A5" refers to a monoclonal antibody, or antigen-binding fragment thereof, that binds to *C. difficile* toxin A, wherein the antibody comprises 1) a heavy chain variable domain comprising the amino acid sequence of SEQ ID NO:74 and a light chain variable domain comprising the amino acid sequence of SEQ ID NO:76; or 2) a heavy chain variable domain comprising a CDR1 comprising the amino acid sequence of SEQ ID NO:78, a CDR2 comprising the amino acid sequence of SEQ ID NO:80, and a CDR3 comprising the amino acid sequence of SEQ ID NO:82 and a light chain variable domain comprising a CDR1 comprising the amino acid sequence of SEQ ID NO:85, a CDR2 comprising the amino acid sequence of SEQ ID NO:87, and a CDR3 comprising the amino acid sequence of SEQ ID NO:89. In one embodiment, the monoclonal antibody comprises a heavy chain variable domain comprising a FR1 comprising the amino acid sequence SEQ ID NO:77, a CDR1 comprising the amino acid sequence of SEQ ID NO:78, a FR2 comprising the amino acid sequence SEQ ID NO:79, a CDR2 comprising the amino acid sequence of SEQ ID NO:80, a FR3 comprising the amino acid sequence SEQ ID NO:81, a CDR3 comprising the amino acid sequence of SEQ ID NO:82, and a FR4 comprising the amino acid sequence SEQ ID NO:83 and a light chain variable domain comprising a FR1 comprising the amino acid sequence SEQ ID NO:84, a CDR1 comprising the amino acid sequence of SEQ ID NO:85, a FR2 comprising the amino acid sequence SEQ ID NO:86, a CDR2 comprising the amino acid sequence of SEQ ID NO:87, a FR3 comprising the amino acid sequence SEQ ID NO:88, a CDR3 comprising the amino acid sequence of SEQ ID NO:89, and a FR4 comprising the amino acid sequence SEQ ID NO:90. In yet another embodiment, the antibody is a monoclonal antibody that binds to a *C. difficile* toxin A epitope that is recognized by the A5 antibody, such that the monoclonal antibody competitively inhibits, or cross-blocks, the binding of the A5 antibody to *C. difficile* toxin A.

Whether an antibody competitively inhibits the binding of an antibody to *C. difficile* toxin A can be assessed using routine methods in the art, including, for example, the Octet methods described in the examples of this application and other routine quantitative methods, such as the Biacore assay. In one embodiment, competitive binding is measured using biolayer interferometry.

The amino acid and nucleotide sequences for the $V_H$ and $V_L$ domains of the A1 antibody are as follows:

```
A1 heavy chain nucleic acid
                                            (SEQ ID NO: 19)
ATGAAACATCTGTGGTTCTTCCTTCTCCTGGTGGCAGCCCCCAGATGGGT

CCTGTCCCAGGTGCACCTGCAGGAGTCGGGCCCAGGACTGGTGAAGCCTT

CGGAGACCCTGTCCCTCACCTGCACTGTCTCCGGTGACTCCATCAGTACT

TACTACTGGAGCTGGATCCGGCAGCCCCCAGGGAAGGGACTGGAGTGGAT

TGGGTATGTCTATTACACTGGGAGCACCAACTACAGCCCTTCCCTCGAGG

GTCGAGTCACCTTATCAGTAGACACGTCCAAGAACCAGTTCTCCCTGAAG

TTGAATTCTGTGAGTGCTGCGGACACGGCCGTGTATTACTGTGCGAGAGG

CGCGGCGGAGTGGCTACGATTCAGGGGGTTCTTTGACTACTGGGGCCAGG

GAATCCTGGTCTCCGTCTCCTCAGCCTCCACCAAGGGCCCATCGGTCTTC

CCCCTGGCACCCTCCTCCAAGAGCACCTCTGGGGGCACAGCGGCCCTGGG

CTGCCTGGTCAAGGACTACTTCCCCGAACCGGTGACGGTGTCGTGGAACT

CAGGCGCCCTGACCAGCGGCGTGCACACCTTCCCGGCTGTCCTACAGTCC

TCAGGACTCTACTCCCTCAGCAGCGTGGTGACCGTGCCCTCCAGCAGCTT

GGGCACCCAGACCTACATCTGCAACGTGAATCACAAGCCCAGCAACACCA

AGGTGGACAAGAAAGTTGAGCCCAAATCTTGTGACAAAACTCACACATGC

CCACCGTGCCCAGCACCTGAACTCCTGGGGGGACCGTCAGTCTTCCTCTT

CCCCCCAAAACCCAAGGACACCCTCATGATCTCCCGGACCCCTGAGGTCA

CATGCGTGGTGGTGGACGTGAGCCACGAAGACCCTGAGGTCAAGTTCAAC

TGGTACGTGGACGGCGTGGAGGTGCATAATGCCAAGACAAAGCCGCGGGA

GGAGCAGTACAACAGCACGTACCGGGTGGTCAGCGTCCTCACCGTCCTGC

ACCAGGACTGGCTGAATGGCAAGGAGTACAAGTGCAAGGTCTCCAACAAA

GCCCTCCCAGCCCCCATCGAGAAAACCATCTCCAAAGCCAAAGGGCAGCC

CCGAGAACCACAGGTGTACACCCTGCCCCCATCCCGGGATGAGCTGACCA

AGAACCAGGTCAGCCTGACCTGCCTGGTCAAAGGCTTCTATCCCAGCGAC

ATCGCCGTGGAGTGGGAGAGCAATGGGCAGCCGGAGAACAACTACAAGAC

CACGCCTCCCGTGCTGGACTCCGACGGCTCCTTCTTCCTCTACAGCAAGC

TCACCGTGGACAAGAGCAGGTGGCAGCAGGGGAACGTCTTCTCATGCTCC
```

-continued

```
GTGATGCATGAGGCTCTGCACAACCACTACACGCAGAAGAGCCTCTCCCT
GTCTCCGGGTAAATGA
```

A1 light chain nucleic acid
(SEQ ID NO: 21)
```
ATGGAAACCCCAGCGCAGCTTCTCTTCCTCCTGCTACTCTGGCTCCCAGA
TACCACCGGAGAAGTTGTGTTGACGCAGTCTCCAGGCACCCTGTCTTTGT
CTCCAGGGGAAAGAGCCACCCTCTCCTGTAGGGCCAGTCAGAGTGTTACC
AACGGCTTCTTAGCCTGGTACCAGCAGAAACCTGGCCAGGCTCCCAGGGT
CCTCATCTATGGTGCGTCCAGCAGGGCCACTGGCATCCCAGACAGGTTCA
GTGGCAGTGGGTCTGGGACAGACTTCACTCTCACCATCAGCAGACTGGAG
CCTGAAGATTTTGCAATGTATTACTGTCAGCAGTATGGTCTCTCAGGGAC
TTTTGGCCAGGGGACCAAGCTGGAGATCAAACGAACTGTGGCTGCACCAT
CTGTCTTCATCTTCCCGCCATCTGATGAGCAGTTGAAATCTGGAACTGCC
TCTGTTGTGTGCCTGCTGAATAACTTCTATCCCAGAGAGGCCAAAGTACA
GTGGAAGGTGGATAACGCCCTCCAATCGGGTAACTCCCAGGAGAGTGTCA
CAGAGCAGGACAGCAAGGACAGCACCTACAGCCTCAGCAGCACCCTGACG
CTGAGCAAAGCAGACTACGAGAAACACAAAGTCTACGCCTGCGAAGTCAC
CCATCAGGGCCTGAGCTCGCCCGTCACAAAGAGCTTCAACAGGGGAGAGT
GTTAG
```

A1 heavy chain amino acid
(SEQ ID NO: 20)
```
MKHLWFFLLLVAAPRWVLSQVHLQESGPGLVKPSETLSLTCTVSGDSIST
YYWSWIRQPPGKGLEWIGYVYYTGSTNYSPSLEGRVTLSVDTSKNQFSLK
LNSVSAADTAVYYCARGAAEWLRFRGFFDYWGQGILVSVSSASTKGPSVF
PLAPSSKSTSGGTAALGCLVKDYFPEPVTVSWNSGALTSGVHTFPAVLQS
SGLYSLSSVVTVPSSSLGTQTYICNVNHKPSNTKVDKKVEPKSCDKTHTC
PPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSD
IAVEWESNGQPENNYKTTPPVLDSDGSFFLYSKLTVDKSRWQQGNVFSCS
VMHEALHNHYTQKSLSLSPGK
```

A1 light chain amino acid
(SEQ ID NO: 22)
```
METPAQLLFLLLLWLPDTTGEVVLTQSPGTLSLSPGERATLSCRASQSVT
NGFLAWYQQKPGQAPRVLIYGASSRATGIPDRFSGSGSGTDFTLTISRLE
PEDFAMYYCQQYGLSGTFGQGTKLEIKRTVAAPSVFIFPPSDEQLKSGTA
SVVCLLNNFYPREAKVQWKVDNALQSGNSQESVTEQDSKDSTYSLSSTLT
LSKADYEKHKVYACEVTHQGLSSPVTKSFNRGEC
```

The amino acid sequences for the FR and CDR sequences of the A1 antibody are as follows:

FRH1:
(SEQ ID NO: 23)
QVHLQESGPGLVKPSETLSLTCTVS

CDRH1:
(SEQ ID NO: 24)
GDSISTYYWS

FRH2:
(SEQ ID NO: 25)
WIRQPPGKGLEWIG

CDRH2:
(SEQ ID NO: 26)
YVYYTGSTN

FRH3:
(SEQ ID NO: 27)
YSPSLEGRVTLSVDTSKNQFSLKLNSVSAADTAVYYCAR

CDRH3:
(SEQ ID NO: 28)
GAAEWLRFRGFFDY

FRH4:
(SEQ ID NO: 29)
WGQGILVSVSS

FRL1:
(SEQ ID NO: 30)
EVVLTQSPGTLSLSPGERATLSC

CDRL1:
(SEQ ID NO: 31)
RASQSVTNGFLA

FRL2:
(SEQ ID NO: 32)
WYQQKPGQAPRVLIY

CDRL2:
(SEQ ID NO: 33)
GASSRAT

FRL3:
(SEQ ID NO: 34)
GIPDRFSGSGSGTDFTLTISRLEPEDFAMYYC

CDRL3:
(SEQ ID NO: 35)
QQYGLSGT

FRL4:
(SEQ ID NO: 36)
FGQGTKLEIK

One aspect is directed to an isolated polypeptide comprising one or more of the CDR sequences of the A1 antibody (i.e., one or more of SEQ ID NOs. 24, 26, 28, 31, 33, or 35). In certain embodiments, the isolated polypeptide further comprises additional amino acid sequences, or other molecules, to form a molecule that binds toxin A, including, but not limited to an anti-toxin A antibody.

The amino acid and nucleotide sequences for the $V_H$ and $V_L$ domains of the A2 antibody are as follows:

A2 heavy chain nucleic acid
(SEQ ID NO: 1)
```
ATGAAACATCTGTGGTTCTTCCTTCTCCTGGTGGCAGCTCCCAGATGGGT
CCTGTCCCAGGTGCAGCTGCAGGAGTCGGGCCCAGGACTGGTGAAGCCTT
CGGAGACCCTGTCCCTCACCTGCACTGTCTCTGGTGGCTCCATCAGTACT
TACTACTGGAGCTGGATCCGGCAGTCCCCAGGGAAGGGACTGGAGTGGAT
GGGGTATATCTATTATAGTGGGAGCACCAACTACAACCCCTCCCTCGAGA
GTCGGGTCACCATAGCAGTGGACACGTCCAAGAATCAGTTCTCCCTGCAG
TTGACCTCTGTGACTGCTGCGGACACGGCCGTGTATTACTGTGCGAGAGG
```

-continued

```
AGCGGCGGAGTGGCTACGGTTCAGGGGGTTCTTTGACTCCTGGGGCCAGG
GAACCCTGGTCACCGTCTCCTCAGCCTCCACCAAGGGCCCATCGGTCTTC
CCCCTGGCACCCTCCTCCAAGAGCACCTCTGGGGGCACAGCGGCCCTGGG
CTGCCTGGTCAAGGACTACTTCCCCGAACCGGTGACGGTGTCGTGGAACT
CAGGCGCCCTGACCAGCGGCGTGCACACCTTCCCGGCTGTCCTACAGTCC
TCAGGACTCTACTCCCTCAGCAGCGTGGTGACCGTGCCCTCCAGCAGCTT
GGGCACCCAGACCTACATCTGCAACGTGAATCACAAGCCCAGCAACACCA
AGGTGGACAAGAAAGTTGAGCCCAAATCTTGTGACAAAACTCACACATGC
CCACCGTGCCCAGCACCTGAACTCCTGGGGGGACCGTCAGTCTTCCTCTT
CCCCCCAAAACCCAAGGACACCCTCATGATCTCCCGGACCCCTGAGGTCA
CATGCGTGGTGGTGGACGTGAGCCACGAAGACCCTGAGGTCAAGTTCAAC
TGGTACGTGGACGGCGTGGAGGTGCATAATGCCAAGACAAAGCCGCGGGA
GGAGCAGTACAACAGCACGTACCGGGTGGTCAGCGTCCTCACCGTCCTGC
ACCAGGACTGGCTGAATGGCAAGGAGTACAAGTGCAAGGTCTCCAACAAA
GCCCTCCCAGCCCCCATCGAGAAAACCATCTCCAAAGCCAAAGGGCAGCC
CCGAGAACCACAGGTGTACACCCTGCCCCCATCCCGGGATGAGCTGACCA
AGAACCAGGTCAGCCTGACCTGCCTGGTCAAAGGCTTCTATCCCAGCGAC
ATCGCCGTGGAGTGGGAGAGCAATGGGCAGCCGGAGAACAACTACAAGAC
CACGCCTCCCGTGCTGGACTCCGACGGCTCCTTCTTCCTCTACAGCAAGC
TCACCGTGGACAAGAGCAGGTGGCAGCAGGGGAACGTCTTCTCATGCTCC
GTGATGCATGAGGCTCTGCACAACCACTACACGCAGAAGAGCCTCTCCCT
GTCTCCGGGTAAATGA
```

A2 light chain nucleic acid
(SEQ ID NO: 3)
```
ATGGAAACCCCAGCGCAGCTTCTCTTCCTCCTGCTACTCTGGCTCCCAGA
GACCACCGGAGAAAATGTGTTGACGCAGTCTCCAGGGACCCTGTCTTTGT
CTCCAGGGGAAAGAGCCACCCTCTCCTGCAGGGCCAGTCACAGTGTTACC
AACAACTTCTTAGCCTGGTACCAGCAAAAACCTGGCCAGGCTCCCAGGCT
CCTCATCTATGGTGTGTCCAGCAGGGCCACTGGCATCCCAGACAGGTTCA
GTGGCAGTGGGTCTGGGACAGACTTCACTCTCACCATCAGCAGACTGGAG
CCTGAAGATTTTGCAGTGTATTACTGTCAGCAATATGGTGTCTCAGGGAC
TTTTGGCCAGGGGACCAAGCTGGAGATCAAACGAACTGTGGCTGCACCAT
CTGTCTTCATCTTCCCGCCATCTGATGAGCAGTTGAAATCTGGAACTGCC
TCTGTTGTGTGCCTGCTGAATAACTTCTATCCCAGAGAGGCCAAAGTACA
GTGGAAGGTGGATAACGCCCTCCAATCGGGTAACTCCCAGGAGAGTGTCA
CAGAGCAGGACAGCAAGGACAGCACCTACAGCCTCAGCAGCACCCTGACG
CTGAGCAAAGCAGACTACGAGAAACACAAAGTCTACGCCTGCGAAGTCAC
CCATCAGGGCCTGAGCTCGCCCGTCACAAAGAGCTTCAACAGGGGAGAGT
GTTAG
```

A2 heavy chain amino acid
(SEQ ID NO: 2)
MKHLWFFLLLVAAPRWVLSQVQLQESGPGLVKPSETLSLTCTVSGGSIST
YYWSWIRQSPGKGLEWMGYIYYSGSTNYNPSLESRVTIAVDTSKNQFSLQ
LTSVTAADTAVYYCARGAAEWLRFRGFFDSWGQGTLVTVSSASTKGPSVF
PLAPSSKSTSGGTAALGCLVKDYFPEPVTVSWNSGALTSGVHTFPAVLQS
SGLYSLSSVVTVPSSSLGTQTYICNVNHKPSNTKVDKKVEPKSCDKTHTC
PPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSD
IAVEWESNGQPENNYKTTPPVLDSDGSFFLYSKLTVDKSRWQQGNVFSCS
VMHEALHNHYTQKSLSLSPGK A2 light chain amino acid
(SEQ ID NO: 4)
METPAQLLFLLLLWLPETTGENVLTQSPGTLSLSPGERATLSCRASHSVT
NNFLAWYQQKPGQAPRLLIYGVSSRATGIPDRFSGSGSGTDFTLTISRLE
PEDFAVYYCQQYGVSGTFGQGTKLEIKRTVAAPSVFIFPPSDEQLKSGTA
SVVCLLNNFYPREAKVQWKVDNALQSGNSQESVTEQDSKDSTYSLSSTLT
LSKADYEKHKVYACEVTHQGLSSPVTKSFNRGEC The amino acid sequences for the FR and CDR sequences of the A2 antibody are as follows:

FRH1:
(SEQ ID NO: 5)
QVQLQESGPGLVKPSETLSLTCTVS

CDRH1:
(SEQ ID NO: 6)
GGSISTYYWS

FRH2:
(SEQ ID NO: 7)
WIRQSPGKGLEWMG

CDRH2:
(SEQ ID NO: 8)
YIYYSGSTN

FRH3:
(SEQ ID NO: 9)
YNPSLESRVTIAVDTSKNQFSLQLTSVTAADTAVYYCAR

CDRH3:
(SEQ ID NO: 10)
GAAEWLRFRGFFDS

FRH4:
(SEQ ID NO: 11)
WGQGTLVTVSS

FRL1:
(SEQ ID NO: 12)
ENVLTQSPGTLSLSPGERATLSC

CDRL1:
(SEQ ID NO: 13)
RASHSVTNNFLA

FRL2:
(SEQ ID NO: 14)
WYQQKPGQAPRLLIY

CDRL2:
(SEQ ID NO: 15)
GVSSRAT

```
FRL3:
                                     (SEQ ID NO: 16)
GIPDRFSGSGSGTDFTLTISRLEPEDFAVYYC

CDRL3:
                                     (SEQ ID NO: 17)
QQYGVSGT

FRL4:
                                     (SEQ ID NO: 18)
FGQGTKLEIK
```

One aspect is directed to an isolated polypeptide comprising one or more of the CDR sequences of the A2 antibody (i.e., one or more of SEQ ID NOs. 6, 8, 10, 13, 15, or 17). In certain embodiments, the isolated polypeptide further comprises additional amino acid sequences, or other molecules, to form a molecule that binds toxin A, including, but not limited to an anti-toxin A antibody.

The amino acid and nucleotide sequences for the $V_H$ and $V_L$ domains of the A3 antibody are as follows:

```
A3 heavy chain nucleic acid
                                     (SEQ ID NO: 37)
ATGCAACTGCTGGAGTCTGGGGGAGGCTTGGTGAAGCCTGGGGGGTCCCT
TAGACTCTCCTGTGCAGCCTCTGGATTCACTTTCAGTAACGCCTGGATGA
GTTGGGTCCGCCAGGGTCCAGGGAAGGGGCTGGAATGGGTTGGCCGTATT
AAAAGTAAAACTGATGGTGGGACAACAGACTACGCTGCACCCGTGAAAGG
CAGATTCAGCATCTCAAGAAATGATTCAAATAACACGCTGTTTCTGCAAA
TGAACAGCCTGAAAACCGAGGACACAGCCGTATATTACTGTACCACAGGT
CCTCAAATTGTAGTTGTAGCAGGTGCTACCAGTCGGGACCAGCCTAACTA
CTACTACTACGGTTTGGACGTCTGGGGCCTAGGGACCACGGTCACCGTCT
CGTCAGCCTCCACCAAGGGCCCATCGGTCTTCCCCCTGGCACCCTCCTCC
AAGAGCACCTCTGGGGGCACAGCGGCCCTGGGCTGCCTGGTCAAGGACTA
CTTCCCCGAACCGGTGACGGTGTCGTGGAACTCAGGCGCCCTGACCAGCG
GCGTGCACACCTTCCCGGCTGTCCTACAGTCCTCAGGACTCTACTCCCTC
AGCAGCGTGGTGACCGTGCCCTCCAGCAGCTTGGGCACCCAGACCTACAT
CTGCAACGTGAATCACAAGCCCAGCAACACCAAGGTGGACAAGAAAGTTG
AGCCCAAATCTTGTGACAAAACTCACACATGCCCACCGTGCCCAGCACCT
GAACTCCTGGGGGGACCGTCAGTCTTCCTCTTCCCCCCAAAACCCAAGGA
CACCCTCATGATCTCCCGGACCCCTGAGGTCACATGCGTGGTGGTGGACG
TGAGCCACGAAGACCCTGAGGTCAAGTTCAACTGGTACGTGGACGGCGTG
GAGGTGCATAATGCCAAGACAAAGCCGCGGGAGGAGCAGTACAACAGCAC
GTACCGGGTGGTCAGCGTCCTCACCGTCCTGCACCAGGACTGGCTGAATG
GCAAGGAGTACAAGTGCAAGGTCTCCAACAAAGCCCTCCCAGCCCCCATC
GAGAAAACCATCTCCAAAGCCAAAGGGCAGCCCCGAGAACCACAGGTGTA
CACCCTGCCCCCATCCCGGGATGAGCTGACCAAGAACCAGGTCAGCCTGA
CCTGCCTGGTCAAAGGCTTCTATCCCAGCGACATCGCCGTGGAGTGGGAG
AGCAATGGGCAGCCGGAGAACAACTACAAGACCACGCCTCCCGTGCTGGA
CTCCGACGGCTCCTTCTTCCTCTACAGCAAGCTCACCGTGGACAAGAGCA
GGTGGCAGCAGGGGAACGTCTTCTCATGCTCCGTGATGCATGAGGCTCTG
CACAACCACTACACGCAGAAGAGCCTCTCCCTGTCTCCGGGTAAATGA A3 light chain nucleic acid
                                     (SEQ ID NO: 39)
ATGGCCAGCTTCCCTCTCCTCCTCACCCTCCTCACTCACTGTGCAGGGTC
CTGGGCCCAGTCTGTGCTGACTCAGCCACCCTCAGCGTCTGGGACCCCCG
GGCAGAGGGTCACCATCTCTTGTTCTGGAAGCAGCTCCAACATCGGCATT
AATACTGTAAACTGGTACCAGCAGCTCCCAGGAACGGCCCCCAAACTCCT
CATATATAAGAGTAATCTGCGACCCTCAGGGGTCCCTGACCGATTCTCTG
GCTCCAAGTCTGGCACCTCAGCCTCCCTGGCCATCAGTGGGCTCCGGTCT
GAGGATGAGGCTGATTATTACTGTGCGGCATGGGATGACAGCCTGACTGG
TCTTTATGTCTTCGGAACTGGGACCAAGGTCACCGTCCTAGGTCAGCCCA
AGGCCAACCCCACTGTCACTCTGTTCCCGCCCTCCTCTGAGGAGCTCCAA
GCCAACAAGGCCACACTAGTGTGTCTGATCAGTGACTTCTACCCGGGAGC
TGTGACAGTGGCTTGGAAGGCAGATGGCAGCCCCGTCAAGGCGGGAGTGG
AGACGACCAAACCCTCCAAACAGAGCAACAACAAGTACGCGGCCAGCAGC
TACCTGAGCCTGACGCCCGAGCAGTGGAAGTCCCACAGAAGCTACAGCTG
CCAGGTCACGCATGAAGGGAGCACCGTGGAGAAGACAGTGGCCCCTACAG
AATGTTCATAG A3 heavy chain amino acid
                                     (SEQ ID NO: 38)
MQLLESGGGLVKPGGSLRLSCAASGFTFSNAWMSWVRQGPGKGLEWVGRI
KSKTDGGTTDYAAPVKGRFSISRNDSNNTLFLQMNSLKTEDTAVYYCTTG
PQIVVVAGATSRDQPNYYYYGLDVWGLGTTVTVSSASTKGPSVFPLAPSS
KSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAP
ELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWE
SNGQPENNYKTTPPVLDSDGSFFLYSKLTVDKSRWQQGNVFSCSVMHEAL
HNHYTQKSLSLSPGK A3 light chain amino acid
                                     (SEQ ID NO: 40)
MASFPLLLTLLTHCAGSWAQSVLTQPPSASGTPGQRVTISCSGSSSNIGI
NTVNWYQQLPGTAPKLLIYKSNLRPSGVPDRFSGSKSGTSASLAISGLRS
EDEADYYCAAWDDSLTGLYVFGTGTKVTVLGQPKANPTVTLFPPSSEELQ
ANKATLVCLISDFYPGAVTVAWKADGSPVKAGVETTKPSKQSNNKYAASS
YLSLTPEQWKSHRSYSCQVTHEGSTVEKTVAPTECS
```

The amino acid sequences for the FR and CDR sequences of the A3 antibody are as follows:

```
FRH1:
                                     (SEQ ID NO: 41)
MQLLESGGGLVKPGGSLRLSCAAS

CDRH1:
                                     (SEQ ID NO: 42)
GFTFSNAWMS
```

FRH2:
(SEQ ID NO: 43)
WVRQGPGKGLEWVG

CDRH2:
(SEQ ID NO: 44)
RIKSKTDGGTTD

FRH3:
(SEQ ID NO: 45)
YAAPVKGRFSISRNDSNNTLFLQMNSLKTEDTAVYYCTT

CDRH3:
(SEQ ID NO: 46)
GPQIVVVA

FRH4:
(SEQ ID NO: 47)
GATSRDQPNYYYYGLDVWGLGTTVTVSS

FRL1:
(SEQ ID NO: 48)
QSVLTQPPSASGTPGQRVTISC

CDRL1:
(SEQ ID NO: 49)
SGSSSNIGINTVN

FRL2:
(SEQ ID NO: 50)
WYQQLPGTAPKLLIY

CDRL2:
(SEQ ID NO: 51)
KSNLRPS

FRL3:
(SEQ ID NO: 52)
GVPDRFSGSKSGTSASLAISGLRSEDEADYYC

CDRL3:
(SEQ ID NO: 53)
AAWDDSLTGLYV

FRL4:
(SEQ ID NO: 54)
FGTGTKVTVLGQPKANPTVT

One aspect is directed to an isolated polypeptide comprising one or more of the CDR sequences of the A3 antibody (i.e., one or more of SEQ ID NOs: 42, 44, 46, 49, 51, or 53). In certain embodiments, the isolated polypeptide further comprises additional amino acid sequences, or other molecules, to form a molecule that binds toxin A, including, but not limited to an anti-toxin A antibody.

The amino acid and nucleotide sequences for the $V_H$ and $V_L$ domains of the A4 antibody are as follows:

A4 heavy chain nucleic acid
(SEQ ID NO: 55)
ATGGAGTTTGGGCTGAGCTGGGTTTTCCTCGTTGCTCTTTTAAGAGGTGT
CCAGTGTCAGGTGCACCTGGTGGAGTCTGGGGGAGGCGTGGTCCAGCCTG
GGAGGTCCCTGAGACTCTCCTGTGCAACCTTTGGACTCAACTTCAGTGAC
TATGGTTTTCACTGGGTCCGCCAGGCTCCAGGCAAGGGGCTGGAGTGGGT
GGCAGTTACATCATATGATGGAAGCAACAAATACTACGCAGAATTCGTGA
AGGGCCGATTCACCATCTCCAGAGACAATTACAAGAATACGGTGTATCTG
CAAATGAACAGCCTGAGACTTGAGGACACGGCTGTGTATTACTGTGCGAG
AGATCTCGCCCCATACAATTTTTGGAGTGGTTATGGGAATAATTGGTTCG
ACCCCTGGGGCCAGGGAACCCTGGTCACCGTCTCCTCAGCCTCCACCAAG
GGCCCATCGGTCTTCCCCCTGGCACCCTCCTCCAAGAGCACCTCTGGGGG
CACAGCGGCCCTGGGCTGCCTGGTCAAGGACTACTTCCCCGAACCGGTGA
CGGTGTCGTGGAACTCAGGCGCCCTGACCAGCGGCGTGCACACCTTCCCG
GCTGTCCTACAGTCCTCAGGACTCTACTCCCTCAGCAGCGTGGTGACCGT
GCCCTCCAGCAGCTTGGGCACCCAGACCTACATCTGCAACGTGAATCACA
AGCCCAGCAACACCAAGGTGGACAAGAAAGTTGAGCCCAAATCTTGTGAC
AAAACTCACACATGCCCACCGTGCCCAGCACCTGAACTCCTGGGGGGACC
GTCAGTCTTCCTCTTCCCCCCAAAACCCAAGGACACCCTCATGATCTCCC
GGACCCCTGAGGTCACATGCGTGGTGGTGGACGTGAGCCACGAAGACCCT
GAGGTCAAGTTCAACTGGTACGTGGACGGCGTGGAGGTGCATAATGCCAA
GACAAAGCCGCGGGAGGAGCAGTACAACAGCACGTACCGGGTGGTCAGCG
TCCTCACCGTCCTGCACCAGGACTGGCTGAATGGCAAGGAGTACAAGTGC
AAGGTCTCCAACAAAGCCCTCCCAGCCCCCATCGAGAAAACCATCTCCAA
AGCCAAAGGGCAGCCCCGAGAACCACAGGTGTACACCCTGCCCCCATCCC
GGGATGAGCTGACCAAGAACCAGGTCAGCCTGACCTGCCTGGTCAAAGGC
TTCTATCCCAGCGACATCGCCGTGGAGTGGGAGAGCAATGGGCAGCCGGA
GAACAACTACAAGACCACGCCTCCCGTGCTGGACTCCGACGGCTCCTTCT
TCCTCTACAGCAAGCTCACCGTGGACAAGAGCAGGTGGCAGCAGGGGAAC
GTCTTCTCATGCTCCGTGATGCATGAGGCTCTGCACAACCACTACACGCA
GAAGAGCCTCTCCCTGTCTCCGGGTAAATGA A4 light chain nucleic acid
(SEQ ID NO: 57)
ATGGAAACCCCAGCGCAGCTTCTCTTCCTCCTGCTACTCTGGCTCCCAGA
TACCACCGGAGAAATTGTGTTGACGCAGTCTCCAGGCACCCTGTCTTTGT
CTCCAGGGGAAAGAGCCACCCTCTCCTGCAGGGCCAGTCAGAGTGTTACT
GGCACCTCCTTAGCCTGGTTCCAGCAGAAACCTGGCCAGGCTCCCCGGCT
CCTCATCTATGGTGCATCCAGCAGGGCCACTGGCATCCCAGACAGGTTCA
GTGGCAGTGGGTCTGGGACAGACTTCACTCTCACCATCAGCAGACTGGAG
CCTGAAGATTTTGCAGTGTATTACTGTCAGCAGTATGGTAGCTCACCTAG
ACTCACTTTCGGCGGAGGGACCAAGGTGGAGATCAAACGAACTGTGGCTG
CACCATCTGTCTTCATCTTCCCGCCATCTGATGAGCAGTTGAAATCTGGA
ACTGCCTCTGTTGTGTGCCTGCTGAATAACTTCTATCCCAGAGAGGCCAA
AGTACAGTGGAAGGTGGATAACGCCCTCCAATCGGGTAACTCCCAGGAGA
GTGTCACAGAGCAGGACAGCAAGGACAGCACCTACAGCCTCAGCAGCACC
CTGACGCTGAGCAAAGCAGACTACGAGAAACACAAAGTCTACGCCTGCGA
AGTCACCCATCAGGGCCTGAGCTCGCCCGTCACAAAGAGCTTCAACAGGG
GAGAGTGTTAG A4 heavy chain amino acid
(SEQ ID NO: 56)
MEFGLSWVFLVALLRGVQCQVHLVESGGGVVQPGRSLRLSCATFGLNFSD
YGFHWVRQAPGKGLEWVAVTSYDGSNKYYAEFVKGRFTISRDNYKNTVYL
QMNSLRLEDTAVYYCARDLAPYNFWSGYGNNWFDPWGQGTLVTVSSASTK

```
GPSVFPLAPSSKSTSGGTAALGCLVKDYFPEPVTVSWNSGALTSGVHTFP

AVLQSSGLYSLSSVVTVPSSSLGTQTYICNVNHKPSNTKVDKKVEPKSCD

KTHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYKC

KVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGN

VFSCSVMHEALHNHYTQKSLSLSPGK

A4 light chain amino acid
                                              (SEQ ID NO: 58)
METPAQLLFLLLLWLPDTTGEIVLTQSPGTLSLSPGERATLSCRASQSVT

GTSLAWFQQKPGQAPRLLIYGASSRATGIPDRFSGSGSGTDFTLTISRLE

PEDFAVYYCQQYGSSPRLTFGGGTKVEIKRTVAAPSVFIFPPSDEQLKSG

TASVVCLLNNFYPREAKVQWKVDNALQSGNSQESVTEQDSKDSTYSLSST

LTLSKADYEKHKVYACEVTHQGLSSPVTKSFNRGEC
```

The amino acid sequences for the FR and CDR sequences of the A4 antibody are as follows:

```
    FRH1:
                                              (SEQ ID NO: 59)
    QVHLVESGGGVVQPGRSLRLSCATF

CDRH1:
                                              (SEQ ID NO: 60)
    GLNFSDYGFH

FRH2:
                                              (SEQ ID NO: 61)
    WVRQAPGKGLEWVA

CDRH2:
                                              (SEQ ID NO: 62)
    VTSYDGSNK

FRH3:
                                              (SEQ ID NO: 63)
    YYAEFVKGRFTISRDNYKNTVYLQMNSLRLEDTAVYYCAR

CDRH3:
                                              (SEQ ID NO: 64)
    DLAPYNFWSGYGNNWFDP

FRH4:
                                              (SEQ ID NO: 65)
    WGQGTLVTVSS

FRL1:
                                              (SEQ ID NO: 66)
    EIVLTQSPGTLSLSPGERATLSC

CDRL1:
                                              (SEQ ID NO: 67)
    RASQSVTGTSLA

FRL2:
                                              (SEQ ID NO: 68)
    WFQQKPGQAPRLLIY

CDRL2:
                                              (SEQ ID NO: 69)
    GASSRAT

FRL3:
                                              (SEQ ID NO: 70)
    GIPDRFSGSGSGTDFTLTISRLEPEDFAVYYC

CDRL3:
                                              (SEQ ID NO: 71)
    QQYGSSPRLT

FRL4:
                                              (SEQ ID NO: 72)
    FGGGTKVEIK
```

One aspect is directed to an isolated polypeptide comprising one or more of the CDR sequences of the A4 antibody (i.e., one or more of SEQ ID NOs. 60, 62, 64, 67, 69, or 71). In certain embodiments, the isolated polypeptide further comprises additional amino acid sequences, or other molecules, to form a molecule that binds toxin A, including, but not limited to an anti-toxin A antibody.

The amino acid and nucleotide sequences for the $V_H$ and $V_L$ domains of the A5 antibody are as follows:

```
A5 heavy chain nucleic acid
                                              (SEQ ID NO: 73)
ATGGAGTTTGGGCTGAGCTGGGTTTTCCTCGTTGCTCTTTTAAGAGGTGT

CCAGTGTCAGGTGCACCTGGTGGAGTCTGGGGGAGGCGTGGTCCAGCCTG

GGAGGTCCCTGAGACTCTCCTGTGCAACCTTTGGACTCAACTTCAGTGAC

TATGGTTTTCACTGGGTCCGCCAGGCTCCAGGCAAGGGGCTGGAGTGGGT

GGCAGTTACATCATATGATGGAAGCAACAAATACTACGCAGAATTCGTGA

AGGGCCGATTCACCATCTCCAGAGACAATTACAAGAATACGGTGTATCTG

CAAATGAACAGCCTGAGACTTGAGGACACGGCTGTGTATTACTGTGCGAG

AGATCTCGCCCCATACAATTTTTGGAGTGGTTATGGGAATAATTGGTTCG

ACCCCTGGGGCCAGGGAACCCTGGTCACCGTCTCCTCAGCCTCCACCAAG

GGCCCATCGGTCTTCCCCCTGGCACCCTCCTCCAAGAGCACCTCTGGGGG

CACAGCGGCCCTGGGCTGCCTGGTCAAGGACTACTTCCCCGAACCGGTGA

CGGTGTCGTGGAACTCAGGCGCCCTGACCAGCGGCGTGCACACCTTCCCG

GCTGTCCTACAGTCCTCAGGACTCTACTCCCTCAGCAGCGTGGTGACCGT

GCCCTCCAGCAGCTTGGGCACCCAGACCTACATCTGCAACGTGAATCACA

AGCCCAGCAACACCAAGGTGGACAAGAAAGTTGAGCCCAAATCTTGTGAC

AAAACTCACACATGCCCACCGTGCCCAGCACCTGAACTCCTGGGGGGACC

GTCAGTCTTCCTCTTCCCCCCAAAACCCAAGGACACCCTCATGATCTCCC

GGACCCCTGAGGTCACATGCGTGGTGGTGGACGTGAGCCACGAAGACCCT

GAGGTCAAGTTCAACTGGTACGTGGACGGCGTGGAGGTGCATAATGCCAA

GACAAAGCCGCGGGAGGAGCAGTACAACAGCACGTACCGGGTGGTCAGCG

TCCTCACCGTCCTGCACCAGGACTGGCTGAATGGCAAGGAGTACAAGTGC

AAGGTCTCCAACAAAGCCCTCCCAGCCCCCATCGAGAAAACCATCTCCAA

AGCCAAAGGGCAGCCCCGAGAACCACAGGTGTACACCCTGCCCCCATCCC

GGGATGAGCTGACCAAGAACCAGGTCAGCCTGACCTGCCTGGTCAAAGGC

TTCTATCCCAGCGACATCGCCGTGGAGTGGGAGAGCAATGGGCAGCCGGA

GAACAACTACAAGACCACGCCTCCCGTGCTGGACTCCGACGGCTCCTTCT

TCCTCTACAGCAAGCTCACCGTGGACAAGAGCAGGTGGCAGCAGGGGAAC

GTCTTCTCATGCTCCGTGATGCATGAGGCTCTGCACAACCACTACACGCA

GAAGAGCCTCTCCCTGTCTCCGGGTAAATGA
```

A5 light chain nucleic acid
(SEQ ID NO: 75)
ATGGAAGCCCCAGCGCAGCTTCTCTTCCTCCTGCTACTCTGGCTCCCAGA

TACCACTGGAGAAATAGTGATGACGCAGTCTCCAGCCACCCTGTCTGTCT

CTCCAGGAGAAAGAGCCACCCTCTCCTGCAGGGCCAGTCAGAGTATTAGC

AGCAACTTAGCCTGGTACCAGCAGAAACCTGGCCAGGCTCCCAGACTCCT

CATCTATGATGCATCCACCAGGGCCACTGGTATCCCAGCCAGGTTCAGTG

GCAGTGGGTCTGGGACAGAGTTCACTCTCACCATCAGCAGCCTGCAGTCT

GAAGATTTTGCAGTTTATTACTGTCAGCAATACAATGACTGGCTTGTGAC

GTTCGGCCAAGGGACCAAAGTGGAAATCAAACGAACTGTGGCTGCACCAT

CTGTCTTCATCTTCCCGCCATCTGATGAGCAGTTGAAATCTGGAACTGCC

TCTGTTGTGTGCCTGCTGAATAACTTCTATCCCAGAGAGGCCAAAGTACA

GTGGAAGGTGGATAACGCCCTCCAATCGGGTAACTCCCAGGAGAGTGTCA

CAGAGCAGGACAGCAAGGACAGCACCTACAGCCTCAGCAGCACCCTGACG

CTGAGCAAAGCAGACTACGAGAAACACAAAGTCTACGCCTGCGAAGTCAC

CCATCAGGGCCTGAGCTCGCCCGTCACAAAGAGCTTCAACAGGGGAGAGT

GTTAG

A5 heavy chain amino acid
(SEQ ID NO: 74)
MEFGLSWVFLVALLRGVQCQVHLVESGGGVVQPGRSLRLSCATFGLNFSD

YGFHWVRQAPGKGLEWVAVTSYDGSNKYYAEFVKGRFTISRDNYKNTVYL

QMNSLRLEDTAVYYCARDLAPYNFWSGYGNNWFDPWGQGTLVTVSSASTK

GPSVFPLAPSSKSTSGGTAALGCLVKDYFPEPVTVSWNSGALTSGVHTFP

AVLQSSGLYSLSSVVTVPSSSLGTQTYICNVNHKPSNTKVDKKVEPKSCD

KTHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYKC

KVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGN

VFSCSVMHEALHNHYTQKSLSLSPGK

A5 light chain amino acid
(SEQ ID NO: 76)
MEAPAQLLFLLLLWLPDTTGEIVMTQSPATLSVSPGERATLSCRASQSIS

SNLAWYQQKPGQAPRLLIYDASTRATGIPARFSGSGSGTEFTLTISSLQS

EDFAVYYCQQYNDWLVTFGQGTKVEIKRTVAAPSVFIFPPSDEQLKSGTA

SVVCLLNNFYPREAKVQWKVDNALQSGNSQESVTEQDSKDSTYSLSSTLT

LSKADYEKHKVYACEVTHQGLSSPVTKSFNRGEC

The amino acid sequences for the FR and CDR sequences of the A5 antibody are as follows:

FRH1:
(SEQ ID NO: 77)
QVHLVESGGGVVQPGRSLRLSCATF

CDRH1:
(SEQ ID NO: 78)
GLNFSDYGFH

FRH2:
(SEQ ID NO: 79)
WVRQAPGKGLEWVA

CDRH2:
(SEQ ID NO: 80)
VTSYDGSNK

FRH3:
(SEQ ID NO: 81)
YYAEFVKGRFTISRDNYKNTVYLQMNSLRLEDTAVYYCAR

CDRH3:
(SEQ ID NO: 82)
DLAPYNFWSGYGNNWFDP

FRH4:
(SEQ ID NO: 83)
WGQGTLVTVSS

FRL1:
(SEQ ID NO: 84)
EIVMTQSPATLSVSPGERATLSC

CDRL1:
(SEQ ID NO: 85)
RASQSISSNLA

FRL2:
(SEQ ID NO: 86)
WYQQKPGQAPRLLIY

CDRL2:
(SEQ ID NO: 87)
DASTRAT

FRL3:
(SEQ ID NO: 88)
GIPARFSGSGSGTEFTLTISSLQSEDFAVYYC

CDRL3:
(SEQ ID NO: 89)
QQYNDWLVT|

FRL4:
(SEQ ID NO: 90)
FGQGTKVEIK

One aspect is directed to an isolated polypeptide comprising one or more of the CDR sequences of the A5 antibody (i.e., one or more of SEQ ID NOs. 78, 80, 82, 85, 87, or 89). In certain embodiments, the isolated polypeptide further comprises additional amino acid sequences, or other molecules, to form a molecule that binds toxin A, including, but not limited to an anti-toxin A antibody.

The SEQ ID NOs corresponding to the sequences of the A1, A2, A3, A4, and A5, antibodies are listed in Table 1.

TABLE 1

| SEQ ID NOs of Anti-Toxin A Antibodies | | | | | | |
|---|---|---|---|---|---|---|
| Region | Type | A1 | A2 | A3 | A4 | A5 |
| VH | DNA | 19 | 1 | 37 | 55 | 73 |
| VH | AA | 20 | 2 | 38 | 56 | 74 |
| VL | DNA | 21 | 3 | 39 | 57 | 75 |
| VL | AA | 22 | 4 | 40 | 58 | 76 |
| FRH TABLE 1-continued SEQ ID NOs of Anti-Toxin A Antibodies

| Region | Type | A1 | A2 | A3 | A4 | A5 |
|---|---|---|---|---|---|---|
| CDRL2 | AA | 33 | 15 | 51 | 69 | 87 |
| FRL3 | AA | 34 | 16 | 52 | 70 | 88 |
| CDRL3 | AA | 35 | 17 | 53 | 71 | 89 |
| FRL4 | AA | 36 | 18 | 54 | 72 | 90 |

6. Anti-Toxin B Antibodies

This disclosure provides antibodies that bind to *C. difficile* toxin B, including human, monoclonal antibodies having 1) high binding affinity, 2) potent in vitro neutralization activity, and 3) optionally a broad spectrum of binding to the toxins of various toxinotypes. Thus, in one embodiment, the antibody has at least one of the following characteristics:

(a) the antibody binds to *C. difficile* toxin B with a dissociation constant ($K_D$) equal to or less than 100 pM;
(b) the antibody neutralizes the in vitro cytotoxicity of *C. difficile* toxin B in the Vero monkey kidney cell line with an NT50 equal to or less than 1000 pM;
(c) the antibody neutralizes the *C. difficile* toxin B induced loss of transepithelial electrical resistance (TEER) in the T-84 cell line with an NT50 equal to or less than 200 pM; and/or
(d) the antibody binds to toxin B produced by at least the strains of toxinotypes 0, III, and V.

The antibody may have at least two, at least three, or all 4 of the above-identified characteristics.

In one embodiment, the human, monoclonal antibody binds to *C. difficile* toxin B with a dissociation constant ($K_D$) equal to or less than 500 pM, 250 pM, 200 pM, 150 pM, 100 pM ($10^{-10}$M), 50 pM, 30 pM, 10 pM ($10^{-11}$M), or 1 pM ($10^{-12}$M). The dissociation constant may be measured using techniques known in the art. In one embodiment, the dissociation constant is measured using biolayer interferometry, as described in the examples of this application.

In another embodiment, the human, monoclonal antibody neutralizes the in vitro cytotoxicity of *C. difficile* toxin B at 17 pg/mL in the Vero monkey kidney cell line with an NT50 of equal to or less than 1000 pM, 500 pM, 100 pM, 60 pM, or 50 pM. For the sake of consistency, when measuring the neutralizing activity in the Vero monkey kidney cell line, Vero cells ($2.5 \times 10^4$ cells/well with 5% heat-inactivated FBS) are seeded in 96-well tissue culture microtiter plates and incubated 37° C. overnight. An equal volume (80 µl) of 34.4 pg/mL (8xMC50) *C. difficile* toxin B solution and individual dilutions of the antibody solutions (80 µl) in Vero cell medium are combined in a new 96-well plate, and incubated at 37° C., 5% $CO_2$ for 1 hour before 100 µl of the toxin/antibody solutions are added to the Vero cells, and incubated at 37° C. for 72 hours. After incubating for 72 hours, the cells are washed twice with 120 µl/each of MEM medium that does not contain phenol, L-glutamine and FBS before adding 100 µl MEM medium that does not contain phenol, L-glutamine and FBS and 10 µl of Alamar Blue® (Life Technologies) to each well. The plates are lightly mixed and incubated at 37° C. for 4 hours before reading fluorescence at 560-590 nm with a cut off at 590 nm.

In yet another embodiment, the human, monoclonal antibody neutralizes the *C. difficile* toxin B (at 75 ng/mL, applied basolaterally) induced loss of transepithelial electrical resistance (TEER) in the T-84 cell line with an NT50 equal to or less than 200 pM, 150 pM, 100 pM, or 70 pM. For the sake of consistency, when measuring TEER, T-84 cells are seeded into 0.4 micron polyester transwell plates at a seeding density of $3.6 \times 10^5$ cells/cm² and maintained at 37° C., 5% $CO_2$ in 10% heat-inactivated FBS in DMEM/F12 culture media for 10-12 days until stable TEER is achieved and media is replaced in both apical and basolateral compartments of the transwells daily from day 6 and on the day of assay. The *C. difficile* toxin B (final concentration of 75 ng/mL) is combined 1:1 with an antibody and incubated at 37° C. with gentle rocking for 30 minutes before replacing the media in the basolateral compartment with the toxin/antibody samples. Transepithelial electrical resistance of the T-84 cells is measured at $T_0$ immediately before sample addition and after 2.5 hours ($T_{150}$) incubation at 37° C. 5% $CO_2$.

In another embodiment, the human, monoclonal anti-toxin B antibody binds to toxin B produced by strains of at least toxinotypes 0, III, and V, toxin B produced by strains of at least toxinotypes 0, III, V, and VIII, toxin B produced by the strains of at least toxinotypes 0, III, V, VIII, and XII, or toxin B produced by the strains of at least toxinotypes 0, III, V, VIII, XII, and XV. Toxinotype binding may be measured using techniques known in the art, including the techniques described in the examples of this application, such as Western analysis. In another embodiment, for antibodies that bind to an epitope in the C-terminal domain (CTD) of toxin A or toxin B, the toxinotype can be measured using a CTD competition assay, as described in the examples of this application.

In another embodiment, the human, monoclonal anti-toxin B antibody has an on rate constant ($K_{on}$) to toxin B of at least $10^5 M^{-1} s^{-1}$. In another embodiment, the human, monoclonal anti-toxin B antibody has an off rate constant ($K_{off}$) to toxin B of $10^{-4} s^{-1}$, $10^{-5} s^{-1}$, $10^{-6} s^{-1}$, $10^{-7} s^{-1}$, or $10^{-8} s^{-1}$, or less. The $K_{on}$ and $K_{off}$ may be measured using techniques known in the art. In one embodiment, the dissociation constant is measured using biolayer interferometry, as described in the examples of this application.

In one embodiment, the antibody is an isolated B1 antibody. As used herein, the term "B1" refers to a monoclonal antibody, or antigen-binding fragment thereof, that binds to *C. difficile* toxin B, wherein the antibody comprises 1) a heavy chain variable domain comprising the amino acid sequence of SEQ ID NO:110 and a light chain variable domain comprising the amino acid sequence of SEQ ID NO:112; or 2) a heavy chain variable domain comprising a CDR1 comprising the amino acid sequence of SEQ ID NO:114, a CDR2 comprising the amino acid sequence of SEQ ID NO:116, and a CDR3 comprising the amino acid sequence of SEQ ID NO:118 and a light chain variable domain comprising a CDR1 comprising the amino acid sequence of SEQ ID NO:121, a CDR2 comprising the amino acid sequence of SEQ ID NO:123, and a CDR3 comprising the amino acid sequence of SEQ ID NO:125. In one embodiment, the monoclonal antibody comprises a heavy chain variable domain comprising a FR1 comprising the amino acid sequence SEQ ID NO:113, a CDR1 comprising the amino acid sequence of SEQ ID NO:114, a FR2 comprising the amino acid sequence SEQ ID NO:115, a CDR2 comprising the amino acid sequence of SEQ ID NO:116, a FR3 comprising the amino acid sequence SEQ ID NO:117, a CDR3 comprising the amino acid sequence of SEQ ID NO:118, and a FR4 comprising the amino acid sequence SEQ ID NO:119 and a light chain variable domain comprising a FR1 comprising the amino acid sequence SEQ ID NO:120, a CDR1 comprising the amino acid sequence of SEQ ID NO:121, a FR2 comprising the amino acid sequence SEQ ID NO:122, a CDR2 comprising the amino acid sequence of SEQ ID NO:123, a FR3 comprising the amino acid sequence SEQ ID NO:124, a CDR3 comprising the amino acid sequence of SEQ ID NO:125, and a FR4 comprising the amino acid sequence SEQ ID NO:126. In yet another embodiment, the antibody is a monoclonal antibody that binds to a *C. difficile* toxin B epitope that is recognized by the B1 antibody, such that the monoclonal antibody competitively inhibits, or cross-blocks, the binding of the B1 antibody to *C. difficile* toxin B.

In another embodiment, the antibody is an isolated B2 antibody. As used herein, the term "B2" refers to a monoclonal antibody, or antigen-binding fragment thereof, that binds to *C. difficile* toxin B, wherein the antibody comprises 1) a heavy chain variable domain comprising the amino acid sequence of SEQ ID NO:92 and a light chain variable domain comprising the amino acid sequence of SEQ ID NO:94; or 2) a heavy chain variable domain comprising a CDR1 comprising the amino acid sequence of SEQ ID NO:96, a CDR2 comprising the amino acid sequence of SEQ ID NO:98, and a CDR3 comprising the amino acid sequence of SEQ ID NO:100 and a light chain variable domain comprising a CDR1 comprising the amino acid sequence of SEQ ID NO:103, a CDR2 comprising the amino acid sequence of SEQ ID NO:105, and a CDR3 comprising the amino acid sequence of SEQ ID NO:107. In one embodiment, the monoclonal antibody comprises a heavy chain variable domain comprising a FR1 comprising the amino acid sequence SEQ ID NO:95, a CDR1 comprising the amino acid sequence of SEQ ID NO:96, a FR2 comprising the amino acid sequence SEQ ID NO:97, a CDR2 comprising the amino acid sequence of SEQ ID NO:98, a FR3 comprising the amino acid sequence SEQ ID NO:99, a CDR3 comprising the amino acid sequence of SEQ ID NO:100, and a FR4 comprising the amino acid sequence SEQ ID NO:101 and a light chain variable domain comprising a FR1 comprising the amino acid sequence SEQ ID NO:102, a CDR1 comprising the amino acid sequence of SEQ ID NO:103, a FR2 comprising the amino acid sequence SEQ ID NO:104, a CDR2 comprising the amino acid sequence of SEQ ID NO:105, a FR3 comprising the amino acid sequence SEQ ID NO:106, a CDR3 comprising the amino acid sequence of SEQ ID NO:107, and a FR4 comprising the amino acid sequence SEQ ID NO:108. In yet another embodiment, the antibody is a monoclonal antibody that binds to a *C. difficile* toxin B epitope that is recognized by the B2 antibody, such that the monoclonal antibody competitively inhibits, or cross-blocks, the binding of the B2 antibody to *C. difficile* toxin B.

In another embodiment, the antibody is an isolated B3 antibody. As used herein, the term "B3" refers to a monoclonal antibody, or antigen-binding fragment thereof, that binds to *C. difficile* toxin B, wherein the antibody comprises 1) a heavy chain variable domain comprising the amino acid sequence of SEQ ID NO:164 and a light chain variable domain comprising the amino acid sequence of SEQ ID NO:166; or 2) a heavy chain variable domain comprising a CDR1 comprising the amino acid sequence of SEQ ID NO:168, a CDR2 comprising the amino acid sequence of SEQ ID NO:170, and a CDR3 comprising the amino acid sequence of SEQ ID NO:172 and a light chain variable domain comprising a CDR1 comprising the amino acid sequence of SEQ ID NO:175, a CDR2 comprising the amino acid sequence of SEQ ID NO:177, and a CDR3 comprising the amino acid sequence of SEQ ID NO:179. In one embodiment, the monoclonal antibody comprises a heavy chain variable domain comprising a FR1 comprising the amino acid sequence SEQ ID NO:167, a CDR1 comprising the amino acid sequence of SEQ ID NO:168, a FR2 comprising the amino acid sequence SEQ ID NO:169, a CDR2 comprising the amino acid sequence of SEQ ID NO:170, a FR3 comprising the amino acid sequence SEQ ID NO:171, a CDR3 comprising the amino acid sequence of SEQ ID NO:172, and a FR4 comprising the amino acid sequence SEQ ID NO:173 and a light chain variable domain comprising a FR1 comprising the amino acid sequence SEQ ID NO:174, a CDR1 comprising the amino acid sequence of SEQ ID NO:175, a FR2 comprising the amino acid sequence SEQ ID NO:176, a CDR2 comprising the amino acid sequence of SEQ ID NO:177, a FR3 comprising the amino acid sequence SEQ ID NO:178, a CDR3 comprising the amino acid sequence of SEQ ID NO:179, and a FR4 comprising the amino acid sequence SEQ ID NO:180. In yet another embodiment, the antibody is a monoclonal antibody that binds to a *C. difficile* toxin B epitope that is recognized by the B3 antibody, such that the monoclonal antibody competitively inhibits, or cross-blocks, the binding of the B3 antibody to *C. difficile* toxin B.

In another embodiment, the antibody is an isolated B4 antibody. As used herein, the term "B4" refers to a monoclonal antibody, or antigen-binding fragment thereof, that binds to *C. difficile* toxin B, wherein the antibody comprises 1) a heavy chain variable domain comprising the amino acid sequence of SEQ ID NO:146 and a light chain variable domain comprising the amino acid sequence of SEQ ID NO:148; or 2) a heavy chain variable domain comprising a CDR1 comprising the amino acid sequence of SEQ ID NO:150, a CDR2 comprising the amino acid sequence of SEQ ID NO:152, and a CDR3 comprising the amino acid sequence of SEQ ID NO:154 and a light chain variable domain comprising a CDR1 comprising the amino acid sequence of SEQ ID NO:157, a CDR2 comprising the amino acid sequence of SEQ ID NO:159, and a CDR3 comprising the amino acid sequence of SEQ ID NO:161. In one embodiment, the monoclonal antibody comprises a heavy chain variable domain comprising a FR1 comprising the amino acid sequence SEQ ID NO:149, a CDR1 comprising the amino acid sequence of SEQ ID NO:150, a FR2 comprising the amino acid sequence SEQ ID NO:151, a CDR2 comprising the amino acid sequence of SEQ ID NO:152, a FR3 comprising the amino acid sequence SEQ ID NO:153, a CDR3 comprising the amino acid sequence of SEQ ID NO:154, and a FR4 comprising the amino acid sequence SEQ ID NO:155 and a light chain variable domain comprising a FR1 comprising the amino acid sequence SEQ ID NO:156, a CDR1 comprising the amino acid sequence of SEQ ID NO:157, a FR2 comprising the amino acid sequence SEQ ID NO:158, a CDR2 comprising the amino acid sequence of SEQ ID NO:159, a FR3 comprising the amino acid sequence SEQ ID NO:160, a CDR3 comprising the amino acid sequence of SEQ ID NO:161, and a FR4 comprising the amino acid sequence SEQ ID NO:162. In yet another embodiment, the antibody is a monoclonal antibody that binds to a *C. difficile* toxin B epitope that is recognized by the B4 antibody, such that the monoclonal antibody competitively inhibits, or cross-blocks, the binding of the B4 antibody to *C. difficile* toxin B.

In another embodiment, the antibody is an isolated B5 antibody. As used herein, the term "B5" refers to a monoclonal antibody, or antigen-binding fragment thereof, that binds to *C. difficile* toxin B, wherein the antibody comprises 1) a heavy chain variable domain comprising the amino acid sequence of SEQ ID NO:182 and a light chain variable domain comprising the amino acid sequence of SEQ ID NO:184; or 2) a heavy chain variable domain comprising a CDR1 comprising the amino acid sequence of SEQ ID NO:186, a CDR2 comprising the amino acid sequence of SEQ ID NO:188, and a CDR3 comprising the amino acid sequence of SEQ ID NO:190 and a light chain variable domain comprising a CDR1 comprising the amino acid sequence of SEQ ID NO:193, a CDR2 comprising the amino acid sequence of SEQ ID NO:195, and a CDR3 comprising the amino acid sequence of SEQ ID NO:197. In one embodiment, the monoclonal antibody comprises a heavy chain variable domain comprising a FR1 comprising the amino acid sequence SEQ ID NO:185, a CDR1 comprising the amino acid sequence of SEQ ID NO:186, a FR2 comprising the amino acid sequence SEQ ID NO:187, a CDR2 comprising the amino acid sequence of SEQ ID NO:188, a FR3 comprising the amino acid sequence SEQ ID NO:189, a CDR3 comprising the amino acid sequence of SEQ ID NO:190, and a FR4 comprising the amino acid sequence SEQ ID NO:191 and a light chain variable domain comprising a FR1 comprising the amino acid sequence SEQ ID NO:192, a CDR1 comprising the amino acid sequence of SEQ ID NO:193, a FR2 comprising the amino acid sequence SEQ ID NO:194, a CDR2 comprising the amino acid sequence of SEQ ID NO:195, a FR3 comprising the amino acid sequence SEQ ID NO:196, a CDR3 comprising the amino acid sequence of SEQ ID NO:197, and a FR4 comprising the amino acid sequence SEQ ID NO:198. In yet another embodiment, the antibody is a monoclonal antibody that binds to a *C. difficile* toxin B epitope that is recognized by the B5 antibody, such that the monoclonal antibody competitively inhibits, or cross-blocks, the binding of the B5 antibody to *C. difficile* toxin B.

In another embodiment, the antibody is an isolated B6 antibody. As used herein, the term "B6" refers to a monoclonal antibody, or antigen-binding fragment thereof, that binds to *C. difficile* toxin B, wherein the antibody comprises 1) a heavy chain variable domain comprising the amino acid sequence of SEQ ID NO:128 and a light chain variable domain comprising the amino acid sequence of SEQ ID NO:130; or 2) a heavy chain variable domain comprising a CDR1 comprising the amino acid sequence of SEQ ID NO:132, a CDR2 comprising the amino acid sequence of SEQ ID NO:134, and a CDR3 comprising the amino acid sequence of SEQ ID NO:136 and a light chain variable domain comprising a CDR1 comprising the amino acid sequence of SEQ ID NO:139, a CDR2 comprising the amino acid sequence of SEQ ID NO:141, and a CDR3 comprising the amino acid sequence of SEQ ID NO:143. In one embodiment, the monoclonal antibody comprises a heavy chain variable domain comprising a FR1 comprising the amino acid sequence SEQ ID NO:131, a CDR1 comprising the amino acid sequence of SEQ ID NO:132, a FR2 comprising the amino acid sequence SEQ ID NO:133, a CDR2 comprising the amino acid sequence of SEQ ID NO:134, a FR3 comprising the amino acid sequence SEQ ID NO:135, a CDR3 comprising the amino acid sequence of SEQ ID NO:136, and a FR4 comprising the amino acid sequence SEQ ID NO:137 and a light chain variable domain comprising a FR1 comprising the amino acid sequence SEQ ID NO:138, a CDR1 comprising the amino acid sequence of SEQ ID NO:139, a FR2 comprising the amino acid sequence SEQ ID NO:140, a CDR2 comprising the amino acid sequence of SEQ ID NO:141, a FR3 comprising the amino acid sequence SEQ ID NO:142, a CDR3 comprising the amino acid sequence of SEQ ID NO:143, and a FR4 comprising the amino acid sequence SEQ ID NO:144. In yet another embodiment, the antibody is a monoclonal antibody that binds to a *C. difficile* toxin B epitope that is recognized by the B6 antibody, such that the monoclonal antibody competitively inhibits, or cross-blocks, the binding of the B6 antibody to *C. difficile* toxin B.

Whether an antibody competitively inhibits the binding of an antibody to *C. difficile* toxin B can be assessed using routine methods in the art, including, for example, the Octet methods described in the examples of this application or other routine quantitative binding assays, such as the Biacore assay. In one embodiment, competitive binding is measured using biolayer interferometry.

The B1, B2, and B3 antibodies bind to an epitope within amino acids 10-520 of SEQ ID NO:231. Thus, one embodiment is directed to an isolated monoclonal antibody that binds to an epitope in the glucosyl transferase domain of *C. difficile* toxin B, wherein the epitope comprises amino acids 10-520 of SEQ ID NO:231. More specifically, the B1 and B3 antibodies bind to an epitope comprising the amino acid sequence SGRNK (SEQ ID NO:234) or amino acids 56-80 of SEQ ID NO:231. Thus, another embodiment is directed to an isolated monoclonal antibody that binds to an epitope in the glucosyl transferase domain of *C. difficile* toxin B, wherein the epitope comprises the amino acid sequence SGRNK (SEQ ID NO:234) or amino acids 56-80 of SEQ ID NO:231.

The B4 antibody binds to an epitope in the N-terminal translocation domain of *C. difficile* toxin B, wherein the epitope comprises amino acids 1110-1530 of SEQ ID NO:231. Thus, another embodiment is directed to an isolated monoclonal antibody that binds to an epitope in the N-terminal translocation domain of *C. difficile* toxin B, wherein the epitope comprises amino acids 1110-1530 of SEQ ID NO:231.

The B6 antibody binds to an epitope in the receptor binding domain of *C. difficile* toxin B, wherein the epitope comprises amino acids 1750-2360 of SEQ ID NO:231. Thus, another embodiment is directed to an isolated monoclonal antibody that binds to an epitope in the receptor binding domain of *C. difficile* toxin B, wherein the epitope comprises amino acids 1750-2360 of SEQ ID NO:231.

The amino acid and nucleotide sequences for the $V_H$ and $V_L$ domains of the B1 antibody are as follows:

```
B1 heavy chain nucleic acid
                                     (SEQ ID NO: 109)
ATGGAGTTTGGGCTGAGCTGGGTTTTCCTTGTTGCCATTTTAAAAGGTGT

CCAGTGTGAGGTGCAGCTGGTGGAGTCCGGGGGAGGCTTAGTTCAGCCTG

GGGGGTCCCTGAGACTCTCCTGTGCAGCCTCTGGATTCACTTTCAGAAGT

TACTGGATGCACTGGGTCCGCCAAGTTCCAGGGAAGGGGCTGGTGTGGGT

GTCATGTATTAATAAAGAAGGGAGTAGCACAACCTACGCGGACTCCGTGA

AGGGCCGATTCACCATCTCCAGAGACAACGCCAAGAACACGCTGTATTTG

GAAATGAACAGTCTGAGAGCCGACGACACGGCTGTGTATTATTGTCTAAG

GGGATACGATGTTGACTACTGGGGCCAGGGAACGCTGGTCACCGTCTCCT

CAGCCTCCACCAAGGGCCCATCGGTCTTCCCCCTGGCACCCTCCTCCAAG

AGCACCTCTGGGGGCACAGCGGCCCTGGGCTGCCTGGTCAAGGACTACTT

CCCCGAACCGGTGACGGTGTCGTGGAACTCAGGCGCCCTGACCAGCGGCG

TGCACACCTTCCCGGCTGTCCTACAGTCCTCAGGACTCTACTCCCTCAGC

AGCGTGGTGACCGTGCCCTCCAGCAGCTTGGGCACCCAGACCTACATCTG
```

```
CAACGTGAATCACAAGCCCAGCAACACCAAGGTGGACAAGAAAGTTGAGC

CCAAATCTTGTGACAAAACTCACACATGCCCACCGTGCCCAGCACCTGAA

CTCCTGGGGGGACCGTCAGTCTTCCTCTTCCCCCCAAAACCCAAGGACAC

CCTCATGATCTCCCGGACCCCTGAGGTCACATGCGTGGTGGTGGACGTGA

GCCACGAAGACCCTGAGGTCAAGTTCAACTGGTACGTGGACGGCGTGGAG

GTGCATAATGCCAAGACAAAGCCGCGGGAGGAGCAGTACAACAGCACGTA

CCGGGTGGTCAGCGTCCTCACCGTCCTGCACCAGGACTGGCTGAATGGCA

AGGAGTACAAGTGCAAGGTCTCCAACAAAGCCCTCCCAGCCCCCATCGAG

AAAACCATCTCCAAAGCCAAAGGGCAGCCCCGAGAACCACAGGTGTACAC

CCTGCCCCCATCCCGGGATGAGCTGACCAAGAACCAGGTCAGCCTGACCT

GCCTGGTCAAAGGCTTCTATCCCAGCGACATCGCCGTGGAGTGGGAGAGC

AATGGGCAGCCGGAGAACAACTACAAGACCACGCCTCCCGTGCTGGACTC

CGACGGCTCCTTCTTCCTCTACAGCAAGCTCACCGTGGACAAGAGCAGGT

GGCAGCAGGGGAACGTCTTCTCATGCTCCGTGATGCATGAGGCTCTGCAC

AACCACTACACGCAGAAGAGCCTCTCCCTGTCTCCGGGTAAATGA
B1 light chain nucleic acid
                                    (SEQ ID NO: 111)
ATGGCCTGGACTCCTCTCCTCCTGTTCCTCTCTCACTGCACAGGTTC

CCTCTCGCAGGCTGTGCTGACTCAGCCGTCCTCCCTCTCTGCATCTCCG

GAGCATCAGTCAGTCTCACCTGCACCTTGCGCAGTGGCATCAATGTTGGT

ACCTACAGGATATACTGGTATCAGCAGAAGCCAGGGAGTCCTCCCCGTTA

TCTCCTGAGGTACAAATCAGGCTTAGATAAACACCAGGGCTCTGGAGTCC

CCAGCCGCTTCTCTGGATCCAAAGATGATTCGGCCAATGCAGGGATTTTA

TTCATTTCTGGGCTCCAGTCTGAGGATGAGGCTGATTATTACTGTTTGAT

TTGGCACAGCAGCGCTGTGGTATTCGGCGGAGGGACCAAGCTGACCGTCC

TAGGTCAGCCCAAGGCTGCCCCCTCGGTCACTCTGTTCCCGCCCTCCTCT

GAGGAGCTTCAAGCCAACAAGGCCACACTAGTGTGTCTGATCAGTGACTT

CTACCCGGGAGCTGTGACAGTGGCTTGGAAGGCAGATGGCAGCCCCGTCA

AGGCGGGAGTGGAGACGACCAAACCCTCCAAACAGAGCAACAACAAGTAC

GCGGCCAGCAGCTACCTGAGCCTGACGCCCGAGCAGTGGAAGTCCCACAG

AAGCTACAGCTGCCAGGTCACGCATGAAGGGAGCACCGTGGAGAAGACAG

TGGCCCCTACAGAATGTTCATAG
B1 heavy chain amino acid
                                    (SEQ ID NO: 110)
MEFGLSWVFLVAILKGVQCEVQLVESGGGLVQPGGSLRLSCAASGFTFRS

YWMHWVRQVPGKGLVWVSCINKEGSSTTYADSVKGRFTISRDNAKNTLYL

EMNSLRADDTAVYYCLRGYDVDYWGQGTLVTVSSASTKGPSVFPLAPSSK

STSGGTAALGCLVKDYFPEPVTVSWNSGALTSGVHTFPAVLQSSGLYSLS

SVVTVPSSSLGTQTYICNVNHKPSNTKVDKKVEPKSCDKTHTCPPCPAPE

LLGGPSVFLFPPKPKDTLMISRTPEVTCVVVDVSHEDPEVKFNWYVDGVE

VHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWES

NGQPENNYKTTPPVLDSDGSFFLYSKLTVDKSRWQQGNVFSCSVMHEALH

NHYTQKSLSLSPGK

B1 light chain amino acid
                                    (SEQ ID NO: 112)
MAWTPLLLLFLSHCTGSLSQAVLTQPSSLSASPGASVSLTCTLRSGINVG

TYRIYWYQQKPGSPPRYLLRYKSGLDKHQGSGVPSRFSGSKDDSANAGIL

FISGLQSEDEADYYCLIWHSSAVVFGGGTKLTVLGQPKAAPSVTLFPPSS

EELQANKATLVCLISDFYPGAVTVAWKADGSPVKAGVETTKPSKQSNNKY

AASSYLSLTPEQWKSHRSYSCQVTHEGSTVEKTVAPTECS
```

The amino acid sequences for the FR and CDR sequences of the B1 antibody are as follows.

```
FRH1:
                                    (SEQ ID NO: 113)
EVQLVESGGGLVQPGGSLRLSCAAS

CDRH1:
                                    (SEQ ID NO: 114)
GFTFRSYWMH

FRH2:
                                    (SEQ ID NO: 115)
WVRQVPGKGLVWVS

CDRH2:
                                    (SEQ ID NO: 116)
CINKEGSSTT

FRH3:
                                    (SEQ ID NO: 117)
YADSVKGRFTISRDNAKNTLYLEMNSLRADDTAVYYCLR

CDRH3:
                                    (SEQ ID NO: 118)
GYDVDYWG

FRH4:
                                    (SEQ ID NO: 119)
QGTLVTVSS

FRL1:
                                    (SEQ ID NO: 120)
QAVLTQPSSLSASPGASVSLTCTLR

CDRL1:
                                    (SEQ ID NO: 121)
SGINVGTYRIY

FRL2:
                                    (SEQ ID NO: 122)
WYQQKPGSPPRYLL

CDRL2:
                                    (SEQ ID NO: 123)
RYKSGLDKH

FRL3:
                                    (SEQ ID NO: 124)
QGSGVPSRFSGSKDDSANAGILFISGLQSEDEADYYCLI

CDRL3:
                                    (SEQ ID NO: 125)
WHSSAVVF

FRL4:
                                    (SEQ ID NO: 126)
GGGTKLTVLGQPKAAPSVT
```

One aspect is directed to an isolated polypeptide comprising one or more of the CDR sequences of the B1 antibody (i.e., one or more of SEQ ID NOs. 114, 116, 118, 121, 123, or 125). In certain embodiments, the isolated polypeptide further comprises additional amino acid sequences, or other molecules, to form a molecule that binds toxin B, including, but not limited to an anti-toxin B antibody.

The amino acid and nucleotide sequences for the $V_H$ and $V_L$ domains of the B2 antibody are as follows:

```
B2 heavy chain nucleic acid
                                          (SEQ ID NO: 91)
ATGAAACACCTGTGGTTCTTCGTCCTCCTGGTGGCAGCTCCCAGATGGGT

CCTGTCCCAGGTGCAACTACTGCAGGGGGGCGCAGGACTGTTGAAGCCTT

CGGAGACCCTGTCCCTCACGTGCGCTGTCTATGGTGGGTCCTTTAGTGAA

CACTATTGGAGTTGGATCCGCCAGCCCCCAGGGAAGGGGCTGGAGTGGAT

TGGGGAAATCAATTATGGTGGAAACACCAACTACAACCCGTCCCTCGAGA

GTCGAATCTCCATCTCAGTGGACACATCAAAGAACCAGGTCTTCCTGAGA

GTGAGATTTGTGACAGCTGCGGACACGGCTGTGTATTTTTGTTCGGGAGG

CCGGCGAGCAGCAGTACATGGCCGGACTTTTGCTATCTGGGGCCAAGGGA

CAATGGTCACCGTCTCTTCAGCCTCCACCAAGGGCCCATCGGTCTTCCCC

CTGGCACCCTCCTCCAAGAGCACCTCTGGGGGCACAGCGGCCCTGGGCTG

CCTGGTCAAGGACTACTTCCCCGAACCGGTGACGGTGTCGTGGAACTCAG

GCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGG

CACCCAGACCTACATCTGCAACGTGAATCACAAGCCCAGCAACACCAAGG

TGGACAAGAAAGTTGAGCCCAAATCTTGTGACAAAACTCACACATGCCCA

CCGTGCCCAGCACCTGAACTCCTGGGGGGACCGTCAGTCTTCCTCTTCCC

CCCAAAACCCAAGGACACCCTCATGATCTCCCGGACCCCTGAGGTCACAT

GCGTGGTGGTGGACGTGAGCCACGAAGACCCTGAGGTCAAGTTCAACTGG

TACGTGGACGGCGTGGAGGTGCATAATGCCAAGACAAAGCCGCGGGAGGA

GCAGTACAACAGCACGTACCGGGTGGTCAGCGTCCTCACCGTCCTGCACC

AGGACTGGCTGAATGGCAAGGAGTACAAGTGCAAGGTCTCCAACAAAGCC

CTCCCAGCCCCCATCGAGAAAACCATCTCCAAAGCCAAAGGGCAGCCCCG

AGAACCACAGGTGTACACCCTGCCCCCATCCCGGGATGAGCTGACCAAGA

ACCAGGTCAGCCTGACCTGCCTGGTCAAAGGCTTCTATCCCAGCGACATC

GCCGTGGAGTGGGAGAGCAATGGGCAGCCGGAGAACAACTACAAGACCAC

GCCTCCCGTGCTGGACTCCGACGGCTCCTTCTTCCTCTACAGCAAGCTCA

CCGTGGACAAGAGCAGGTGGCAGCAGGGGAACGTCTTCTCATGCTCCGTG

ATGCATGAGGCTCTGCACAACCACTACACGCAGAAGAGCCTCTCCCTGTC

TCCGGGTAAATGA

B2 light chain nucleic acid
                                          (SEQ ID NO: 93)
ATGAGGCTCCCTGCTCAGCTCCTGGGGCTGCTAATGCTCTGGGTCTCCGG

GTCCAGTGGGGATATTGTGATGACGCAGTCTCCACTCTCCCTGCCCGTCA

CCCCTGGAGAGCCGGCCTCCATCTCCTGCAGGTCTAGTCAGAGCCTGCTT

CATACTAATGGAAACAACTATTTGGTATGGTATCTGCAGAAGCCAGGGCA

GGCTCCACATCTCCTGATCTATCTGGGATCTAATCGGGCCTCCGGGGTCC

CTGGCAGGTTCAGTGGCAGTGGATCAGGCACAGATTTTACACTGAAAATC
```

-continued

```
AGCAGAGTGGAGGTCGAGGATGTTGGGGTTTATTACTGCATGCAATCTCT

ACAAACTCCTCCCACTTTTGGCCAGGGGACCAAGCTGGAGATCAAACGAA

CTGTGGCTGCACCATCTGTCTTCATCTTCCCGCCATCTGATGAGCAGTTG

AAATCTGGAACTGCCTCTGTTGTGTGCCTGCTGAATAACTTCTATCCCAG

AGAGGCCAAAGTACAGTGGAAGGTGGATAACGCCCTCCAATCGGGTAACT

CCCAGGAGAGTGTCACAGAGCAGGACAGCAAGGACAGCACCTACAGCCTC

AGCAGCACCCTGACGCTGAGCAAAGCAGACTACGAGAAACACAAAGTCTA

CGCCTGCGAAGTCACCCATCAGGGCCTGAGCTCGCCCGTCACAAAGAGCT

TCAACAGGGGAGAGTGTTAG

B2 heavy chain amino acid
                                          (SEQ ID NO: 92)
MKHLWFFVLLVAAPRWVLSQVQLLQGGAGLLKPSETLSLTCAVYGGSFSE

HYWSWIRQPPGKGLEWIGEINYGGNTNYNPSLESRISISVDTSKNQVFLR

VRFVTAADTAVYFCSGGRRAAVHGRTFAIWGQGTMVTVSSASTKGPSVFP

LAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCP

PCPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKA

LPAPIEKTISKAKGQPREPQVYTLPPSRDELTKNQVSLTCLVKGFYPSDI

AVEWESNGQPENNYKTTPPVLDSDGSFFLYSKLTVDKSRWQQGNVFSCSV

MHEALHNHYTQKSLSLSPGK

B2 light chain amino acid
                                          (SEQ ID NO: 94)
MRLPAQLLGLLMLWVSGSSGDIVMTQSPLSLPVTPGEPASISCRSSQSLL

HTNGNNYLVWYLQKPGQAPHLLIYLGSNRASGVPGRFSGSGSGTDFTLKI

SRVEVEDVGVYYCMQSLQTPPTFGQGTKLEIKRTVAAPSVFIFPPSDEQL

KSGTASVVCLLNNFYPREAKVQWKVDNALQSGNSQESVTEQDSKDSTYSL

SSTLTLSKADYEKHKVYACEVTHQGLSSPVTKSFNRGEC
```

The amino acid sequences for the FR and CDR sequences of the B2 antibody are as follows:

```
FRH1:
                                    (SEQ ID NO: 95)
QVQLLQGGAGLLKPSETLSLTCAVY

CDRH1:
                                    (SEQ ID NO: 96)
GGSFSEHYWS

FRH2:
                                    (SEQ ID NO: 97)
WIRQPPGKGLEWIG

CDRH2:
                                    (SEQ ID NO: 98)
EINYGGNTN

FRH3:
                                    (SEQ ID NO: 99)
YNPSLESRISISVDTSKNQVFLRVRFVTAADTAVYFCSG

CDRH3:
                                   (SEQ ID NO: 100)
GRRAAVHGRTFAI
```

```
FRH4:
                                  (SEQ ID NO: 101)
WGQGTMVTVSS

FRL1:
                                  (SEQ ID NO: 102)
DIVMTQSPLSLPVTPGEPASISC

CDRL1:
                                  (SEQ ID NO: 103)
RSSQSLLHTNGNNYLV

FRL2:
                                  (SEQ ID NO: 104)
WYLQKPGQAPHLLIY

CDRL2:
                                  (SEQ ID NO: 105)
LGSNRAS

FRL3:
                                  (SEQ ID NO: 106)
GVPGRFSGSGSGTDFTLKISRVEVEDVGVYYC

CDRL3:
                                  (SEQ ID NO: 107)
MQSLQTPPT

FRL4:
                                  (SEQ ID NO: 108)
FGQGTKLEIK
```

One aspect is directed to an isolated polypeptide comprising one or more of the CDR sequences of the B2 antibody (i.e., one or more of SEQ ID NOs. 96, 98, 100, 103, 105, or 107). In certain embodiments, the isolated polypeptide further comprises additional amino acid sequences, or other molecules, to form a molecule that binds toxin B, including, but not limited to an anti-toxin B antibody.

The amino acid and nucleotide sequences for the $V_H$ and $V_L$ domains of the B3 antibody are as follows:

```
B3 heavy chain nucleic acid
                                  (SEQ ID NO: 163)
ATGGAGTTTGGGCTGAGCTGGGTTTTCCTTGTTGCCATTTTAAAAGGTGT

CCAGTGTGAGGTGCAGCTGGTGGAGTCCGGGGGAGGCTTAGTTCAGCCTG

GGGGGTCCCTGAGACTCTCCTGTTCAGCCTCTGGATTCACTTTCAGAAGT

TACTGGATGCACTGGGTCCGCCAAGTTCCAGGGAAGGGGCTGGTATGGGT

CTCATGTATTAATAAAGAAGGGAGTAGCACAACCTACGCGGACTCCGTGA

AGGGCCGATTCACCATCTCCAGAGACAACGCCAAGAACACGCTGTATTTG

CAAATGAACAGTCTGAGAGCCGACGACACGGCTGTGTATTACTGTCTAAG

GGGATACGATGTTGACTACTGGGGCCAGGGAACCCTGGTCACCGTCTCCT

CAGCCTCCACCAAGGGCCCATCGGTCTTCCCCCTGGCACCCTCCTCCAAG

AGCACCTCTGGGGGCACAGCGGCCCTGGGCTGCCTGGTCAAGGACTACTT

CCCCGAACCGGTGACGGTGTCGTGGAACTCAGGCGCCCTGACCAGCGGCG

TGCACACCTTCCCGGCTGTCCTACAGTCCTCAGGACTCTACTCCCTCAGC

AGCGTGGTGACCGTGCCCTCCAGCAGCTTGGGCACCCAGACCTACATCTG

CAACGTGAATCACAAGCCCAGCAACACCAAGGTGGACAAGAAAGTTGAGC

CCAAATCTTGTGACAAAACTCACACATGCCCACCGTGCCCAGCACCTGAA

CTCCTGGGGGGACCGTCAGTCTTCCTCTTCCCCCCAAAACCCAAGGACAC

CCTCATGATCTCCCGGACCCCTGAGGTCACATGCGTGGTGGTGGACGTGA
```
```
GCCACGAAGACCCTGAGGTCAAGTTCAACTGGTACGTGGACGGCGTGGAG

GTGCATAATGCCAAGACAAAGCCGCGGGAGGAGCAGTACAACAGCACGTA

CCGGGTGGTCAGCGTCCTCACCGTCCTGCACCAGGACTGGCTGAATGGCA

AGGAGTACAAGTGCAAGGTCTCCAACAAAGCCCTCCCAGCCCCCATCGAG

AAAACCATCTCCAAAGCCAAAGGGCAGCCCCGAGAACCACAGGTGTACAC

CCTGCCCCCATCCCGGGATGAGCTGACCAAGAACCAGGTCAGCCTGACCT

GCCTGGTCAAAGGCTTCTATCCCAGCGACATCGCCGTGGAGTGGGAGAGC

AATGGGCAGCCGGAGAACAACTACAAGACCACGCCTCCCGTGCTGGACTC

CGACGGCTCCTTCTTCCTCTACAGCAAGCTCACCGTGGACAAGAGCAGGT

GGCAGCAGGGGAACGTCTTCTCATGCTCCGTGATGCATGAGGCTCTGCAC

AACCACTACACGCAGAAGAGCCTCTCCCTGTCTCCGGGTAAATGA

B3 light chain nucleic acid
                                  (SEQ ID NO: 165)
ATGGCCTGGACTCCTCTCCTCCTCCTGTTCCTCTCTCACTGCACAGGTTC

CCTCTCGCAGGCTGTGCTGACTCAGCCGTCCTCCCTCTCTGCATCTCCCG

GAGCATCAGTCAGTCTCACCTGCACCTTGCGCAGTGGCGTCAATGTTGGT

TCCTACAGGATATACTGGTATCAGCAGAAGCCAGGGAGTCCTCCCCGGTA

TCTCCTGAGGTACAAATCAGGCTTAGATAAACACCAGGGCTCTGGAGTCC

CCAGCCGCTTCTCTGGATCCAAAGATGATTCGGCCAATGCAGGGATTTTA

TTCATTTCTGGGCTCCAGTCTGAGAATGATGCTGATTATTACTGTTTGAT

TTGGCACAACAGCGCTGTGGTATTCGGCGGAGGGACCAAGCTGACCGTCC

TAGGTCAGCCCAAGGCTGCCCCCTCGGTCACTCTGTTCCCGCCCTCCTCT

GAGGAGCTTCAAGCCAACAAGGCCACACTGGTGTGTCTGATCAGTGACTT

CTACCCGGGAGCTGTGACAGTGGCTTGGAAGGCAGATGGCAGCCCCGTCA

AGGCGGGAGTGGAGACGACCAAACCCTCCAAACAGAGCAACAACAAGTAC

GCGGCCAGCAGCTACCTGAGCCTGACGCCCGAGCAGTGGAAGTCCCACAG

AAGCTACAGCTGCCAGGTCACGCATGAAGGGAGCACCGTGGAGAAGACAG

TGGCCCCTACAGAATGTTCATAG

B3 heavy chain amino acid
                                  (SEQ ID NO: 164)
MEFGLSWVFLVAILKGVQCEVQLVESGGGLVQPGGSLRLSCSASGFTFRS

YWMHWVRQVPGKGLVWVSCINKEGSSTTYADSVKGRFTISRDNAKNTLYL

QMNSLRADDTAVYYCLRGYDVDYWGQGTLVTVSSASTKGPSVFPLAPSSK

STSGGTAALGCLVKDYFPEPVTVSWNSGALTSGVHTFPAVLQSSGLYSLS

SVVTVPSSSLGTQTYICNVNHKPSNTKVDKKVEPKSCDKTHTCPPCPAPE

LLGGPSVFLFPPKPKDTLMISRTPEVTCVVVDVSHEDPEVKFNWYVDGVE

VHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWES

NGQPENNYKTTPPVLDSDGSFFLYSKLTVDKSRWQQGNVFSCSVMHEALH

NHYTQKSLSLSPGK

B3 light chain amino acid
                                  (SEQ ID NO: 166)
MAWTPLLLLFLSHCTGSLSQAVLTQPSSLSASPGASVSLTCTLRSGVNVG

SYRIYWYQQKPGSPPRYLLRYKSGLDKHQGSGVPSRFSGSKDDSANAGIL
```

-continued

```
FISGLQSENDADYYCLIWHNSAVVFGGGTKLTVLGQPKAAPSVTLFPPSS

EELQANKATLVCLISDFYPGAVTVAWKADGSPVKAGVETTKPSKQSNNKY

AASSYLSLTPEQWKSHRSYSCQVTHEGSTVEKTVAPTECS
```

The amino acid sequences for the FR and CDR sequences of the B3 antibody are as follows:

```
FRH1:
                                        (SEQ ID NO: 167)
EVQLVESGGGLVQPGGSLRLSCSAS

CDRH1:
                                        (SEQ ID NO: 168)
GFTFRSYWMH

FRH2:
                                        (SEQ ID NO: 169)
WVRQVPGKGLVWVS

CDRH2:
                                        (SEQ ID NO: 170)
CINKEGSSTT

FRH3:
                                        (SEQ ID NO: 171)
YADSVKGRFTISRDNAKNTLYLQMNSLRADDTAVYYCLR

CDRH3:
                                        (SEQ ID NO: 172)
GYDVDYWG

FRH4:
                                        (SEQ ID NO: 173)
QGTLVTVSS

FRL1:
                                        (SEQ ID NO: 174)
QAVLTQPSSLSASPGASVSLTCTLR

CDRL1:
                                        (SEQ ID NO: 175)
SGVNVGSYRIY

FRL2:
                                        (SEQ ID NO: 176)
WYQQKPGSPPRYLL

CDRL2:
                                        (SEQ ID NO: 177)
RYKSGLDKH

FRL3:
                                        (SEQ ID NO: 178)
QGSGVPSRFSGSKDDSANAGILFISGLQSENDADYYCLI

CDRL3:
                                        (SEQ ID NO: 179)
WHNSAVVF

FRL4:
                                        (SEQ ID NO: 180)
GGGTKLTVLGQPKAAPSVT
```

One aspect is directed to an isolated polypeptide comprising one or more of the CDR sequences of the B3 antibody (i.e., one or more of SEQ ID NOs. 168, 170, 172, 175, 177, or 179). In certain embodiments, the isolated polypeptide further comprises additional amino acid sequences, or other molecules, to form a molecule that binds toxin B, including, but not limited to an anti-toxin B antibody.

The amino acid and nucleotide sequences for the $V_H$ and $V_L$ domains of the B4 antibody are as follows:

```
B4 heavy chain nucleic acid
                                        (SEQ ID NO: 145)
ATGGAACTGGGCTCCGCTGGGTTTTCCTTGTTGCTATTTTAGAAGGTGT

CCAGTGTGAGGTGCAGCTGGTGGAGTCTGGGGGAGGCCTGGTCAAGCCTG

GGGGGTCCCTGAGAGTCTCCTGTGCAGCCTCTGGATTCACCTTCAGTAGC

TATAGCATGAACTGGATCCGCCAGGCTCCAGGGAAGGGGCTGGAGTGGGT

CTCATCCATTAGTAGTAATAGTAGTTACATATACTACGCAGACTCAGTTA

AGGGCCGATTCACCATCTCCAGAGACAACGCCAAGAACTCACTGTATCTG

CAAATGAACAGCCTGAGAGCCGAGGACACGGCTGTTTATTACTGTGCGAG

AGATCGGGACTACAGTAACTACCTTACCGCGTGGGGCCAGGGAACCCTGG

TCACCGTCTCCTCAGCCTCCACCAAGGGCCCATCGGTCTTCCCCCTGGCA

CCCTCCTCCAAGAGCACCTCTGGGGGCACAGCGGCCCTGGGCTGCCTGGT

CAAGGACTACTTCCCCGAACCGGTGACGGTGTCGTGGAACTCAGGCGCCC

TGACCAGCGGCGTGCACACCTTCCCGGCTGTCCTACAGTCCTCAGGACTC

TACTCCCTCAGCAGCGTGGTGACCGTGCCCTCCAGCAGCTTGGGCACCCA

GACCTACATCTGCAACGTGAATCACAAGCCCAGCAACACCAAGGTGGACA

AGAAAGTTGAGCCCAAATCTTGTGACAAAACTCACACATGCCCACCGTGC

CCAGCACCTGAACTCCTGGGGGGACCGTCAGTCTTCCTCTTCCCCCCAAA

ACCCAAGGACACCCTCATGATCTCCCGGACCCCTGAGGTCACATGCGTGG

TGGTGGACGTGAGCCACGAAGACCCTGAGGTCAAGTTCAACTGGTACGTG

GACGGCGTGGAGGTGCATAATGCCAAGACAAAGCCGCGGGAGGAGCAGTA

CAACAGCACGTACCGGGTGGTCAGCGTCCTCACCGTCCTGCACCAGGACT

GGCTGAATGGCAAGGAGTACAAGTGCAAGGTCTCCAACAAAGCCCTCCCA

GCCCCCATCGAGAAAACCATCTCCAAAGCCAAAGGGCAGCCCCGAGAACC

ACAGGTGTACACCCTGCCCCCATCCCGGGATGAGCTGACCAAGAACCAGG

TCAGCCTGACCTGCCTGGTCAAAGGCTTCTATCCCAGCGACATCGCCGTG

GAGTGGGAGAGCAATGGGCAGCCGGAGAACAACTACAAGACCACGCCTCC

CGTGCTGGACTCCGACGGCTCCTTCTTCCTCTACAGCAAGCTCACCGTGG

ACAAGAGCAGGTGGCAGCAGGGGAACGTCTTCTCATGCTCCGTGATGCAT

GAGGCTCTGCACAACCACTACACGCAGAAGAGCCTCTCCCTGTCTCCGGG

TAAATGA

B4 light chain nucleic acid
                                        (SEQ ID NO: 147)
ATGGCCTGGTCTCCTCTCCTCCTCACTCTCCTCGCTCACTGCACAGGGTC

CTGGGCCCAGTCTGTGCTGACGCAGCCGCCCTCAGTGTCTGGGGCCCCAG

GGCAGAGGGTCACCATCTCCTGCACTGGGAGCAGCTCCAACATCGGGGCA

GGTTATGATGTACACTGGTACCGCCAACTTCCAGGAACAGCCCCCAAACT

CCTCATCTATGGTAAGAACAATCGGCCCTCAGGGGTCCCTAACCGATTCT

CTGGCTCCAAGTCTGGCACCTCAGCCTCCCTGGCCATCACTGGCCTCCAG

GCTGAGGATGAGGCTGATTATTACTGTCAGTCCTATGACAGCAGCCTGAG

TGGTTCGGTATTCGGCGGAGGGACCAAGCTGACCGTCCTAGGTCAGCCCA

AGGCTGCCCCCTCGGTCACTCTGTTCCCGCCCTCCTCTGAGGAGCTTCAA

GCCAACAAGGCCACACTAGTGTGTCTGATCAGTGACTTCTACCCGGGAGC
```

```
TGTGACAGTGGCTTGGAAGGCAGATGGCAGCCCCGTCAAGGCGGGAGTGG

AGACGACCAAACCCTCCAAACAGAGCAACAACAAGTACGCGGCCAGCAGC

TACCTGAGCCTGACGCCCGAGCAGTGGAAGTCCCACAGAAGCTACAGCTG

CCAGGTCACGCATGAAGGGAGCACCGTGGAGAAGACAGTGGCCCCTACAG

AATGTTCATAG

B4 heavy chain amino acid
                                           (SEQ ID NO: 146)
MELGLRWVFLVAILEGVQCEVQLVESGGGLVKPGGSLRVSCAASGFTFSS

YSMNWIRQAPGKGLEWVSSISSNSSYIYYADSVKGRFTISRDNAKNSLYL

QMNSLRAEDTAVYYCARDRDYSNYLTAWGQGTLVTVSSASTKGPSVFPLA

PSSKSTSGGTAALGCLVKDYFPEPVTVSWNSGALTSGVHTFPAVLQSSGL

YSLSSVVTVPSSSLGTQTYICNVNHKPSNTKVDKKVEPKSCDKTHTCPPC

PAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALP

APIEKTISKAKGQPREPQVYTLPPSRDELTKNQVSLTCLVKGFYPSDIAV

EWESNGQPENNYKTTPPVLDSDGSFFLYSKLTVDKSRWQQGNVFSCSVMH

EALHNHYTQKSLSLSPGK

B4 light chain amino acid
                                           (SEQ ID NO: 148)
MAWSPLLLTLLAHCTGSWAQSVLTQPPSVSGAPGQRVTISCTGSSSNIGA

GYDVHWYRQLPGTAPKLLIYGKNNRPSGVPNRFSGSKSGTSASLAITGLQ

AEDEADYYCQSYDSSLSGSVFGGGTKLTVLGQPKAAPSVTLFPPSSEELQ

ANKATLVCLISDFYPGAVTVAWKADGSPVKAGVETTKPSKQSNNKYAASS

YLSLTPEQWKSHRSYSCQVTHEGSTVEKTVAPTECS
```

The amino acid sequences for the FR and CDR sequences of the B4 antibody are as follows:

```
FRH1:
                                           (SEQ ID NO: 149)
EVQLVESGGGLVKPGGSLRVSCAAS

CDRH1:
                                           (SEQ ID NO: 150)
GFTFSSYSMN

FRH2:
                                           (SEQ ID NO: 151)
WIRQAPGKGLEWVS

CDRH2:
                                           (SEQ ID NO: 152)
SISSNSSYI

FRH3:
                                           (SEQ ID NO: 153)
YYADSVKGRFTISRDNAKNSLYLQMNSLRAEDTAVYYCAR

CDRH3:
                                           (SEQ ID NO: 154)
DRDYSNYLTA

FRH4:
                                           (SEQ ID NO: 155)
WGQGTLVTVSS

FRL1:
                                           (SEQ ID NO: 156)
QSVLTQPPSVSGAPGQRVTISC

CDRL1:
                                           (SEQ ID NO: 157)
TGSSSNIGAGYDVH

FRL2:
                                           (SEQ ID NO: 158)
WYRQLPGTAPKLLIY

CDRL2:
                                           (SEQ ID NO: 159)
GKNNRPS

FRL3:
                                           (SEQ ID NO: 160)
GVPNRFSGSKSGTSASLAITGLQAEDEADYYC

CDRL3:
                                           (SEQ ID NO: 161)
QSYDSSLSGSV

FRL4:
                                           (SEQ ID NO: 162)
FGGGTKLTVLGQPKAAPSVT
```

One aspect is directed to an isolated polypeptide comprising one or more of the CDR sequences of the B4 antibody (i.e., one or more of SEQ ID NOs. 150, 152, 154, 157, 159, or 161). In certain embodiments, the isolated polypeptide further comprises additional amino acid sequences, or other molecules, to form a molecule that binds toxin B, including, but not limited to an anti-toxin B antibody.

The amino acid and nucleotide sequences for the $V_H$ and $V_L$ domains of the B5 antibody are as follows:

```
B5 heavy chain nucleic acid
                                           (SEQ ID NO: 181)
ATGAAACACCTGTGGTTCTTCCTCCTCCTGGTGGCAGCTCCCAGATGGGT

CCTGTCTCAGGTGCATCTGCAGGAGTCGGGCCCAGGACTGGTGAAGCCTT

CGGGGACCCTGTCCCTCACCTGCGCTGTCTCTGGTGGCTCCATCAGTTAC

ACTAACTGGTGGAGTTGGGTCCGCCTGCCCCCAGGGAAGGGGCTGGAGTG

GATAGGGGAAATCTATCATAGTAGGAGCACCAACTACAACCCGTCCCTCA

AGAGTCGAGTCACCATGTCAATAGACAAGTCCAAGAATCTGTTCTCCCTG

AAGCTGAACTCTGTGACCGCCGCGGACACGGCCATCTATTACTGTGCTAA

AGCCGCTTACACAAGGGATGGAATACAGCCTTTTGACAACTGGGGCCAGG

GAACCCTGGTCACCGTCTCCTCAGCCTCCACCAAGGGCCCATCGGTCTTC

CCCCTGGCACCCTCCTCCAAGAGCACCTCTGGGGGCACAGCGGCCCTGGG

CTGCCTGGTCAAGGACTACTTCCCCGAACCGGTGACGGTGTCGTGGAACT

CAGGCGCCCTGACCAGCGGCGTGCACACCTTCCCGGCTGTCCTACAGTCC

TCAGGACTCTACTCCCTCAGCAGCGTGGTGACCGTGCCCTCCAGCAGCTT

GGGCACCCAGACCTACATCTGCAACGTGAATCACAAGCCCAGCAACACCA

AGGTGGACAAGAAAGTTGAGCCCAAATCTTGTGACAAAACTCACACATGC

CCACCGTGCCCAGCACCTGAACTCCTGGGGGGACCGTCAGTCTTCCTCTT

CCCCCCAAAACCCAAGGACACCCTCATGATCTCCCGGACCCCTGAGGTCA

CATGCGTGGTGGTGGACGTGAGCCACGAAGACCCTGAGGTCAAGTTCAAC

TGGTACGTGGACGGCGTGGAGGTGCATAATGCCAAGACAAAGCCGCGGGA

GGAGCAGTACAACAGCACGTACCGGGTGGTCAGCGTCCTCACCGTCCTGC
```

```
ACCAGGACTGGCTGAATGGCAAGGAGTACAAGTGCAAGGTCTCCAACAAA

GCCCTCCCAGCCCCCATCGAGAAAACCATCTCCAAAGCCAAAGGGCAGCC

CCGAGAACCACAGGTGTACACCCTGCCCCCATCCCGGGATGAGCTGACCA

AGAACCAGGTCAGCCTGACCTGCCTGGTCAAAGGCTTCTATCCCAGCGAC

ATCGCCGTGGAGTGGGAGAGCAATGGGCAGCCGGAGAACAACTACAAGAC

CACGCCTCCCGTGCTGGACTCCGACGGCTCCTTCTTCCTCTACAGCAAGC

TCACCGTGGACAAGAGCAGGTGGCAGCAGGGGAACGTCTTCTCATGCTCC

GTGATGCATGAGGCTCTGCACAACCACTACACGCAGAAGAGCCTCTCCCT

GTCTCCGGGTAAATGA

B5 light chain nucleic acid
                                              (SEQ ID NO: 183)
ATGGTGTTGCAGACCCAGGTCTTCATTTCTCTGTTGCTCTGGATCTCTGG

TGCCTACGGGGACATCGTGATGACCCAGTCTCCAGACTCCCTGGCTGTGT

CTCTGGGCGAGAGGGCCACCATCAACTGCAAGTCCAGCCAGAGTGTTTTA

AAGAGCTCCAACAATAAGAACTACTTAGCTTGGTACCAGCAGAAACCAGG

ACAGCCTCCTAAGCTGCTCATTTTCTGGGCATCGACCCGGGAATCCGGGG

TCCCTGACCGATTCAGTGGCAGCGGGTCTGGGACAGATTTCACTCTCACC

ATCAGCAGCCTGCAGGCTGAAGATGTGGCAGTTTATTACTGTCAGCAATA

TTCTAGTGCTCCTCGAACTTTCGGCGGAGGGACCAACGTAGAAATCAGAC

GAACTGTGGCTGCACCATCTGTCTTCATCTTCCCGCCATCTGATGAGCAG

TTGAAATCTGGAACTGCCTCTGTTGTGTGCCTGCTGAATAACTTCTATCC

CAGAGAGGCCAAAGTACAGTGGAAGGTGGATAACGCCCTCCAATCGGGTA

ACTCCCAGGAGAGTGTCACAGAGCAGGACAGCAAGGACAGCACCTACAGC

CTCAGCAGCACCCTGACGCTGAGCAAAGCAGACTACGAGAAACACAAAGT

CTACGCCTGCGAAGTCACCCATCAGGGCCTGAGCTCGCCCGTCACAAAGA

GCTTCAACAGGGGAGAGTGTTAG

B5 heavy chain amino acid
                                              (SEQ ID NO: 182)
MKHLWFFLLLVAAPRWVLSQVHLQESGPGLVKPSGTLSLTCAVSGGSISY

TNWWSWVRLPPGKGLEWIGEIYHSRSTNYNPSLKSRVTMSIDKSKNLFSL

KLNSVTAADTAIYYCAKAAYTRDGIQPFDNWGQGTLVTVSSASTKGPSVF

PLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHTC

PPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNK

ALPAPIEKTISKAKGQPREPQVYTLPPSRDELTKNQVSLTCLVKGFYPSD

IAVEWESNGQPENNYKTTPPVLDSDGSFFLYSKLTVDKSRWQQGNVFSCS

VMHEALHNHYTQKSLSLSPGK

B5 light chain amino acid
                                              (SEQ ID NO: 184)
MVLQTQVFISLLLWISGAYGDIVMTQSPDSLAVSLGERATINCKSSQSVL

KSSNNKNYLAWYQQKPGQPPKLLIFWASTRESGVPDRFSGSGSGTDFTLT

ISSLQAEDVAVYYCQQYSSAPRTFGGGTNVEIRRTVAAPSVFIFPPSDEQ

LKSGTASVVCLLNNFYPREAKVQWKVDNALQSGNSQESVTEQDSKDSTYS

LSSTLTLSKADYEKHKVYACEVTHQGLSSPVTKSFNRGEC
```

The amino acid sequences for the FR and CDR sequences of the B5 antibody are as follows:

FRH1:
(SEQ ID NO: 185)
QVHLQESGPGLVKPSGTLSLTCAVS

CDRH1:
(SEQ ID NO: 186)
GGSISYTNWWS

FRH2:
(SEQ ID NO: 187)
WVRLPPGKGLEWIG

CDRH2:
(SEQ ID NO: 188)
EIYHSRSTN

FRH3:
(SEQ ID NO: 189)
YNPSLKSRVTMSIDKSKNLFSLKLNSVTAADTAIYYCAK

CDRH3:
(SEQ ID NO: 190)
AAYTRDGIQPFDN

FRH4:
(SEQ ID NO: 191)
WGQGTLVTVSS

FRL1:
(SEQ ID NO: 192)
DIVMTQSPDSLAVSLGERATINC

CDRL1:
(SEQ ID NO: 193)
KSSQSVLKSSNNKNYLA

FRL2:
(SEQ ID NO: 194)
WYQQKPGQPPKLLIF

CDRL2:
(SEQ ID NO: 195)
WASTRES

FRL3:
(SEQ ID NO: 196)
GVPDRFSGSGSGTDFTLTISSLQAEDVAVYYC

CDRL3:
(SEQ ID NO: 197)
QQYSSAPRT

FRL4:
(SEQ ID NO: 198)
FGGGTNVEIR

One aspect is directed to an isolated polypeptide comprising one or more of the CDR sequences of the B5 antibody (i.e., one or more of SEQ ID NOs. 186, 188, 190, 193, 195, or 197). In certain embodiments, the isolated polypeptide further comprises additional amino acid sequences, or other molecules, to form a molecule that binds toxin B, including, but not limited to an anti-toxin B antibody.

The amino acid and nucleotide sequences for the $V_H$ and $V_L$ domains of the B6 antibody are as follows:

B6 heavy chain nucleic acid
(SEQ ID NO: 127)
ATGGAGTTGGGGCTGTGCTGGGTTTTCCTTGTTGCTATTTTAGAAGGTGT
CCAGTGTGAGGTGCAGCTGGTGGAGTCTGGGGGAGGCTTGGTACAGCCGG
GGGGGTCCCTGAGACTCTCCTGTGCAGCCTCTGGATTCACCTTCACTACC
TCTACCATGAACTGGGTCCGCCAGGCTCCAGGGAAGGGGCTGGAGTGGGT
TTCATACATTACTAGGACCAGCACTGTCATATACTATGCAGACTCTGTGA
AGGGCCGATTCACCATCTCCAGAGACAATGCCAAGAACTCACTGTATCTG
CAAATGAGCAGCCTGAGAGCCGAGGACACGGCTGTGTATTATTGTGCGAG
AGGGGTGAGGGACATTGGCGGAAACGGTTTTGACTACTGGGGCCAGGGAA
CCCTGGTCACCGTCTCCTCAGCCTCCACCAAGGGCCCATCGGTCTTCCCC
CTGGCACCCTCCTCCAAGAGCACCTCTGGGGGCACAGCGGCCCTGGGCTG
CCTGGTCAAGGACTACTTCCCCGAACCGGTGACGGTGTCGTGGAACTCAG
GCGCCCTGACCAGCGGCGTGCACACCTTCCCGGCTGTCCTACAGTCCTCA
GGACTCTACTCCCTCAGCAGCGTGGTGACCGTGCCCTCCAGCAGCTTGGG
CACCCAGACCTACATCTGCAACGTGAATCACAAGCCCAGCAACACCAAGG
TGGACAAGAAAGTTGAGCCCAAATCTTGTGACAAAACTCACACATGCCCA
CCGTGCCCAGCACCTGAACTCCTGGGGGGACCGTCAGTCTTCCTCTTCCC
CCCAAAACCCAAGGACACCCTCATGATCTCCCGGACCCCTGAGGTCACAT
GCGTGGTGGTGGACGTGAGCCACGAAGACCCTGAGGTCAAGTTCAACTGG
TACGTGGACGGCGTGGAGGTGCATAATGCCAAGACAAAGCCGCGGGAGGA
GCAGTACAACAGCACGTACCGGGTGGTCAGCGTCCTCACCGTCCTGCACC
AGGACTGGCTGAATGGCAAGGAGTACAAGTGCAAGGTCTCCAACAAAGCC
CTCCCAGCCCCCATCGAGAAAACCATCTCCAAAGCCAAAGGGCAGCCCCG
AGAACCACAGGTGTACACCCTGCCCCCATCCCGGGATGAGCTGACCAAGA
ACCAGGTCAGCCTGACCTGCCTGGTCAAAGGCTTCTATCCCAGCGACATC
GCCGTGGAGTGGGAGAGCAATGGGCAGCCGGAGAACAACTACAAGACCAC
GCCTCCCGTGCTGGACTCCGACGGCTCCTTCTTCCTCTACAGCAAGCTCA
CCGTGGACAAGAGCAGGTGGCAGCAGGGGAACGTCTTCTCATGCTCCGTG
ATGCATGAGGCTCTGCACAACCACTACACGCAGAAGAGCCTCTCCCTGTC
TCCGGGTAAATGA B6 light chain nucleic acid
(SEQ ID NO: 129)
ATGGAAACCCCAGCGCAGCTTCTCTTCCTCCTGCTACTCTGGCTCCCAGA
TACCACCGGAGAAATTGTGTTGACGCAGTCTCCAGGCACCCTCTCTTTGT
CTCCAGGGGAAAGAGCCACCCTCTCCTGCAGGGCCAGTCAGAGTGTAACC
AGCAGTTACTTAGCCTGGTACCAGCAGAAAACTGGCCAGGCTCCCAGGCT
CCTCATCTACGGCGCATCCAGCAGGGCCACTGGCATCCCAGACAGGTTCA
GTGGCAGTGGGTCTGGGACAGACTTCACTCTCACCATCGCCAGACTGGAG
CCTGAAGATTTTGCGGTGTATTACTGTCAGCAGTATGGTAGCTCGCCTCC
GTACACTTTTGGCCAGGGGACCAAGCTGGAGATCAAACGAACTGTGGCTG
CACCATCTGTCTTCATCTTCCCGCCATCTGATGAGCAGTTGAAATCTGGA
ACTGCCTCTGTTGTGTGCCTGCTGAATAACTTCTATCCCAGAGAGGCCAA
AGTACAGTGGAAGGTGGATAACGCCCTCCAATCGGGTAACTCCCAGGAGA
GTGTCACAGAGCAGGACAGCAAGGACAGCACCTACAGCCTCAGCAGCACC
CTGACGCTGAGCAAAGCAGACTACGAGAAACACAAAGTCTACGCCTGCGA
AGTCACCCATCAGGGCCTGAGCTCGCCCGTCACAAAGAGCTTCAACAGGG
GAGAGTGTTAG B6 heavy chain amino acid
(SEQ ID NO: 128)
MELGLCWVFLVAILEGVQCEVQLVESGGGLVQPGGSLRLSCAASGFTFTT
STMNWVRQAPGKGLEWVSYITRTSTVIYYADSVKGRFTISRDNAKNSLYL
QMSSLRAEDTAVYYCARGVRDIGGNGFDYWGQGTLVTVSSASTKGPSVFP
LAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCP
PCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKA
LPAPIEKTISKAKGQPREPQVYTLPPSRDELTKNQVSLTCLVKGFYPSDI
AVEWESNGQPENNYKTTPPVLDSDGSFFLYSKLTVDKSRWQQGNVFSCSV
MHEALHNHYTQKSLSLSPGK B6 light chain amino acid
(SEQ ID NO: 130)
METPAQLLFLLLLWLPDTTGEIVLTQSPGTLSLSPGERATLSCRASQSVT
SSYLAWYQQKTGQAPRLLIYGASSRATGIPDRFSGSGSGTDFTLTIARLE
PEDFAVYYCQQYGSSPPYTFGQGTKLEIKRTVAAPSVFIFPPSDEQLKSG
TASVVCLLNNFYPREAKVQWKVDNALQSGNSQESVTEQDSKDSTYSLSST
LTLSKADYEKHKVYACEVTHQGLSSPVTKSFNRGEC The amino acid sequences for the FR and CDR sequences of the B6 antibody are as follows:

FRH1:
(SEQ ID NO: 131)
EVQLVESGGGLVQPGGSLRLSCAAS

CDRH1:
(SEQ ID NO: 132)
GFTFTTSTMN

FRH2:
(SEQ ID NO: 133)
WVRQAPGKGLEWVS

CDRH2:
(SEQ ID NO: 134)
YITRTSTVI

FRH3:
(SEQ ID NO: 135)
YYADSVKGRFTISRDNAKNSLYLQMSSLRAEDTAVYYCAR

CDRH3:
(SEQ ID NO: 136)
GVRDIGGNGFDY

FRH4:
(SEQ ID NO: 137)
WGQGTLVTVSS

```
FRL1:
                                      (SEQ ID NO: 138)
EIVMTQSPATLSVSPGERATLSC

CDRL1:
                                      (SEQ ID NO: 139)
RASQSISSNLA

FRL2:
                                      (SEQ ID NO: 140)
WYQQKPGQAPRLLIY

CDRL2:
                                      (SEQ ID NO: 141)
DASTRAT

FRL3:
                                      (SEQ ID NO: 142)
GIPARFSGSGSGTEFTLTISSLQSEDFAVYYC

CDRL3:
                                      (SEQ ID NO: 143)
QQYNDWLVT

FRL4:
                                      (SEQ ID NO: 144)
FGQGTKVEIK
```

One aspect is directed to an isolated polypeptide comprising one or more of the CDR sequences of the B6 antibody (i.e., one or more of SEQ ID NOs.132, 134, 136, 139, 141, or 143). In certain embodiments, the isolated polypeptide further comprises additional amino acid sequences, or other molecules, to form a molecule that binds toxin B, including, but not limited to an anti-toxin B antibody.

The SEQ ID NOs corresponding to the sequences of the B1, B2, B3, B4, B5, and B6 antibodies are listed in Table 2.

TABLE 2

| SEQ ID NOs of Anti-Toxin B Antibodies | | | | | | | |
|---|---|---|---|---|---|---|---|
| Region | Type | B1 | B2 | B3 | B4 | B5 | B6 |
| VH | DNA | 109 | 91 | 163 | 145 | 181 | 127 |
| VH | AA | 110 | 92 | 164 | 146 | 182 | 128 |
| VL | DNA | 111 | 93 | 165 | 147 | 183 | 129 |
| VL | AA | 112 | 94 | 166 | 148 | 184 | 130 |
| FRH1 | AA | 113 | 95 | 167 | 149 | 185 | 131 |
| CDRH1 | AA | 114 | 96 | 168 | 150 | 186 | 132 |
| FRH2 | AA | 115 | 97 | 169 | 151 | 187 | 133 |
| CDRH2 | AA | 116 | 98 | 170 | 152 | 188 | 134 |

TABLE 2-continued

| SEQ ID NOs of Anti-Toxin B Antibodies | | | | | | | |
|---|---|---|---|---|---|---|---|
| Region | Type | B1 | B2 | B3 | B4 | B5 | B6 |
| FRH3 | AA | 117 | 99 | 171 | 153 | 189 | 135 |
| CDRH3 | AA | 118 | 100 | 172 | 154 | 190 | 136 |
| FRH4 | AA | 119 | 101 | 173 | 155 | 191 | 137 |
| FRL1 | AA | 120 | 102 | 174 | 156 | 192 | 138 |
| CDRL1 | AA | 121 | 103 | 175 | 157 | 193 | 139 |
| FRL2 | AA | 122 | 104 | 176 | 158 | 194 | 140 |
| CDRL2 | AA | 123 | 105 | 177 | 159 | 195 | 141 |
| FRL3 | AA | 124 | 106 | 178 | 160 | 196 | 142 |
| CDRL3 | AA | 125 | 107 | 179 | 161 | 197 | 143 |
| FRL4 | AA | 126 | 108 | 180 | 162 | 198 | 144 |

7. Modified Antibodies

Modified versions of the A1, A2, A3, A4, A5, B1, B2, B3, B4, B5, and B6 antibodies are also provided. Typically modifications to an antibody can be introduced through the nucleic acids that encode the heavy or light chain variable domains of the antibody. These modifications can include deletions, insertions, point mutations, truncations, and amino acid substitutions and addition of amino acids or non-amino acid moieties. For example, random mutagenesis of the disclosed $V_H$ or $V_L$ sequences can be used to generate variant $V_H$ or $V_L$ domains still capable of binding C. difficile toxin A or B. A technique using error-prone PCR is described by Gram et al. (Proc. Nat. Acad. Sci. U.S.A. (1992) 89: 3576-3580). Another method uses direct mutagenesis of the disclosed $V_H$ or $V_L$ sequences. Such techniques are disclosed by Barbas et al. (Proc. Nat. Acad. Sci. U.S.A. (1994) 91: 3809-3813) and Schier et al. (J. Mol. Biol. (1996) 263: 551-567). Modifications can also be made directly to the amino acid sequence, such as by cleavage, addition of a linker molecule or addition of a detectable moiety, such as biotin, addition of a fatty acid, and the like.

In one embodiment, the antibody is a monoclonal antibody that binds to C. difficile toxin A and comprises 1) a heavy chain variable domain that is at least about 70%, at least about 80%, at least about 90%, at least about 95%, at least about 98% identical, or 100% identical to the amino acid sequence of the heavy chain variable domain of the A1, A2, A3, A4, or A5 antibody, and 2) a light chain variable domain that is at least about 70%, at least about 80%, at least about 90%, at least about 95%, at least about 98% identical, or 100% identical to the amino acid sequence of the light chain variable domain of the A1, A2, A3, A4, or A5 antibody, wherein the heavy chain and light chain variable domains from the same antibody are combined as shown in Table 3.

TABLE 3

| Modified Anti-Toxin A Antibodies | |
|---|---|
| C. difficile Toxin A Antibody | |
| $V_H$ | $V_L$ |
| At least about 70%, at least about 80%, at least about 90%, at least about 95%, at least about 98% identical, or 100% identical to SEQ ID NO: 20 (A1) | At least about 70%, at least about 80%, at least about 90%, at least about 95%, at least about 98% identical, or 100% identical to SEQ ID NO: 22 (A1) |
| At least about 70%, at least about 80%, at least about 90%, at least about 95%, at least about 98% identical, or 100% identical to SEQ ID NO: 2 (A2) | At least about 70%, at least about 80%, at least about 90%, at least about 95%, at least about 98% identical, or 100% identical to SEQ ID NO: 4 (A2) |
| At least about 70%, at least about 80%, at least about 90%, at least about 95%, at least about 98% identical, or 100% identical to SEQ ID NO: 38 (A3) | At least about 70%, at least about 80%, at least about 90%, at least about 95%, at least about 98% identical, or 100% identical to SEQ ID NO: 40 (A3) |
| At least about 70%, at least about 80%, at least about 90%, at least about 95%, at least | At least about 70%, at least about 80%, at least about 90%, at least about 95%, at least |

TABLE 3-continued

Modified Anti-Toxin A Antibodies
C. difficile Toxin A Antibody

| $V_H$ | $V_L$ |
|---|---|
| about 98% identical, or 100% identical to SEQ ID NO: 56 (A4) | about 98% identical, or 100% identical to SEQ ID NO: 58 (A4) |
| At least about 70%, at least about 80%, at least about 90%, at least about 95%, at least about 98% identical, or 100% identical to SEQ ID NO: 74 (A5) | At least about 70%, at least about 80%, at least about 90%, at least about 95%, at least about 98% identical, or 100% identical to SEQ ID NO: 76 (A5) |

In another embodiment, the antibody is a monoclonal antibody binds to C. difficile toxin B and comprises 1) a heavy chain variable domain that is at least about 70%, at least about 80%, at least about 90%, at least about 95%, at least about 98% identical, or 100% identical to the amino acid sequence of the heavy chain variable domain of the B1, B2, B3, B4, B5, or B6 antibody, and 2) a light chain variable domain that is at least about 70%, at least about 80%, at least about 90%, at least about 95%, at least about 98% identical, or 100% identical to the amino acid sequence of the light chain variable domain of the B1, B2, B3, B4, B5, or B6 antibody, wherein the heavy chain and light chain variable domains from the same antibody are combined as shown in Table 4.

TABLE 4

Modified Anti-Toxin B Antibodies
C. difficile Toxin B Antibody

| $V_H$ | $V_L$ |
|---|---|
| At least about 70%, at least about 80%, at least about 90%, at least about 95%, at least about 98% identical, or 100% identical to SEQ ID NO: 110 (B1) | At least about 70%, at least about 80%, at least about 90%, at least about 95%, at least about 98% identical, or 100% identical to SEQ ID NO: 112 (B1) |
| At least about 70%, at least about 80%, at least about 90%, at least about 95%, at least about 98% identical, or 100% identical to SEQ ID NO: 92 (B2) | At least about 70%, at least about 80%, at least about 90%, at least about 95%, at least about 98% identical, or 100% identical to SEQ ID NO: 94 (B2) |
| At least about 70%, at least about 80%, at least about 90%, at least about 95%, at least about 98% identical, or 100% identical to SEQ ID NO: 164 (B3) | At least about 70%, at least about 80%, at least about 90%, at least about 95%, at least about 98% identical, or 100% identical to SEQ ID NO: 166 (B3) |
| At least about 70%, at least about 80%, at least about 90%, at least about 95%, at least about 98% identical, or 100% identical to SEQ ID NO: 146 (B4) | At least about 70%, at least about 80%, at least about 90%, at least about 95%, at least about 98% identical, or 100% identical to SEQ ID NO: 148 (B4) |
| At least about 70%, at least about 80%, at least about 90%, at least about 95%, at least about 98% identical, or 100% identical to SEQ ID NO: 182 (B5) | At least about 70%, at least about 80%, at least about 90%, at least about 95%, at least about 98% identical, or 100% identical to SEQ ID NO: 184 (B5) |
| At least about 70%, at least about 80%, at least about 90%, at least about 95%, at least about 98% identical, or 100% identical to SEQ ID NO: 128 (B6) | At least about 70%, at least about 80%, at least about 90%, at least about 95%, at least about 98% identical, or 100% identical to SEQ ID NO: 130 (B6) |

In another embodiment, the monoclonal antibody binds to C. difficile toxin A and comprises six CDRs (H1, H2, H3, L1, L2, and L3) that are at least about 70%, at least about 80%, at least about 90%, at least about 95% or at least about 98% identical to the amino acid sequences of the six CDRs (H1, H2, H3, L1, L2, and L3) of the heavy and light chain variable domains of the A1, A2, A3, A4, or A5 antibody.

In yet another embodiment, the monoclonal antibody binds to C. difficile toxin B and comprises six CDRs (H1, H2, H3, L1, L2, and L3) that are at least about 70%, at least about 80%, at least about 90%, at least about 95% or at least about 98% identical to the amino acid sequences of the six CDRs (H1, H2, H3, L1, L2, and L3) of the heavy and light chain variable domains of the B1, B2, B3, B4, B5, or B6 antibody.

In another embodiment, the monoclonal antibody binds to C. difficile toxin A and comprises a heavy chain variable domain identical to SEQ ID NO:20 (A1), SEQ ID NO:2 (A2), SEQ ID NO:38 (A3), SEQ ID NO:56 (A4), or SEQ ID NO:74 (A5) except for 1, up to 2, up to 3, up to 4, up to 5, up to 6, up to 7, and in certain cases, up to 10 amino acid substitutions in the CDR sequences. In another embodiment, the monoclonal antibody binds to C. difficile toxin A and comprises a light chain variable domain identical to SEQ ID NO:22 (A1), SEQ ID NO:4 (A2), SEQ ID NO:40 (A3), SEQ ID NO:58 (A4), or SEQ ID NO:76 (A5) except for 1, up to 2, up to 3, up to 4, up to 5, up to 6, up to 7, and in certain cases, up to 10 amino acid substitutions in the CDR sequences.

In yet another embodiment, the monoclonal antibody binds to C. difficile toxin B and comprises a heavy chain variable domain identical to SEQ ID NO:110 (B1), SEQ ID NO:92 (B2), SEQ ID NO:164 (B3), SEQ ID NO:146 (B4), SEQ ID NO:182 (B5), or SEQ ID NO:128 (B6) except for 1, up to 2, up to 3, up to 4, up to 5, up to 6, up to 7, and in certain cases, up to 10 amino acid substitutions in the CDR sequences. In another embodiment, the monoclonal antibody binds to C. difficile toxin A and comprises a light chain variable domain identical to SEQ ID NO:112 (B1), SEQ ID NO:94 (B2), SEQ ID NO:166 (B3), SEQ ID NO:148 (B4), SEQ ID NO:184 (B5), or SEQ ID NO:130 (B6) except for 1, up to 2, up to 3, up to 4, up to 5, up to 6, up to 7, and in certain cases, up to 10 amino acid substitutions in the CDR sequences.

The specific amino acid positions that can be substituted in a CDR, as well as the donor amino acid that can be substituted into those positions can be readily determined by one of skill in the art using known methods, such as those disclosed in published U.S. Application 2006/0099204, the disclosure of which is hereby incorporated by reference in its entirety. Typically, this involves substitution of an amino acid with an amino acid having similar charge, hydrophobic, or stereochemical characteristics. More drastic substitutions in FR regions, in contrast to CDR regions, may also be made as long as they do not adversely affect (e.g., reduce affinity by more than 50% as compared to unsubstituted antibody) the binding properties of the antibody.

Modified versions of the A1, A2, A3, A4, A5, B1, B2, B3, B4, B5, and B6 antibodies can also be screened to identify which mutation provides a modified antibody that retains a desired property, such as high affinity binding of the parent antibody for either C. difficile toxin A or B and/or potent in vitro neutralizing activity.

Thus, in one embodiment, the modified antibody, including those described in Table 3, binds to C. difficile toxin A with a dissociation constant ($K_D$) equal to or less than 10 pM ($10^{-11}$M), 1 pM ($10^{-12}$M), 0.1 pM ($10^{-13}$M), 0.01 pM ($10^{-14}$M), or 0.001 pM ($10^{-15}$M). In another embodiment, the modified antibody, including those described in Table 4, binds to C. difficile toxin B with a dissociation constant ($K_D$) equal to or less than 250 pM, 200 pM, 150 pM, 100 pM, 50 pM, 30 pM, 10 pM, 1 pM ($10^{-12}$M), or 0.1 pM ($10^{-13}$M). The dissociation constant may be measured using techniques known in the art, including biolayer interferometry, as described in the examples of this application.

In one embodiment, the modified antibody, including those described in Table 3, neutralizes the in vitro cytotoxicity of C. difficile toxin A at 2.4 ng/mL in the Vero monkey kidney cell line with an NT50 equal to or less than 3000 pM, 2000 pM, 1000 pM, 100 pM, 60 pM, or 50 pM. In another embodiment, the modified antibody, including those described in Table 4, neutralizes the in vitro cytotoxicity of C. difficile toxin B at 17 pg/mL in the Vero monkey kidney cell line with an NT50 of equal to or less than 1000 pM, 100 pM, 60 pM, or 50 pM. For the sake of consistency, when measuring the neutralizing activity in the Vero monkey kidney cell line, Vero cells ($2.5 \times 10^4$ cells/well with 5% heat-inactivated FBS) are seeded in a 96-well tissue culture microtiter plates and incubated 37° C., 5% $CO_2$ overnight. An equal volume (80 µl) of 4.8 ng/mL (8×MC50) C. difficile toxin A solution or 34.4 pg/mL (8×MC50) C. difficile toxin B solution and individual dilutions of the antibody solutions (80 µl) in Vero cell medium are combined in a new 96-well plate, and incubated at 37° C., 5% $CO_2$ for 1 hour before 100 µl of the toxin/antibody solutions are added to the Vero cells, and incubated at 37° C. for 72 hours. After incubating for 72 hours, the cells are washed twice with 120 µl/each of MEM medium that does not contain phenol, L-glutamine and FBS before adding 100 µl MEM medium that does not contain phenol, L-glutamine and FBS and 10 µl of Alamar Blue® (Life Technologies) to each well. The plates are lightly mixed and incubated at 37° C. for 4 hours before reading fluorescence at 560-590 nm with a cut off at 590 nm.

In one embodiment, the modified antibody, including those described in Table 3, neutralizes the C. difficile toxin A (at 200 ng/mL, applied apically) induced loss of transepithelial resistance (TEER) in the T-84 cell line with an NT50 equal to or less than 6 nM, 5 nM, 2 nM, or 1.5 nM. In another embodiment, the modified antibody, including those described in Table 4, neutralizes the C. difficile toxin B (at 75 ng/mL, applied basolaterally) induced loss of TEER in the T-84 cell line with an NT50 equal to or less than 200 pM, 150 pM, 100 pM, or 70 pM. For the sake of consistency, when measuring TEER, T-84 cells are seeded into 0.4 micron polyester transwell plates at a seeding density of $3.6 \times 10^5$ cells/cm$^2$ and maintained at 37° C., 5% $CO_2$ in 10% heat-inactivated FBS in DMEM/F12 culture media for 10-12 days until stable TEER is achieved and media is replaced in both apical and basolateral compartments of the transwells daily from day 6 and on the day of assay. The C. difficile toxin A (final concentration 200 ng/mL) or toxin B (final concentration of 75 ng/mL) is combined 1:1 with an antibody and incubated at 37° C. with gentle rocking for 30 minutes before replacing the media in the apical compartment with the toxin A/antibody samples or the media in the basolateral compartment with the toxin B/antibody samples. Transepithelial electrical resistance of the T-84 cells is measured at $T_0$ immediately before sample addition and after 2.5 hours ($T_{150}$) incubation at 37° C. 5% $CO_2$.

In one embodiment, the modified antibody is a monoclonal antibody, including, but not limited to, a bispecific antibody, that cross-blocks the binding of at least one of the A1, A2, A3, A4, or A5 antibodies to toxin A, using a routine quantitative cross-blocking assay, such as the Biacore assay discussed above. In one embodiment, the modified antibody is a monoclonal antibody, including, but not limited to, a bispecific antibody, that cross-blocks the binding of the A1 antibody to toxin A. In another embodiment, the modified antibody is a monoclonal antibody, including, but not limited to, a bispecific antibody, that cross-blocks the binding of the A2 antibody to toxin A. In another embodiment, the modified antibody is a monoclonal antibody, including, but not limited to, a bispecific antibody, that cross-blocks the binding of the A3 antibody to toxin A. In another embodiment, the modified antibody is a monoclonal antibody, including, but not limited to, a bispecific antibody, that cross-blocks the binding of the A4 antibody to toxin A. In another embodiment, the modified antibody is a monoclonal antibody, including, but not limited to, a bispecific antibody, that cross-blocks the binding of the A5 antibody to toxin A.

In one embodiment, the modified antibody is a monoclonal antibody, including, but not limited to, a bispecific antibody, that cross-blocks the binding of at least one of the B1, B2, B3, B4, B5, or B6 antibodies to toxin B, using a routine quantitative cross-blocking assay, such as the Biacore assay discussed above. In another embodiment, the modified antibody is a monoclonal antibody, including, but not limited to, a bispecific antibody, that cross-blocks the binding of the B1 antibody to toxin B. In another embodiment, the modified antibody is a monoclonal antibody, including, but not limited to, a bispecific antibody, that cross-blocks the binding of the B2 antibody to toxin B. In another embodiment, the modified antibody is a monoclonal antibody, including, but not limited to, a bispecific antibody, that cross-blocks the binding of the B3 antibody to toxin B. In another embodiment, the modified antibody is a monoclonal antibody, including, but not limited to, a bispecific antibody, that cross-blocks the binding of the B4 antibody to toxin B. In another embodiment, the modified antibody is a monoclonal antibody, including, but not limited to, a bispecific antibody, that cross-blocks the binding of the B5 antibody to toxin B. In another embodiment, the modified antibody is a monoclonal antibody, including, but not limited to, a bispecific antibody, that cross-blocks the binding of the B6 antibody to toxin B.

8. Nucleic Acids, Cloning and Expression Systems

The present disclosure further provides isolated nucleic acids encoding the A1, A2, A3, A4, A5, B1, B2, B3, B4, B5, and B6 antibodies or portions thereof. The nucleic acids may comprise DNA or RNA and may be wholly or partially synthetic or recombinant. Reference to a nucleotide sequence as set out herein encompasses a DNA molecule with the specified sequence, and encompasses a RNA molecule with the specified sequence in which U is substituted for T, unless context requires otherwise.

The nucleic acids provided herein encode at least one CDR, all six CDRs (i.e., H1, H2, H3, L1, L2, and L3), a $V_L$ domain, and/or a $V_L$ domain of one of the A1, A2, A3, A4, A5, B1, B2, B3, B4, B5, or B6 antibodies.

The present disclosure also provides expression vectors (or plasmids) comprising at least one nucleic acid encoding a CDR, all six CDRs (i.e., H1, H2, H3, L1, L2, and L3), a $V_H$ domain, and/or a $V_L$ domain of one of the A1, A2, A3, A4, A5, B1, B2, B3, B4, B5, or B6 antibodies, as well as other nucleic acid sequences useful for regulating polypeptide expression. Suitable expression vectors can be chosen or constructed, so that they contain appropriate regulatory sequences, including promoter sequences, terminator sequences, polyadenylation sequences, enhancer sequences, marker genes and other sequences as appropriate.

The expression vectors can be introduced into a host cell to produce the desired antibody. Systems for cloning and expression of a polypeptide in a variety of different host cells are well known in the art. For cells suitable for producing antibodies, see Gene Expression Systems, Academic Press, eds. Fernandez et al., 1999. Any protein compatible expression system may be used to produce the disclosed antibodies. Suitable expression systems include transgenic animals described in Gene Expression Systems, Academic Press, eds. Fernandez et al., 1999.

A further aspect of the disclosure provides an isolated host cell comprising a nucleic acid (or expression vector) as disclosed herein. A still further aspect provides a method comprising introducing such nucleic acid (or expression vector) into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g., vaccinia or, for insect cells, baculovirus. For bacterial cells, suitable techniques may include calcium chloride transformation, electroporation and transfection using bacteriophage. The introduction of the nucleic acid into the cells may be followed by causing or allowing expression from the nucleic acid, e.g., by culturing host cells under conditions for expression of the gene. Following production by expression an antibody may be isolated and/or purified using any suitable technique, then used as appropriate.

9. Methods of Making Antibodies

Numerous methods known to those skilled in the art are available for obtaining antibodies or antigen-binding fragments thereof. Antibodies can also be produced using recombinant DNA methods. See, e.g., U.S. Pat. No. 4,816,567, EPO 8430268.0; EPO 85102665.8; EPO 85305604.2; PCT/GB 85/00392; EPO 85115311.4; PCT/US86/002269; and Current Trends in Monoclonal Antibody Development (Steven Shire et al., Eds. Springer, 2010), the disclosures of which are incorporated herein by reference in their entirety. Given the disclosure in this application of specific nucleic acid sequences and the $V_H$ and $V_L$ (or CDR) amino acid sequences encoded thereby, it is possible, using recombinant DNA techniques, to insert a nucleic acid of interest into an expression vector or otherwise express the nucleic acid of interest in a host cell to produce the desired antibody. In addition, as disclosed elsewhere in this application, modified versions of the antibodies described herein can be produced using known techniques, including, for example, random mutagenesis, error-prone PCR, and direct mutagenesis.

Monoclonal antibodies may also be produced by preparing immortalized cell lines capable of producing antibodies having desired specificity, for example against an antigen expressing a desired epitope, such as the specific *C. difficile* toxin A and B epitopes disclosed in this application. Such immortalized cell lines may be produced in a variety of ways. Conveniently, a small non-human animal, such as a mouse, is hyperimmunized with the desired immunogen. The vertebrate is then sacrificed, usually several days after the final immunization, the spleen cells removed, and the spleen cells immortalized. The most common technique is fusion with a myeloma cell fusion partner, as first described by Kohler and Milstein (1975) Nature 256:495-497. Other techniques, including EBV transformation, transformation with bare DNA, e.g., oncogenes, retroviruses, etc., or any other method which provides for stable maintenance of the cell line and production of monoclonal antibodies. Specific techniques for preparing monoclonal antibodies are described in Antibodies: A Laboratory Manual, Harlow and Lane, eds., Cold Spring Harbor Laboratory, 1988, the full disclosure of which is incorporated herein by reference.

In one embodiment, the non-human animal includes at least a part of a human immunoglobulin gene. For example, it is possible to engineer transgenic mouse strains that express human heavy and light chain genes, but are incapable of expressing the endogenous mouse immunoglobulin heavy and light chain genes. Using the hybridoma technology, antigen-specific monoclonal antibodies derived from the genes with the desired specificity may be produced and selected. See, e.g., XENOMOUSE™, Green et al. (1994) *Nature Genetics* 7:13-21, US 2003-0070185, U.S. Pat. No. 5,225,539, WO 96/34096, published Oct. 31, 1996, and PCT Application No. PCT/US96/05928, filed Apr. 29, 1996, the disclosures of which are incorporated herein by reference in their entirety.

Immortalized cell lines can be screened using standard methods, such as enzyme-linked immunosorbent assay (ELISA) or surface plasmon resonance analysis, to identify one or more hybridomas that produce an antibody that specifically binds with a specified antigen and/or epitope. Any form of the specified antigen may be used as the immunogen, e.g., recombinant antigen, naturally occurring forms, any variants or fragments thereof, as well as antigenic peptide thereof.

Another exemplary method of making antibodies includes screening protein expression libraries, e.g., phage or ribosome display libraries. Phage display technology mimics the mammalian immune system by cloning large libraries of antibody genes and selecting for binding to a desired target, such as the specific *C. difficile* toxin A and B epitopes disclosed in this application. Phage display is described, for example, in Ladner et al., U.S. Pat. No. 5,223,409; Smith (1985) *Science* 228:1315-1317; Clackson et al. (1991) *Nature,* 352: 624-628; Marks et al. (1991) *J. Mol. Biol.,* 222: 581-597WO 92/18619; WO 91/17271; WO 92/20791; WO 92/15679; WO 93/01288; WO 92/01047; WO 92/09690; and WO 90/02809, the disclosures of which are incorporated herein by reference in their entirety. It is also possible to produce antibodies that bind a specific antigen, such as one of the specific *C. difficile* epitopes disclosed in this application, by using a variable heavy domain (e.g., SEQ ID NO:4, SEQ ID NO:22, SEQ ID NO:40, SEQ ID NO:58, SEQ ID NO:76, SEQ ID NO:94, SEQ ID NO:112, SEQ ID NO:130, SEQ ID NO:148, SEQ ID NO:166, or SEQ ID NO:184) and screening a library of complimentary variable domains to identify antibodies that retain the desired binding specificity. See Portolano et al., The Journal of Immunology (1993) 150:880-887 and Clarkson et al., Nature (1991) 352:624-628, the disclosures of which are incorporated herein by reference in their entirety.

10. Methods of Use

The antibodies described in this application that bind to *C. difficile* toxin A or toxin B can be used in a variety of research and medical applications. In one aspect, the disclosure provides a method of treating a *C. difficile* infection in a subject, comprising administering to the subject one or more of the A1, A2, A3, A4, A5, B1, B2, B3, B4, B5, or B6 antibodies in an amount effective to treat the *C. difficile* infection. In another embodiment, the method of treating a *C. difficile* infection in a subject, comprises administering at least one antibody that binds to *C. difficile* toxin A selected from the A1, A2, A3, A4, and A5 antibodies and at least one antibody that binds to *C. difficile* toxin B selected from the B1, B2, B3, B4, B5, and B6 antibodies. In one embodiment, the at least one antibody that binds to *C. difficile* toxin A is the A2 antibody and the at least one antibody that binds to *C. difficile* toxin B is one or more of the B1, B2, B3, B4, B5, and B6 antibodies, preferably one or more of B1, B2, or B4. In another embodiment, the method comprises administering the A2 antibody and at least two antibodies that binds to *C. difficile* toxin B, wherein the at least two antibodies that binds to *C. difficile* toxin B are the B1 and B2 antibodies, the B2 and B4 antibodies, or the B2 and B6 antibodies. In another embodiment, the method comprises administering the 1) A2 antibody and 2) a bispecific B1+B2 antibody, a bispecific B2+B4 antibody, or a bispecific B2+B6 antibody. The antibodies may be administered at the same time or sequentially.

In another embodiment, the method of treating a *C. difficile* infection comprises administering a composition to the subject in an amount effective to treat the *C. difficile* infection, wherein the composition comprises at least one antibody that binds to *C. difficile* toxin A selected from the A1, A2, A3, A4, and A5 antibodies and at least one antibody that binds to *C. difficile* toxin B selected from the B1, B2, B3, B4, B5, and B6 antibodies. In another embodiment, the composition comprises at least one antibody that binds to *C. difficile* toxin A and at least one antibody that binds to *C. difficile* toxin B selected from the B1, B2, B3, B4, B5, and B6 antibodies. In another embodiment, the composition comprises at least one antibody that binds to *C. difficile* toxin A selected from the A1, A2, A3, A4, and A5 antibodies and at least one antibody that binds to *C. difficile* toxin B.

In one embodiment, the at least one antibody that binds to *C. difficile* toxin A is the A2 antibody and the at least one antibody that binds to *C. difficile* toxin B is one or more of the B1, B2, B3, B4, B5, and B6 antibodies, preferably one or more of B1, B2, or B4. In one embodiment, the composition comprises the A2 antibody and the B4 antibody. In another embodiment, the composition comprises the A2 antibody and the B2 antibody. In another embodiment, the composition comprises the A2 antibody and the B1 antibody.

In another embodiment, the composition comprises the A2 antibody and two antibodies that bind to *C. difficile* toxin B, wherein the two antibodies that bind to *C. difficile* toxin B are selected from the B1, B2, B3, B4, B5, and B6 antibodies. In one embodiment, the composition comprises the A2, B1, and B2 antibodies. In another embodiment, the composition comprises the A2, B2, and B4 antibodies. In another embodiment the composition comprises the A2, B2, and B6 antibodies.

In yet another embodiment, the composition comprises the 1) A2 antibody and 2) a bispecific B1+B2 antibody, a bispecific B2+B4 antibody, or a bispecific B2+B6 antibody.

Subjects that can be treated with the antibodies disclosed in this application include humans and non-human mammals, including, but not limited to, non-human primates, dogs, cats, horses, cows, sheep, pigs, goats, mice, rats, hamsters, and guinea pigs.

In addition, one or more of the A1, A2, A3, A4, and A5 antibodies can be used to detect *C. difficile* toxin A in a sample, while one or more of the B1, B2, B3, B4, B5, or B6 antibodies can be used to detect *C. difficile* toxin B in a sample. In one embodiment, the method comprises contacting one or more of the A1, A2, A3, A4, A5, B1, B2, B3, B4, B5, or B6 antibodies with the sample and analyzing the sample to detect binding of the antibody to toxin A or toxin B in the sample, wherein binding of the antibody to toxin A or toxin B in the sample indicates the presence of *C. difficile* in the biological sample. In one embodiment, the sample comprises a non-biological sample, such as soil, water, or food products such as meat. In other embodiments, the sample comprises a biological sample, such as blood, serum, tissue, or stool. Such methods can be used to detect a *C. difficile* infection in a patient, wherein binding of the antibody to toxin A or toxin B in a sample from the patient indicates the presence of the *C. difficile* infection in the patient.

Any appropriate label may be used in the detection methods and compositions described herein. A label is any molecule or composition bound to an antibody, or a secondary molecule that is conjugated thereto, and that is detectable by spectroscopic, photochemical, biochemical, immunochemical, electrical, optical or chemical means. Examples of labels, including enzymes, colloidal gold particles, colored latex particles, have been disclosed (U.S. Pat. Nos. 4,275,149; 4,313,734; 4,373,932; and 4,954,452, each incorporated by reference herein). Additional examples of useful labels include, without limitation, haptens (e.g., biotin, digoxigenin (DIG), dintrophenol (DNP), etc.), radioactive isotopes, co-factors, ligands, chemiluminescent or fluorescent agents, protein-adsorbed silver particles, protein-adsorbed iron particles, protein-adsorbed copper particles, protein-adsorbed selenium particles, protein-adsorbed sulphur particles, protein-adsorbed tellurium particles, protein-adsorbed carbon particles, and protein-coupled dye sacs. The attachment of a compound to a label can be through any means, including covalent bonds, adsorption processes, hydrophobic and/or electrostatic bonds, as in chelates and the like, or combinations of these bonds and interactions and/or may involve a linking group.

11. Formulations and Administration

The disclosure provides compositions comprising an antibody described herein that binds to *C. difficile* toxin A or toxin B. In certain embodiments, the compositions are suitable for pharmaceutical use and administration to patients. These compositions comprise one or more of the A1, A2, A3, A4, A5, B1, B2, B3, B4, B5, or B6 antibodies and a pharmaceutically acceptable excipient. In one embodiment, the composition comprises at least one antibody that binds to *C. difficile* toxin A selected from the A1, A2, A3, A4, and A5 antibodies and at least one antibody that binds to *C.*

*difficile* toxin B. In another embodiment, the composition comprises at least one antibody that binds to *C. difficile* toxin A and at least one antibody that binds to *C. difficile* toxin B, wherein the at least one antibody that binds to *C. difficile* toxin B is preferably one or more of the B1, B2, B3, B4, B5, and B6 antibodies.

In one embodiment, the at least one antibody that binds to *C. difficile* toxin A is the A2 antibody or A1 antibody and the at least one antibody that binds to *C. difficile* toxin B is one or more of the B1, B2, B3, B4, B5, or B6 antibodies, preferably one or more of B1, B2, or B4. In one embodiment, the composition comprises the A2 antibody and the B4 antibody. In another embodiment, the composition comprises the A2 antibody and the B2 antibody. In another embodiment, the composition comprises the A2 antibody and the B1 antibody. In another embodiment, the composition comprises the A1 antibody and the B1 antibody. In another embodiment, the composition comprises the A1 antibody and the B2 antibody. In another embodiment, the composition comprises the A1 antibody and the B4 antibody. In another embodiment, the composition comprises the A1 antibody and the B6 antibody.

In another embodiment, the composition comprises the A2 antibody or A1 antibody and two antibodies that bind to *C. difficile* toxin B, wherein the two antibodies that bind to *C. difficile* toxin B are selected from the B1, B2, B3, B4, B5, and B6 antibodies. In one embodiment, the composition comprises the A2, B1, and B2 antibodies. In another embodiment, the composition comprises the A2, B2, and B4 antibodies. In another embodiment the composition comprises the A2, B2, and B6 antibodies. In yet another embodiment, the composition comprises the 1) A2 antibody and 2) a bispecific B1+B2 antibody, a bispecific B2+B4 antibody, or a bispecific B2+B6 antibody. In one embodiment, the composition comprises the A1, B1, and B2 antibodies. In another embodiment, the composition comprises the A1, B2, and B4 antibodies. In another embodiment the composition comprises the A1, B2, and B6 antibodies. In yet another embodiment, the composition comprises the 1) A1 antibody and 2) a bispecific B1+B2 antibody, a bispecific B2+B4 antibody, or a bispecific B2+B6 antibody.

In one embodiment, the composition comprises one or more of the A1, A2, A3, A4, A5, B1, B2, B3, B4, B5, or B6 antibodies for use in treating a *C. difficile* infection. Preferably, the composition comprises at least one antibody that binds to *C. difficile* toxin A selected from the A1, A2, A3, A4, and A5 antibodies and at least one antibody that binds to *C. difficile* toxin B selected from the B1, B2, B3, B4, B5, and B6 antibodies for use in treating a *C. difficile* infection. In one embodiment, the composition comprises the A2 antibody or A1 antibody and the at least one antibody that binds to *C. difficile* toxin B selected from the B1, B2, B3, B4, B5, or B6 antibodies, preferably one or more of B1, B2, or B4 for use in treating a *C. difficile* infection. In one embodiment, the composition comprises the A2 antibody and the B4 antibody for use in treating a *C. difficile* infection. In another embodiment, the composition comprises the A2 antibody and the B2 antibody for use in treating a *C. difficile* infection. In another embodiment, the composition comprises the A2 antibody and the B1 antibody for use in treating a *C. difficile* infection. In another embodiment, the composition comprises the A1 antibody and the B4 antibody for use in treating a *C. difficile* infection. In another embodiment, the composition comprises the A1 antibody and the B2 antibody for use in treating a *C. difficile* infection. In another embodiment, the composition comprises the A1 antibody and the B1 antibody for use in treating a *C. difficile* infection. In another embodiment, the composition comprises the A1 antibody and the B6 antibody for use in treating a *C. difficile* infection.

In yet another embodiment, the composition comprises the A2 or A1 antibody and two antibodies that bind to *C. difficile* toxin B for use in treating a *C. difficile* infection, wherein the two antibodies that bind to *C. difficile* toxin B are selected from the B1, B2, B3, B4, B5, and B6 antibodies. In one embodiment, the composition comprises the A2 antibody, the B1 antibody, and the B2 antibody for use in treating a *C. difficile* infection. In another embodiment, the composition comprises the A2 antibody, the B2 antibody, and the B4 antibody for use in treating a *C. difficile* infection. In another embodiment, the composition comprises the A2 antibody, the B2 antibody, and the B6 antibody for use in treating a *C. difficile* infection. In yet another embodiment, the composition comprises the 1) A2 antibody and 2) a bispecific B1+B2 antibody, a bispecific B2+B4 antibody, or a bispecific B2+B6 antibody for use in treating a *C. difficile* infection. In one embodiment, the composition comprises the A1 antibody, the B1 antibody, and the B2 antibody for use in treating a *C. difficile* infection. In another embodiment, the composition comprises the A1 antibody, the B2 antibody, and the B4 antibody for use in treating a *C. difficile* infection. In another embodiment, the composition comprises the A1 antibody, the B2 antibody, and the B6 antibody for use in treating a *C. difficile* infection. In yet another embodiment, the composition comprises the 1) A1 antibody and 2) a bispecific B1+B2 antibody, a bispecific B2+B4 antibody, or a bispecific B2+B6 antibody, or a bispecific B2+B6 antibody for use in treating a *C. difficile* infection.

The compositions may also contain other active compounds providing supplemental, additional, or enhanced therapeutic functions. In one embodiment, the other active compound is an antibiotic, including, but not limited to, metronidazole, fidaxomicin, or vanomycin. The pharmaceutical compositions may also be included in a container, pack, or dispenser together with instructions for administration.

Pharmaceutically acceptable excipients include, but are not limited to a carrier or diluent, such as a gum, a starch (e.g. corn starch, pregeletanized starch), a sugar (e.g. lactose, mannitol, sucrose, dextrose), a cellulosic material (e.g. microcrystalline cellulose), an acrylate (e.g. polymethylacrylate), calcium carbonate, magnesium oxide, talc, or mixtures thereof; a binder (e.g. acacia, cornstarch, gelatin, carbomer, ethyl cellulose, guar gum, hydroxypropyl cellulose, hydroxypropyl methyl cellulose, povidone); a disintegrating agent (e.g. cornstarch, potato starch, alginic acid, silicon dioxide, croscarmelose sodium, crospovidone, guar gum, sodium starch glycolate), a buffer (e.g. Tris-HCl, acetate, phosphate) of various pH and ionic strength; and additive such as albumin or gelatin to prevent absorption to surfaces; a detergent (e.g. Tween 20, Tween 80, Pluronic F68, bile acid salts); a protease inhibitor; a surfactant (e.g. sodium lauryl sulfate); a permeation enhancer; a solubilizing agent (e.g. glycerol, polyethylene glycerol); an anti-oxidants (e.g. ascorbic acid, sodium metabisulfite, butylated hydroxyanisole); a stabilizer (e.g. hydroxypropyl cellulose, hydroxypropylmethyl cellulose); a viscosity increasing agent (e.g. carbomer, colloidal silicon dioxide, ethyl cellulose, guar gum); a sweetener (e.g. aspartame, citric acid); a preservative (e.g. Thimerosal, benzyl alcohol, parabens); a lubricant (e.g. stearic acid, magnesium stearate, polyethylene glycol, sodium lauryl sulfate); a flow-aid (e.g. colloidal silicon dioxide), a plasticizer (e.g. diethyl phthalate, triethyl citrate); an emulsifier (e.g. carbomer, hydroxypropyl cellulose, sodium lauryl sulfate); a polymer coating (e.g. poloxamers or poloxamines); a coating and film forming agent (e.g. ethyl cellulose, acrylates, polymethacrylates); an adjuvant; a pharmaceutically acceptable carrier for liquid formulations, such as an aqueous (water, alcoholic/aqueous solution, emulsion or suspension, including saline and buffered media) or non-aqueous (e.g., propylene glycol, polyethylene glycol, and injectable organic esters such as ethyl oleate) solution, suspension, emulsion or oil; and a parenteral vehicle (for subcutaneous, intravenous, intraarterial, or intramuscular injection), including but not limited to, sodium chloride solution, Ringer's dextrose, dextrose and sodium chloride, lactated Ringer's and fixed oils.

Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

A pharmaceutical composition of the invention is formulated to be compatible with its intended route of administration. Methods to accomplish the administration are known to those of ordinary skill in the art. This includes, for example, injections, by parenteral routes such as intravenous, intravascular, intraarterial, subcutaneous, intramuscular, intraperitoneal, intraventricular, intraepidural, or others as well as oral, nasal, ophthalmic, rectal, or topical. Sustained release administration is also specifically contemplated, by such means as depot injections or erodible implants. Localized delivery is particularly contemplated, by such means as delivery via a catheter to one or more arteries, such as the renal artery or a vessel supplying a localized site of interest.

In one embodiment a subject antibody is administered to a patient by intravenous, intramuscular or subcutaneous injection. An antibody may be administered within a dose range between about 1 μg/kg to about 100 mg/kg. A therapeutically effective amount of antibody may include, but is not limited to, dosage ranges of about 0.1 mg/kg to about 100 mg/kg; 0.1 mg/kg to about 10 mg/kg; about 0.5 mg/kg to 75 mg/kg; 1 mg/kg to about 50 mg/kg; 1 mg/kg to about 10 mg/kg; 0.5 mg/kg to about 25 mg/kg; or about 1 mg/kg to about 5 mg/kg. The antibody may be administered, for example, by bolus injunction or by slow infusion. The dosage may depend on the type and severity of the infection and/or on the characteristics of the individual, such as general health, age, sex, body weight and tolerance to drugs and should be adjusted, as needed, according to individual need and professional judgment. The dosage may also vary depending upon factors, such as route of administration, target site, or other therapies administered. The skilled artisan will be able to determine appropriate doses depending on these and other factors.

Toxicity and therapeutic efficacy of the composition can be determined by standard pharmaceutical procedures in cell cultures or experimental animals, e.g., determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Antibodies that exhibit large therapeutic indices may be less toxic and/or more therapeutically effective.

12. Kits

In some embodiments, at least one antibody described herein that binds to *C. difficile* toxin A or toxin B is supplied in the form of a kit useful, for example, for performing the treatment or diagnostic methods described in this application. In one embodiment, an appropriate amount of one or more of the A1, A2, A3, A4, A5, B1, B2, B3, B4, B5, or B6 antibodies is provided in one or more containers. In other embodiments, one or more of the A1, A2, A3, A4, A5, B1, B2, B3, B4, B5, or B6 antibodies is provided suspended in an aqueous solution or as a freeze-dried or lyophilized powder, for instance. The container(s) in which the at least one antibody is supplied can be any conventional container that is capable of holding the supplied form, for instance, microfuge tubes, ampoules, or bottles. The amount of antibody supplied can be any appropriate amount.

Other kit embodiments include means for detecting one or more of the A1, A2, A3, A4, A5, B1, B2, B3, B4, B5, or B6 antibodies, such as secondary antibodies. In some such instances, the secondary antibody is directly labeled with a detectable moiety (as described elsewhere in this disclosure). In other instances, the primary or secondary (or higher-order) antibody is conjugated to a hapten (such as biotin, DNP, DIG, etc.), which is detectable by a detectably labeled cognate hapten-binding molecule (e.g., streptavidin (SA)-horse radish peroxidase, SA-alkaline phosphatase, SA-QDot® (Invitrogen, Carlsbad, Calif.), etc.). In some embodiments, the primary or secondary antibody in conjugated with a fluorescent detection moiety (e.g., FITC, rhodamine, ALEXA FLUOR® (Invitrogen, Carlsbad, Calif.) dyes, Cy designated fluorophores, etc.). Some kit embodiments may include colorimetric reagents (e.g., DAB, AEC, etc.) in suitable containers to be used in concert with primary or secondary (or higher-order) antibodies that are labeled with enzymes for the development of such colorimetric reagents.

In one embodiment, a kit includes instructional materials disclosing methods of use of the kit contents (e.g., an antibody described herein that binds to *C. difficile* toxin A or toxin B) in a disclosed method. The instructional materials may be provided in any number of forms, including, but not limited to, written form (e.g., hardcopy paper, etc.), in an electronic form (e.g., computer diskette or compact disk) or may be visual (e.g., video files). The kits may also include additional components to facilitate the particular application for which the kit is designed. Thus, for example, the kits may additionally include buffers and other reagents routinely used for the practice of a particular method. Such kits and appropriate contents are well known to those of skill in the art.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1

Antibody Screening

Blood donor selection. Serum was collected from 3000 healthy donors and assessed for its capacity to neutralize *C.*

*difficile* toxin A and/or toxin B by cytotoxicity assay on IMR90 cells as described by Babcock et al. (Infection and Immunity, November 2006, p. 6339-6347). Briefly, IMR90 cells were seeded in a 96 well plate (half size well plates) at a cell density of $1\times10^4$ cells/well in a 50 µl volume. The plates were incubated for 24 hours at 37° C., 5% $CO_2$, before removing the supernatant from the wells. Sera were diluted in IMR90 cell culture medium 1/25 and 1/100 for toxin A and 1/100 and 1/500 for toxin B and incubated for 60 minutes with either 4× MC50 of toxin A or 2× MC50 of toxin B. This mixture was then added to the wells of the 96 well plate and incubated for 16-24 hours at 37° C., 5% $CO_2$ before assessing the cytopathic effect. The cytopathic effect was determined microscopically and scored as 0 (0% rounded cells), 1 (25% rounded cells), 2 (50% rounded cells), 3 (75% rounded cells), 4 (100% rounded cells). Sera exhibiting a neutralizing activity were further tested with the same assay in a series of dilutions ranging from 1/25 to 1/3200. In parallel, neutralizing sera were also tested by ELISA to determine their titers against both toxins, as well as their cross-reactivity for the toxinotypes 0, III, V, VIII, XII, XIV, and XV. Peripheral Blood Mononuclear Cells (PBMCs) from the 12 best donors were used for the screening campaigns to maximize the probability to isolate B cells secreting high quality antibodies.

Antigens. Untoxoided *C. difficile* toxins A and B were purified from the supernatant of a culture of strain VPI10463 (ATCC 43255).

Antibody Screening. The A2, A4, A5, B6, B4 antibodies were obtained by implementing the method described in Jin et al. (2011, Nature Protocols Vol. 6, N° 5 pp668-676) and named ISAAC (ImmunoSpot Array Assay on a Chip). In brief, *C. difficile* toxin A or B antigen was coated on the chip. The anti-toxin A or B human antibodies, secreted from wells containing one human B cell, diffuse onto the chip surface and bind to the antigen coated on the chip surface. Bound antibodies were visualized using Cyanine 3 anti-human IgG monoclonal antibody. The B cells secreting specific anti-toxin A or B antibodies were isolated and the heavy and light chains of human monoclonal antibodies were obtained by single cell reverse transcriptase polymerase chain reaction (RT-PCR). The amplified VH and VL fragments were subsequently cloned into expression vectors for production in Human Embryonic Kidney (HEK) 293T cells or Chinese Hamster Ovary Cells and recombinant antibody testing.

The A1, A3, B1, B2, B3, B5 antibodies were obtained by implementing the method described in the patent application WO2013/000982 named VIVASCREEN. B-lymphocytes from the best donors were isolated, activated and expanded in vitro. Supernatants from expanded B-lymphocyte pools were then screened using a binding assay against *C. difficile* toxin A or toxin B. B-cell pools that secreted antibodies against toxin A or B were further screened with a functional assay. Notably, the functional hits were identified using a cytotoxicity assay on IMR90 cells as described by Babcock et al. 2006. Briefly, IMR90 cells were seeded in a 96 well plate (half size well plates) at a cell density of 1×10E4 cells/well in a 50 µl volume. The plates were incubated during 24 hours at 37° C., 5% $CO_2$, before removing the supernatant from the wells. 150 µl of supernatants from each of the expanded B cell pools were incubated for 60 minutes with either 8× MC50 of toxin A or 2× MC50 of B. This mixture was then added to the wells of the 96 well plate and incubated for 16-24 hours at 37° C.+$CO_2$ before assessing the cytopathic effect. The cytopathic effect was determined microscopically and scored as 0 (0% rounded cells), 1 (25% rounded cells), 2 (50% rounded cells), 3 (75% rounded cells), 4 (100% rounded cells).

The single B cells secreting specific anti-toxin A or B antibodies from each relevant B-cell pool were further isolated by the ISAAC (ImmunoSpot Array Assay on a Chip) method on toxin A- or toxin B-coated chips, and the heavy and light chains of the monoclonal antibodies were obtained by single cell reverse transcriptase polymerase chain reaction (RT-PCR). The amplified VH and VL fragments were subsequently cloned into expression vectors for production and further recombinant antibody characterization. Using these processes, tens of millions of antibody producing B lymphocytes were screened and characterized to identify extremely rare antibodies having high binding affinity for and strong neutralizing activity against either *C. difficile* toxin A or *C. difficile* toxin B, and preferably with a broad spectrum of binding to strains of various *C. difficile* toxinotypes, such as 0, III, V, VIII, XII, and XV.

Example 2

Binding Affinity of Anti-Toxin A and B Antibodies

The binding affinities of all antibodies were determined by Bio-Layer Interferometry using a Octet® Red96 (FortéBio). Bio-Layer Interferometry is an optical analytical technique that analyzes the interference pattern of white light reflected from two surfaces: a layer of immobilized protein (e.g., antibody) on the biosensor tip, and an internal reference layer. Any change in the number of molecules bound to the biosensor tip causes a shift in the interference pattern that can be measured in real-time. Abdiche et al., *Analytical Biochemistry*, 2009, 386(2), 172-180.

Sensors coated with Protein A were first wet for 10 minutes in FortéBio kinetics buffer (KB), PBS pH 7.4 containing 0.002% Tween-20 and 0.1 mg/ml BSA. The sensors were then transferred to wells containing antibody at a concentration of 10 µg/ml in KB and the accumulation of antibody on the sensors was measured for 300 seconds. The sensors were then transferred to wells containing KB for 300 seconds to wash off contaminants. Binding of toxin to the antibody was initiated by transferring the antibody-coated sensors into wells containing *C. difficile* toxin A or B at concentrations ranging from 0.7 to 20 µg/ml. After 400 seconds, the sensors were moved into KB buffer for 900 seconds to monitor the dissociation of the bound toxin. Throughout the experiment, samples were agitated at 30° C. and 1000 rpm. The changes in thickness of the protein layer over time at four different concentrations of toxin were fit to the equations of equilibrium kinetics to calculate association and dissociation constants. The dissociation constants, on rate constants, and off rate constants of the anti-toxin A and anti-toxin B antibodies are provided in Table 5.

TABLE 5

| mAb | $K_D$ (M) | $K_{on}$ (1/Ms) | $K_{on}$ error | $K_{off}$ (1/s) | $K_{off}$ error |
|---|---|---|---|---|---|
| A1 | $6.81 \times 10^{-14}$* | $3.75 \times 10^5$ | $2.19 \times 10^3$ | $2.55 \times 10^{-8}$ | $3.05 \times 10^{-6}$ |
| A2 | $4.43 \times 10^{-12}$* | $3.56 \times 10^5$ | $2.16 \times 10^3$ | $1.58 \times 10^{-6}$ | $3.16 \times 10^{-6}$ |

TABLE 5-continued

| mAb | $K_D$ (M) | $K_{on}$ (1/Ms) | $K_{on}$ error | $K_{off}$ (1/s) | $K_{off}$ error |
|---|---|---|---|---|---|
| A3 | $4.61 \times 10^{-10}$ | $1.69 \times 10^5$ | $5.25 \times 10^2$ | $7.77 \times 10^{-5}$ | $1.38 \times 10^{-6}$ |
| A4 | $5.57 \times 10^{-13}$* | $5.55 \times 10^5$ | $5.07 \times 10^3$ | $3.09 \times 10^{-7}$ | $4.62 \times 10^{-6}$ |
| A5 | $1.44 \times 10^{-10}$ | $3.12 \times 10^5$ | $2.90 \times 10^3$ | $4.49 \times 10^{-5}$ | $4.84 \times 10^{-6}$ |
| B1 | $4.77 \times 10^{-11}$ | $5.85 \times 10^5$ | $4.34 \times 10^3$ | $2.79 \times 10^{-5}$ | $3.73 \times 10^{-6}$ |
| B2 | $7.97 \times 10^{-11}$ | $4.20 \times 10^5$ | $3.18 \times 10^3$ | $3.35 \times 10^{-5}$ | $3.92 \times 10^{-6}$ |
| B3 | $4.87 \times 10^{-10}$ | $1.93 \times 10^5$ | $1.45 \times 10^3$ | $9.40 \times 10^{-5}$ | $3.73 \times 10^{-6}$ |
| B4 | $1.21 \times 10^{-10}$ | $5.31 \times 10^5$ | $4.46 \times 10^3$ | $6.44 \times 10^{-5}$ | $4.26 \times 10^{-6}$ |
| B5 | $2.02 \times 10^{-10}$ | $4.77 \times 10^5$ | $2.15 \times 10^3$ | $9.62 \times 10^{-5}$ | $2.35 \times 10^{-6}$ |
| B6 | $7.26 \times 10^{-13}$* | $7.30 \times 10^5$ | $4.61 \times 10^3$ | $5.30 \times 10^{-7}$ | $3.13 \times 10^{-6}$ |

The $K_D$ of the A3 and A5 antibodies for toxin A was 461 pM and 144 pM, respectively. The $K_D$ of the A1, A2, and A4 antibodies for toxin A are shown in Table 5. All were less than 10 pM. The lower limit of quantification by the Octet® Red96 (FortéBio) system is about 10 pM. These results demonstrate that the A1, A2, A3, A4, and A5 antibodies bound C. difficile toxin A with at least picomolar affinities. Some of the antibody affinities may be in the subpicomolar range if measured with a more sensitive system.

The $K_D$ of the B1, B2, B3, B4, and B5 antibodies for toxin B was 48, 80, 487, 121, and 202 pM, respectively. The $K_D$ of the B6 antibody for toxin B is shown in Table 5 and was less than the lower limit of quantification by the Octet® Red96 (FortéBio) system, which is about 10 pM. These results demonstrate that the B1, B2, B3, B4, B5, and B6 antibodies bound C. difficile toxin B with at least picomolar affinities. Some of the antibody affinities may be in the subpicomolar range if measured with a more sensitive system.

Example 3

In Vitro Vero Cell Cytotoxicity Based Toxin Neutralization Assay

Cell-based neutralization assays in either Vero monkey kidney cells or T-84 human colon epithelial cell monolayer were used to evaluate the ability of the anti-toxin A and anti-toxin B antibodies to neutralize the activity of toxin A or toxin B. The first assay uses Vero cells, a cell line which was derived from the kidney of a normal adult African green monkey. The Vero cell assay assesses the ability of anti-toxin A or anti-toxin B antibodies to inhibit toxin A or toxin B induced killing of Vero cells. This assay uses an Alamar Blue® (Life Technologies) readout to assess cell viability. Resazurin, the active ingredient of Alamar Blue® (Life Technologies), is a non-toxic, cell permeable blue compound. Only living cells are able to reduce Resazurin to a red fluorescent compound, consequently viable cell number is directly proportional red fluorescence. Therefore the lower the fluorescence reading, the fewer viable cells present.

Vero cells ($2.5 \times 10^4$ cells/well with 5% heat-inactivated FBS) were seeded in a 96-well tissue culture microtiter plates and incubated 37° C., 5% $CO_2$ overnight. Stock solutions of 8×MC50 (concentration inducing 50% of the maximum response) C. difficile toxin A or B were prepared in Vero cell medium. One MC50 dose was 0.6 ng/mL and 4.3 pg/mL for toxin A and B, respectively.

Various dilutions of the A1, A2, A3, A4, A5, B1, B2, B3, B4, B5, or B6 antibodies were prepared in Vero cell medium and added to a 96-well tissue culture plate. An equal volume (80 µl) of 8×MC50 C. difficile toxin A or toxin B solution and individual dilutions of the antibody solutions (80 µl) were combined in a new 96-well tissue culture plate, and incubated at 37° C. with 5% $CO_2$ and humidity for 1 hour with appropriate controls (toxin A or B without antibody or media). The resulting toxin/antibody solution has a toxin A or B concentration of 4×MC50. After incubating for 1 hour, 100 µl of the toxin/antibody solutions was added to the Vero cells in 96-well tissue culture microtiter plates. The Vero cells were incubated with the toxin/antibody solution at 37° C. for 72 hours.

After incubating for 72 hours of incubation, the cells were washed twice with 120 µl/each of MEM medium that does not contain phenol, L-glutamine and FBS. Next 100 µl MEM medium that does not contain phenol, L-glutamine & FBS and 10 µl of Alamar Blue® (Life Technologies) was added to each well. The plates were lightly mixed and incubated at 37° C. for 4 hours before reading fluorescence at 560-590 nm with a cut off at 590 nm.

Percent survival was plotted over antibody concentration. Cell survival in toxin/antibody treated cells was compared to cells treated with toxin A or B without antibody and NT50 was calculated for each antibody. NT50 is the concentration of antibody that results in 50% reduction in survival as compared to control cells treated with toxin A or B but no antibody.

The results obtained with the A1, A2, A3, A4, A5, B1, B2, B3, B4, B5, and B6 antibodies are summarized in Table 6, depicting both the potency of the neutralizing activity (Cytotox NT50) and the percent completion of the antibody-induced neutralization (% completion cytotox).

TABLE 6

| | mAb | | | | | | | | | | |
|---|---|---|---|---|---|---|---|---|---|---|---|
| | A1 | A2 | A3 | A4 | A5 | B1 | B2 | B3 | B5 | B4 | B6 |
| Cytotox NT50, pM | 48 | 55 | 980 | 3400 | 2700 | 49 | 63 | 100 | 2900 | 70 as combo | |
| % completion cytotox | <90 | 100 | 90 | <90 | 75 | 95 | 75 | 100 | 95 | 95 as combo | |

All five anti-toxin A antibodies exhibited a cytotoxic NT50 of less than 3500 pM. The A1, A2, A3, and A5 exhibited a cytotoxic NT50 of less than 3000 pM, and remarkably A1, A2, and A3 exhibited a cytotoxic NT50 of less than 1000 pM, with A2 and A1 showing the greatest potency at 55 pM and 48 pM, respectively. All five anti-toxin A antibodies also showed a high completion percentage of at least 75%, with A2 and A3 showing the greatest percent completion of 100% and 90%, respectively.

Figures 1A, 1B:
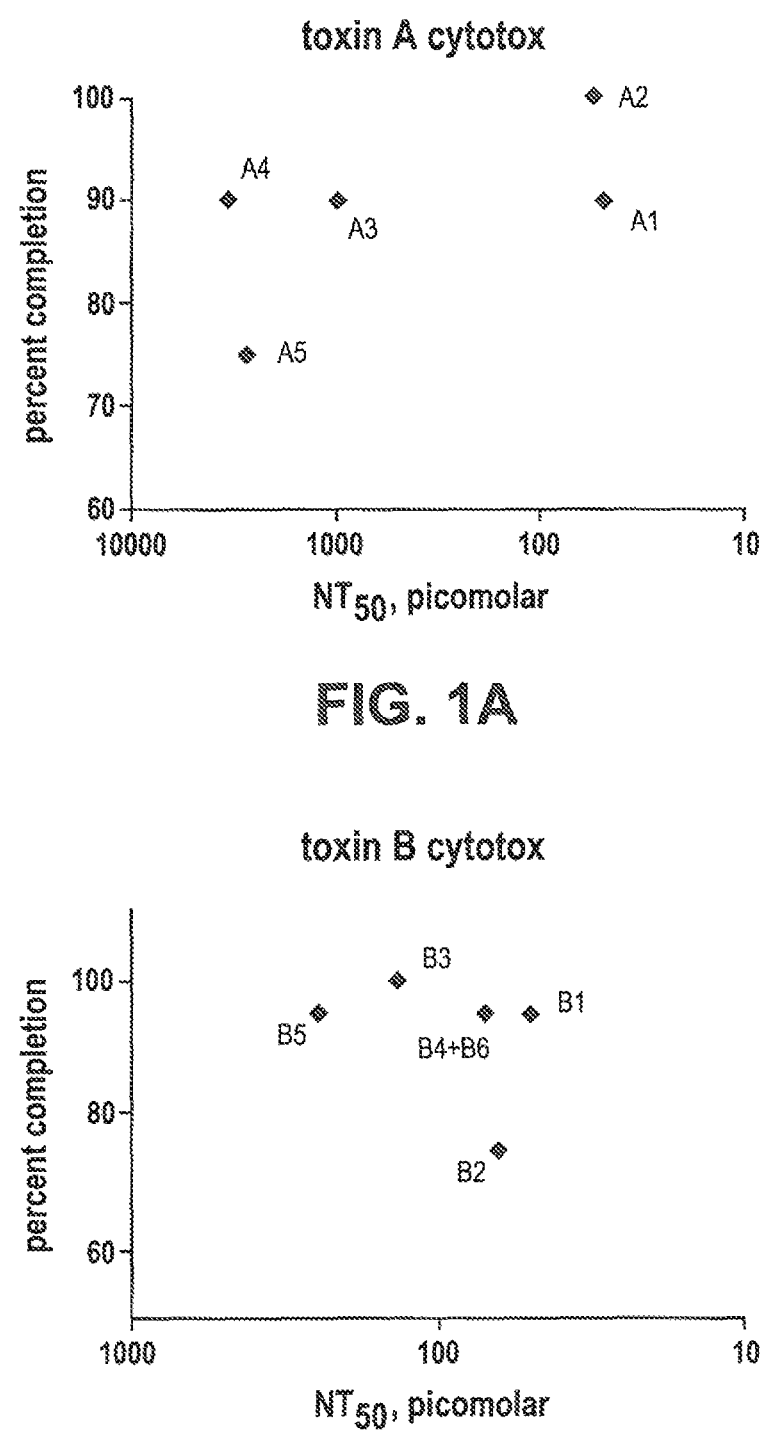

The anti-toxin B antibodies similarly exhibited high potency in the Vero cell neutralization assay, with all but the B5 antibody having a cytotoxic NT50 of 100 pM or less (B6 and B4 were tested as a combination). All six anti-toxin B antibodies also showed a high completion percentage of at least 75%, with B1, B3, B5, and B6 and B4 (tested as a combination) having a percent completion of at least 95%. The results of the Vero cell neutralization assays for the anti-toxin A and anti-toxin B antibodies are also graphically illustrated in FIGS. 1A and 1B, with potency represented on the x axis and percent completion represented on the y axis.

Example 4

In Vitro TEER Based Toxin Neutralization Assay

The second cell-based neutralization assay uses a T-84 human carcinoma cell line derived from a lung metastasis of a colon carcinoma (ATCC CCL-248). This assay assesses the ability of anti-toxin A or anti-toxin B antibodies to inhibit toxin A or toxin B induced loss of transepithelial electrical resistance (TEER) in T-84 cells.

T-84 cells were seeded into 0.4 micron polyester transwell plates at a seeding density of $3.6 \times 10^5$ cells/cm$^2$ and maintained at 37° C., 5% $CO_2$ in 10% heat-inactivated FBS in DMEM/F12 culture media for 10-12 days until stable TEER was achieved. Transepithelial electrical resistance was measured using Millipore Millicell® ERS-2 Volt-Ohm Meter. Media was replaced in both apical and basolateral compartments daily from day 6 and on the day of assay. Final concentration of toxin A used for challenge dose was equivalent to 6 times challenge dose required to produce loss of transepithelial resistance of 50% (TER50). One TER50 dose was 33 ng/mL and 15 ng/mL for toxin A and toxin B, respectively. Toxin A challenge was performed in the apical compartment of the transwell. The final concentration of toxin B used for challenge dose was equivalent to 5 times TER50. Toxin B challenge was performed in basolateral compartment.

Toxin A or toxin B and one of the A1, A2, A3, A4, A5, B1, B2, B3, B4, B5, or B6 antibodies were combined at 1:1 ratio and incubated at 37° C. with gentle rocking for 30 minutes, with appropriate controls (toxin A or B without antibody or media). Media was removed from the appropriate apical or basolateral compartment and the toxin/antibody samples were added to the T-84 cells in the transwell plates. Transepithelial resistance of the T-84 cells is measured at $T_0$ immediately before sample addition and after 2.5 hours ($T_{150}$) incubation at 37° C. 5% $CO_2$.

Percent TEER loss is calculated for each sample using the following equation: % TEER loss=$[(T_0-T_{150}) \div T_0]$ *100%–% TEER loss Negative well. Percent protection for antibody is calculated for each treatment using the following equation: % Protection=[(% TEER loss Toxin Challenge)–(% TEER loss Toxin with Treatment)].

Percent TEER loss was plotted over antibody concentration. TEER loss in toxin/antibody treated cells was compared to cells treated with toxin A or B without antibody and $NT_{50}$ was calculated for each antibody. $NT_{50}$ is the concentration of antibody that results in 50% reduction in TEER loss as compared to control cells treated with toxin A or B but no antibody.

The results obtained with the A1, A2, A3, A4, A5, B1, B2, B3, B4, B5, and B6 antibodies are summarized in Table 7, depicting both the potency of the neutralizing activity (TEER NT50) and the percent completion of the antibody-induced neutralization (% completion TEER).

TABLE 7

|  | mAb | | | | | | | | | | |
| --- | --- | --- | --- | --- | --- | --- | --- | --- | --- | --- | --- |
|  | A1 | A2 | A3 | A4 | A5 | B1 | B2 | B3 | B5 | B4 | B6 |
| TEER NT50, nM | <1.3 | 1.8 | 1.3 | 4.7 | 7.3 | 270 | 70 | 600 | 200 | 130 | 100 |
| % completion TEER | 80 | 75 | 80 | ND | ND | 91 | 98 | 95 | 70 | 93 | 92 |

All five anti-toxin A antibodies exhibited a TEER NT50 of less than 10 nM. The A1, A2, A3, and A4 antibodies exhibited a TEER NT50 of less than 5 nM, and remarkably A1, A2, and A3 exhibited a TEER NT50 of less than 2 nM. The A1, A2, and A3 antibodies also showed a high completion percentage (TEER) of at least 75%. The plateau for the A4 and A5 antibodies was never reached.

Figure 2B:
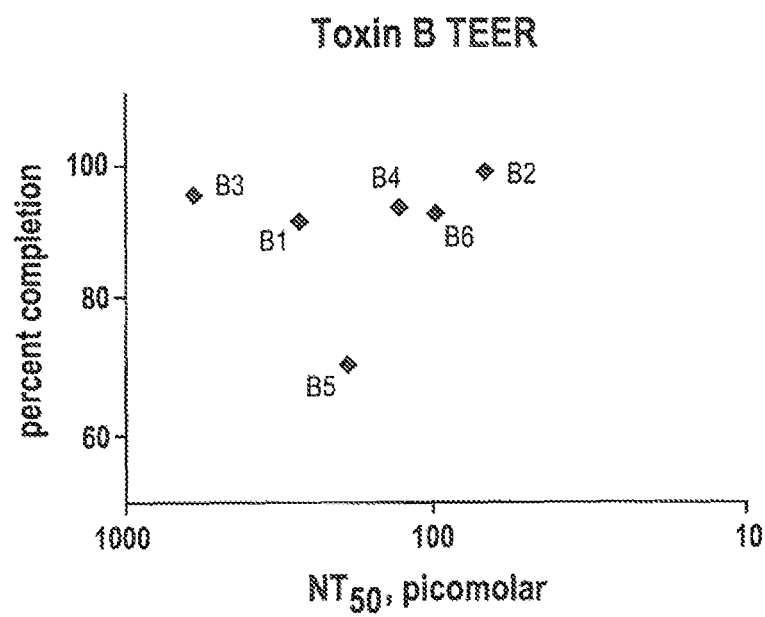

The anti-toxin B antibodies similarly exhibited high potency in the TEER neutralization assay, with all but the B3 antibody having a TEER NT50 of 300 pM or less, and the B2, B4, B5, and B6 antibodies having a TEER NT50 of 200 pM or less, with B6, B4, and B2 showing the greatest potency at 100 pM, 130 pM, and 70 pM, respectively. All 6 anti-toxin B antibodies also showed a high completion percentage of at least 70%, with B1, B2, B3, B4, and B6 having a percent completion of at least 90%. The results of the TEER neutralization assays for the anti-toxin A and anti-toxin B antibodies are also graphically illustrated in FIGS. 2A and 2B, with potency represented on the x axis and percent completion represented on the y axis.

Example 5

Toxinotype Analysis by Western Blotting

The breadth of protection against various C. difficile toxinotypes was assessed using two different assays. In the first, toxinotype binding was measured using Western analysis. C. difficile strains representative of toxinotypes 0, III, V, VIII, XII, and XV were grown anaerobically at 250 ml scale. The representative strain of toxinotype 0 is VPI10463 or ATCC 43255, the C. difficile reference strain. The representative toxinotype III strain (CDC #2005099) is a hypervirulent NAP1/027 strain isolated from an outbreak in Montreal. The representative toxinotype V strain is CDC #2004255. The representative toxinotype VIII strain is CDC #2005195. The representative toxinotype XII strain is CDC #2004097. The representative toxinotype XV strain is CDC #2004012.

The supernatants were recovered by tangential flow filtration through a 0.2 µm membrane and adjusted to 0.4 M ammonium sulfate using a 3.7 M stock solution. The supernatant was loaded on a 1 ml Phenyl Sepharose FF (hi-sub) column (GE Healthcare) and the column was washed with Buffer A (45 mM Tris-HCl, 45 mM NaCl, 0.4 M NH$_4$SO$_4$, 1 mM DTT, 0.2 mM EDTA, pH 7.5). The crude toxins were eluted using a 200 ml gradient to Buffer B (50 mM Tris-HCl, 50 mM NaCl, 1 mM DTT, 0.2 mM EDTA, pH 7.5). Fractions containing toxins were identified by SDS-PAGE. Fractions were stored in SDS-PAGE loading buffer to prevent autoproteolysis prior to Western blot analysis.

Purified toxins (about 20 ng) were analyzed using SDS-PAGE on a NuPAGE® (Life Technologies) 4-12% polyacrylamide gel run at 200V using SeeBlue2® standards (Invitrogen). The proteins in the gel were transferred to a nitrocellulose membrane in 6 min, using the iBlot® (Invitrogen) gel blotting system. The blot was blocked with PBST (10 mM sodium phosphate, 2 mM potassium phosphate, 2.7 mM potassium chloride, 137 mM sodium chloride, 0.1% Tween 20) containing 5% nonfat dry milk (NFDM) for 1 h at room temperature. The blot was probed with the mAb diluted 1:5000 in 2.5% NFDM/PBST for 1 h at RT, then washed 3×5 min with PBST. The blot was incubated with goat anti-human Alkaline Phosphatase conjugate (Sigma, A1543) [1:6600 in 2.5% NFDM/PBST,] for 1 h at RT. The blot was washed 3×5 min with PBST and developed with 1 BCIP/NBT tablet (Sigma, B5655) in 10 ml water. Development was stopped by putting the blot into deionized water.

Each of the anti-toxin A antibodies, A1, A2, A3, A4, and A5, demonstrated binding to toxinotypes 0, III, V, XII, and XV by Western analysis. Of the anti-toxin B antibodies, B3 and B6 bound to toxinotypes 0, III, V, VIII, XII, and XV, while B1 bound to at least toxinotypes 0, III, V, VIII, XII, and B2 bound to toxinotypes 0, III, V, and VIII. B4 bound to toxinotypes 0, III, and V, while B5 bound to toxinotype 0 and III. The toxinotype binding results for the anti-toxin A and anti-toxin B antibodies are summarized below in Table 8.

TABLE 8

| | Anti A mAb | | | | |
|---|---|---|---|---|---|
| | A1 | A2 | A3 | A4 | A5 |
| Toxinotype Binding | 0, III, V, XII, XV | 0, III, V, XII, XV | 0, III, V, XII, XV | 0, III, V, XII, XV | 0, III, V, XII, XV |

| | Anti B mAb | | | | | |
|---|---|---|---|---|---|---|
| | B1 | B2 | B3 | B4 | B5 | B6 |
| Toxinotype Binding | 0, III, V, VIII, XII | 0, III, V, VIII | 0, III, V, VIII, XII, XV | 0, III, V | 0, III | 0, III, V, VIII, XII, XV |

Example 6

Toxinotype Analysis by CTD Competition Assay

Toxinotyping by Western analysis can be biased by low toxin production in some strains. Therefore a more sensitive CTD (C Terminal Domain) competition assay was developed. For the CTD competition assay, the CTDs of *C. difficile* toxin A and toxin B from genomic DNA of toxinotypes 0, III, V, VIII, XII and XV were cloned, expressed, and purified and combined with anti-toxin A or anti-toxin B antibodies to measure the effect on cytotoxicity or TEER in cell based neutralization assays (as described in previous example). The CTD competition assay only works for antibodies that recognize an epitope in the CTD of toxin A or toxin B.

Briefly, for toxin A, a QuickExtract™ DNA Extraction Kit (Epicentre) was used to isolate genomic DNA from 1 ml samples of cultures of each of the six *C. difficile* strains representing five toxinotypes (0, III, V, XII and XV). The following primers were used for amplification of the toxin A C-terminal domains (CTDs):

```
FP:
                                    (SEQ ID NO: 235)
5'-CACCATGGGATTTAAAATAATAGATAATAAAACTTATTAC-3'

RP:
                                    (SEQ ID NO: 236)
5'-GCCATATATCCCAGGGGC-3'
```

The primers were designed to amplify the last 900 amino acids (amino acids 1811-2710 in the VPI10463 reference sequence), or 2700 bp of the toxin A toxinotype 0 CTD. Amplification was performed using Pfx50 DNA Polymerase and a standard touchdown PCR protocol. In the case where multiple bands were amplified, the band of the correct size (about 2700 bp for toxinotypes 0, III, V, XII and XV was purified by excision of the band of the correct size from an agarose gel followed by gel extraction. Purified or unpurified PCR product was directionally cloned into the expression plasmid pET101-D-Topo, using a ligation-independent cloning strategy, as per the manufacturer's instructions (Invitrogen, Champion™ pET Directional TOPO® Expression Kit).

Directionality and sequence were confirmed by traditional DNA sequencing, using the forward and reverse cloning primers. Due to the highly repetitive nature of the intervening sequences the sequence of the entire CTD was not confirmed. The translation start site is at the ATG in the forward primer sequence. Expression continues through the reverse primer sequence and the C-terminal tags encoded by the expression plasmid. Recombinant expression of these proteins yields a protein of the following sequence as previously described: Met-GFKIIDNKTYY-[toxinotype-specific A CTD aa's 1823-2704]-APGIYG-[V5 epitope]-RTG-[6× His] (SEQ ID NO:237).

For toxin B, DNA samples were isolated from the six *C. difficile* strains representing six toxinotypes (0, III, V, VIII, XII and XV). The following primers were used for amplification of the toxin B CTD's:

FP:
(SEQ ID NO: 238)
5'-CGGATCC<u>GAATTC</u>ATTCTTA*TGTCAACTAGTGAAGAAAATAAGG*-3'

RP:
(SEQ ID NO: 239)
5'-GTGGTGGTG<u>CTCGAG</u>*AGCTGTATCAGGATCAAAATAATAC*-3'

The primers were designed to amplify the last 615 amino acids excluding the final 6 amino acids of the Toxin B CTD (aa 1752-2360), or 1827 bp of the toxin B toxinotype 0 CTD.

Amplification was performed using TaKaRa LA Taq DNA Polymerase and a standard touchdown PCR protocol. In the case where multiple bands were amplified, the band of the correct size (about 1827 bp for all toxinotypes) was purified by excision of the band of the correct size from an agarose gel followed by gel extraction. Purified or unpurified PCR product was directionally cloned into the expression plasmid pET24A+, using traditional restriction digest and ligation-dependent cloning strategy. Directionality and sequence were confirmed by traditional DNA sequencing, using the forward and reverse cloning primers. Due to the highly repetitive nature of the intervening sequences the sequence of the entire CTD was not confirmed. The translation start site is at the ATG in the forward primer sequence. Expression continues through the reverse primer sequence and the C-terminal tags encoded by the expression plasmid. Recombinant expression of these proteins yields a protein of the following sequence: Met-STSEENK-[toxinotype-specific B CTD aa's 1760-2352]-YYFDPDTA-LE-[6× His] (SEQ ID NO:240).

The cloned toxin A and B CTD proteins were expressed as soluble full-length His-tagged proteins by recombinant expression in the *E. coli* strain BL21 Star (DE3) using the IPTG-free Overnight Express Autoinduction System 1 as per the manufacturer's instructions (Novagen). Proteins were purified under native conditions by bind-and-elute affinity chromatography on Ni-NTA resin, followed by anion exchange in the negative purification mode. Purified CTD proteins were used in cell-based, in vitro neutralization assays to determine the toxinotype specificity of certain antibodies.

The A2 antibody was tested in the Vero cell competition assay to measure the impact of toxin A CTDs of toxinotype 0, III, V, XII, and XV on the neutralizing activity of A2. The Vero cell neutralization was carried out as described above with varying dilutions of the antibodies, plus the addition of 1 µg/ml of toxinotype 0, III, V, XII, or XV toxin A CTDs. A2 neutralizes toxin A induced cytotoxicity in Vero cells with high potency. Toxinotype 0, III, V, XII, and XV CTDs strongly inhibited the neutralizing activity of A2 at low concentrations of antibody (0.625 µg and below) but had minimal, if any effect, at A2 concentrations above 1.25 µg/ml. FIG. 3.

The A2 antibody was also tested in a T-84 cell neutralization assay to measure the impact of toxin A CTDs of toxinotypes 0, III, V, XII, and XV on TEER in T-84 cells. The T-84 cell neutralization assay was carried out as described above with varying dilutions of A2, plus the addition of 0.4 µg/ml or 1 µg/ml of toxinotype 0, III, V, XII, and XV toxin A CTDs. A2 neutralizes toxin A induced loss of TEER in T-84 cells with high potency. CTDs from toxinotypes 0, III, V, XII, and XV strongly inhibited the neutralizing activity of A2 in the TEER assay. FIG. 4A. Thus, the neutralizing activity of the A2 antibody was strongly inhibited by CTDs from five toxinotypes CTDs (0, III, V, XII, and XV), revealing a broad spectrum of protection against *C. difficile* toxinotypes with the more sensitive in vitro functional assays.

The B6 antibody was similarly tested in the T-84 cell neutralization assay. Toxin B CTDs from toxinotypes 0, III, V, VIII, XII, and XV strongly inhibited the neutralizing activity of B6. FIG. 4B.

Example 7

Epitope Mapping of Toxin B Antibodies by Western Blot

Epitope mapping of anti-toxin B antibodies was conducted by Western analysis using recombinant domains from *C. difficile* toxin A and toxin B. The recombinant domains from toxin A were used as negative controls. Segments of the genes for toxin A and toxin B were cloned by PCR from *C. difficile* DNA of strain VPI10463. The amino acid sequences of toxin A and toxin B from *C. difficile* strain VPI10463 are set forth in SEQ ID NO:230 and SEQ ID NO:230, respectively. The corresponding amino acid residues for the cloned gene segments of toxin A and B are set forth in the table below:

| Toxin Fragment | Amino Acid Residues | Domain |
|---|---|---|
| A2 | 300-660 of SEQ ID NO: 230 | Glucosyltransferase/protease |
| A3 | 660-1100 of SEQ ID NO: 230 | Protease/translocation |
| B1 | 510-1110 of SEQ ID NO: 231 | Protease |
| B2 | 1110-1530 of SEQ ID NO: 231 | Translocation N-terminal |
| B3 | 1750-2360 of SEQ ID NO: 231 | Receptor binding |
| B4 | 10-520 of SEQ ID NO: 231 | Glucosyltransferase |
| B5 | 1530-1750 of SEQ ID NO: 231 | Translocation C-terminal |

A methionine start codon was added to the N-terminus and a 6× His tag (SEQ ID NO:332) followed by a stop codon was added to the C-terminus. The resulting PCR products were ligated into the multiple cloning site of plasmid pET24+. The constructs were transformed into *E. coli* BL21 (DE3) and induced by addition of IPTG.

Constructs A2 and A3 were expressed but were insoluble and were purified by denaturing chromatography, while constructs B1-B5 were at least partly soluble and purified by non-denaturing chromatography. Soluble constructs were grown to liter scale in LB medium at 37° C. Cells were pelleted by centrifugation and lysed by microfluidization (Microfluidics Corp, Newton Mass.) in 50 mM NaHPO$_4$, 300 mM NaCl, 20 mM imidazole, pH 8.0. Insoluble material was removed by centrifugation and the cleared lysate was loaded onto a Ni-NTA column (Qiagen). The column was washed with 50 mM NaHPO$_4$, 300 mM NaCl, 20 mM imidazole, pH 8.0 and eluted with 50 mM NaHPO$_4$, 300 mM NaCl, 250 mM imidazole, pH 8.0. Insoluble constructs were grown and harvested as for soluble ones, but the cell pellet was resuspended in 8M Urea, 100 mM NaHPO$_4$, 10 mM Tris-HCl, pH 8.0 before microfluidization. Insoluble material was removed by centrifugation and the cleared lysate was loaded onto a Ni-NTA column and washed with 8M Urea, 100 mM NaHPO$_4$, 10 mM Tris-HCl, pH 6.3. The column was eluted with 8M Urea, 100 mM NaHPO$_4$, 10 mM Tris-HCl, pH 4.5 and protein-containing fractions were dialysed with multiple changes against 50 mM NaHPO$_4$, 300 mM NaCl, 250 mM imidazole, pH 8.0.

The binding of the B1, B2, B4, and B6 antibodies to the recombinant domains was assessed by Western analysis. Purified recombinant domains (about 400 ng) were analyzed using SDS-PAGE on a NuPAGE® (Life Technologies) 4-12% polyacrylamide gel run at 200V using SeeBlue2® standards (Invitrogen). The proteins in the gel were transferred to a nitrocellulose membrane in 6 min, using the iBlot® (Invitrogen) gel blotting system. The blot was blocked with PBST (10 mM sodium phosphate, 2 mM potassium phosphate, 2.7 mM potassium chloride, 137 mM sodium chloride, 0.1% Tween 20) containing 5% nonfat dry milk (NFDM) for 1 h at room temperature. The blot was probed with the antibody diluted 1:5000 in 2.5% NFDM/PBST for 1 h at RT, then washed 3×5 min with PBST. The blot was incubated with goat anti-human Alkaline Phosphatase conjugate (Sigma, A1543) [1:6600 in 2.5% NFDM/PBST,] for 1 h at RT. The blot was washed 3×5 min with PBST and developed with 1 BCIP/NBT tablet (Sigma, B5655) in 10 ml water. Development was stopped by putting the blot into deionized water.

Western analysis revealed that B1 and B2 bound to an epitope in the glucosyl transferase domain (amino acids 10-520 of SEQ ID NO:231) of toxin B, while B4 bound to an epitope in the N-terminal translocation domain (amino acids 1110-1530 of SEQ ID NO:231) of toxin B. The B6 antibody bound to an epitope in the receptor binding domain (amino acids 1750-2360 of SEQ ID NO:231) of toxin B.

Example 8

Epitope Mapping Using PepSet ELISA

The PepSet ELISA was used to identify linear epitopes of toxin A recognized by the A2 antibody. For the CTD, the following non-overlapping peptides of varying length were designed to cover the repetitive oligopeptide units:

```
1
                                  (SEQ ID NO: 199)
SGSGHLGFKIIDNKTYYYDEDSKL 2
                                  (SEQ ID NO: 200)
SGSGVTGWQTINGKKYYFDINTGA 3
                                  (SEQ ID NO: 201)
SGSGLTSYKIINGKHFYFNNDGVM 4
                                  (SEQ ID NO: 202)
SGSGQSKFLTLNGKKYYFDNNSKA 5
                                  (SEQ ID NO: 203)
SGSGVTGWRIINNEKYYFNPNNAI 6
                                  (SEQ ID NO: 204)
SGSGAVGLQVIDNNKYYFNPDTAI 7
                                  (SEQ ID NO: 205)
SGSGSKGWQTVNGSRYYFDTDTAI 8
                                  (SEQ ID NO: 206)
SGSGFNGYKTIDGKHFYFDSDCVV 9
                                  (SEQ ID NO: 207)
SGSGVTGLQTIDSKKYYFNTNTAE 10
                                  (SEQ ID NO: 208)
SGSGATGWQTIDGKKYYFNTNTAE 11
                                  (SEQ ID NO: 209)
SGSGATGWQTIDGKKYYFNTNTAI 12
                                  (SEQ ID NO: 210)
SGSGSTGYTIINGKHFYFNTDGIM 13
                                  (SEQ ID NO: 211)
SGSGQNEFLTLNGKKYYFGSDSKA 14
                                  (SEQ ID NO: 212)
SGSGVTGWRIINNKKYYFNPNNAI 15
                                  (SEQ ID NO: 213)
SGSGAIHLCTINNDKYYFSYDGIL 16
                                  (SEQ ID NO: 214)
SGSGQNGYITIERNNFYFDANNES 17
                                  (SEQ ID NO: 215)
SGSGQNKFLTLNGKKYYFDNDSKA 18
                                  (SEQ ID NO: 216)
SGSGVTGWQTIDGKKYYFNLNTAE 19
                                  (SEQ ID NO: 217)
SGSGATGWQTIDGKKYYFNLNTAE 20
                                  (SEQ ID NO: 218)
SGSGATGWQTIDGKKYYFNTNTFI 21
                                  (SEQ ID NO: 219)
SGSGSTGYTSINGKHFYFNTDGIM 22
                                  (SEQ ID NO: 220)
SGSGQNKFLTLNGKKYYFGSDSKA 23
                                  (SEQ ID NO: 221)
SGSGVTGLRTIDGKKYYFNTNTAV 24
                                  (SEQ ID NO: 222)
SGSGVTGWQTINGKKYYFNTNTSI 25
                                  (SEQ ID NO: 223)
SGSGSTGYTIISGKHFYFNTDGIM 26
                                  (SEQ ID NO: 224)
SGSGQNRFLYLHDNIYYFGNNSKA 27
                                  (SEQ ID NO: 225)
SGSGATGWVTIDGNRYYFEPNTAM 28
                                  (SEQ ID NO: 226)
SGSGANGYKTIDNKNFYFRNGLPQ 29
                                  (SEQ ID NO: 227)
SGSGQNRFLHLLGKIYYFGNNSKA 30
                                  (SEQ ID NO: 228)
SGSGVTGWQTINGKVYYFMPDTAM 31
                                  (SEQ ID NO: 229)
SGSGAGGLFEIDGVIYFFGVDGVK
```

15 amino acid sequences with overlapping 5 amino acids domains and a moving window of 10 amino acids were also designed to cover the gaps between those repetitive units. All peptides were synthesized and probed for binding to A2.

Peptide binding was measured by ELISA. Briefly, 100 µl of 5 µg/ml streptavidin (Southern Biotech) in a sodium carbonate/sodium bicarbonate coating buffer solution (pH 9.6) was added to each well of NUNC Maxisorp® (eBiosciences) 96 well plates and incubated at 4° C. overnight. The plates were washed 4 times with PBS Tween 20 (PBST) using a volume of 304 µl/well before blocking with 3% BSA solution for 60 minutes. Biotinylated *C. difficile* toxin A CTD peptides were diluted to a concentration of 100 ng/ml, in diluent (3% BSA in PBST), added to each well (100 µl/well), and incubated at 25° C. for 60 minutes. The plates were then washed 4 times with PBST using a volume of 300 µl/well. The antibody solution was diluted to the appropriate dilution in diluent buffer (3% BSA in PBST), added to the plates (100 µl/well), and incubated at 25° C. for 60 minutes. Following the incubation with antibody, the plates were again washed 4 times with PBST using a volume of 300 µl/well.

For the secondary antibody reaction, horseradish peroxidase (HRP)-goat anti human IgG (Jackson ImmunoResearch) was diluted to 1:2000 in diluent buffer, added to the plates (100 µl/well), and incubated at 25° C. for 60 minutes. Following the incubation with secondary antibody, the plates were again washed 4 times with PBST using a volume of 300 µl/well. SureBlue Reserve™ TMB peroxidase substrate (KPL Inc.) was then added to each well (100 µl/well) and incubated at 25° C. for 10 minutes. The reaction was stopped by adding 100 µl/well of TMB stop solution (KPL Inc.). The plates were read at a wavelength of 450 nm at 25° C. using a Molecular Devices, Model Spectra Max M5.

No binding was observed between A2 and the longer, overlapping peptide sequences. The A2 antibody bound to non-overlapping peptides 2, 18, 19, 20, 24 and 30:

```
P2:
                                    (SEQ ID NO: 241)
VTGWQTINGKKYYFDINTGA

P18:
                                    (SEQ ID NO: 242)
VTGWQTIDGKKYYFNLNTAE

P19:
                                    (SEQ ID NO: 333)
ATGWQTIDGKKYYFNLNTAE

P20:
                                    (SEQ ID NO: 334)
ATGWQTIDGKKYYFNTNTFI

P24:
                                    (SEQ ID NO: 335)
VTGWQTINGKKYYFNTNTSI

P30
                                    (SEQ ID NO: 243)
VTGWQTINGKVYYFMPDTAM
```

Thus, the A2 antibody recognizes a minimal linear epitope in the C-terminal domain of toxin A comprising the amino acid sequence $X_1$TGWQTI (SEQ ID NO:232), where $X_1$ is A or V. The A2 antibody also recognizes a longer consensus sequence comprising the amino acid sequence of: $X_2$TGWQTI$X_3$GK$X_4$YYF (SEQ ID NO:233), where $X_2$ is A or V, $X_3$ is N or D and $X_4$ is K or V.

As discussed above, it was determined by Western analysis that the B1 and B2 antibodies bound to an epitope in the glucosyl transferase domain (GTD) of toxin B. In addition, sequence analysis showed that B1 and B3 light and heavy chains differed by only 3 CDR and 2 FR mutations in the light chain and 2 FR mutations in the heavy chain and predicted that the B1 and B3 antibodies would bind to the same epitope. Thus, the PepSet peptide binding assay was also used to identify linear epitopes in the GTD of toxin B recognized by B1, B2, and B3, using the general protocol described above for the A2 antibody. For the GTD, the following peptides with 15 amino acid sequences and 5 amino acid overlap were designed to cover the N terminal domain of the molecule:

```
179
                                    (SEQ ID NO: 247)
SGSGMSLVNRKQLEKMANV 180
                                    (SEQ ID NO: 248)
SGSGRKQLEKMANVRFRTQ 181
                                    (SEQ ID NO: 249)
SGSGKMANVRFRTQEDEYV 182
                                    (SEQ ID NO: 250)
SGSGRFRTQEDEYVAILDA 183
                                    (SEQ ID NO: 251)
SGSGEDEYVAILDALEEYH 184
                                    (SEQ ID NO: 252)
SGSGAILDALEEYHNMSEN 185
                                    (SEQ ID NO: 253)
SGSGLEEYHNMSENTVVEK 186
                                    (SEQ ID NO: 254)
SGSGNMSENTVVEKYLKLK 187
                                    (SEQ ID NO: 255)
SGSGTVVEKYLKLKDINSL 188
                                    (SEQ ID NO: 256)
SGSGYLKLKDINSLTDICI 189
                                    (SEQ ID NO: 257)
SGSGDINSLTDICIDTYKK 190
                                    (SEQ ID NO: 258)
SGSGTDICIDTYKKSGRNK 191
                                    (SEQ ID NO: 259)
SGSGDTYKKSGRNKALKKF 192
                                    (SEQ ID NO: 260)
SGSGSGRNKALKKFKEYLV 193
                                    (SEQ ID NO: 261)
SGSGALKKFKEYLVTEVLE 194
                                    (SEQ ID NO: 262)
SGSGKEYLVTEVLELKNNN 195
                                    (SEQ ID NO: 263)
SGSGTEVLELKNNNLTPVE
```

-continued 196 (SEQ ID NO: 264)
SGSGLKNNNLTPVEKNLHF 197 (SEQ ID NO: 265)
SGSGKNLHFVWIGGQINDT 198 (SEQ ID NO: 266)
SGSGVWIGGQINDTAINYI 199 (SEQ ID NO: 267)
SGSGQINDTAINYINQWKD 200 (SEQ ID NO: 268)
SGSGAINYINQWKDVNSDY 201 (SEQ ID NO: 269)
SGSGNQWKDVNSDYNVNVF 202 (SEQ ID NO: 270)
SGSGVNSDYNVNVFYDSNA 203 (SEQ ID NO: 271)
SGSGLKKTVVESAINDTLE 204 (SEQ ID NO: 272)
SGSGVESAINDTLESFREN 205 (SEQ ID NO: 273)
SGSGNDTLESFRENLNDPR 206 (SEQ ID NO: 274)
SGSGSFRENLNDPRFDYNK 207 (SEQ ID NO: 275)
SGSGLNDPRFDYNKFFRKR 208 (SEQ ID NO: 276)
SGSGFDYNKFFRKRMEIIY 209 (SEQ ID NO: 277)
SGSGFFRKRMEIIYDKQKN 210 (SEQ ID NO: 278)
SGSGMEIIYDKQKNFINYY 211 (SEQ ID NO: 279)
SGSGDKQKNFINYYKAQRE 212 (SEQ ID NO: 280)
SGSGFINYYKAQREENPEL 213 (SEQ ID NO: 281)
SGSGKAQREENPELIIDDI 214 (SEQ ID NO: 282)
SGSGENPELIIDDIVKTYL 215 (SEQ ID NO: 283)
SGSGIIDDIVKTYLSNEYS 216 (SEQ ID NO: 284)
SGSGVKTYLSNEYSKEIDE 217 (SEQ ID NO: 285)
SGSGSNEYSKEIDELNTYI 218 (SEQ ID NO: 286)
SGSGKEIDELNTYIEESLN 219 (SEQ ID NO: 287)
SGSGLNTYIEESLNKITQN 220 (SEQ ID NO: 288)
SGSGEESLNKITQNSGNDV 221 (SEQ ID NO: 289)
SGSGKITQNSGNDVRNFGE 222 (SEQ ID NO: 290)
SGSGSGNDVRNFGEFKNGE 223 (SEQ ID NO: 291)
SGSGRNFGEFKNGESFNLY 224 (SEQ ID NO: 292)
SGSGFKNGESFNLYEQELV 225 (SEQ ID NO: 293)
SGSGDVDMLPGIQPDLFES 226 (SEQ ID NO: 294)
SGSGPGIQPDLFESIEKPS 227 (SEQ ID NO: 295)
SGSGDLFESIEKPSSVTVD 228 (SEQ ID NO: 296)
SGSGIEKPSSVTVDFWEMT 229 (SEQ ID NO: 297)
SGSGSVTVDFWEMTKLEAI 230 (SEQ ID NO: 298)
SGSGKLEAIMKYKEYIPEY 231 (SEQ ID NO: 299)
SGSGMKYKEYIPEYTSEHF 232 (SEQ ID NO: 300)
SGSGYIPEYTSEHFDMLDE 233 (SEQ ID NO: 301)
SGSGTSEHFDMLDEEVQSS 234 (SEQ ID NO: 302)
SGSGDMLDEEVQSSFESVL 235 (SEQ ID NO: 303)
SGSGEVQSSFESVLASKSD -continued 236 (SEQ ID NO: 304)
SGSGFESVLASKSDKSEIF 237 (SEQ ID NO: 305)
SGSGASKSDKSEIFSSLGD 238 (SEQ ID NO: 306)
SGSGKSEIFSSLGDMEASP 239 (SEQ ID NO: 307)
SGSGSSLGDMEASPLEVKI 240 (SEQ ID NO: 308)
SGSGMEASPLEVKIAFNSK 241 (SEQ ID NO: 309)
SGSGLEVKIAFNSKGIINQ 242 (SEQ ID NO: 310)
SGSGAFNSKGIINQGLISV 243 (SEQ ID NO: 311)
SGSGKDSYCSNLIVKQIEN 244 (SEQ ID NO: 312)
SGSGKQIENRYKILNNSLN 245 (SEQ ID NO: 313)
SGSGRYKILNNSLNPAISE 246 (SEQ ID NO: 314)
SGSGNNSLNPAISEDNDFN 247 (SEQ ID NO: 315)
SGSGPAISEDNDFNTTTNT 248 (SEQ ID NO: 316)
SGSGDNDFNTTTNTFIDSI 249 (SEQ ID NO: 317)
SGSGTTTNTFIDSIMAEAN 250 (SEQ ID NO: 318)
SGSGFIDSIMAEANADNGR 251 (SEQ ID NO: 319)
SGSGMAEANADNGRFMMEL 252 (SEQ ID NO: 320)
SGSGADNGRFMMELGKYLR 253 (SEQ ID NO: 321)
SGSGLLMFKEGSMNIHLIE 254 (SEQ ID NO: 322)
SGSGEGSMNIHLIEADLRN 255 (SEQ ID NO: 323)
SGSGIHLIEADLRNFEISK 256 (SEQ ID NO: 324)
SGSGADLRNFEISKTNISQ 257 (SEQ ID NO: 325)
SGSGFEISKTNISQSTEQE 258 (SEQ ID NO: 326)
SGSGTNISQSTEQEMASLW 259 (SEQ ID NO: 327)
SGSGSTEQEMASLWSFDDA 260 (SEQ ID NO: 328)
SGSGMASLWSFDDARAKAQ 261 (SEQ ID NO: 329)
SGSGSFDDARAKAQFEEYK 262 (SEQ ID NO: 330)
SGSGRAKAQFEEYKRNYFE All peptides were synthesized and probed for binding to B1, B2, and B3.

The B1 and B3 antibodies both bound to peptides 190, 191, and 192 from the toxin B GTD:

P190:
(SEQ ID NO: 244)
aa 56-70 TDICIDTYKKSGRNK

P191:
(SEQ ID NO: 245)
aa 61-75 DTYKKSGRNKALKKF

P192:
(SEQ ID NO: 246)
aa 66-80 SGRNKALKKFKEYLV

Thus, the B1 and B3 antibodies both recognize a minimal linear epitope in the GTD of toxin B comprising the amino acid sequence SGRNK (SEQ ID NO:234). This epitope maps to amino acids 56-80 of SEQ ID NO:231. The B2 antibody binds very weakly to the P190, P191, and P192 peptides but did not bind strongly to any of the GTD short repeat sequences. The B1 and B3 antibodies were also shown to bind to the same epitope by Octet analysis (data not shown).

The N-terminal 91 amino acids of the GTD shares homology with a domain found in cholera toxin and other pathogens. In cholera, this domain, referred to as the 4-helix bundle (4 HB) or membrane localization domain (MLD), has been shown to be involved in direct binding of the toxin to the cell membrane and mutagenesis of several amino acids in the MLD abolishes this function (Geissler et al, PNAS, 2010). The SGRNK (SEQ ID NO:234) sequence identified through peptide binding analysis is located in a loop between alpha helices 3 and 4 of the MLD.

Amino acids 1-91 of toxin B were cloned into a pET28a expression construct (GeneArt) with an LPETG (SEQ ID NO:336) motif (which allows for sortase-catalyzed conjugation of labels, such as biotin) and a C-terminal 6× His tag both with the wild-type SGRNK (SEQ ID NO:234) sequence and a mutated version: AGANK (SEQ ID NO:337). These constructs had the following amino acid sequences:

```
WT Toxin B MLD (1-91) + LPETGG + 6X HIS
                                        (SEQ ID NO: 338)
MSGLVPRGSHMSLVNRKQLEKMANVRFRTQEDEYVAILDALEEYHN

MSENTVVEKYLKLKDINSLTDIYIDTYKKSGRNKALKKFKEYLVTEVLEL

KNNNLLPETGGHHHHHH

Mutant Toxin B MLD (1-91) + LPETGG + 6X HIS
                                        (SEQ ID NO: 339)
MSGLVPRGSHMSLVNRKQLEKMANVRFRTQEDEYVAILDALEEYHN

MSENTVVEKYLKLKDINSLTDIYIDTYKKAGANKALKKFKEYLVTEVLEL

KNNNLLPETGGHHHHHH
```

The GTD enzymatic domain (amino acids 95-586; "ASE") was also cloned into a pET28a expression construct (GeneArt) with an LPETG motif and a C-terminal 6× His tag. This construct has the following amino acid sequence:

```
WT Toxin B ASE (95-586) + LPETGG + 6X HIS
                                        (SEQ ID NO: 340)
MEKNLHFVWIGGQINDTAINYINQWKDVNSDYNVNVFYDSNAFLINT

LKKTVVESAINDTLESFRENLNDPRFDYNKFFRKRMEIIYDKQKNFINYY

KAQREENPELIIDDIVKTYLSNEYSKEIDELNTYIEESLNKITQNSGNDV

RNFEEFKNGESFNLYEQELVERWNLAAASDILRISALKEIGGMYLDVDML

PGIQPDLFESIEKPSSVTVDFWEMTKLEAIMKYKEYIPEYTSEHFDMLDE

EVQSSFESVLASKSDKSEIFSSLGDMEASPLEVKIAFNSKGIINQGLISV

KDSYCSNLIVKQIENRYKILNNSLNPAISEDNDFNTTTNTFIDSIMAEAN

ADNGRFMMELGKYLRVGFFPDVKTTINLSGPEAYAAAYQDLLMFKEGSMN

IHLIEADLRNFEISKTNISQSTEQEMASLWSFDDARAKAQFEEYKRNYFE

GSLGELPETGGHHHHHH
```

Using both Western and dot blot analysis, B2 was found to bind strongly to the wild type MLD sequence and to the mutant MLD sequence to a much lesser extent. The B1 and B3 antibodies did not bind to either the wild type or mutant MLD sequence by Western or dot blot analysis. No binding to the ASE domain was observed with any of the antibodies.

Binding of the B1, B2, and B3 antibodies to the wild type and mutant toxin B MLD sequences and the wild type toxin B ASE sequence was also assessed using Bio-Layer Interferometry on a Octet® RED96 (FortéBio) at 30° C., as described above in Example 2. As expected, all three antibodies bind to the full length toxin B and toxin B GTD by Octet analysis. B2 bound to the wild type and mutant MLD sequences, while neither B1 nor B3 bound to either MLD sequence. Unexpectedly, all three antibodies were found to bind the toxin B ASE domain by Octet analysis, suggesting that the non-denatured ASE domain may possess some non-specific binding activity due to misfolding or a hydrophobic surface generated by separating the ASE domain from the MLD. In the Western analysis, under denaturing conditions, only the positive control (6× His) antibody bound the ASE domain.

The Octet analysis was also conducted for the B1 and B2 antibodies using the cloned GTD (aa 1-586) with the wild-type SGRNK (SEQ ID NO:234) sequence and a mutated version: AGANK (SEQ ID NO:337). Both antibodies bind strongly to the wild type GTD. B2 binding was reduced by the mutations to the SGRNK motif (SEQ ID NO:234, leading to an approximately 100-fold difference in $K_d$. B1 binding was unaffected by the mutations.

Hydrogen-Deuterium Exchange Mass Spectroscopy shows that the binding of the B2 antibody strongly reduces solvent exchange of the N-terminal helix of the GTD, while the SGRNK (SEQ ID NO:234) sequence is barely protected by B2 binding (data not shown). Saturation binding on the Octet shows that B1 and B2 do not interfere with each other's ability to bind toxin B, thus suggesting that the two antibodies recognize different epitopes.

In summary, while PepSet ELISA showed that the B1 and B3 antibodies bind strongly to a linear epitope comprising the SGRNK (SEQ ID NO:234) motif of the MLD, neither antibody bound to the toxin B MLD by Western, dot blot, or Octet analysis. However, the B1 and B3 antibodies do bind to the toxin B GTD by Western and Octet analysis, suggesting that the conformational epitope recognized by the B1 and B3 antibodies may not be exposed or present when the MLD is expressed separately from the ASE domain. On the other hand, the B2 antibody, which binds very weakly to linear epitopes comprising the SGRNK (SEQ ID NO:234) motif, was found to bind the toxin B MLD by Western, dot blot, and Octet analysis. Mutating the SGRNK (SEQ ID NO:234) sequence in the toxin B MLD and GTD reduces the binding of the B2 antibody. Together, these observations suggest that the B2 antibody binds to a conformational epitope within the MLD. The SGRNK (SEQ ID NO:234) motif within the MLD may play a role in contributing to the tertiary structure of the epitope recognized by B2 or may interact non-specifically with the B2 antibody.

Example 9

In Vivo Efficacy of Antibodies in Hamster Model

The hamster model is widely recognized as the optimal choice for the evaluation of novel treatment strategies against *C. difficile* (Best et al. Gut, 2012, 3(2):145-167; Babcock et al. Infection & Immunity, 2006,74(11):6339-6347). Once the normal intestinal flora of these animals is compromised by antibiotic treatment, challenge with live toxigenic *C. difficile* bacteria or viable spores from a toxigenic strain leads to colonization followed by lethal cecitis. Diarrhea, histological damage and cecitis result from the action of *C. difficile* toxin A and B and the stimulation of local inflammation. These symptoms are very similar to the symptoms observed in human suffering from *C. difficile*-associated diarrhea (CDAD). Thus, the in vivo efficacy of the human anti-toxin A and anti-toxin B antibodies was evaluated in a hamster CDAD model (also known as the hamster *C. difficile* infection (CDI) model).

Female Golden Syrian hamsters (*Mesocricetus auratus*), obtained from Charles River Laboratories, were individually caged and allowed to acclimate to the animal facility for at least 48 hours prior to any treatment, challenge, or other manipulation. All procedures involving animals were conducted under protocols approved by the Institutional Animal Care and Use Committee (IACUC).

For the primary challenge, animals were intraperitoneally (IP) injected with anti-toxin A and B antibodies at doses ranging from 6-50 mg/kg, every day for 4 consecutive days on days −3, −2, −1, and 0 relative to bacterial challenge on day 0. The test antibodies were injected as a combination of one human anti-toxin A antibody and one human anti-toxin B antibody. Combinations tested included 1) A2 (anti toxin A) and B6 (anti toxin B), 2) A2 (anti toxin A) and B4 (anti toxin B), 3) A2 (anti toxin A) and B1 (anti toxin B), and 4) A2 (anti toxin A) and B2 (anti toxin B). Control animals were also injected on the same 4-day injection schedule with 2 ml of PBS. In addition, 24 hours prior to bacterial challenge all animals were weighed and IP injected with 1 ml of a 1 mg/ml clindamycin solution. This antibiotic pretreatment disrupts the normal intestinal flora and facilitates gut colonization with C. difficile.

On the day of challenge, animals received their final IP injection of antibodies or PBS prior to intragastric (IG) challenge with a LD100 dose of C. difficile spores (toxinotype 0 strain 630). To prepare C. difficile spores, the bacteria were grown for 24 hours in thioglycollate medium. This culture was used to inoculate anaerobic blood agar plates which were incubated at 37° C. until the bacterial were confluent (3-4 days). After reaching confluence, plates were incubated for an additional 3 days to induce spore formation. Spores were harvested into PBS without Ca or Mg, washed once and then heat shocked at 56° C. for 10 minutes to kill the vegetative cells. The spore suspension was centrifuged at 500 g for 30 minutes and re-suspended in 20% glycerol in PBS. Spore preparations were frozen at −65° C. or less for long term storage. Viable spore counts (CFU ml$^{-1}$) were assessed by thawing the spore stock at 37° C. and performing serial 10-fold dilutions in water. Dilutions were plated in triplicate onto pre-reduced CDSA agar plates. Plates were incubated under anaerobic conditions at 37° C. for no less than 48 hours. The colonies were counted and CFU ml$^{-1}$ was calculated. After completion of IP injection and IG challenge, animals were housed individually in sterile caging that consists of autoclaved sterilized bedding, autoclaved sterilized water, and irradiated food.

After challenge, animals were observed at least twice a day for morbidity and mortality and were weighed as per approved protocol. Both diarrheal disease and animal behavior were assessed. Diarrheal disease was scored numerically on a scale of 0-3: 0—no disease, 1—loose feces, 2—wet tail and perianal region, 3—wet perianal region, belly and hind paws. Behavior is evaluated categorically using the following criteria: N—animal appears normal; QAR—animal appears slightly lethargic, but alert and arousable; I—animal appears severely dehydrated, immobile, and exhibits hunched posture and/or ruffled fur. If an animal received a behavior score of I, the animal was immediately euthanized via CO$_2$ overdose. Percent weight loss was also calculated and if the animal lost >30% of its pre-challenge body weight it was considered moribund and was immediately euthanized via CO$_2$ overdose. All animals in a study were observed until all animals had either died or been euthanized or there was a period of at least 48 hours with no animals displaying any diarrheal symptoms or behaviors of illness.

In initial tests, the A2 antibody was paired with either the B4 or B6 antibody. Control hamsters that did not receive an antibody usually died by day 4 of the study. With these antibody combinations, a dose of 50 mg/kg provided optimal results (data not shown). At a dose of 50 mg/kg, A2+B4 conferred survival on all animals tested through the end of the study (15 days post challenge), whereas only 60% of animals treated with A2 and B6 survived. FIG. 5A. The animals treated with A2+B4 also showed no disease symptoms and had less weight loss than those treated with A2+B6. FIGS. 5B and 5C.

Figure 6A:
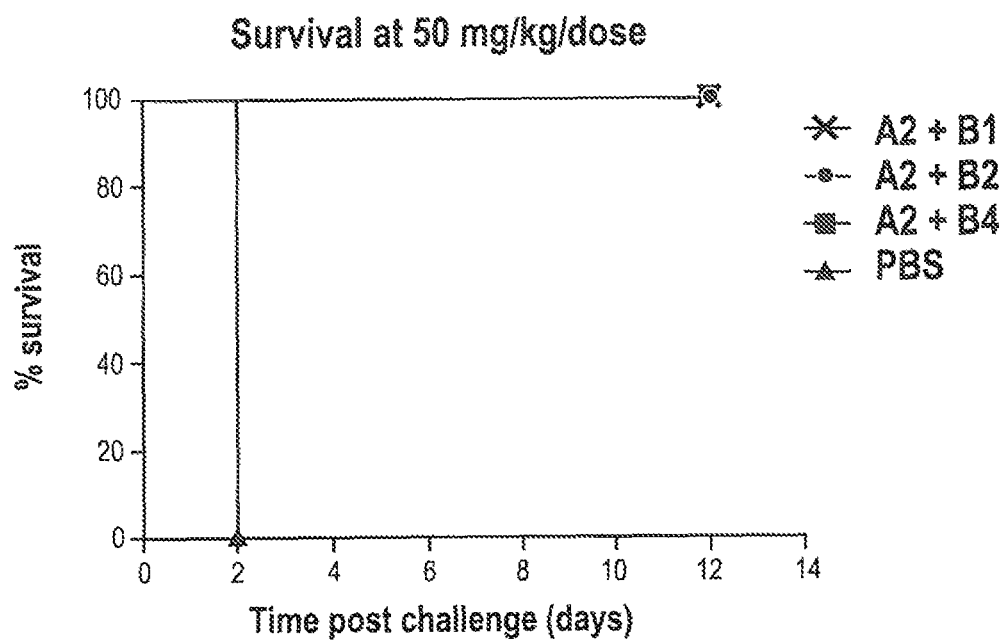
FIGS. 6A-B show the survival of hamsters treated with antibody combinations A2+B1, A2+B2, A2+B4, or control (PBS) at an antibody dose of either 50 mg/kg (FIG. 6A), or 6 mg/kg (FIG. 6B) following an initial challenge with *C. difficile* spores (toxinotype 0 strain 630).
Figure 6B:
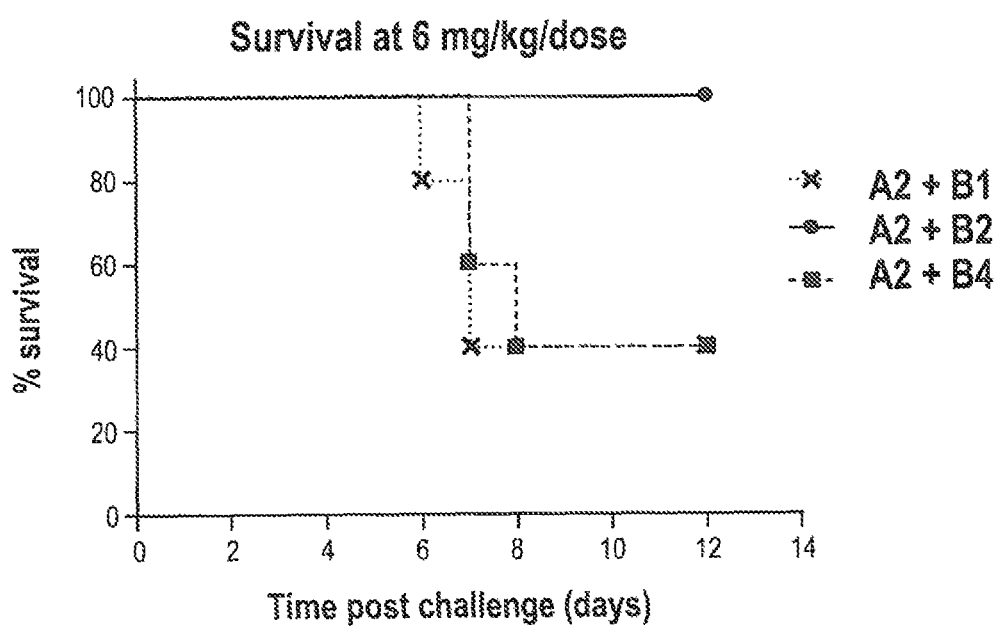
Figure 7A:
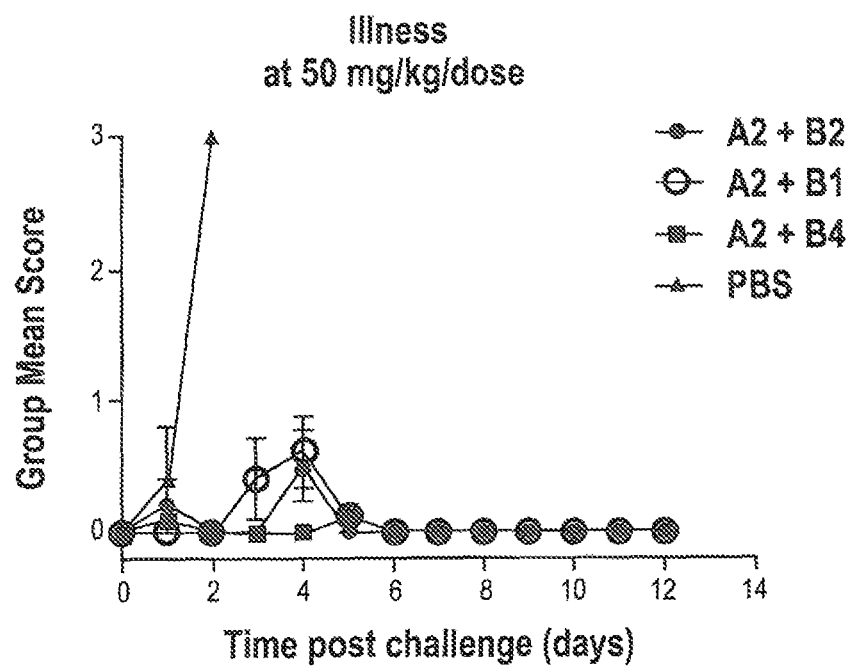
FIGS. 7A-B show the disease symptoms of hamsters treated with antibody combinations A2+B1, A2+B2, A2+B4, or control (PBS) at an antibody dose of either 50 mg/kg (FIG. 7A), or 6 mg/kg (FIG. 7B) following an initial challenge with *C. difficile* spores (toxinotype 0 strain 630), where 0=no illness, 1=loose feces, 2=wet tail and perianal region, and 3=wet tail and lower abdomen.
Figure 7B:
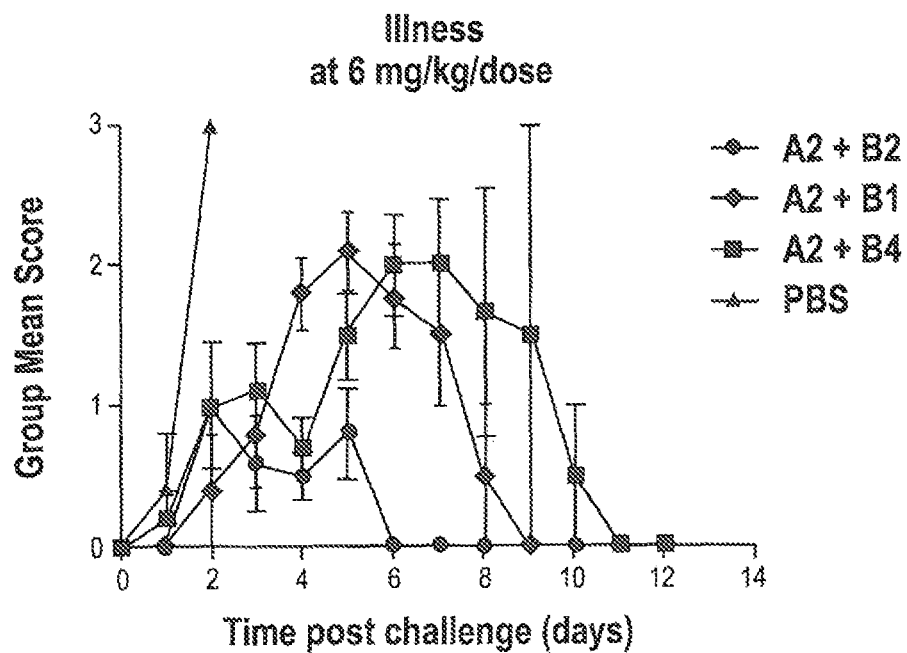
Figure 8A:
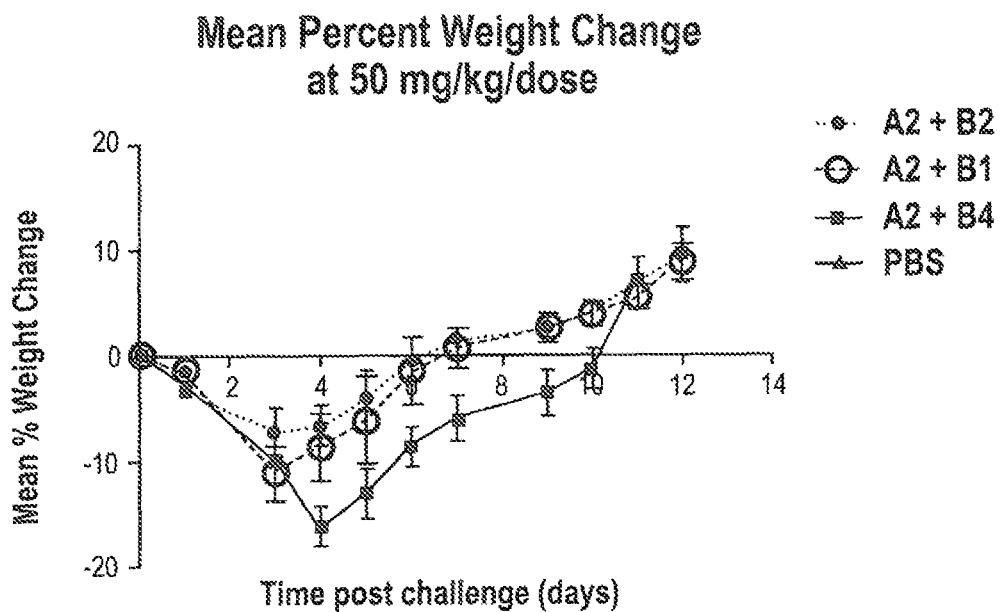
FIGS. 8A-B show the mean weight change post-challenge with *C. difficile* spores (toxinotype 0 strain 630) of hamsters treated with antibody combinations A2+B1, A2+B2, A2+B4, or control (PBS) at an antibody dose of either 50 mg/kg (FIG. 8A), or 6 mg/kg (FIG. 8B).
Figure 8B:
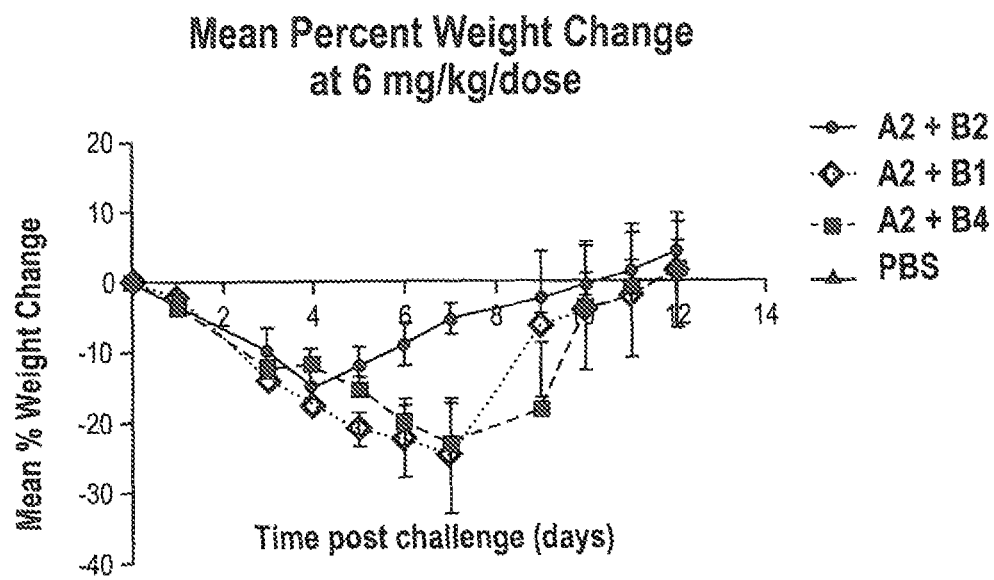

Subsequent testing in the CDAD model compared A2+B4 to A2+B1 and A2+B2. At the 50 mg/kg dose, both A2+B1 and A2+B2 conferred survival on all animals tested through the end of the study (12 days post challenge). FIG. 6A. The antibody pairs were also tested at lower doses. At the 6 mg/kg dose, A2+B2 conferred 100% survival through the end of the study (12 days post challenge), whereas A2+B1 and A2+B4, at the lower dose, conferred only 40% survival. FIG. 6B. The animals treated with 50 mg/kg of each of the three antibody combinations showed minimal disease symptoms, with A2+B2 showing superior protection against illness at the lower dosage (6 mg/kg). FIGS. 7A and 7B. The A2+B2 combination also conferred less weight loss than the A2+B1 and A2+B4 combinations. FIGS. 8A and 8B.

Fecal pellets were collected from challenged animals throughout the study, usually but not always on days 4, 7 and 12 post-challenge. In order to ensure collection of fresh fecal pellets, fecal matter was collected 1 day after animals were transferred into clean cages. Fecal matter was cultured to determine the C. difficile colonization status of animals. To culture fecal matter, fecal pellets were weighed and at least 40 mg of feces were homogenized with 5×volumes of DPBS and 5×volumes ethanol per mg of sample. Material was serially diluted and 100 μl of diluted homogenized fecal matter was cultured on reduced C. difficile selective Agar plates (CDSA plates) at 37° C. in an anaerobic jar. After 56-72 hours of growth, colonies, which should appear as flat to low umbonate yellow colonies with ground glass-like appearance and a slightly filamentous edge, were counted.

Figure 9A:
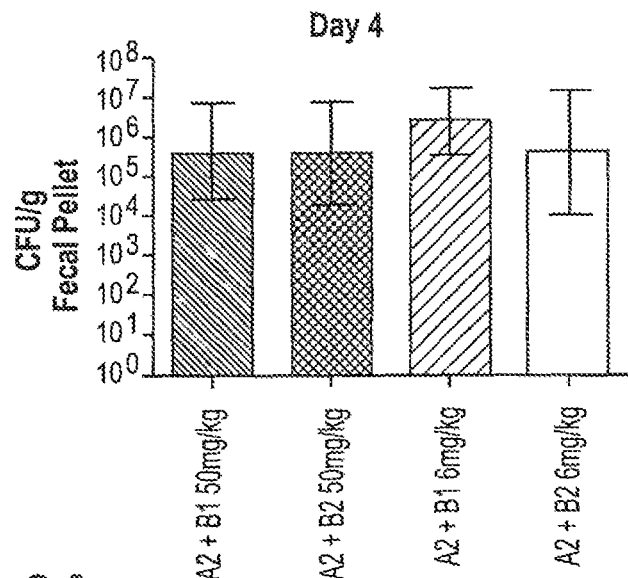
FIGS. 9A-C show the *C. difficile* load in fecal pellets (CFU/g) collected from hamsters treated with antibody combinations (6 mg/kg) A2+B1 or A2+B2 at day 4 post challenge with *C. difficile* spores (toxinotype 0 strain 630) (FIG. 9A), at day 7 post challenge (FIG. 9B), and as a time course (FIG. 9C), showing that by day 13 none of the antibody-treated hamsters showed any detectable fecal shedding.
Figure 9B:
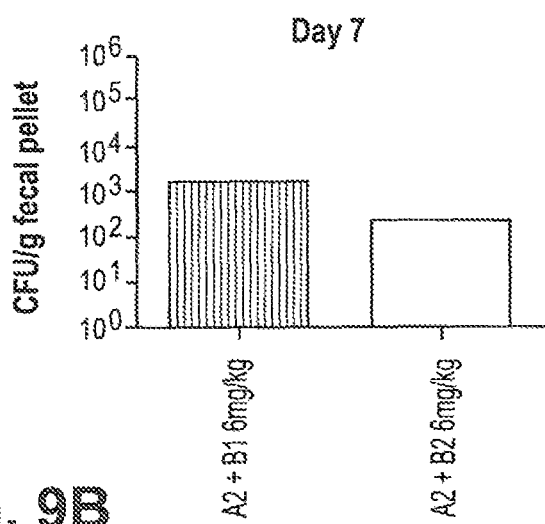
Figure 9C:
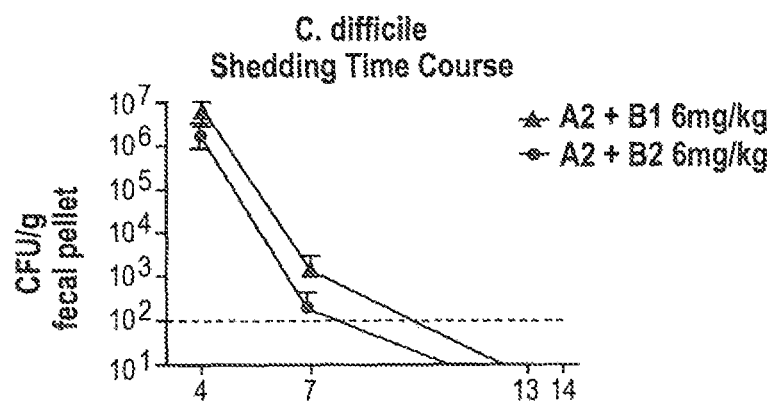

Treatment with 6 mg/kg A2+B1 or A2+B2 did not affect the initial colonization and C. difficile burden, as measured by a C. difficile fecal culture tested on Day 4 post challenge. FIG. 9A. However, when measured at Day 7 post challenge, both antibody combinations reduced C. difficile load as measured by fecal shedding of C. difficile. FIG. 9B. By Day 13 post challenge neither the A2+B1 nor the A2+B2 combination showed any detectable fecal shedding. FIG. 9C.

Example 10

In Vivo Efficacy of Antibodies Against Highly Virulent Strains

Figure 10A:
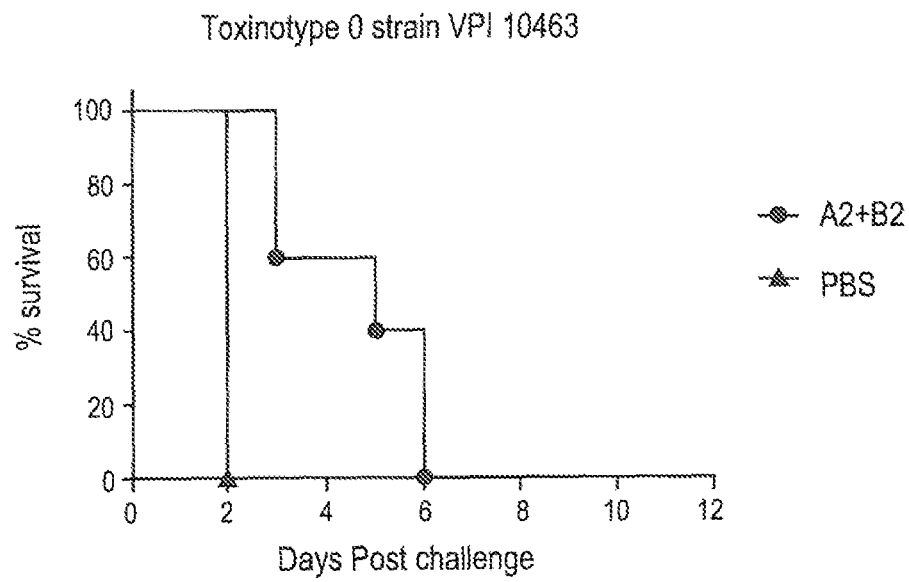
FIGS. 10A-B show the therapeutic effects of antibody combinations A2+B2 at a dosage of 6 mg/kg in a hamster model of CDAD using highly virulent *C. difficile* strains.
Figure 10B:
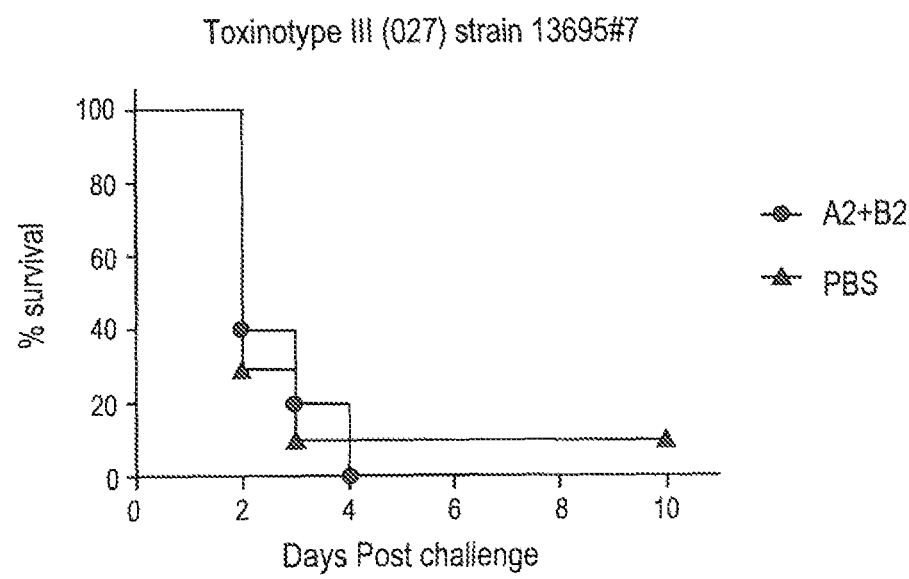

Based on the results from Example 9, the A2+B2 antibody combination was tested against highly virulent strains of C. difficile: the toxinotype 0 strain VPI10463 and toxinotype III (ribotype 027) strain 13695 #7. The hamster CDAD model was used as described in Example 9. At the 6 mg/kg dose, A2+B2 prolonged life as compared to the PBS control but resulted in 0% survival at days 6 and 4, respectively for the VPI10463 and 13695 #7 strains. FIGS. 10A and 10B.

Figure 11A:
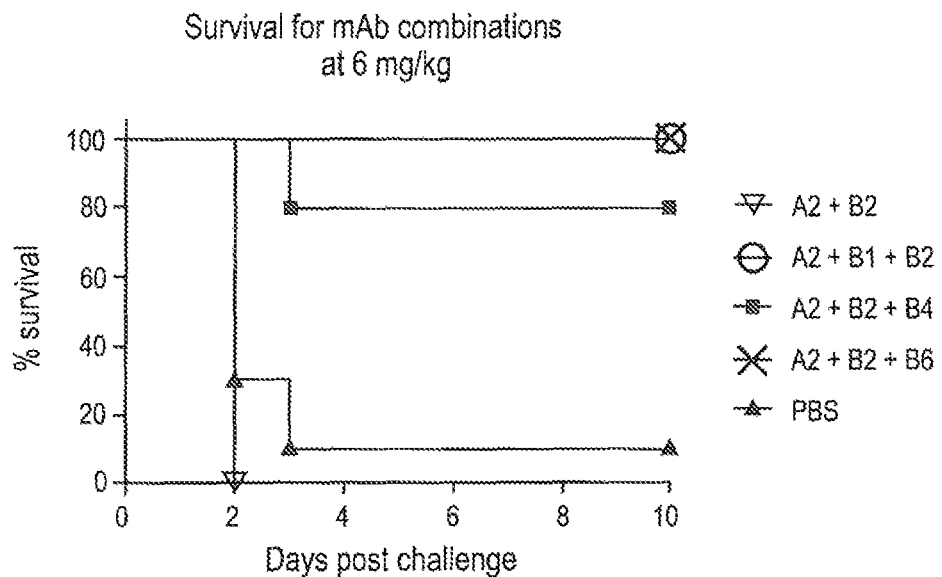
FIGS. 11A-B show the therapeutic effects of antibody combinations A2+B2; A2+B1+B2; A2+B2+B4; and A2+B2+B6 in a hamster model of CDAD using the highly virulent toxinotype III (ribotype 027) strain 13695 #7.
Figure 11B:
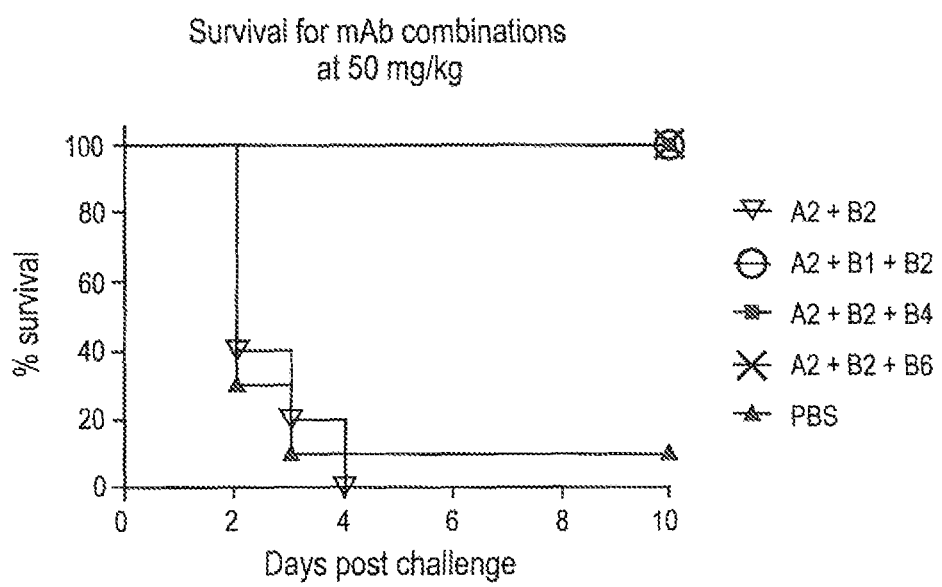
Figure 12A:
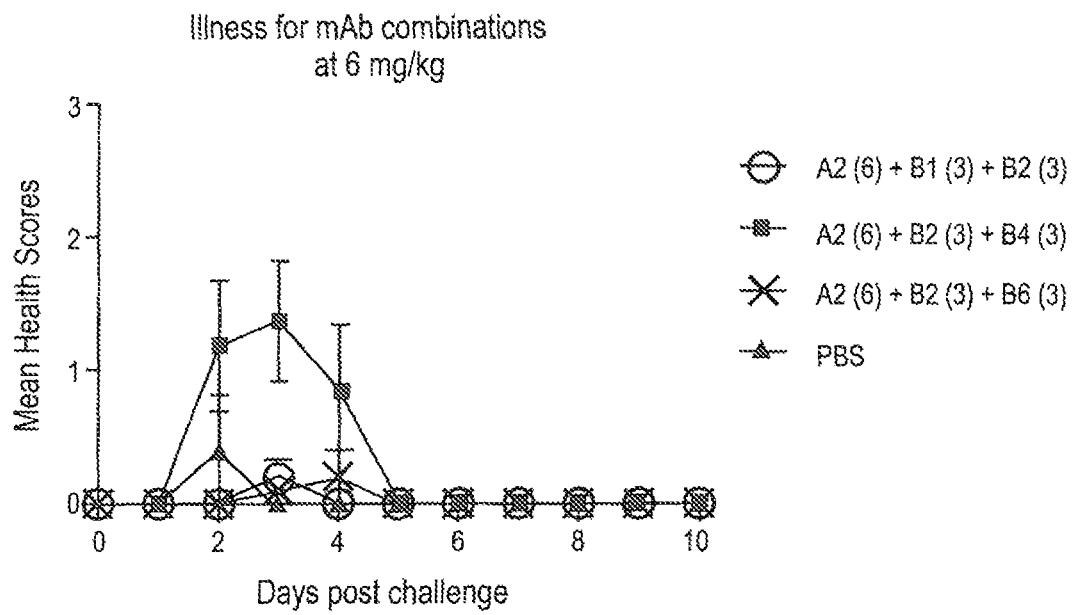
FIGS. 12A-B show the therapeutic effects of antibody combinations A2+B1+B2; A2+B2+B4; and A2+B2+B6 in a hamster model of CDAD using the highly virulent toxinotype III (ribotype 027) strain 13695 #7.
Figure 12B:
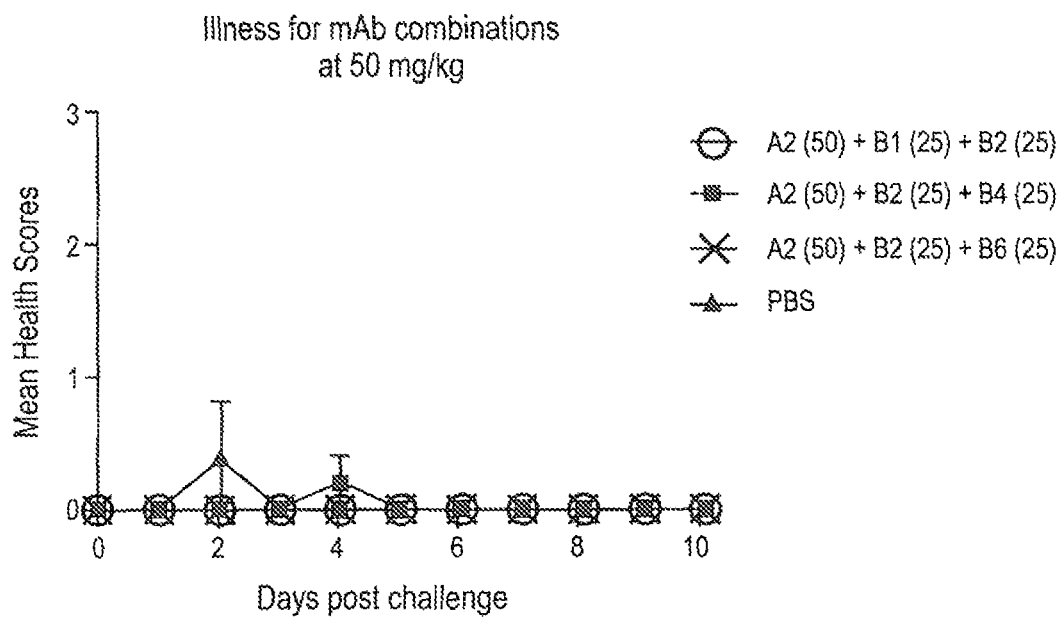

Adding a third antibody to the A2+B2 combination significantly enhances survival in the hamster CDAD model. The following three antibody combinations were tested at low (6 mg/kg) and high doses (50 mg/kg) using epidemic highly virulent strain 13695 #7: A2 (6 mg/kg or 50 mg/kg)+B1 (3 mg/kg or 25 mg/kg)+B2 (3 mg/kg or 25 mg/kg), A2 (6 mg/kg or 50 mg/kg)+B2 (3 mg/kg or 25 mg/kg)+B4 (3 mg/kg or 25 mg/kg), and A2 (6 mg/kg or 50 mg/kg)+B2 (3 mg/kg or 25 mg/kg)+B6 (3 mg/kg or 25 mg/kg). All three combinations conferred survival on all animals tested through the end of the study (10 days post challenge) except for the low dose of A2+B2+B4, which conferred 80% survival through the end of the study. FIGS. 11A and 11B. All three combinations showed strong protection against illness, with two combinations (A2+B1+B2 and A2+B2+B6) showing no disease symptoms and the third combination (A2+B2+B4) showing no disease symptoms after day 5 post challenge. FIGS. 12A and 12B. Similar results were observed for the VPI10463 strain (data not shown).

While this invention has been particularly shown and described with references to preferred embodiments thereof, it will be understood by those skilled in the art that various changes in form and details may be made therein without departing from the scope of the invention encompassed by the appended claims.

What is claimed is:

1. An isolated recombinant monoclonal antibody that binds to *Clostridium difficile* toxin B, wherein said antibody comprises a heavy chain variable domain and a light chain variable domain, and:
   (a) wherein the heavy chain variable domain comprises a complementarity determining region 1 (CDR1) comprising the amino acid sequence of SEQ ID NO:96; a CDR2 comprising the amino acid sequence of SEQ ID NO:98; and a CDR3 comprising the amino acid sequence of SEQ ID NO:100; and wherein the light chain variable domain comprises: a CDR1 comprising the amino acid sequence of SEQ ID NO:103; a CDR2 comprising the amino acid sequence of SEQ ID NO:105; and a CDR3 comprising the amino acid sequence of SEQ ID NO:107;
   (b) wherein the heavy chain variable domain comprises a CDR1 comprising the amino acid sequence of SEQ ID NO:114; a CDR2 comprising the amino acid sequence of SEQ ID NO:116; and a CDR3 comprising the amino acid sequence of SEQ ID NO:118; and wherein the light chain variable domain comprises: a CDR1 comprising the amino acid sequence of SEQ ID NO:121; a CDR2 comprising the amino acid sequence of SEQ ID NO:123; and a CDR3 comprising the amino acid sequence of SEQ ID NO:125;
   (c) wherein the heavy chain variable domain comprises a CDR1 comprising the amino acid sequence of SEQ ID NO:132; a CDR2 comprising the amino acid sequence of SEQ ID NO:134; and a CDR3 comprising the amino acid sequence of SEQ ID NO:136; and wherein the light chain variable domain comprises: a CDR1 comprising the amino acid sequence of SEQ ID NO:139; a CDR2 comprising the amino acid sequence of SEQ ID NO:141; and a CDR3 comprising the amino acid sequence of SEQ ID NO:143;
   (d) wherein the heavy chain variable domain comprises a CDR1 comprising the amino acid sequence of SEQ ID NO:150; a CDR2 comprising the amino acid sequence of SEQ ID NO:152; and a CDR3 comprising the amino acid sequence of SEQ ID NO:154; and wherein the light chain variable domain comprises: a CDR1 comprising the amino acid sequence of SEQ ID NO:157; a CDR2 comprising the amino acid sequence of SEQ ID NO:159; and a CDR3 comprising the amino acid sequence of SEQ ID NO:161;
   (e) wherein the heavy chain variable domain comprises a CDR1 comprising the amino acid sequence of SEQ ID NO:168; a CDR2 comprising the amino acid sequence of SEQ ID NO:170; and a CDR3 comprising the amino acid sequence of SEQ ID NO:172; and wherein the light chain variable domain comprises: a CDR1 comprising the amino acid sequence of SEQ ID NO:175; a CDR2 comprising the amino acid sequence of SEQ ID NO:177; and a CDR3 comprising the amino acid sequence of SEQ ID NO:179; or
   (f) wherein the heavy chain variable domain comprises a CDR1 comprising the amino acid sequence of SEQ ID NO:186; a CDR2 comprising the amino acid sequence of SEQ ID NO:188; and a CDR3 comprising the amino acid sequence of SEQ ID NO:190; and wherein the light chain variable domain comprises: a CDR1 comprising the amino acid sequence of SEQ ID NO:193; a CDR2 comprising the amino acid sequence of SEQ ID NO:195; and a CDR3 comprising the amino acid sequence of SEQ ID NO:197.

2. The isolated recombinant monoclonal antibody of claim 1,
   (a) wherein the heavy chain variable domain comprises the amino acid sequence of SEQ ID NO:92 and the light chain variable domain comprises the amino acid sequence of SEQ ID NO:94;
   (b) wherein the heavy chain variable domain comprises the amino acid sequence of SEQ ID NO:110 and the light chain variable domain comprises the amino acid sequence of SEQ ID NO:112;
   (c) wherein the heavy chain variable domain comprises the amino acid sequence of SEQ ID NO:128 and the light chain variable domain comprises the amino acid sequence of SEQ ID NO:130;
   (d) wherein the heavy chain variable domain comprises the amino acid sequence of SEQ ID NO:146 and the light chain variable domain comprises the amino acid sequence of SEQ ID NO:148;

(e) wherein the heavy chain variable domain comprises the amino acid sequence of SEQ ID NO:164 and the light chain variable domain comprises the amino acid sequence of SEQ ID NO:166; or (f) wherein the heavy chain variable domain comprises the amino acid sequence of SEQ ID NO:182 and the light chain variable domain comprises the amino acid sequence of SEQ ID NO:184.

3. The isolated recombinant monoclonal antibody of claim 1, wherein the antibody comprises at least one of the following characteristics:

(a) the antibody binds to *C. difficile* toxin B with a dissociation constant ($K_D$) equal to or less than 100 pM;

(b) the antibody neutralizes the in vitro cytotoxicity of *C. difficile* toxin B in the Vero monkey kidney cell line with an NT50 equal to or less than 1000 pM;

(c) the antibody neutralizes the *C. difficile* toxin B induced loss of transepithelial resistance (TEER) in the T-84 cell line with an NT50 equal to or less than 200 pM; or (d) the antibody binds to toxin B produced by at least the strains of toxinotypes 0, III, and V.

4. The isolated recombinant monoclonal antibody of claim 3, wherein the antibody binds to toxin B produced by at least the strains of toxinotypes 0, III, V, and VIII, toxin B produced by at least the strains of toxinotypes 0, III, V, VIII, and XII, or toxin B produced by at least the strains of toxinotypes 0, III, V, VIII, XII, and XV.

5. The isolated recombinant monoclonal antibody of claim 1, wherein the antibody is a human antibody.

6. The isolated recombinant monoclonal antibody of claim 1, wherein the antibody is a bispecific antibody, wherein the bispecific antibody comprises 1) a first antigen binding site comprising a heavy chain variable domain and a light chain variable domain (a) wherein the heavy chain variable domain comprises a complementarity determining region 1 (CDR1) comprising the amino acid sequence of SEQ ID NO:6; a CDR2 comprising the amino acid sequence of SEQ ID NO:8; and a CDR3 comprising the amino acid sequence of SEQ ID NO:10; and wherein the light chain variable domain comprises: a CDR1 comprising the amino acid sequence of SEQ ID NO:13; a CDR2 comprising the amino acid sequence of SEQ ID NO:15; and a CDR3 comprising the amino acid sequence of SEQ ID NO:17;

(b) wherein the heavy chain variable domain comprises a CDR1 comprising the amino acid sequence of SEQ ID NO:24; a CDR2 comprising the amino acid sequence of SEQ ID NO:26; and a CDR3 comprising the amino acid sequence of SEQ ID NO:28; and wherein the light chain variable domain comprises: a CDR1 comprising the amino acid sequence of SEQ ID NO:31; a CDR2 comprising the amino acid sequence of SEQ ID NO:33; and a CDR3 comprising the amino acid sequence of SEQ ID NO:35;

(c) wherein the heavy chain variable domain comprises a CDR1 comprising the amino acid sequence of SEQ ID NO:42; a CDR2 comprising the amino acid sequence of SEQ ID NO:44; and a CDR3 comprising the amino acid sequence of SEQ ID NO:46; and wherein the light chain variable domain comprises: a CDR1 comprising the amino acid sequence of SEQ ID NO:49; a CDR2 comprising the amino acid sequence of SEQ ID NO:51; and a CDR3 comprising the amino acid sequence of SEQ ID NO:53;

(d) wherein the heavy chain variable domain comprises a CDR1 comprising the amino acid sequence of SEQ ID NO:60; a CDR2 comprising the amino acid sequence of SEQ ID NO:62; and a CDR3 comprising the amino acid sequence of SEQ ID NO:64; and wherein the light chain variable domain comprises: a CDR1 comprising the amino acid sequence of SEQ ID NO:67; a CDR2 comprising the amino acid sequence of SEQ ID NO:69; and a CDR3 comprising the amino acid sequence of SEQ ID NO:71; or (e) wherein the heavy chain variable domain comprises a CDR1 comprising the amino acid sequence of SEQ ID NO:78; a CDR2 comprising the amino acid sequence of SEQ ID NO:80; and a CDR3 comprising the amino acid sequence of SEQ ID NO:82; and wherein the light chain variable domain comprises: a CDR1 comprising the amino acid sequence of SEQ ID NO:85; a CDR2 comprising the amino acid sequence of SEQ ID NO:87; and a CDR3 comprising the amino acid sequence of SEQ ID NO:89, and wherein the heavy chain variable domain of said antibody is linked to a human constant region, and 2) a second antigen binding site comprising the heavy chain variable domain and light chain variable domain of the antibody of claim 1.

7. The isolated recombinant monoclonal antibody of claim 1, wherein the antibody is a bispecific antibody, wherein the bispecific antibody comprises 1) a first antigen binding site comprising the heavy chain variable domain and light chain variable domain of a B1 antibody and 2) a second antigen binding site comprising the heavy chain variable domain and light chain variable domain of a B2 antibody.

8. A composition comprising the isolated recombinant monoclonal antibody of claim 1 that binds to *C. difficile* toxin B.

9. The composition of claim 8, further comprising at least one antibody that binds to *C. difficile* toxin A, wherein the at least one antibody that binds to *C. difficile* toxin A is one or more of A1, A2, A3, A4, and A5 antibodies.

10. The composition of claim 8, further comprising at least one antibody that binds to *C. difficile* toxin A and wherein the antibody that binds to *C. difficile* toxin B is one or more of a B1, B2, B3, B4, B5, and B6 antibody.

11. The composition of claim 8, further comprising a pharmaceutically acceptable excipient.

12. A method of treating a *C. difficile* infection, comprising administering to a subject one or more of the isolated recombinant monoclonal antibodies of claim 1 in an amount effective to treat the *C. difficile* infection.

13. A method of treating a *C. difficile* infection, comprising administering to a subject the composition of claim 8 in an amount effective to treat the *C. difficile* infection.

14. The method of claim 12, wherein the subject is a human.

15. The isolated recombinant monoclonal antibody of claim 1, wherein the antibody is expressed from a transgenic animal.

16. The isolated recombinant monoclonal antibody of claim 1, wherein the antibody is expressed from an insect cell, a Chinese Hamster Ovary cell or a Human Embryonic Kidney 293T cell.

17. The isolated recombinant monoclonal antibody of claim 1, wherein the antibody is expressed from a Chinese Hamster Ovary cell.

18. The isolated recombinant monoclonal antibody of claim 1, wherein the heavy chain variable domain of the antibody is linked to a human constant region and wherein a source of the heavy chain variable domain and the light chain variable domain is different from a source of the human constant region.

19. The isolated recombinant monoclonal antibody of claim 1, wherein the antibody is labeled.

* * * * *